(12) United States Patent
Hert et al.

(10) Patent No.: US 10,676,446 B2
(45) Date of Patent: Jun. 9, 2020

(54) BICYCLIC QUINAZOLINONE DERIVATIVES

(71) Applicant: Hoffmann-La Roche Inc., Little Falls, NJ (US)

(72) Inventors: Jerome Hert, Basel (CH); Daniel Hunziker, Moehlin (CH); Christoph Kuratli, Moehlin (CH); Rainer E. Martin, Basel (CH); Patrizio Mattei, Riehen (CH); Alexander Lee Satz, Schoenenbuch (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/728,894

(22) Filed: Oct. 10, 2017

(65) Prior Publication Data

US 2018/0029996 A1    Feb. 1, 2018

Related U.S. Application Data

(63) Continuation of application No. PCT/EP2016/057549, filed on Apr. 7, 2016.

(30) Foreign Application Priority Data

Apr. 10, 2015 (EP) .................................. 15163133

(51) Int. Cl.

| | |
|---|---|
| *C07D 239/90* | (2006.01) |
| *A61K 31/517* | (2006.01) |
| *A61P 27/06* | (2006.01) |
| *C07D 401/04* | (2006.01) |
| *C07D 471/04* | (2006.01) |
| *C07D 401/12* | (2006.01) |
| *C07D 403/04* | (2006.01) |
| *C07D 403/12* | (2006.01) |
| *C07D 405/12* | (2006.01) |
| *C07D 413/12* | (2006.01) |
| *A61P 27/02* | (2006.01) |

(52) U.S. Cl.
CPC ......... *C07D 239/90* (2013.01); *C07D 401/04* (2013.01); *C07D 401/12* (2013.01); *C07D 403/04* (2013.01); *C07D 403/12* (2013.01); *C07D 405/12* (2013.01); *C07D 413/12* (2013.01); *C07D 471/04* (2013.01)

(58) Field of Classification Search
CPC ... C07D 239/88; C07D 239/91; C07D 239/90
USPC .......................... 544/287; 514/266.22, 266.2
See application file for complete search history.

(56) References Cited

U.S. PATENT DOCUMENTS

| | | | |
|---|---|---|---|
| 3,392,149 A | 7/1968 | von der Emden et al. | |
| 5,202,322 A | 4/1993 | Allen et al. | |
| 5,238,942 A | 8/1993 | Chakravarty et al. | |
| 5,240,928 A | 8/1993 | Allen et al. | |
| 5,290,780 A | 3/1994 | Venkatesan et al. | |
| 5,304,565 A | 4/1994 | Morimoto et al. | |
| 5,358,951 A | 10/1994 | Levin et al. | |
| 5,470,975 A | 11/1995 | Atwal | |
| 5,472,961 A | 12/1995 | Gottschlich et al. | |
| 5,532,243 A | 7/1996 | Gilligan | |
| 6,821,964 B2 | 11/2004 | Colon-Cruz et al. | |
| 6,841,560 B2 | 1/2005 | Thompson et al. | |
| 7,271,260 B2 | 9/2007 | Lee et al. | |
| 8,329,907 B2 | 12/2012 | Schultz et al. | |
| 8,697,883 B2 | 4/2014 | Abouabdellah et al. | |
| 8,841,324 B2 | 9/2014 | Staehle et al. | |
| 9,029,387 B2 | 5/2015 | Staehle et al. | |
| 9,493,486 B2 | 11/2016 | Hunziker et al. | |
| 9,802,944 B2 | 10/2017 | Di Giorgio et al. | |
| 10,208,052 B1 | 2/2019 | Zheng et al. | |

(Continued)

FOREIGN PATENT DOCUMENTS

| | | |
|---|---|---|
| CA | 2 768 095 | 1/2011 |
| CA | 2878442 A1 | 4/2014 |

(Continued)

OTHER PUBLICATIONS 1206969-43-8,Database Registry [retrieved online May 25, 2016] Chemical Abstracts Service, Feb. 22, 2010 (Feb. 22, 2010), BroadPharm: XP002707619, retrieved from STN Database accession No. 1206969-43-8 the whole document.
959567-58-9,Database Registry [retrieved online May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patent review" Expert Opin Ther Patents 23(9):1123-1132 ( 2013).

(Continued)

*Primary Examiner* — Susanna Moore
(74) *Attorney, Agent, or Firm* — Katherine J. Mackenzie

(57) ABSTRACT

The invention provides novel compounds having the general formula (I)

(I)

[Chemical structure diagram showing formula (I) with substituents $R^1, A^2, R^{13}, R^7, O, R^2, R^3, R^4, R^{10}, R^{12}, A^1, N, R^5, R^6, A^3, N, R^{14}, R^9$]

wherein $R^1$, $R^2$, $R^3$, $R^4$, $R^5$, $R^6$, $R^7$, $R^8$, $R^9$, $R^{10}$, $R^{12}$, $R^{13}$, $R^{14}$, $A^1$, $A^2$, $A^3$, n and m are as described herein.

39 Claims, No Drawings

(56) References Cited

U.S. PATENT DOCUMENTS

| | | |
|---|---|---|
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Anand et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |

FOREIGN PATENT DOCUMENTS

| | | |
|---|---|---|
| CN | 1751047 | 3/2006 |
| CN | 102459207 A | 5/2012 |
| EP | 0 417 631 A2 | 3/1991 |
| EP | 2 301 936 A1 | 3/2011 |
| EP | 3 187 492 A1 | 7/2017 |
| EP | 3385261 A1 | 10/2018 |
| JP | 2001039950 | 2/2001 |
| JP | 2005-239708 | 9/2005 |
| JP | 2007-176809 | 7/2007 |
| JP | 2008-501743 | 1/2008 |
| JP | 2008-31064 | 2/2008 |
| JP | 2008-531533 | 8/2008 |
| JP | 2008-540547 | 11/2008 |
| JP | 2009-161449 | 7/2009 |
| JP | 2011-502150 | 1/2011 |
| RU | 2 375 352 C2 | 12/2009 |
| WO | 99/40070 | 8/1999 |
| WO | 01/30780 | 5/2001 |
| WO | 02/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008-31064 A | 2/2008 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 | 6/2010 |
| WO | 2010/063352 A1 | 6/2010 |
| WO | 2010/099938 | 9/2010 |
| WO | 2010/108651 | 9/2010 |
| WO | 2010/112116 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2009/154132 | 12/2011 |
| WO | 2011/151461 A2 | 12/2011 |
| WO | 2012/020008 | 2/2012 |
| WO | 2012/024620 | 2/2012 |
| WO | 2012/028243 | 3/2012 |
| WO | 2012/080727 | 6/2012 |
| WO | 2012/166415 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/133112 A1 | 9/2014 |
| WO | 2014/139324 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 A1 | 5/2015 |
| WO | 2015/078803 | 6/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/154023 A1 | 10/2015 |
| WO | 2013/031987 | 3/2016 |
| WO | 2016/061160 A1 | 4/2016 |
| WO | 2016/128529 A1 | 8/2016 |
| WO | 2016/162390 | 10/2016 |
| WO | 2017/005073 | 1/2017 |
| WO | 2017/037146 | 3/2017 |
| WO | 2017/037670 A1 | 3/2017 |
| WO | 2017/050732 | 3/2017 |
| WO | 2017/050747 | 3/2017 |
| WO | 2017/050791 | 3/2017 |
| WO | 2017/050792 | 3/2017 |
| WO | 2017/053722 A1 | 3/2017 |
| WO | 2017/091673 A2 | 6/2017 |
| WO | 2017/139978 | 8/2017 |
| WO | 2018/167001 A1 | 9/2018 |
| WO | 2018/167113 | 9/2018 |

OTHER PUBLICATIONS

Benesh et al., FEBS Lett 588:2712-2727 (2014).
CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.
CAS Registry Database, 1352926-14-7,Database Registry [retrieved online May 25, 2016] Chemical Abstracts Service Jan. 12, 2012 (Jan. 12, 2012), All i chern LLC: XP002707617, retrieved from STN Database accession No. 1352926-14-7 see also RN: 135295-74-6; the whole document.
Database Capulus (online) Chemical Abstracts Service Columbus Ohio, 1993, Database accession No. 1994:483155 RN156411-73-3, 156411-74-4 (1993).

(56) References Cited

OTHER PUBLICATIONS

Garcia-Gutierrez et al., "Novel inhibitors to Taenia solium Cu/Zn superoxide dismutase identifed by virtual screening" J. Computer. Aided Molecular Design 25:1135-1145 ( 2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Harald M.H.G. Albers et al., "Discovery and Optimization of Boronic Acid Based Inhibitors of Autotaxin" Journal of Medicinal Chemistry 53(13):4958-4967 (Jul. 8, 2010).
Hoeglund et al., "Optimization of a pidemidic acid autotaxin inhibitor" Journal of Medicinal Chemistry 53:1056-1066 (Dec. 30, 2009).
International Search Report for International Patent Application No. PCT/EP2014/075360 dated Feb. 9, 2015.
ISR for PCT/EP2013/061890, dated Sep. 17, 2013.
ISR for PCT/EP2013/069679, dated Nov. 8, 2013.
Jones et al., ACS Med Chem Lett 7:857-861 ( 2016).
Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).
Litherland et al., "The Amino-derivatives of Pentuerythritol. Part I. Preparation." (Published on Jan. 1, 1938. Downloaded by Roche Group on May 24, 2016; 17:23:15.),:1588-1595.
Mayo Clinic Staff, (Lupus[online], retrieved from the internet on Jan. 24, 2017; http://www.mayoclinic.org/diseases-conditions/lupus basics/definition/CON-20019676) 2017.
Orr et al., "One-pot synthesis of chiral azetidines from chloroaldehyde and chiral amines" Tetrahedron Letters (XP055073241), 52:3618-3620 ( 2011).
Overberger et al., "Absolute Configuration of 2,7-Diazaspiro[4.4]nonane. A Reassignment" J. Org. Chem. (XP055072840), 46:2757-2764 ( 1981).
Sippy et al., "Preparation and characterization of N-(3-pyridinyl) spirocyclic diamines as ligands for nicotinic acetylcholine receptors" Bioorganic & Medicinal Chemistry Letters 19:1682-1685 (2009).
Stocks et al., "A Practical Method for Targeted Library Design Balancing Lead-like Properties with Diversity" Chem Med Chem (XP002707616), 4:800-808 ( 2009).
Written Opinion for PCT/EP2013/061890, dated Sep. 17, 2013.
Written Opinion for PCT/EP2013/069679, dated Nov. 8, 2013.
pp. 1-13 (STN Columbus (STN International) dated Oct. 9, 2015).
Sheridan et al., "The Most Common Chemical Replacements in Drug-Like Compounds" J. Chem. Inf. Comput. Sci. 42(1):103-108 (2002).
Database Registry Numbers, Chemical Abstract Service (CAS), 38 pages (Dec. 26, 2007).
Harald M.H.G. Albers et al., "Structure-Based Design of Novel Boronic Acid-Based Inhibitors of Autotaxin" Journal of Medicinal Chemistry 54(13):4619-4626 (2011).
Patani et al., "Bioisosterism: A Rational Approach in Drug Design," Chem.Ref. (1996), vol. 96, pp. 3147-3176.
Anderson, "The Process of Structure-Based Drug Design" Chemistry & Biology 10:787-797 (Sep. 2003).
Bora, Rajesh O., et al., "[1, 2, 4]-Oxadiazoles: Synthesis and Biological Applications" Mini-Reviews in Med. Chem 14(4):355-369 (Mar. 13, 2014).
Erdik, Ender, "Transition Metal Catalyzed Reactions of Organozinc Reagents" Tetrahedron Report No. 23 48(44):9577-9648 (Jan. 1, 1992).
Farina, V. et al. Organic Reactions "The Stille Reaction" Paquette, Leo A., New York-US:Wiley and Sons, vol. 50:1-704 (Apr. 1, 1997).
Green et al. Protective Groups in Organic Synthesis (Table of Contents only, in 4 pages), Second edition, New York:John Wiley & Sons, Inc., (1991).
Hall, Dennis.. ed. et al. Boronic Acids: Preparation, Applications in Organic Synthesis and Medicine (Description and table of contents only, 2 pages), Hall, Dennis,Wiley,:1-571 (Jan. 1, 2006).
Hemming, K. Science of Synthesis, Product 13: 1, 2, 3-Triazoles "Product Class 6:1,2,4-Oxadiazoles" Storr, R.C. & Gilchrist, T.L., eds., Stuttgart-DE:Thieme Verlagsgruppe, vol. 13:127-184 (Jan. 1, 2004).
Henke, Brad R., et al., "Optimization of 3-(1H-Indazol-3-ylmethl)-1,5-benzodiazepines as Potent, Orally Active CCK-A Agonists" J Med Chem 40:2706-2725 (Apr. 22, 1997).
International Search Report for PCT/EP2016/072277, pp. 1-5 (Dec. 8, 2016).
Li, Jie Jack et al. Name Reactions for Homologation, Part 1 "Name Reactions for Homologation, Part 1" (Abstract of text, author information, and table of contents only, 2 pages),Wiley and Sons,:1-685 (May 1, 2009).
Matralis et al., "Development and therapeutic potential of autotaxin small molecule inhibitors: From bench to advanced clinical trials" Med. Res. Rev.:1-38 (2018).
Mitchell, Terence N., "Palladium-Catalysed Reactions of Organotin Compounds" Synthesis 9:803-815 (Aug. 16, 1991).
Negishi, Ei-ichi, et al. Metal-Catalyzed Cross-Coupling Reactions "Chapter 1: Palladium or NickelCatalyzed CrossCoupling with Organometals Containing Zinc, Magnesium, Aluminum, and Zirconium" (Preface, table of contents, list of contributors only, 22 pages), Diederich, Francois, Stang, Peter J., eds., Weinheim, DE:Wiley-VCH Verlag GmbH,:1-47 (Jan. 1, 2004).
Polshettiwar, Vivek, et al., "Suzuki-Miyaura Cross-Coupling Reations in Aqueous Media: Green and Sustainable Syntheses of Biaryles" ChemSUSChem 3:502-522 (Jan. 1, 2010).
Pouliot, Marie-France, et al., "Syntheses of 1,3,4-oxadiazoles from 1,2-diacylhydrazines using [Et2NSF2]BF4 as a practical cyclodehydration agent" Org. Biomol. Chem 10:988-993 (Oct. 27, 2012).
Schlaeger, "The Protein Hydrolysate, Primatone RL, is a Cost-effective Multiple Growth Promoter of Mammalian Cell Culture in Serum-contianing and Serum-free Media and Displays Anti-apoptosis Properties" J Immunol Methods 194:191-199 (1996).
Sheridan et al., "Cautious optimism surrounds early clinical data for PD-1 blocker" Nature Biotechnology 30:729-730 (2012).
Stille, John K., "The Palladium-Catalyzed Cross-Coupling Reactions of Organotin Reagents with Organic Electrophiles" Angew Chem. Int. Ed. Engl. 25:508-524 (Jan. 1, 1986).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).
Suzuki, A., et al., "Synthetic Studies via the cross-coupling reaction of organoboron derivatives with organic halides" Pure Appl Chem 63(3):419-422 (Jan. 1, 1991).
Thiel, "Structure-aided drug design's next generaton" Nature Biotechnology 22(5):513-519 (2004).
Tucker, Thomas J., et al., "Discovery of 3-{5-[(6-Amino-1H-pyrazolo [3,4-b]pyridine-3-yl)methoxy] 2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
WO:ISR, pp. 1-6 (International Search Report from PCT/EP2016/070561 dated Oct. 23, 2016 Oct. 12, 2016).

BICYCLIC QUINAZOLINONE DERIVATIVES

RELATED APPLICATIONS

This application is a continuation of International Application No. PCT/EP2016/057549, filed Apr. 7, 2016, claiming priority to EP Application Number 15163133.0 filed Apr. 10, 2015, each of which are incorporated herein by reference in its entirety.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

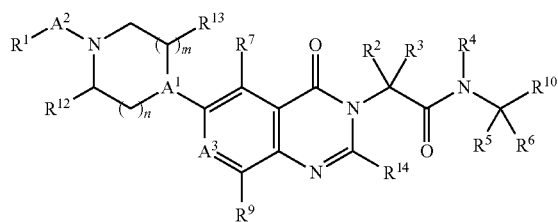

(I)

$R^1$ is hydroxyalkyl, dihydroxyalkyl, hydroxycycloalkyl, alkoxy, haloalkoxy, alkoxyalkoxyalkyl, alkoxyalkyl, haloalkoxyalkyl, alkyl, haloalkyl, alkylsulfonyl, haloalkylsulfonyl, aminosulfonylalkyl, cyanoalkyl, nitratealkyl, substituted cycloalkyl, substituted cycloalkylalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, halohaloxy, alkylcarbonyl, carboxy, halogen and cyano;

$R^2$ and $R^3$ are independently selected from H, alkyl and cycloalkyl;

or $R^2$ and $R^3$ together with the carbon to which they are attached form a cycloalkyl;

$A^1$ is —CH—, —C(OH)— or —N—;

$A^2$ is —C(O)—, —C(O)CH$_2$—, —CH$_2$—, —NR$^{11}$C(O)—, —NR$^{11}$C(O)CH$_2$—, —S(O)$_2$—;

$A^3$ is —CR$^8$— or —N—;

one of $R^4$ and $R^5$ is H or alkyl and the other is H, alkoxyalkyl, alkoxycarbonylalkyl, haloalkoxycarbonylalkyl, alkyl, haloalkyl, carboxyalkyl, cycloalkyl or substituted aminocarbonylalkyl, wherein substituted aminocarbonylalkyl is substituted on the nitrogen atom by two substituents independently selected from H, alkyl, cycloalkyl and substituted phenyl, wherein substituted phenyl is substituted with one to three substituents independently selected from H, alkyl, haloalkyl and cycloalkyl;

or $R^4$ and $R^5$ together with the nitrogen and carbon atoms to which they are attached form a heterocycloalkyl;

$R^6$ is H or alkyl;

$R^7$, $R^8$ and $R^9$ are independently H, alkyl, cycloalkyl, halogen or cyano;

$R^{10}$ is substituted aryl or substituted heteroaryl, wherein substituted aryl or substituted heteroaryl are substituted with one to three substituents selected from H, alkyl, haloalkyl, alkoxy, haloalkoxy, halogen, nitro, cyano, alkylsulfonyl, haloalkylsulfonyl and pentafluoro-λ$^6$-sulfanyl;

$R^{11}$ is H, alkyl or cycloalkyl;

$R^{12}$ and $R^{13}$ are both H or $R^{12}$ and $R^{13}$ together form —(CH$_2$)$_p$—;

$R^{14}$ is H, alkyl or hydroxy;

n, m and p are independently zero, 1 or 2;

or pharmaceutically acceptable salts.

Autotaxin (ATX) is a secreted enzyme also called ectonucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and -chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particulary, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular example is methoxy The term "alkoxyalkyl" denotes an alkyl group wherein at least one of the hydrogen atoms of the alkyl group is replaced by an alkoxy group. Particular examples are methoxymethyl, methoxyethyl, ethoxymethyl, ethoxyethyl, iso-propoxymethyl and iso-propoxyethyl.

The term "alkoxycarbonyl" denotes a group of the formula —C(O)—R', wherein R' is an alkoxy group. Particular example is a group of formula —C(O)—R', wherein R' is methoxy.

The term "alkoxycarbonylalkyl" denotes an alkyl group wherein at least one of the hydrogen atoms of the alkyl group is replaced by an alkoxycarbonyl group. Particular example is methoxycarbonylethyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, tert-butyl and pentyl. Particular alkyl groups include methyl, ethyl, isopropyl, n-butyl and sec-butyl.

The term "alkylcarbonyl" denotes a group of the formula —C(O)—R', wherein R' is an alkyl group.

The term "alkylsulfonyl" denotes a group of the formula —S(O)$_2$—R', wherein R' is an alkyl group. Particular example is methylsulfonyl.

The term "amino" denotes a —NH$_2$ group.

The term "aminosulfonyl" denotes —S(O)$_2$—NH$_2$ group.

The term "aminosulfonylalkyl" denotes an alkyl group wherein at least one of the hydrogen atoms of the alkyl group is replaced by an aminosulfonyl group. Examples are aminosulfonylmethyl, aminosulfonylethyl and aminosulfonylpropyl. Particular examples are aminosulfonylmethyl and aminosulfonylpropyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "carbonyl" denotes a —C(O)— group.

The term "carboxy" denotes a —COOH group.

The term "carboxyalkyl" denotes an alkyl group wherein at least one of the hydrogen atoms of the alkyl group is replaced by a carboxy group. Particular example is carboxyethyl.

The term "cyano" denotes a —C≡N group.

The term "cyanoalkyl" denotes an alkyl group wherein one of the hydrogen atoms of the alkyl group is replaced by a cyano group. Particular examples are cyanomethyl and cyanoethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl.

The term "cycloalkylalkyl" denotes an alkyl group wherein at least one of the hydrogen atoms of the alkyl group is replaced by a cycloalkyl group. Particular example of cycloalkylalkyl is cyclobutylmethyl.

The term "dihydroxyalkyl" denotes an alkyl group wherein two of the hydrogen atoms of the alkyl group are each replaced by a hydroxy group. Particular examples are dihydroxyethyl and dihydroxypropyl.

The term "haloalkoxy" denotes an alkoxy group wherein at least one of the hydrogen atoms of the alkoxy group has been replaced by the same or different halogen atoms. Particular examples are trifluoromethoxy and trifluoroethyl.

The term "haloalkoxyalkyl" denotes an alkyl group wherein at least one of the hydrogen atoms of the alkyl group has been replaced by a haloalkoxy group.

The term "haloalkoxycarbonyl" denotes a group of the formula —C(O)—R', wherein R' is an haloalkoxy group.

The term "haloalkoxycarbonylalkyl" denotes an alkyl group wherein at least one of the hydrogen atoms of the alkyl group is replaced by a haloalkoxycarbonyl group.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl.

Particular haloalkyl group is trifluoromethyl.

The term "haloalkylsulfonyl" denotes a group of the formula —S(O)$_2$—R', wherein R' is an haloalkyl group.

The term "halogen" and "halo" are used interchangeably herein and denote fluoro, chloro, bromo or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are furanyl, oxazodiazolyl, oxazolyl, isoxazolyl, pyrrolyl, imidazolyl, benzodioxolyl and pyridinyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are dioxanyl, 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Particular example of heterocycloalkyl groups are dioxanyl, morpholinyl, tetrahydropyranyl, tetrahydrofuranyl, azetidinyl and oxetanyl.

The term "hydroxy" denotes a —OH group.

The term "hydroxyalkyl" denotes an alkyl group wherein one of the hydrogen atoms of the alkyl group is replaced by a hydroxy group. Particular examples are hydroxymethyl, hydroxyethyl, hydroxypropyl and hydroxybutyl.

The term "hydroxycyloalkyl" denotes a cycloalkyl group wherein one of the hydrogen atoms of the cycloalkyl group is replaced by a hydroxy group. Particular examples are hydroxycyclopropyl and hydroxycyclobutyl The term "nitrate" denotes a —NO3 group.

The term "nitratealkyl" denotes an alkyl group wherein one of the hydrogen atoms of the alkyl group is replaced by a nitrate group. Particular example is nitratemethyl.

The term "nitro" denotes a —NO$_2$ group. The term "sulfonyl" denotes a —S(O)$_2$ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention are compounds according to formula (I) as described herein, wherein

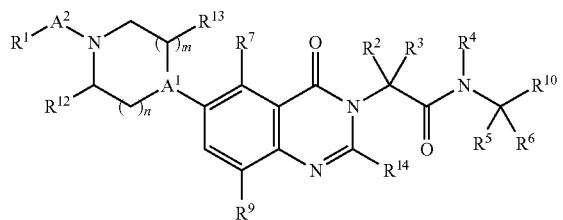

(I)

R¹ is alkoxy, haloalkoxy, alkoxyalkyl, haloalkoxyalkyl, alkyl, haloalkyl, alkylsulfonyl, haloalkylsulfonyl, aminosulfonylalkyl, substituted cycloalkyl, substituted cycloalkylalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, halohalkoxy, alkylcarbonyl, carboxy, halogen and cyano;

R² and R³ are independently selected from H, alkyl and cycloalkyl;

or R² and R³ together with the carbon to which they are attached form a cycloalkyl;

A¹ is —CH— or —N—;

A² is —C(O)—, —C(O)CH₂—, —CH₂—, —NR¹¹C(O)—, —NR¹¹C(O)CH₂—, —S(O)₂—;

one of R⁴ and R⁵ is H or alkyl and the other is H, alkoxycarbonylalkyl, haloalkoxycarbonylalkyl, alkyl, haloalkyl, carboxyalkyl, cycloalkyl or substituted aminocarbonylalkyl, wherein substituted aminocarbonylalkyl is substituted on the nitrogen atom by two substituents independently selected from H, alkyl, cycloalkyl and substituted phenyl, wherein substituted phenyl is substituted with one to three substituents independently selected from H, alkyl, haloalkyl and cycloalkyl;

or R⁴ and R⁵ together with the nitrogen and carbon atoms to which they are attached form a heterocycloalkyl;

R⁶ is H or alkyl;

R⁷, R⁸ and R⁹ are independently H, alkyl, cycloalkyl, halogen or cyano;

R¹⁰ is substituted aryl or substituted heteroaryl, wherein substituted aryl or substituted heteroaryl are substituted with one to three substituents selected from H, alkyl, haloalkyl, alkoxy, haloalkoxy, halogen, nitro, cyano, alkylsulfonyl, haloalkylsulfonyl and pentafluoro-λ⁶-sulfanyl;

R¹¹ is H, alkyl or cycloalkyl;

R¹² and R¹³ are both H or R¹² and R¹³ together form —(CH₂)ₚ—;

R¹⁴ is H, alkyl or hydroxy;

n, m and p are independently zero, 1 or 2;

or pharmaceutically acceptable salts. Another embodiment of the present invention are compounds according to formula (I) as described herein, wherein R¹ is hydroxyalkyl, dihydroxyalkyl, hydroxycycloalkyl, alkoxy, alkoxyalkoxyalkyl, alkoxyalkyl, alkyl, alkylsulfonyl, aminosulfonylalkyl, cyano, nitratealkyl, substituted cycloalkyl, substituted cycloalkylalkyl, haloalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, alkylcarbonyl, carboxy and halogen.

Another embodiment of the present invention are compounds according to formula (I) as described herein, wherein R¹ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, alkylcarbonyl, carboxy and halogen.

A particular embodiment of the present invention are compounds according to formula (I) as described herein, wherein R¹ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted dioxanyl, substituted azetidinyl, substituted morpholinyl and or substituted phenyl, wherein, substituted cycloalkyl, substituted cycloalkylalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted dioxanyl, substituted azetidinyl, substituted morpholinyl and substituted phenyl are substituted with one to three substituents selected from H, amino, alkyl, haloalkyl, alkoxy, alkylcarbonyl, carboxy and halogen.

A particular embodiment of the present invention are compounds according to formula (I) as described herein, wherein R¹ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted azetidinyl, substituted morpholinyl and or substituted phenyl, wherein, substituted cycloalkyl, substituted cycloalkylalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted azetidinyl, substituted morpholinyl and substituted phenyl are substituted with one to three substituents selected from H, amino, alkyl, haloalkyl, alkoxy, alkylcarbonyl, carboxy and halogen.

A further particular embodiment of the present invention are compounds according to formula (I) as described herein, wherein R¹ is alkoxyalkyl, alkyl, substituted cycloalkyl or substituted cycloalkylalkyl, wherein substituted cycloalkyl and substituted cycloalkylalkyl are substituted with one to three substituents selected from H, haloalkyl and halogen.

A more particular embodiment of the present invention are compounds according to formula (I) as described herein, wherein $R^1$ is alkoxyalkyl or alkyl.

A furthermore particular embodiment of the present invention are compounds according to formula (I) as described herein, wherein $R^1$ is alkyl.

Another particular embodiment of the present invention are compounds according to formula (I) as described herein, wherein $A^1$ is —CH— or —N—.

Another particular embodiment of the present invention are compounds according to formula (I) as described herein, wherein $R^2$ is H or alkyl.

Also a particular embodiment of the present invention are compounds according to formula (I) as described herein, wherein $R^3$ is H.

Also a furthermore particular embodiment of the present invention are compounds according to formula (I) as described herein, wherein $R^2$ and $R^3$ are H.

A particular embodiment of the present invention are compounds according to formula (I) as described herein, wherein $R^4$ is H, alkoxycarbonylalkyl, alkyl, carboxyalkyl, cycloalkyl or aminocarbonylalkyl substituted on the nitrogen atom by one H and one alkyl.

Another particular embodiment of the present invention are compounds according to formula (I) as described herein, wherein $R^5$ is H, alkoxyalkyl, alkyl aminocarbonylalkyl substituted on the nitrogen atom by two substitutents independently selected from H and alkyl.

Another particular embodiment of the present invention are compounds according to formula (I) as described herein, wherein $R^5$ is H, alkyl aminocarbonylalkyl substituted on the nitrogen atom by two substitutents independently selected from H and alkyl.

A furthermore particular embodiment of the present invention are compounds according to formula (I) as described herein, wherein $R^4$ is H or alkyl and $R^5$ is H.

Also an embodiment of the present invention are compounds according to formula (I) as described herein, wherein $R^6$ is H.

Another particular embodiment of the present invention are compounds according to formula (I) as described herein, wherein $R^7$, $R^8$ and $R^9$ are H.

Another embodiment of the present invention are compounds according to formula (I) as described herein, wherein $R^{10}$ is substituted phenyl, substituted benzodioxolyl, substituted isoxazolyl, substituted oxadiazolyl or substituted pyridinyl, wherein substituted phenyl, substituted benzodioxolyl, substituted isoxazolyl, substituted oxadiazolyl or substituted pyridinyl are substituted with one to three substitutents selected from H, alkyl, haloalkyl, alkoxy, halohalkoxy, halogen, nitro, cyano, alkylsulfonyl and pentafluoro-$\lambda^6$-sulfanyl.

A more particular embodiment of the present invention are compounds according to formula (I) as described herein, wherein $R^{10}$ is phenyl substituted with one to three substitutents selected from H, halogen and cyano.

An embodiment of the present invention are compounds according to formula (I) as described herein, wherein $R^{11}$ is H and alkyl.

Another embodiment of the present invention are compounds according to formula (I) as described herein, wherein n is 1 and m is 1 or 2.

A further particular embodiment of the present invention are compounds according to formula (I) as described herein, wherein n and m are 1.

A particular embodiment of the present invention are compounds according to formula (I) as described herein, wherein p is 1.

Another embodiment of the present invention are compounds according to formula (I) as described herein, wherein $R^{12}$ and $R^{13}$ are both H.

A particular embodiment of the present invention are compounds according to formula (I) as described herein, wherein $R^{14}$ is H.

A particular embodiment of the present invention are compounds according to formula (I) as described herein, wherein $A^2$ is —C(O)—.

A particular embodiment of the present invention are compounds according to formula (I) as described herein, wherein $A^3$ is —$CR^8$—.

A furthermore particular embodiment of the present invention are compounds according to formula (I) as described herein, wherein $R^1$ is alkoxyalkyl or alkyl;
$R^2$ and $R^3$ are H;
$A^1$ is —CH— or —N—;
$A^2$ is —C(O)—;
$R^4$ is H or alkyl and $R^5$ is H;
or $R^4$ and $R^5$ together with the nitrogen and carbon atoms to which they are attached form a heterocycloalkyl;
$R^6$ is H;
$R^7$, $R^8$ and $R^9$ are H;
$R^{10}$ is substituted aryl or substituted heteroaryl, wherein substituted aryl or substituted heteroaryl are substituted with one to three substituents selected from H, alkyl, haloalkyl, alkoxy, halohalkoxy, halogen, nitro, cyano, alkylsulfonyl, haloalkylsulfonyl and pentafluoro-$\lambda^6$-sulfanyl;
$R^{11}$ is H, alkyl or cycloalkyl;
$R^{12}$ and $R^{13}$ are both H or $R^{12}$ and $R^{13}$ together form —$(CH_2)_p$—;
$R^{14}$ is H, alkyl or hydroxy;
n, m and p are independently zero, 1 or 2;
or pharmaceutically acceptable salts.

Particular examples of compounds of formula (I) as described herein are selected from (3R)-3-[[2-[6-(4-acetylpiperazin-1-yl)-4-oxoquinazolin-3-yl]acetyl]amino]-3-(4-chlorophenyl)-N-methylpropanamide;

(3R)-3-[[2-[6-(4-acetylpiperazin-1-yl)-4-oxoquinazolin-3-yl]acetyl]amino]-3-(4-chlorophenyl)-N,N-dimethylpropanamide;

(3R)-3-[[2-[6-(4-acetylpiperazin-1-yl)-4-oxoquinazolin-3-yl]acetyl]amino]-3-(4-chlorophenyl)-N-phenylpropanamide;

(3R)-3-[[2-[6-(4-acetylpiperazin-1-yl)-4-oxoquinazolin-3-yl]acetyl]amino]-N-methyl-3-[4-(trifluoromethyl)phenyl]propanamide;

(3R)-3-[[2-[6-(4-acetylpiperazin-1-yl)-4-oxoquinazolin-3-yl]acetyl]amino]-N,N-dimethyl-3-[4-(trifluoromethyl)phenyl]propanamide;

(3R)-3-[[2-[6-(4-acetylpiperazin-1-yl)-4-oxoquinazolin-3-yl]acetyl]amino]-N-(2-methylpropyl)-3-[4-(trifluoromethyl)phenyl]propanamide;

(3R)-3-[[2-[6-(4-acetylpiperazin-1-yl)-4-oxoquinazolin-3-yl]acetyl]amino]-N-phenyl-3-[4-(trifluoromethyl)phenyl]propanamide;

(3R)-3-[[2-[6-(4-acetylpiperazin-1-yl)-4-oxoquinazolin-3-yl]acetyl]amino]-N-benzyl-3-[4-(trifluoromethyl)phenyl]propanamide;

(3R)-3-[[2-[6-(4-acetylpiperazin-1-yl)-4-oxoquinazolin-3-yl]acetyl]amino]-N-methyl-3-(4-nitrophenyl)propanamide;

2-[6-(4-acetylpiperazin-1-yl)-4-oxoquinazolin-3-yl]-N-[(4-chlorophenyl)methyl]acetamide;

2-[6-(4-acetylpiperazin-1-yl)-4-oxoquinazolin-3-yl]-N-[(6-chloropyridin-3-yl)methyl]acetamide;

2-[6-(4-acetylpiperazin-1-yl)-4-oxoquinazolin-3-yl]-N-[(5-chloropyridin-2-yl)methyl]acetamide;

2-[6-(4-acetylpiperazin-1-yl)-4-oxoquinazolin-3-yl]-N-[1-(4-chlorophenyl)ethyl]acetamide;

2-[6-(4-acetylpiperazin-1-yl)-4-oxoquinazolin-3-yl]-N-[(4-fluorophenyl)methyl]acetamide;

2-[6-(4-acetylpiperazin-1-yl)-4-oxoquinazolin-3-yl]-N-(1,3-benzodioxol-5-ylmethyl)acetamide;

2-[6-(4-acetylpiperazin-1-yl)-4-oxoquinazolin-3-yl]-N-[[6-(trifluoromethyl)pyridin-3-yl]methyl]acetamide;

2-[6-(4-acetylpiperazin-1-yl)-4-oxoquinazolin-3-yl]-N-[[4-(trifluoromethyl)phenyl]methyl]acetamide;

2-[6-(4-acetylpiperazin-1-yl)-4-oxoquinazolin-3-yl]-N-[(6-cyanopyridin-3-yl)methyl]acetamide;

2-[6-(4-acetylpiperazin-1-yl)-4-oxoquinazolin-3-yl]-N-[(4-cyanophenyl)methyl]acetamide;

2-[6-(4-acetylpiperazin-1-yl)-4-oxoquinazolin-3-yl]-N-[[4-(trifluoromethoxy)phenyl]methyl]acetamide;

2-[6-(4-acetylpiperazin-1-yl)-4-oxoquinazolin-3-yl]-N-[(4-nitrophenyl)methyl]acetamide;

2-[6-(4-acetylpiperazin-1-yl)-4-oxoquinazolin-3-yl]-N-[(3,4-dichlorophenyl)methyl]acetamide;

2-[6-(4-acetylpiperazin-1-yl)-4-oxoquinazolin-3-yl]-N-[(2,4-dichlorophenyl)methyl]acetamide;

2-[6-(4-acetylpiperazin-1-yl)-4-oxoquinazolin-3-yl]-N-[(4-chloro-3-fluorophenyl)methyl]acetamide;

2-[6-(4-acetylpiperazin-1-yl)-4-oxoquinazolin-3-yl]-N-[(3-chloro-4-cyanophenyl)methyl]acetamide;

2-[6-(4-acetylpiperazin-1-yl)-4-oxoquinazolin-3-yl]-N-[[4-fluoro-3-(trifluoromethoxy)phenyl]methyl]acetamide;

(3R)-3-[[2-[6-(4-acetylpiperazin-1-yl)-4-oxoquinazolin-3-yl]acetyl]amino]-3-(4-chlorophenyl)propanamide;

2-[6-(4-acetylpiperazin-1-yl)-4-oxoquinazolin-3-yl]-N-[(4-cyano-3-fluorophenyl)methyl]acetamide;

2-[6-(4-acetylpiperazin-1-yl)-4-oxoquinazolin-3-yl]-N-[(2-chloro-4-cyanophenyl)methyl]acetamide;

2-[6-(4-acetylpiperazin-1-yl)-4-oxoquinazolin-3-yl]-N-[(4-cyano-2-fluorophenyl)methyl]acetamide;

2-[6-(4-acetylpiperazin-1-yl)-4-oxoquinazolin-3-yl]-N-[(4-cyano-2,6-difluorophenyl)methyl]acetamide;

2-[6-(4-acetylpiperazin-1-yl)-4-oxoquinazolin-3-yl]-N-[(4-cyano-2-methoxyphenyl)methyl]acetamide;

2-[6-(4-acetylpiperazin-1-yl)-4-oxoquinazolin-3-yl]-N-[[4-cyano-2-(2,2,2-trifluoroethoxy)phenyl]methyl]acetamide;

2-[6-(4-acetylpiperazin-1-yl)-4-oxoquinazolin-3-yl]-N-[[4-chloro-3-(trifluoromethyl)phenyl]methyl]acetamide;

2-[6-(4-acetylpiperazin-1-yl)-4-oxoquinazolin-3-yl]-N-[(3-cyano-2-methylphenyl)methyl]acetamide;

2-[6-(4-acetylpiperazin-1-yl)-4-oxoquinazolin-3-yl]-N-[(2-chloropyridin-4-yl)methyl]acetamide;

2-[6-(4-acetylpiperazin-1-yl)-4-oxoquinazolin-3-yl]-N-[(3-nitrophenyl)methyl]acetamide;

2-[6-(4-acetylpiperazin-1-yl)-4-oxoquinazolin-3-yl]-N-[[4-chloro-3-(trifluoromethoxy)phenyl]methyl]acetamide;

2-[6-(4-acetylpiperazin-1-yl)-4-oxoquinazolin-3-yl]-N-[[4-(pentafluoro-$\lambda^6$-sulfanyl)phenyl]methyl]acetamide;

2-[6-(4-acetylpiperazin-1-yl)-4-oxoquinazolin-3-yl]-N-[(3-methyl-4-methylsulfonylphenyl)methyl]acetamide;

2-[6-(4-acetylpiperazin-1-yl)-4-oxoquinazolin-3-yl]-N-[(4,5-dichloropyridin-2-yl)methyl]acetamide;

2-[6-(4-acetylpiperazin-1-yl)-4-oxoquinazolin-3-yl]-N-[(3-chloro-4-methylphenyl)methyl]acetamide;

2-[6-(4-acetylpiperazin-1-yl)-4-oxoquinazolin-3-yl]-N-[(4-chlorophenyl)methyl]-N-methylacetamide;

2-[6-(4-acetylpiperazin-1-yl)-4-oxoquinazolin-3-yl]-N-[(3,4-dichlorophenyl)methyl]-N-methylacetamide;

2-[6-(4-acetylpiperazin-1-yl)-4-oxoquinazolin-3-yl]-N-[(4-cyano-3-fluorophenyl)methyl]-N-methylacetamide;

2-[6-(4-acetylpiperazin-1-yl)-4-oxoquinazolin-3-yl]-N-[(2,6-dichloropyridin-4-yl)methyl]-N-methylacetamide;

6-(4-acetylpiperazin-1-yl)-3-[2-[2-(4-chlorophenyl)pyrrolidin-1-yl]-2-oxoethyl]quinazolin-4-one;

6-(4-acetylpiperazin-1-yl)-3-[2-[(2R)-2-(4-methylphenyl)pyrrolidin-1-yl]-2-oxoethyl]quinazolin-4-one;

2-[6-(4-acetylpiperazin-1-yl)-4-oxoquinazolin-3-yl]-N-[2-(3,4-dichlorophenyl)ethyl]acetamide;

2-[6-(4-acetylpiperazin-1-yl)-4-oxoquinazolin-3-yl]-N-[[3-(4-chlorophenyl)-1,2-oxazol-5-yl]methyl]acetamide;

2-[6-(4-acetylpiperazin-1-yl)-4-oxoquinazolin-3-yl]-N-[[5-(4-chlorophenyl)-1,2,4-oxadiazol-3-yl]methyl]acetamide;

3-[[2-[6-(4-acetylpiperazin-1-yl)-4-oxoquinazolin-3-yl]acetyl]amino]-3-(3,4-dichlorophenyl)-N-methylpropanamide;

methyl 3-[[2-[6-(4-acetylpiperazin-1-yl)-4-oxoquinazolin-3-yl]acetyl]-[(3,4-dichlorophenyl)methyl]amino]propanoate;

3-[[2-[6-(4-acetylpiperazin-1-yl)-4-oxoquinazolin-3-yl]acetyl]-[(3,4-dichlorophenyl)methyl]amino]propanoic acid;

3-[[2-[6-(4-acetylpiperazin-1-yl)-4-oxoquinazolin-3-yl]acetyl]-[(3,4-dichlorophenyl)methyl]amino]-N-methylpropanamide;

2-[6-(4-acetylpiperazin-1-yl)-4-oxoquinazolin-3-yl]-N-[(3-chloro-4-cyanophenyl)methyl]-N-methylacetamide;

2-[6-(4-acetylpiperazin-1-yl)-4-oxoquinazolin-3-yl]-N-[(4-chloro-3-cyanophenyl)methyl]-N-methylacetamide;

2-[6-(4-acetylpiperazin-1-yl)-4-oxoquinazolin-3-yl]-N-[(4-cyano-3,5-difluorophenyl)methyl]-N-methylacetamide;

N-[(3,4-dichlorophenyl)methyl]-2-[6-[4-(3-methylbutanoyl)piperazin-1-yl]-4-oxoquinazolin-3-yl]acetamide;

N-[(3,4-dichlorophenyl)methyl]-2-[4-oxo-6-(4-pentanoylpiperazin-1-yl)quinazolin-3-yl]acetamide;

N-[(3,4-dichlorophenyl)methyl]-2-[6-[4-(2-methoxyacetyl)piperazin-1-yl]-4-oxoquinazolin-3-yl]acetamide;

N-[(3,4-dichlorophenyl)methyl]-2-[4-oxo-6-[4-(2,2,2-trifluoroacetyl)piperazin-1-yl]quinazolin-3-yl]acetamide;

2-[6-[4-(cyclobutanecarbonyl)piperazin-1-yl]-4-oxoquinazolin-3-yl]-N-[(3,4-dichlorophenyl)methyl]acetamide;

2-[6-[4-(cyclopentanecarbonyl)piperazin-1-yl]-4-oxoquinazolin-3-yl]-N-[(3,4-dichlorophenyl)methyl]acetamide;

2-[6-[4-(cyclohexanecarbonyl)piperazin-1-yl]-4-oxoquinazolin-3-yl]-N-[(3,4-dichlorophenyl)methyl]acetamide;

N-[(3,4-dichlorophenyl)methyl]-2-[6-[4-(oxane-4-carbonyl)piperazin-1-yl]-4-oxoquinazolin-3-yl]acetamide;

N-[(3,4-dichlorophenyl)methyl]-2-[6-[4-(1,2-oxazole-5-carbonyl)piperazin-1-yl]-4-oxoquinazolin-3-yl]acetamide;

N-[(3,4-dichlorophenyl)methyl]-N-methyl-2-[4-oxo-6-(4-propanoylpiperazin-1-yl)quinazolin-3-yl]acetamide;

N-[(3,4-dichlorophenyl)methyl]-N-methyl-2-[6-[4-(2-methylpropanoyl)piperazin-1-yl]-4-oxoquinazolin-3-yl]acetamide;

2-[6-[4-(3-aminooxetane-3-carbonyl)piperazin-1-yl]-4-oxo-quinazolin-3-yl]-N-[(3,4-dichlorophenyl)methyl]acet-amide;

N-[(3,4-dichlorophenyl)methyl]-2-[4-oxo-6-[4-(2-sulfa-moylacetyl)piperazin-1-yl]quinazolin-3-yl]acetamide;

N-[(3,4-dichlorophenyl)methyl]-2-[4-oxo-6-[4-(4-sulfa-moylbutanoyl)piperazin-1-yl]quinazolin-3-yl]acetamide;

2-[6-[4-(cyclobutanecarbonyl)piperazin-1-yl]-4-oxoqui-nazolin-3-yl]-N-[(3,4-dichlorophenyl)methyl]-N-methyl-acetamide;

N-[(3,4-dichlorophenyl)methyl]-2-[6-[4-(3-fluorocyclobu-tanecarbonyl)piperazin-1-yl]-4-oxoquinazolin-3-yl]-N-methylacetamide;

N-[(3,4-dichlorophenyl)methyl]-2-[6-[4-(3,3-difluorocy-clobutanecarbonyl)piperazin-1-yl]-4-oxoquinazolin-3-yl]-N-methylacetamide;

N-[(3,4-dichlorophenyl)methyl]-N-methyl-2-[4-oxo-6-[4-[1-(trifluoromethyl)cyclobutanecarbonyl]piperazin-1-yl]quinazolin-3-yl]acetamide;

2-[6-[4-(3-chlorocyclobutanecarbonyl)piperazin-1-yl]-4-oxoquinazolin-3-yl]-N-[(3,4-dichlorophenyl)methyl]-N-methylacetamide;

N-[(3,4-dichlorophenyl)methyl]-2-[6-[4-(3-methoxycy-clobutanecarbonyl)piperazin-1-yl]-4-oxoquinazolin-3-yl]-N-methylacetamide;

N-[(3,4-dichlorophenyl)methyl]-N-methyl-2-[6-[4-(oxet-ane-3-carbonyl)piperazin-1-yl]-4-oxoquinazolin-3-yl]ac-etamide;

N-[(3,4-dichlorophenyl)methyl]-N-methyl-2-[6-[4-(3-meth-yloxetane-3-carbonyl)piperazin-1-yl]-4-oxoquinazolin-3-yl]acetamide;

2-[6-[4-(1-acetylazetidine-3-carbonyl)piperazin-1-yl]-4-oxoquinazolin-3-yl]-N-[(3,4-dichlorophenyl)methyl]-N-methylacetamide;

4-[3-[2-[(3,4-dichlorophenyl)methylamino]-2-oxoethyl]-4-oxoquinazolin-6-yl]-N-propan-2-ylpiperazine-1-carbox-amide;

N-cyclopropyl-4-[3-[2-[(3,4-dichlorophenyl)methylamino]-2-oxoethyl]-4-oxoquinazolin-6-yl]piperazine-1-carbox-amide;

N-cyclopentyl-4-[3-[2-[(3,4-dichlorophenyl)methylamino]-2-oxoethyl]-4-oxoquinazolin-6-yl]piperazine-1-carbox-amide;

4-[3-[2-[(3,4-dichlorophenyl)methylamino]-2-oxoethyl]-4-oxoquinazolin-6-yl]-N-(2-methoxyethyl)piperazine-1-carboxamide;

4-[3-[2-[(3,4-dichlorophenyl)methylamino]-2-oxoethyl]-4-oxoquinazolin-6-yl]-N-(3,5-dimethyl-1,2-oxazol-4-yl)piperazine-1-carboxamide;

4-[3-[2-[(3,4-dichlorophenyl)methylamino]-2-oxoethyl]-4-oxoquinazolin-6-yl]-N-pyridin-3-ylpiperazine-1-carbox-amide;

N-[(3,4-dichlorophenyl)methyl]-2-[6-(4-methylsulfonylpip-erazin-1-yl)-4-oxoquinazolin-3-yl]acetamide;

2-[6-(4-cyclopentylsulfonylpiperazin-1-yl)-4-oxoquinazo-lin-3-yl]-N-[(3,4-dichlorophenyl)methyl]acetamide;

2-[6-(4-cyclohexylsulfonylpiperazin-1-yl)-4-oxoquinazo-lin-3-yl]-N-[(3,4-dichlorophenyl)methyl]acetamide;

2-[6-(4-cyclopropyl sulfonylpiperazin-1-yl)-4-oxoquinazo-lin-3-yl]-N-[(3,4-dichlorophenyl)methyl]-N-methylacet-amide;

2-[6-[4-(cyclobutylmethylsulfonyl)piperazin-1-yl]-4-oxo-quinazolin-3-yl]-N-[(3,4-dichlorophenyl)methyl]-N-methylacetamide;

methyl 2-[4-[3-[2-[(3,4-dichlorophenyl)methylamino]-2-oxoethyl]-4-oxoquinazolin-6-yl]piperazin-1-yl]acetate;

N-[(3,4-dichlorophenyl)methyl]-2-[6-[4-(2-hydroxyethyl)piperazin-1-yl]-4-oxoquinazolin-3-yl]acetamide;

N-[(3,4-dichlorophenyl)methyl]-2-[6-[4-(2,3-dihydroxypro-pyl)piperazin-1-yl]-4-oxoquinazolin-3-yl]acetamide;

2-[6-[4-(cyclobutylmethyl)piperazin-1-yl]-4-oxoquinazo-lin-3-yl]-N-[(3,4-dichlorophenyl)methyl]acetamide;

N-[(3,4-dichlorophenyl)methyl]-2-[4-oxo-6-[4-(oxolan-3-ylmethyl)piperazin-1-yl]quinazolin-3-yl]acetamide;

N-[(3,4-dichlorophenyl)methyl]-2-[6-[4-(oxan-4-ylmethyl)piperazin-1-yl]-4-oxoquinazolin-3-yl]acetamide;

N-[(3,4-dichlorophenyl)methyl]-2-[6-[4-[(1-methylpyrrol-2-yl)methyl]piperazin-1-yl]-4-oxoquinazolin-3-yl]acet-amide;

N-[(3,4-dichlorophenyl)methyl]-2-[6-[4-(1H-imidazol-2-ylmethyl)piperazin-1-yl]-4-oxoquinazolin-3-yl]acetamide;

N-[(3,4-dichlorophenyl)methyl]-2-[6-[4-(1H-imidazol-5-ylmethyl)piperazin-1-yl]-4-oxoquinazolin-3-yl]acetamide;

3-[[4-[3-[2-[(3,4-dichlorophenyl)methylamino]-2-oxo-ethyl]-4-oxoquinazolin-6-yl]piperazin-1-yl]methyl]furan-2-carboxylic acid;

N-[(3,4-dichlorophenyl)methyl]-2-[6-[4-[(2,4-dimethyl-1,3-oxazol-5-yl)methyl]piperazin-1-yl]-4-oxoquinazolin-3-yl]acetamide;

2-[6-[4-(cyclopropylmethyl)piperazin-1-yl]-4-oxoquinazo-lin-3-yl]-N-[(3,4-dichlorophenyl)methyl]-N-methylacet-amide;

N-[(3,4-dichlorophenyl)methyl]-2-[6-[4-(2-methoxyethyl)piperazin-1-yl]-4-oxoquinazolin-3-yl]-N-methylacet-amide;

N-[(3,4-dichlorophenyl)methyl]-N-methyl-2-[6-[4-(oxetan-3-ylmethyl)piperazin-1-yl]-4-oxoquinazolin-3-yl]acet-amide;

N-[(3,4-dichlorophenyl)methyl]-N-methyl-2-[6-[4-[2-(methylamino)-2-oxoethyl]piperazin-1-yl]-4-oxoqui-nazolin-3-yl]acetamide;

N-[(3,4-dichlorophenyl)methyl]-2-[6-[4-[2-(dimethyl-amino)-2-oxoethyl]piperazin-1-yl]-4-oxoquinazolin-3-yl]-N-methylacetamide;

N-[(3,4-dichlorophenyl)methyl]-N-methyl-2-[4-oxo-6-[4-[2-oxo-2-(propan-2-ylamino)ethyl]piperazin-1-yl]qui-nazolin-3-yl]acetamide;

N-[(3,4-dichlorophenyl)methyl]-2-[6-[4-[2-(diethylamino)-2-oxoethyl]piperazin-1-yl]-4-oxoquinazolin-3-yl]-N-methylacetamide;

N-[(3,4-dichlorophenyl)methyl]-N-methyl-2-[6-[4-(2-mor-pholin-4-yl-2-oxoethyl)piperazin-1-yl]-4-oxoquinazolin-3-yl]acetamide;

2-[6-[4-(2-anilino-2-oxoethyl)piperazin-1-yl]-4-oxoqui-nazolin-3-yl]-N-[(3,4-dichlorophenyl)methyl]-N-methyl-acetamide;

N-[(2-chloro-4-cyanophenyl)methyl]-2-[6-[4-(oxetane-3-carbonyl)piperazin-1-yl]-4-oxoquinazolin-3-yl]acet-amide;

N-[(3-chloro-4-cyanophenyl)methyl]-N-methyl-2-[4-oxo-6-[4-(oxolan-3-ylmethyl)piperazin-1-yl]quinazolin-3-yl]ac-etamide;

N-[(4-chloro-3-cyanophenyl)methyl]-N-methyl-2-[4-oxo-6-[4-(oxolan-3-ylmethyl)piperazin-1-yl]quinazolin-3-yl]ac-etamide;

2-[6-(4-acetylpiperazin-1-yl)-4-oxoquinazolin-3-yl]-N-[(3,4-dichlorophenyl)methyl]-N-ethylacetamide;

2-[6-(4-acetylpiperazin-1-yl)-4-oxoquinazolin-3-yl]-N-[(3,4-dichlorophenyl)methyl]-N-propan-2-ylacetamide;

2-[6-(4-acetyl-1,4-diazepan-1-yl)-4-oxoquinazolin-3-yl]-N-[(3,4-dichlorophenyl)methyl]acetamide;

2-[6-(4-acetyl-1,4-diazepan-1-yl)-4-oxoquinazolin-3-yl]-N-[[4-(trifluoromethyl)phenyl]methyl]acetamide;

2-[6-(4-acetyl-1,4-diazepan-1-yl)-4-oxoquinazolin-3-yl]-N-[(3-chloro-4-cyanophenyl)methyl]-N-methylacetamide;
2-[6-(4-acetyl-1,4-diazepan-1-yl)-4-oxoquinazolin-3-yl]-N-[(4-chloro-3-cyanophenyl)methyl]-N-methylacetamide;
2-[6-(1-acetylpiperidin-4-yl)-4-oxoquinazolin-3-yl]-N-[(3,4-dichlorophenyl)methyl]acetamide;
2-[6-(1-acetylpiperidin-4-yl)-4-oxoquinazolin-3-yl]-N-[[4-(trifluoromethyl)phenyl]methyl]acetamide;
2-[6-(1-acetylpiperidin-4-yl)-4-oxoquinazolin-3-yl]-N-[(3,4-dichlorophenyl)methyl]-N-methylacetamide;
2-[6-(1-acetylpiperidin-4-yl)-4-oxoquinazolin-3-yl]-N-[(3-chloro-4-cyanophenyl)methyl]-N-methylacetamide;
2-[6-(1-acetylpiperidin-4-yl)-4-oxoquinazolin-3-yl]-N-[(4-chloro-3-cyanophenyl)methyl]-N-methylacetamide;
2-[6-(1-acetylpiperidin-4-yl)-4-oxoquinazolin-3-yl]-N-[(4-cyano-3-fluorophenyl)methyl]-N-methylacetamide;
2-[6-(1-acetylpiperidin-4-yl)-4-oxoquinazolin-3-yl]-N-[[4-chloro-3-(trifluoromethoxy)phenyl]methyl]-N-methylacetamide;
N-[(3-chloro-4-cyanophenyl)methyl]-N-methyl-2-[4-oxo-6-[4-(oxolan-3-ylmethyl)-1,4-diazepan-1-yl]quinazolin-3-yl]acetamide;
N-[(4-chloro-3-cyanophenyl)methyl]-N-methyl-2-[4-oxo-6-[4-(oxolan-3-ylmethyl)-1,4-diazepan-1-yl]quinazolin-3-yl]acetamide;
N-[(3-chloro-4-cyanophenyl)methyl]-2-[6-[1-(2-hydroxyacetyl)piperidin-4-yl]-4-oxoquinazolin-3-yl]-N-methylacetamide;
N-[(3-chloro-4-cyanophenyl)methyl]-2-[6-[1-(2-methoxyacetyl)piperidin-4-yl]-4-oxoquinazolin-3-yl]-N-methylacetamide;
N-[(3-chloro-4-cyanophenyl)methyl]-2-[6-[1-(2-methoxypropanoyl)piperidin-4-yl]-4-oxoquinazolin-3-yl]-N-methylacetamide;
N-[(3-chloro-4-cyanophenyl)methyl]-2-[6-[1-(3-methoxypropanoyl)piperidin-4-yl]-4-oxoquinazolin-3-yl]-N-methylacetamide;
N-[(3-chloro-4-cyanophenyl)methyl]-N-methyl-2-[4-oxo-6-[1-(2-propan-2-yloxyacetyl)piperidin-4-yl]quinazolin-3-yl]acetamide;
N-[(3-chloro-4-cyanophenyl)methyl]-2-[6-[1-(cyclopropanecarbonyl)piperidin-4-yl]-4-oxoquinazolin-3-yl]-N-methylacetamide;
N-[(3-chloro-4-cyanophenyl)methyl]-2-[6-[1-(cyclobutanecarbonyl)piperidin-4-yl]-4-oxoquinazolin-3-yl]-N-methylacetamide;
N-[(3-chloro-4-cyanophenyl)methyl]-2-[6-[1-(3-fluorocyclobutanecarbonyl)piperidin-4-yl]-4-oxoquinazolin-3-yl]-N-methylacetamide;
N-[(3-chloro-4-cyanophenyl)methyl]-2-[6-[1-(3-chlorocyclobutanecarbonyl)piperidin-4-yl]-4-oxoquinazolin-3-yl]-N-methylacetamide;
N-[(3-chloro-4-cyanophenyl)methyl]-2-[6-[1-(3,3-difluorocyclobutanecarbonyl)piperidin-4-yl]-4-oxoquinazolin-3-yl]-N-methylacetamide;
N-[(3-chloro-4-cyanophenyl)methyl]-N-methyl-2-[6-[1-(oxetane-2-carbonyl)piperidin-4-yl]-4-oxoquinazolin-3-yl]acetamide;
N-[(3-chloro-4-cyanophenyl)methyl]-N-methyl-2-[6-[1-(oxetane-3-carbonyl)piperidin-4-yl]-4-oxoquinazolin-3-yl]acetamide;
N-[(3-chloro-4-cyanophenyl)methyl]-N-methyl-2-[4-oxo-6-[1-(oxolan-3-ylmethyl)piperidin-4-yl]quinazolin-3-yl]acetamide;
N-[(4-chloro-3-cyanophenyl)methyl]-N-methyl-2-[4-oxo-6-[1-(oxolan-3-ylmethyl)piperidin-4-yl]quinazolin-3-yl]acetamide;
N-[(3-chloro-4-cyanophenyl)methyl]-N-methyl-2-[6-(1-methylsulfonylpiperidin-4-yl)-4-oxoquinazolin-3-yl]acetamide;
N-cyclopropyl-N-[(3,4-dichlorophenyl)methyl]-2-[6-[1-(2-methoxyacetyl)piperidin-4-yl]-4-oxoquinazolin-3-yl]acetamide;
2-[6-[2-acetyl-2-azabicyclo[2.2.1]heptan-5-yl]-4-oxoquinazolin-3-yl]-N-[(3,4-dichlorophenyl)methyl]acetamide;
2-[6-(4-acetylpiperazin-1-yl)-4-oxoquinazolin-3-yl]-N-[(3,4-dichlorophenyl)methyl]propanamide;
2-[6-(4-acetylpiperazin-1-yl)-4-oxoquinazolin-3-yl]-N-[(3,4-dichlorophenyl)methyl]-N-methylpropanamide;
1-[6-(4-acetylpiperazin-1-yl)-4-oxoquinazolin-3-yl]-N-[(3,4-dichlorophenyl)methyl]cyclopropane-1-carboxamide;
2-[6-(4-acetylpiperazin-1-yl)-2-methyl-4-oxoquinazolin-3-yl]-N-[(3,4-dichlorophenyl)methyl]acetamide;
2-[6-(4-acetylpiperazin-1-yl)-2,4-dioxo-1H-quinazolin-3-yl]-N-[(3,4-dichlorophenyl)methyl]acetamide
and pharmaceutically acceptable salts thereof.

Also particular examples of compounds of formula (I) as described herein are selected from
2-(6-(4-acetylpiperazin-1-yl)-4-oxoquinazolin-3(4H)-yl)-N-(1-(3,4-dichlorophenyl)-3-methoxypropyl)acetamide;
N-(3-chloro-4-cyanobenzyl)-2-(6-(1-(2-cyanoacetyl)piperidin-4-yl)-4-oxoquinazolin-3(4H)-yl)-N-methylacetamide;
N-(3-chloro-4-cyanobenzyl)-2-(6-(1-(3-cyanopropanoyl)piperidin-4-yl)-4-oxoquinazolin-3(4H)-yl)-N-methylacetamide;
(R)—N-(3-chloro-4-cyanobenzyl)-2-(6-(1-(2-hydroxypropanoyl)piperidin-4-yl)-4-oxoquinazolin-3(4H)-yl)-N-methylacetamide;
(R)—N-(3-chloro-4-cyanobenzyl)-2-(6-(1-(2-hydroxy-3-methylbutanoyl)piperidin-4-yl)-4-oxoquinazolin-3(4H)-yl)-N-methylacetamide;
(R)—N-(3-chloro-4-cyanobenzyl)-2-(6-(1-(2-methoxypropanoyl)piperidin-4-yl)-4-oxoquinazolin-3(4H)-yl)-N-methylacetamide;
(S)—N-(3-chloro-4-cyanobenzyl)-2-(6-(1-(2-methoxypropanoyl)piperidin-4-yl)-4-oxoquinazolin-3(4H)-yl)-N-methylacetamide;
methyl 4-(3-(2-((3-chloro-4-cyanobenzyl)(methyl)amino)-2-oxoethyl)-4-oxo-3,4-dihydroquinazolin-6-yl)piperidine-1-carboxylate;
2-(6-(1-acetylpiperidin-4-yl)-4-oxoquinazolin-3(4H)-yl)-N-(3-chloro-5-(trifluoromethyl)benzyl)acetamide;
2-(6-(1-acetylpiperidin-4-yl)-4-oxoquinazolin-3(4H)-yl)-N-(4-fluoro-3-(trifluoromethyl)benzyl)acetamide;
2-(6-(1-acetylpiperidin-4-yl)-4-oxoquinazolin-3(4H)-yl)-N-(4-chloro-3-(trifluoromethyl)benzyl)acetamide;
2-(6-(1-acetylpiperidin-4-yl)-4-oxoquinazolin-3(4H)-yl)-N-(3,5-dichlorobenzyl)acetamide;
N-(3,4-dichlorobenzyl)-N-methyl-2-(4-oxo-6-(1-(2-sulfamoylacetyl)piperidin-4-yl)quinazolin-3(4H)-yl)acetamide;
N-(3,4-dichlorobenzyl)-2-(6-(1-(2-(2-methoxyethoxy)acetyl)piperidin-4-yl)-4-oxoquinazolin-3(4H)-yl)-N-methylacetamide;
(R)—N-(3,4-dichlorobenzyl)-2-(6-(1-(2-methoxypropanoyl)piperidin-4-yl)-4-oxoquinazolin-3(4H)-yl)-N-methylacetamide;
(S)—N-(3,4-dichlorobenzyl)-2-(6-(1-(2-methoxypropanoyl)piperidin-4-yl)-4-oxoquinazolin-3(4H)-yl)-N-methylacetamide;
(R)—N-(3,4-dichlorobenzyl)-2-(6-(1-(2-hydroxy-3-methylbutanoyl)piperidin-4-yl)-4-oxoquinazolin-3(4H)-yl)-N-methylacetamide;

(S)—N-(3,4-dichlorobenzyl)-2-(6-(1-(2-hydroxy-3-methylbutanoyl)piperidin-4-yl)-4-oxoquinazolin-3(4H)-yl)-N-methylacetamide;

N-(3,4-dichlorobenzyl)-2-(6-(1-(2-methoxyacetyl)piperidin-4-yl)-4-oxoquinazolin-3(4H)-yl)-N-methylacetamide;

N-(3,4-dichlorobenzyl)-2-(6-(1-(2-hydroxy-2-methylpropanoyl)piperidin-4-yl)-4-oxoquinazolin-3(4H)-yl)-N-methylacetamide;

N-(3,4-dichlorobenzyl)-2-(6-(1-(2-methoxypropanoyl)piperidin-4-yl)-4-oxoquinazolin-3(4H)-yl)-N-methylacetamide;

(R)—N-(3,4-dichlorobenzyl)-2-(6-(1-(2-hydroxypropanoyl)piperidin-4-yl)-4-oxoquinazolin-3(4H)-yl)-N-methylacetamide;

(S)—N-(3,4-dichlorobenzyl)-2-(6-(1-(2-hydroxypropanoyl)piperidin-4-yl)-4-oxoquinazolin-3(4H)-yl)-N-methylacetamide;

N-(3,4-dichlorobenzyl)-2-(6-(1-(1-hydroxycyclobutanecarbonyl)piperidin-4-yl)-4-oxoquinazolin-3(4H)-yl)-N-methylacetamide;

N-(3,4-dichlorobenzyl)-2-(6-(1-(2,3-dihydroxypropanoyl)piperidin-4-yl)-4-oxoquinazolin-3(4H)-yl)-N-methylacetamide;

2-(6-(1-(1,4-dioxane-2-carbonyl)piperidin-4-yl)-4-oxoquinazolin-3(4H)-yl)-N-(3,4-dichlorobenzyl)-N-methylacetamide;

N-(3,4-dichlorobenzyl)-2-(6-(1-(1-hydroxycyclopropanecarbonyl)piperidin-4-yl)-4-oxoquinazolin-3(4H)-yl)-N-methylacetamide;

N-(3,4-dichlorobenzyl)-N-methyl-2-(4-oxo-6-(1-(tetrahydrofuran-2-carbonyl)piperidin-4-yl)quinazolin-3(4H)-yl)acetamide;

N-(3,4-dichlorobenzyl)-N-methyl-2-(6-(1-(2-methyltetrahydrofuran-2-carbonyl)piperidin-4-yl)-4-oxoquinazolin-3(4H)-yl)acetamide;

N-(3,4-dichlorobenzyl)-N-methyl-2-(4-oxo-6-(1-(tetrahydrofuran-3-carbonyl)piperidin-4-yl)quinazolin-3(4H)-yl)acetamide;

N-(3,4-dichlorobenzyl)-N-methyl-2-(6-(1-(oxazole-5-carbonyl)piperidin-4-yl)-4-oxoquinazolin-3(4H)-yl)acetamide;

2-[6-(1-acetyl-4-hydroxypiperidin-4-yl)-4-oxoquinazolin-3-yl]-#N!-[(3,4-dichlorophenyl)methyl]-#N!-methylacetamide;

2-[6-(1-acetyl-4-hydroxypiperidin-4-yl)-4-oxoquinazolin-3-yl]-#N!-[(3-chloro-4-cyanophenyl)methyl]-#N!-methylacetamide;

[2-[4-[3-[2-[(3-chloro-4-cyanophenyl)methyl-methylamino]-2-oxoethyl]-4-oxoquinazolin-6-yl]piperidin-1-yl]-2-oxoethyl]nitrate;

2-(6-(1-acetylpiperidin-4-yl)-8-fluoro-4-oxoquinazolin-3(4H)-yl)-N-(3-chloro-4-cyanobenzyl)-N-methylacetamide;

N-(3-chloro-4-cyanobenzyl)-2-(8-fluoro-6-(1-(3-methoxypropanoyl)piperidin-4-yl)-4-oxoquinazolin-3(4H)-yl)-N-methylacetamide;

2-(6-(1-acetylpiperidin-4-yl)-4-oxopyrido[3,4-d]pyrimidin-3(4H)-yl)-N-(3-chloro-4-cyanobenzyl)-N-methylacetamide;

N-(3-chloro-4-cyanobenzyl)-2-(6-(1-(3-methoxypropanoyl)piperidin-4-yl)-4-oxopyrido[3,4-d]pyrimidin-3(4H)-yl)-N-methylacetamide;

and pharmaceutically acceptable salts thereof.

Further particular examples of compounds of formula (I) as described herein are selected from 2-[6-(4-acetylpiperazin-1-yl)-4-oxoquinazolin-3-yl]-N-[(4-chloro-3-fluorophenyl)methyl]acetamide;

2-[6-(4-acetylpiperazin-1-yl)-4-oxoquinazolin-3-yl]-N-[(3-chloro-4-cyanophenyl)methyl]acetamide;

2-[6-(4-acetylpiperazin-1-yl)-4-oxoquinazolin-3-yl]-N-[(4-cyano-3-fluorophenyl)methyl]acetamide;

2-[6-(4-acetylpiperazin-1-yl)-4-oxoquinazolin-3-yl]-N-[(3,4-dichlorophenyl)methyl]-N-methylacetamide;

2-[6-(4-acetylpiperazin-1-yl)-4-oxoquinazolin-3-yl]-N-[(3-chloro-4-cyanophenyl)methyl]-N-methylacetamide;

2-[6-(1-acetylpiperidin-4-yl)-4-oxoquinazolin-3-yl]-N-[(3-chloro-4-cyanophenyl)methyl]-N-methylacetamide;

N-[(3-chloro-4-cyanophenyl)methyl]-2-[6-[1-(2-methoxyacetyl)piperidin-4-yl]-4-oxoquinazolin-3-yl]-N-methylacetamide and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I), wherein $R^5$ is substituted aminocarbonylalkyl, can be prepared by amide coupling reaction between carboxylic acid building blocks of structure A ($A^1$=N) and amines 1a, wherein $R^{15}$ and $R^{16}$ are independently selected from H, alkyl, cycloalkyl and substituted phenyl, wherein substituted phenyl is substituted with one to three substituents independently selected from H, alkyl, haloalkyl and cycloalkyl, in the presence of a coupling agent (Scheme 1). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and are well known to persons skilled in the art. Amide bond formations can be accomplished by usage of appropriate coupling agents such as O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU), N,N'-carbonyldiimidazole (CDI), N,N'-dicyclohexylcarbodiimide (DCC), N-(3-dimethylaminopropyl)-N'-ethyl-carbodiimide-hydrochloride (EDCI), 1-hydroxy-1,2,3-benzotriazole (HOBT), 2-chloro-1-methylpyridinium iodide (Mukaiyama reagent; E. Bald, K. Saigo, T. Mukaiyama, *Chem. Lett.* 1975, 4, 1163-1166) or benzotriazol-1-yloxytris(dimethylamino) phosphonium hexafluorophoshate (BOP). Suitable bases for this transformation are diisopropylethylamine (DIPEA, Huenig's base), triethylamine, N-methylmorpholine or 4-(dimethylamino)pyridine. The reaction is carried out in appropriate solvents such as for example N,N-dimethylformamide (DMF), dimethylacetamide (DMAc), dichloromethane and dioxane or mixtures thereof at room temperature or elevated temperatures (typically not exceeding 150° C.). Thereby, heating can be accomplished by conventional means such as by using an oil bath or preferably with microwave irradiation.

Scheme 1

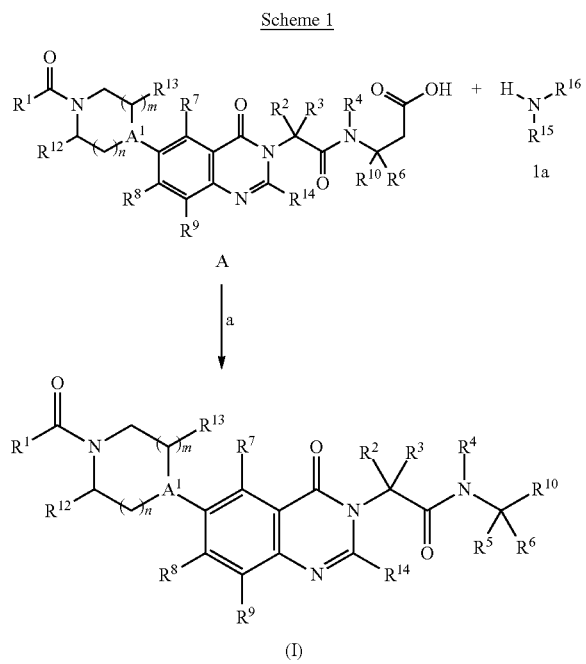

In general, amide bond formation reactions can be conducted using either batch or by employing continuous mode (flow) reaction protocols. Continuous mode synthesis is conducted using a custom-made, integrated flow synthesis and preparative HPLC purification system. A commercial R4 flow reactor module from Vapourtec is connected to a preparative HPLC purification system that is assembled from of a Gilson LH 215 auto-sampler, two Gilson 819 injection modules, two Agilent 1100 Series pumps, one Agilent 1200 series DADA detector, two Varian prep star pumps, one Dionex UV detector, one Polymer Laboratory light-scattering detector and one Dionex P-680 pump. Reagents and starting materials are injected via the LH 215 auto-sampler onto the flow reactor reagent loops (Gilson 819 injection modules) and from there onto the PFA (perfluoroalkoxy polymer) tube reactor coil (10 mL) fitted with a 100 psi back pressure regulator (BPR). In order to limit dispersion effects and to maintain a consistent concentration within the reaction zone as it progresses through the flow reactor, small air bubbles are injected before and after the reaction segment. After completion of the flow reaction, the crude reaction mixture is directly loaded onto the preparative HPLC injection loop to undergo HPLC purification. Purified compounds are collected via the LH 215 auto-sampler. The entire process is controlled using the chromatography management system software Chromeleon version 6.80 from Dionex. The integrated flow synthesis and purification platform has been described in M. Werner, C. Kuratli, R. E. Martin, R. Hochstrasser, D. Wechsler, T. Enderle, A. I. Alanine, H. Vogel, Angew. Chem. Int. Ed. 2014, 53, 1704-1708.

Alternatively, compounds of general formula (I) can be prepared from carboxylic acid building blocks of structure B ($A^1$=N) or C ($A^1$=C) following the sequence outlined in Schemes 2a and 2b. Coupling of carboxylic acid B or C with amines 1a using the aforementioned methods (Scheme 2a, step a) and subsequent cleavage of the amine protection group (e.g., PG=Fmoc, Boc) by using standard methods well known to persons skilled in the art (Scheme 2a, step b) lead to intermediate 3. Subsequent reaction of amine 3 with the appropriate derivatives provides compounds of formula (I) (Scheme 2b). Reaction with carboxylic acids 4 provides access to compounds of general formula (I) wherein $A^2$ is —C(O)— (Scheme 2b, step c). Alternatively, target structures of general formula (I) wherein $A^2$ is —C(O)— can be obtained by coupling of intermediate 3 with acid chlorides 5 in an appropriate solvent such as for example dichloromethane or DMF and a base such as for example diisopropylethylamine (DIPEA, Huenig's base), triethylamine, N-methylmorpholine or 4-(dimethylamino)pyridine, whereby these reactions can take place over a wide range of temperatures ranging from ambient temperature to the reflux temperature of the solvent employed (Scheme 2b, step d).

Scheme 2a

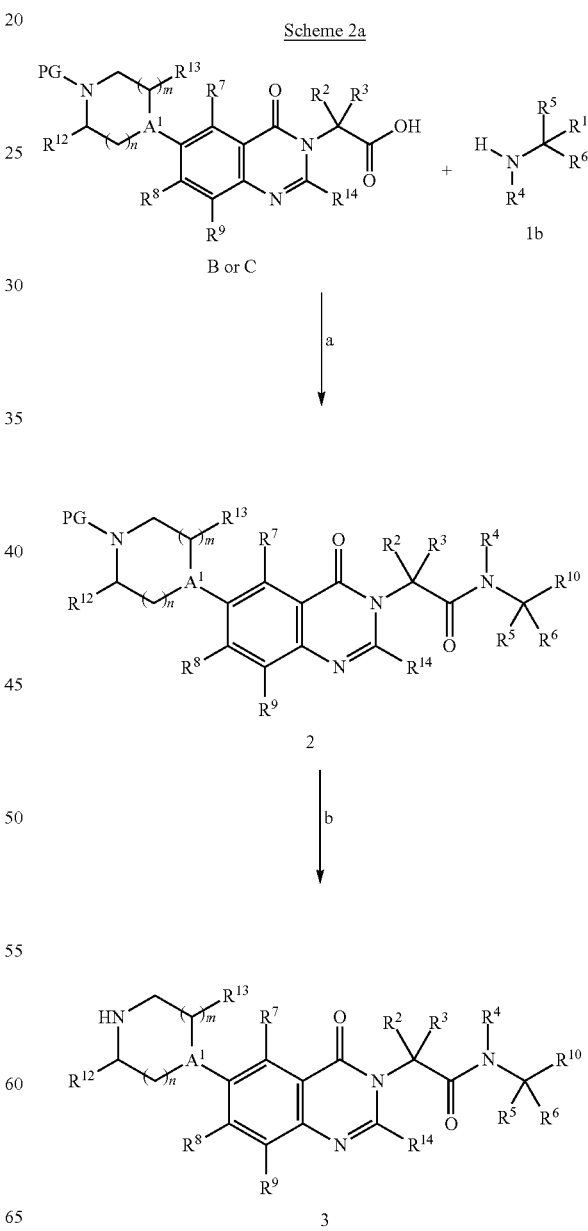

Scheme 2b

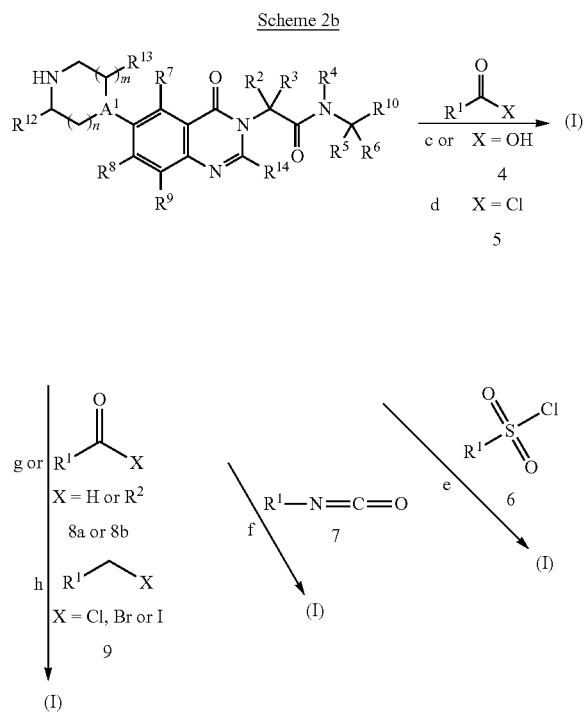

If required, acid chlorides 5 can be prepared from carboxylic acids 4 upon treatment with, e.g., thionyl chloride or oxalyl chloride, in the presence of catalytic amounts of DMF. A further method of accessing compounds of formula (I) wherein $A^2$ is —C(O)— is the reaction of carboxylic acid anhydrides [($R^1$—C═O)$_2$O] with amine 3 in an appropriate solvent such as for example dichloromethane or DMF in the presence of a base such as for example diisopropylethylamine (DIPEA, Huenig's base), triethylamine, N-methylmorpholine or 4-(dimethylamino)pyridine, all methods well known to persons skilled in the art. Alternatively, target structures of general formula (I) can be obtained from carboxylic alkyl esters (e.g., compound 14 in Scheme 3 which is a methyl ester of building block B with PG=acetyl) and amines 1a by treatment for example with bis(trimethylaluminium) or bis(trimethylaluminium)-1,4-diazabicyclo[2.2.2]octane adduct in a solvent like THF and heating at elevated temperatures.

Compounds of general formula (I) wherein $A^2$ is —S(O)$_2$— can be prepared from intermediate 3 and sulfonyl chlorides 6 by employing typical solvents such as for example dichloromethane, DMF or THF in the presence a base such as for example diisopropylethylamine (DIPEA, Huenig's base), triethylamine, N-methylmorpholine or 4-(dimethylamino)pyridine at temperatures between 0° C. and the boiling point of the solvent using conventional heating methods or by microwave irradiation (Scheme 2b, step e).

Compounds of general formula (I), wherein $A^2$ is —$NR^{11}$C(O)— and $R^{11}$ is H, can be prepared from amines of structure 3 and isocyanates 7 by employing typical solvents such as for example dichloromethane or THF at temperatures between 0° C. and the boiling point of the solvent using conventional heating methods or by microwave irradiation (Scheme 2b, step f).

Compounds of general formula (I), wherein $A^2$ is —CH$_2$—, can be prepared by reductive amination procedures (e.g., Leuckart-Wallach reaction) from amines of structure 3 and aldehydes 8a or ketones 8b upon treatment with a suitable reducing agent such as NaBH$_4$, LiBH$_4$, NaBH$_3$CN or NaBH(OAc)$_3$ in a one-step procedure in a solvent like methanol, ethanol, isopropanol or THF in the presence of catalytic amounts of acids such as acetic acid preferably around room temperature to reflux temperature of the solvent (Scheme 2b, step g). Alternatively, the reaction might also be conducted in a two-step procedure by first treatment of aldehyde 8a or ketone 8b with amine 3 in the presence of titanium (IV) isopropoxide with no additional solvent between 0° C. and room temperature or in solvents like methanol or toluene preferably at temperatures between ambient temperature and the reflux temperature of the solvents employed and the subsequent addition of the reducing agent such NaBH$_4$ preferably between 0° C. and room temperature.

In another embodiment, compounds of general formula (I), wherein $A^2$ is —CH$_2$—, can be accessed by alkylation of intermediate 3 with alkyl halides 9 (e.g., methyl 2-bromoacetate or bromomethylcyclopropane) in the presence of a base such as sodium hydride or potassium carbonate in an appropriate solvent like DMF, acetonitrile or THF or mixtures thereof, at rt to elevated temperatures (Scheme 2b, step h). Target compounds of general formula (I) can be purified by classical means such as silica column chromatography, MPLC or preparative HPLC.

Synthesis of carboxylic acid building blocks of general structure B can be accomplished as outlined in Scheme 3. Amide coupling reaction between carboxylic acids 10 (e.g., PG=Fmoc; prepared as described in US2010/0069307A1, pp. 9) and appropriately protected amino acids (e.g., PG$^1$=methyl, ethyl, tert-butyl) like 11 (e.g., glycine methyl ester, tert-butyl 2-aminoacetate) using previously discussed methods provide access to amides of general structure 12 (Scheme 3, step a). Reduction of the nitro group in compounds 12 using typical standard procedures known to those skilled in the art (e.g., Zn, HCl; SnCl$_2$.2H$_2$O, HCl or HOAc) provides anthranilic acids of type 13 (Scheme 3, step b). Reaction of compounds 12 with e.g., trimethyl orthoformate ($R^{14}$=H) in the presence of acetic acid at ambient to elevated temperatures (Scheme 3, step c) followed by cleavage of the carboxylic acid protection group (e.g., PG$^1$=methyl, ethyl, tert-butyl) of quinazolinones 14 by using known methods in the art give access to quinazolinone building blocks of general structure B (Scheme 3, step d). In another embodiment, further quinazolinone building blocks of general structure B were prepared employing a similar reaction sequence replacing trimethyl orthoformate with e.g., trimethyl orthoacetate ($R^{14}$=CH$_3$) or N,N'-carbonyldiimidazole ($R^{14}$=OH) (Scheme 3, step d).

Scheme 3

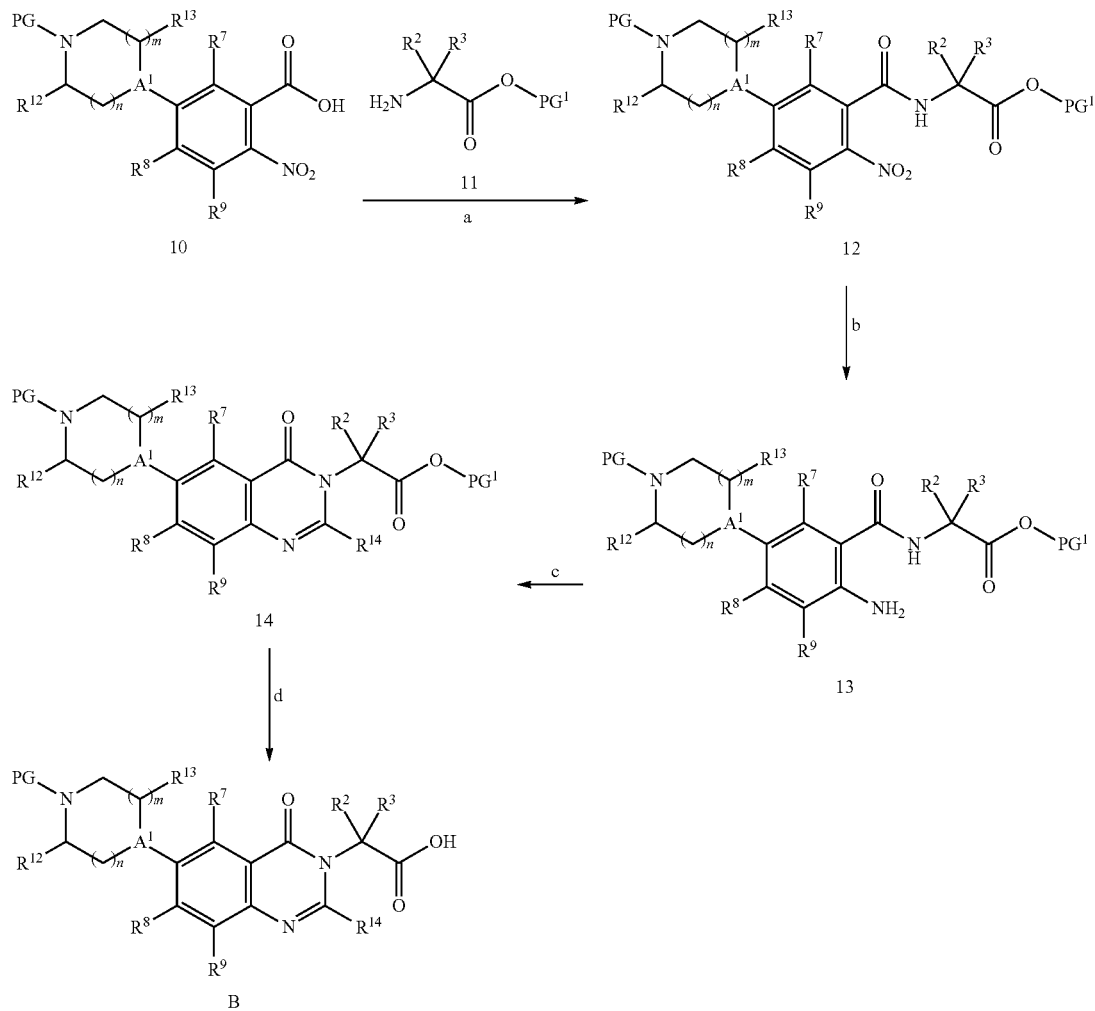

Synthesis of carboxylic acid building blocks of general structure A can be accomplished as described in Scheme 4. Cleavage of the amine protection group (e.g., PG=Fmoc, Boc) by using known methods to persons skilled in the art gives access to quinazolinone building blocks of type 15 (Scheme 4, step a), which upon coupling with carboxylic acids employing previously discussed methods yields carboxylic acid intermediates 16 (Scheme 4, step b). Reaction of compounds 16 with appropriately protected (e.g., benzyl esters) amino acids 17 using standard amide coupling methods provides access to amides of general structure 18 (Scheme 4, step c).

Scheme 4

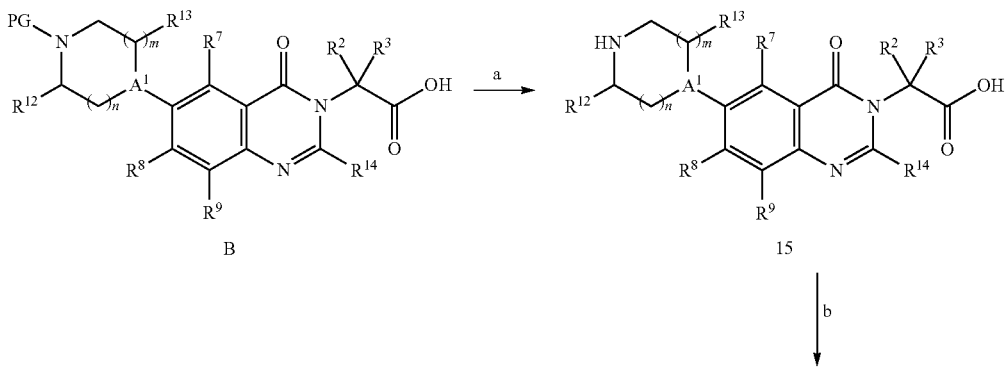

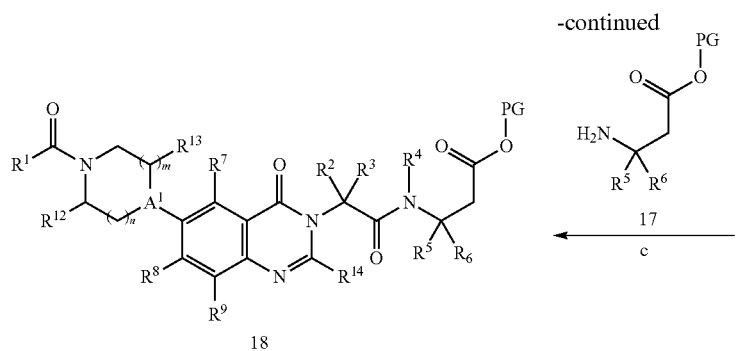

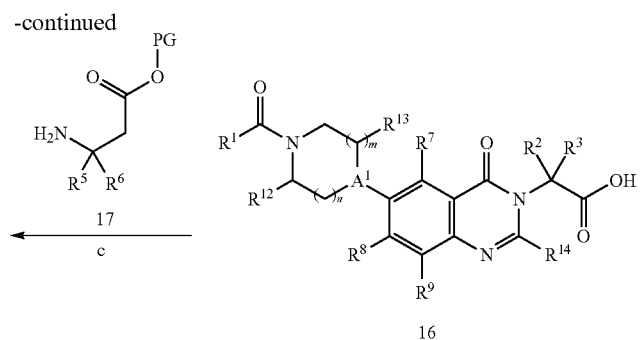

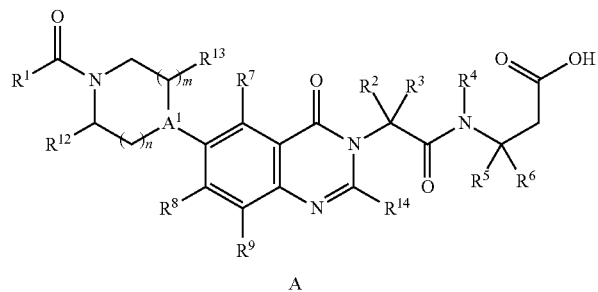

A

Removal of the protection group by using standard methods well known to persons skilled in the art furnishes quinazolinone building blocks of general structure A (Scheme 4, step d).

Preparation of carboxylic acid building blocks of general structure C can be achieved as outlined in Scheme 5. Amide coupling reaction between carboxylic acids 19 (e.g., X=Br, I, OTf) and appropriately protected amino acids (e.g., $PG^1$=methyl, ethyl, tert-butyl) like 11 (e.g., glycine methyl ester, tert-butyl 2-aminoacetate) using previously discussed methods provide access to amides of general structure 20 (Scheme 5, step a). Suzuki-Miyaura reaction (N. Miyaura, K. Yamada, A. Suzuki, *Tetrahedron Lett.* 1979, 20, 3437-3440; N. Miyaura, A. Suzuki, *Chem. Rev.* 1995, 95, 2457-2483) between aryls 20 and a boronic acid or boronic alkyl ester of type 21 (PG=Fmoc, Boc) under palladium (0) or nickel (0) catalysis (e.g., $Pd(OAc)_2$, $Pd(PPh_3)_4$, $PdCl_2$(dppf), $NiCl_2$(dppf)) and in the presence of a suitable ligand (e.g., $PPh_3$, JohnPhos, Xphos, dppf; see: R. Martin, S. L. Buchwald, *Acc. Chem. Res.* 2008, 41, 1461-1473) in typical solvents such as for example dioxane, THF, 1,2-dimethoxyethane and water or mixtures thereof in the presence of a base such as for example potassium carbonate, sodium carbonate or potassium phosphate at temperatures between 0° C. and the boiling point of the solvent using conventional heating methods or by microwave irradiation provides coupling products of general type 22 (Scheme 5, step b). If desired, the reaction might be tuned in such a way that by careful selection of reaction conditions (e.g., nature of base, solvent, reaction temperature and time) simultaneous hydrolysis of the carboxyl acid protection group (e.g., $PG^1$=methyl, ethyl) in compounds 22 can be achieved. Concomitant reduction of the alkene and nitro group in compound 22 by using well known methods to persons skilled in the art such as for instance hydrogenation (e.g., $H_2$, Pd/C) furnishes quinazolinone intermediates 23 (Scheme 5, step c). Treatment of aniline compounds 23 with e.g., trimethyl orthoformate ($R^{14}$=H) in the presence of acetic acid at ambient to elevated temperatures (Scheme 5, step d) followed by cleavage of the carboxylic acid protection group (e.g., $PG^1$=methyl, ethyl, tert-butyl) of quinazolinones 24 by using known methods in the art give access to quinazolinones 25 (Scheme 5, step e). Finally, a switch of protection group PG to $PG^2$ provides access to building blocks of general structure C (Scheme 5, step f).

Scheme 5

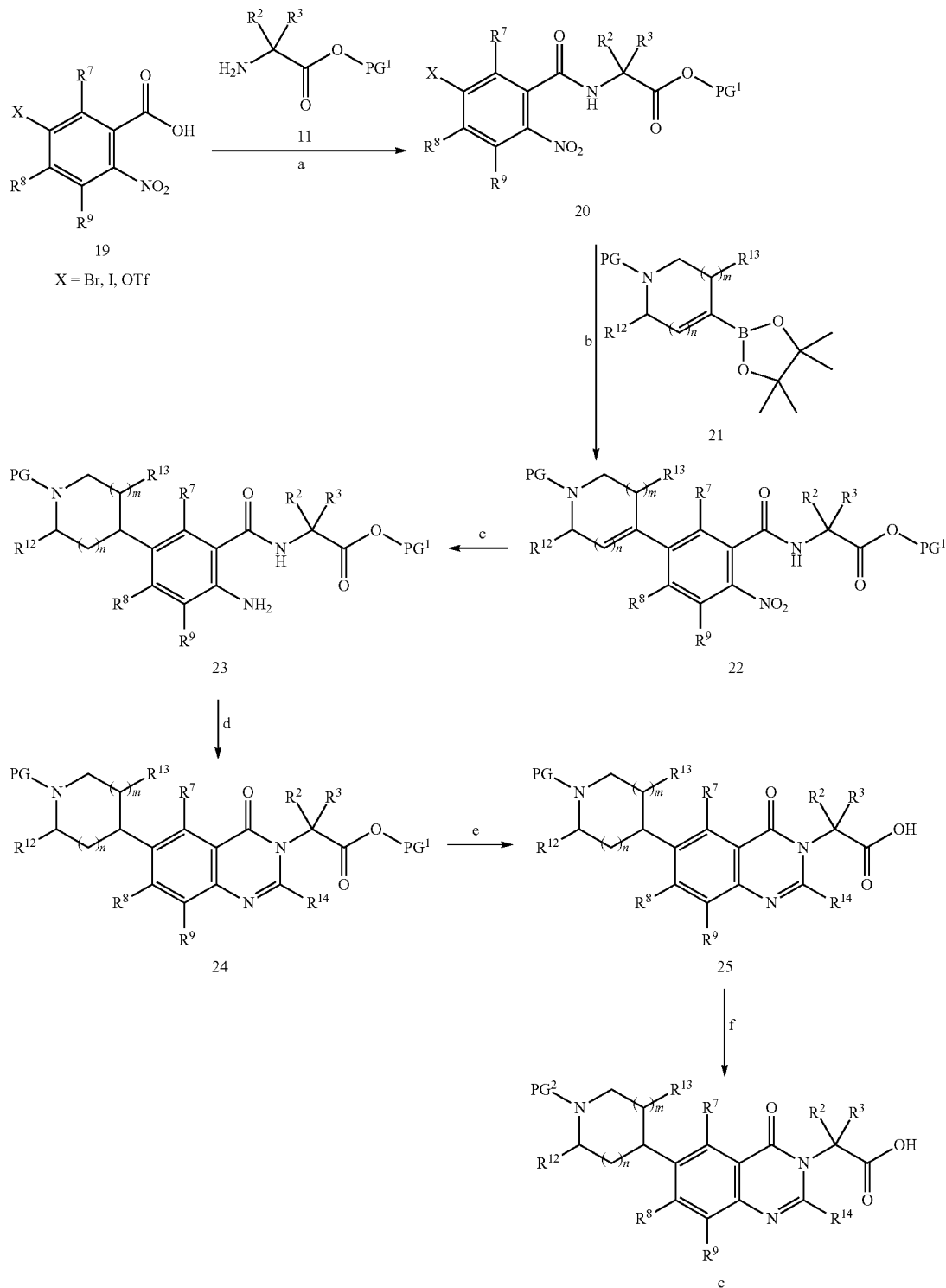

Amines 1b, wherein $R^{10}$ is substituted aryl and $R^5$ and $R^6$ are H, that are not commercially available can be prepared as described in Scheme 6. Radical substitution of compounds 26 with chlorine or bromine by using for example N-chlorosuccinimide or N-bromosuccinimide in a solvent like carbon tetrachloride and a radical initiator like benzoyl peroxide or azobisisobutyronitrile (AIBN) and irradiation with UV-light (e.g., λ=365 nm) at temperatures between 0° C. and the boiling point of the solvent provides benzyl halogenides of type 27 (X=Cl, Br) (Scheme 6, step a). Treatment of compounds 27 with amines of general structure 28 in an appropriate solvent like DMF, acetonitrile or THF or mixtures thereof at rt to elevated temperatures gives access to benzylamines of general structure 1 (Scheme 6, step b). Alternatively, compounds 1b can be accessed from benzaldehydes 28 by reductive amination procedures with amines 29 employing previously discussed methods well known to persons skilled in the art.

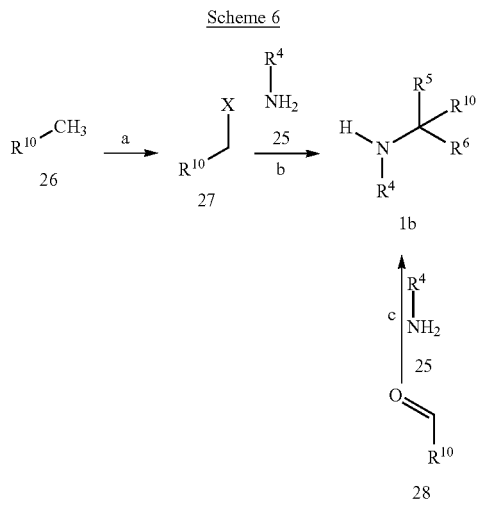

Scheme 6

Also an embodiment of the present invention is a process to prepare a compound of compound of formula (VI) in the presence of a compound of formula (VII), wherein $R^1$, $R^2$, $R^3$, $R^4$, $R^5$, $R^6$, $R^7$, $R^8$, $R^9$, $R^{10}$, $R^{12}$, $R^{13}$, $R^{14}$, $A^1$, $A^3$, n and m are as defined in any one of claims 1 to 25 and $A^2$ is —C(O)—.

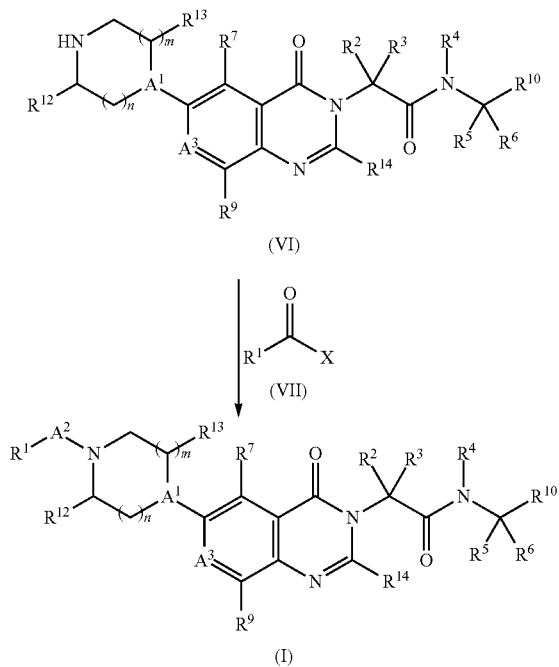

In particular, in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, particularly O-(7-azabenzotriazol-1-yl)-N,N,N',N'-tetramethyluronium hexafluoro-phosphate, in an aprotic solvent such as dichloromethane, tetrahydrofuran, N,N-dimethylformamide, N-methylpyrrolidinone and mixtures thereof, particularly N,N-dimethylformamide, in the presence or absence of a base such as triethylamine, diisopropylethylamine, 4-methylmorpholine and/or 4-(dimethylamino)pyridine, particularly in the presence of 4-methylmorpholine and at a temperature comprised between −78° C. and reflux, particularly between −10° C. and rt.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

Also an object of the invention is a method for the treatment or prophylaxis of ocular conditions, particularly glaucoma, which method comprises administering an effective amount of a compound according to formula (I) as described herein.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g., astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

Also an embodiment of the present invention are compounds of formula (I) as described herein, when manufactured according to any one of the described processes.

Assay Procedures

Production of Human Full Length ATX, with and without his Tag
Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (*J. Immunol. Methods* 1996, 194, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 L of culture supernatant were conditioned for ultrafiltration by adding Brij 35 to a final concentration of 0.02% and by adjusting the pH to 7.0 using 1 M HCl. Then the supernatant was first microfiltred through a 0.2 m Ultran-Pilot Open Channel PES filter (Whatman) and afterwards concentrated to 1 L through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100; GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., *Org. Lett.* 2006, 8, 2023) was labeled with MR121 fluorophore [CAS RN 185308-24-1], 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C. Fluorescence was then measured every 2 min for 1 h (Perkin Elmer plate: vision multimode reader); light intensity: 2.5%; exp. time: 1.4 s, Filter: Fluo_630/690 nm) and $IC_{50}$ values were calculated from these readouts.

| Example | IC50 (µM) |
| --- | --- |
| 1 | 0.269 |
| 2 | 0.360 |
| 3 | 0.198 |
| 4 | 0.170 |
| 5 | 0.121 |
| 6 | 0.979 |
| 7 | 0.084 |
| 8 | 0.279 |
| 9 | 0.054 |
| 10 | 0.096 |
| 11 | 0.119 |
| 12 | 0.148 |
| 13 | 0.478 |
| 14 | 1.471 |
| 15 | 0.415 |
| 16 | 0.207 |
| 17 | 0.137 |
| 18 | 0.014 |
| 19 | 0.130 |
| 20 | 0.005 |
| 21 | 0.052 |
| 22 | 0.091 |
| 23 | 0.072 |
| 24 | 0.033 |
| 25 | 0.016 |
| 26 | 0.051 |
| 27 | 0.340 |
| 28 | 0.027 |
| 29 | 0.175 |
| 30 | 0.139 |
| 31 | 0.331 |
| 32 | 0.089 |
| 33 | 0.245 |
| 34 | 0.024 |
| 35 | 0.071 |
| 36 | 0.346 |
| 37 | 0.073 |
| 38 | 0.004 |
| 39 | 0.012 |
| 40 | 1.557 |
| 41 | 0.021 |
| 42 | 0.140 |
| 43 | 0.112 |
| 44 | 0.017 |
| 45 | 0.038 |
| 46 | 0.184 |
| 47 | 0.341 |
| 48 | 1.580 |
| 49 | 0.179 |
| 50 | 0.456 |
| 51 | 0.051 |
| 52 | 0.072 |
| 53 | 0.018 |
| 54 | 0.831 |
| 55 | 0.038 |
| 56 | 0.008 |
| 57 | 0.008 |
| 58 | 0.015 |
| 59 | 0.070 |
| 60 | 0.010 |
| 61 | 0.016 |
| 62 | 0.011 |
| 63 | 0.011 |
| 64 | 0.004 |
| 65 | 0.010 |
| 66 | 0.190 |
| 67 | 0.015 |
| 68 | 0.004 |
| 69 | 0.003 |
| 70 | 0.318 |
| 71 | 0.026 |
| 72 | 0.010 |
| 73 | 0.006 |
| 74 | 0.007 |
| 75 | 0.005 |
| 76 | 0.010 |
| 77 | 0.003 |
| 78 | 0.009 |
| 79 | 0.010 |
| 80 | 0.012 |
| 81 | 0.073 |
| 82 | 0.043 |
| 83 | 0.030 |
| 84 | 0.002 |
| 85 | 0.061 |
| 86 | 0.133 |
| 87 | 0.076 |
| 88 | 0.088 |
| 89 | 0.020 |
| 90 | 0.035 |
| 91 | 0.030 |
| 92 | 0.007 |
| 93 | 0.029 |
| 94 | 0.067 |
| 95 | 0.068 |
| 96 | 0.011 |
| 97 | 0.004 |
| 98 | 0.044 |
| 99 | 0.031 |
| 100 | 0.204 |
| 101 | 0.064 |
| 102 | 0.195 |
| 103 | 0.288 |
| 104 | 0.064 |
| 105 | 0.059 |
| 106 | 0.132 |
| 107 | 0.067 |
| 108 | 0.055 |
| 109 | 0.035 |
| 110 | 0.034 |
| 111 | 0.035 |
| 112 | 0.071 |
| 113 | 0.202 |
| 114 | 0.026 |
| 115 | 0.029 |
| 116 | 0.016 |
| 117 | 0.016 |
| 118 | 0.035 |
| 119 | 0.649 |
| 120 | 0.009 |
| 121 | 0.020 |
| 122 | 0.012 |
| 123 | 0.067 |
| 124 | 0.007 |
| 125 | 0.007 |
| 126 | 0.012 |
| 127 | 0.009 |
| 128 | 0.015 |
| 129 | 0.026 |
| 130 | 0.111 |
| 131 | 0.001 |
| 132 | 0.012 |
| 133 | 0.001 |
| 134 | 0.001 |
| 135 | 0.001 |
| 136 | 0.001 |

-continued

| Example | IC50 (µM) |
|---|---|
| 137 | 0.002 |
| 138 | 0.003 |
| 139 | 0.018 |
| 140 | 0.047 |
| 141 | 0.002 |
| 142 | 0.060 |
| 143 | 0.046 |
| 144 | 0.086 |
| 145 | 0.082 |
| 146 | 0.001 |
| 147 | 0.140 |
| 148 | 0.015 |
| 149 | 0.039 |
| 150 | 0.091 |
| 151 | 0.021 |
| 152 | 0.180 |
| 153 | 0.036 |
| 154 | 0.002 |
| 155 | 0.153 |
| 156 | 0.561 |
| 157 | 0.010 |
| 158 | 0.002 |
| 159 | 0.001 |
| 160 | 0.158 |
| 161 | 0.028 |
| 162 | 0.044 |
| 163 | 0.001 |
| 164 | 0.025 |
| 165 | 0.020 |
| 166 | 0.627 |
| 167 | 0.004 |
| 168 | 0.027 |
| 169 | 0.035 |
| 170 | 0.014 |
| 171 | 0.003 |
| 172 | 0.021 |
| 173 | 0.008 |
| 174 | 0.002 |
| 175 | 0.015 |
| 176 | 0.046 |
| 177 | 0.036 |
| 178 | 0.034 |
| 179 | 0.156 |
| 180 | 0.005 |
| 181 | 0.008 |
| 182 | 0.008 |
| 183 | 0.028 |
| 184 | 0.086 |
| 185 | 0.125 |
| 186 | 0.004 |
| 187 | 0.001 |
| 188 | 0.001 |
| 189 | 0.001 |
| 190 | 0.001 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

CDI=N,N'-carbonyldiimidazole [CAS RN 530-62-1], DCC=N,N'-dicyclohexylcarbodiimide [CAS RN 538-75-0], DCM=dichloromethane, DIPEA=diisopopylethylamine=iPr$_2$NEt=N-ethyl diisopropylamine=Huenig's base, DMF=N,N-dimethylformamide, dppf=1,1'-bis(diphenylphosphino)ferrocen [CAS RN 12150-46-8], EtOAc=ethyl acetate, h=hour, HATU=1-[bis(dimethylamino) methylene]-1H-1,2,3-triazolo[4,5-b]

pyridinium-3-oxide hexafluorophosphate [CAS RN 148893-10-1], HOBT=1-hydroxy-1,2,3-benzotriazole [CAS RN 123333-53-9], HPLC=high performance liquid chromatography, MPLC=medium pressure liquid chromatography, MS=mass spectrometry, NaBH$_3$CN=sodium cyanoborohydride, NaBH(OAc)$_3$=sodium triacetoxyborohydride, NH$_4$OAc=ammonium acetate, OAc=acetate, PFA=perfluoroalkoxy polymer, Ph=phenyl, PYBOP=(benzotriazol-1-yloxy)tripyrrolidinophosphonium hexafluorophosphate [CAS RN 128625-52-5], rt=room temperature, TBTU=O-benzotriazol-1-yl-N,N,N',N'-tetramethyluronium tetrafluoroborate [CAS RN 125700-67-6], THF=tetrahydrofuran.

Intermediate A-1

2-[6-[4-(9H-Fluoren-9-ylmethoxycarbonyl)piperazin-1-yl]-4-oxoquinazolin-3-yl]acetic acid

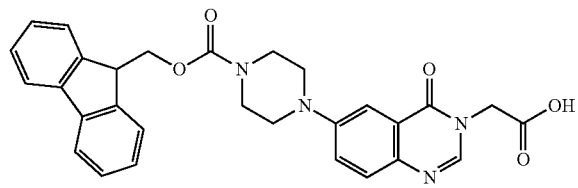 [SMILES: O=C(O)Cn1cnc2ccc(N3CCN(C(=O)OCC4c5ccccc5-c5ccccc54)CC3)cc2c1=O]

[A] 2-Nitro-5-piperazin-1-ylbenzoic acid

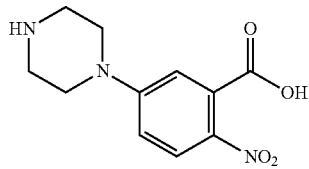

A mixture of 5-chloro-2-nitrobenzoic acid (5.0 g, 24.87 mmol; [CAS RN 2516-95-2]) and piperazin (5.34 g, 62.19 mmol; [CAS RN 110-85-0]) in DMF (10 mL) was heated at 110° C. for 6 h. The reaction mixture was cooled to rt followed by the addition of ice water (50 mL) into the reaction mixture and stirred for 15 min at rt. The precipitated solid was collected by filtration, washed with water (3×50 mL) and dried under vacuum. The title compound was obtained as yellow solid and used directly in the consecutive reaction step without further purification (4.3 g, 69%). MS: m/e=252.1 [M+H]$^+$.

[B] 5-[4-(9H-Fluoren-9-ylmethoxycarbonyl)piperazin-1-yl]-2-nitrobenzoic acid

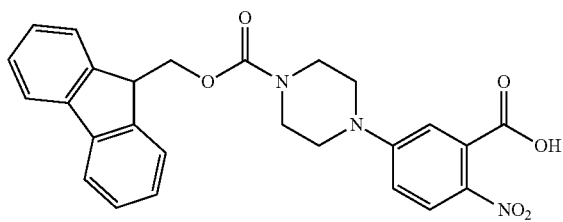 [SMILES: O=C(O)c1cc(N2CCN(C(=O)OCC3c4ccccc4-c4ccccc43)CC2)ccc1[N+](=O)[O-]]

To a suspension of 2-nitro-5-piperazin-1-ylbenzoic acid (4.0 g, 15.94 mmol) in dioxane (40 mL) and aq. 10% NaHCO$_3$ solution (30 mL) was added dropwise 9-fluorenylmethyl chloroformate (4.4 g, 16.73 mmol; [CAS RN 28920-43-6]) in dioxane (40 mL) at 0° C. for 15 min. The resulting mixture was stirred at rt for 20 h. The crude reaction mixture was concentrated under reduce pressure and partitioned between water (50 mL) and EtOAc (50 mL). The organic phase was separated and the aqueous phase extracted with EtOAc (2×50 mL). After that the aqueous phase was neutralized by addition of 35% conc. HCl (2.0 mL) to get a solid precipitate. The obtained solid was collected by filtration, followed by washing with water (2×25 mL) and dried under vacuum. The title compound was obtained as yellow solid and used directly in the consecutive reaction step without further purification (4.8 g, 62%). MS: m/e=474.2 [M+H]$^+$.

[C] 9H-Fluoren-9-ylmethyl 4-[3-[[2-[(2-methylpropan-2-yl)oxy]-2-oxoethyl]carbamoyl]-4-nitrophenyl]piperazine-1-carboxylate

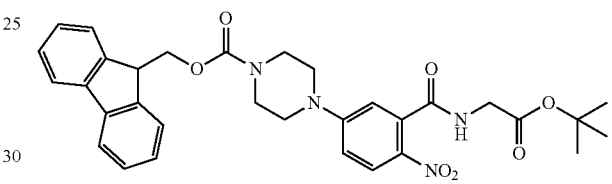

To a solution of 5-[4-(9H-fluoren-9-ylmethoxycarbonyl)piperazin-1-yl]-2-nitrobenzoic acid (4.5 g, 9.53 mmol) in DMF (50 mL) were added TBTU (5.4 g, 14.30 mmol; [CAS RN 125700-67-6]) and DIPEA (4.0 mL, 28.60 mmol) under an atmosphere of nitrogen. Then, tert-butyl 2-aminoacetate (1.87 g, 14.30 mmol; [CAS RN 6456-74-2]) was added and the reaction mixture stirred at rt for 18 h. Ice water (50 mL) was added into the reaction mass and stirred for 30 min at rt. The solid precipitated out, was collected by filtration followed by washing with water (3×50 mL) and dried under vacuum. The title compound was obtained as light yellow solid and used directly in the consecutive reaction step without further purification (3.0 g, 54%). MS: m/e=587.0 [M+H]$^+$.

[D] 9H-Fluoren-9-ylmethyl 4-[4-amino-3-[[2-[(2-methylpropan-2-yl)oxy]-2-oxoethyl]carbamoyl]phenyl]piperazine-1-carboxylate

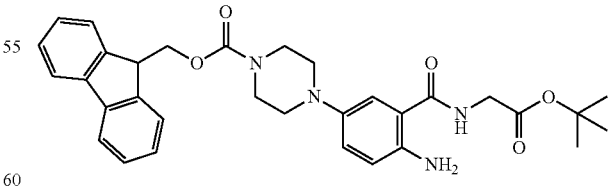

To a stirred solution of 9H-fluoren-9-ylmethyl 4-[3-[[2-[(2-methylpropan-2-yl)oxy]-2-oxoethyl]carbamoyl]-4-nitrophenyl]piperazine-1-carboxylate (2.75 g, 4.69 mmol) in acetic acid (25 mL) was added zinc powder (1.5 g, 23.46 mmol; [CAS RN: 7440-66-6]) portion wise over a period of 10 min and then vigorously stirred at rt for 6 h. The reaction mixture was filtered through Celite® followed by washing with acetic acid (2×10 mL). The filtrate was concentrated under reduce pressure to afford a viscous liquid, which was partitioned between water (25 mL) and EtOAc (25 mL). The aqueous phase was extracted with EtOAc (2×25 mL), the combined organic phases dried over anhydrous Na₂SO₄ and concentrated under reduced pressure. The crude reaction product was purified by column chromatography (100-200 mesh size silica gel) using 40% EtOAc-hexane as eluent affording the title compound as off-white solid (1.3 g, 50%). MS: m/e=557.2 [M+H]⁺.

[E] 9H-Fluoren-9-ylmethyl 4-[3-[2-[(2-methylpropan-2-yl)oxy]-2-oxoethyl]-4-oxoquinazolin-6-yl]piperazine-1-carboxylate

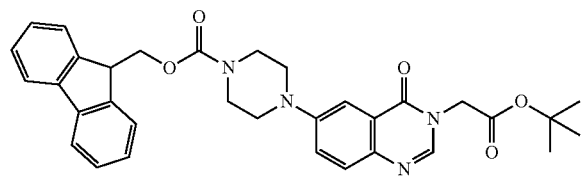 [SMILES: CC(C)(C)OC(=O)Cn1cnc2ccc(N3CCN(C(=O)OCC4c5ccccc5-c5ccccc54)CC3)cc2c1=O]

A mixture of 9H-fluoren-9-ylmethyl 4-[4-amino-3-[[2-[(2-methylpropan-2-yl)oxy]-2-oxoethyl]carbamoyl]phenyl]piperazine-1-carboxylate (1.2 g, 2.16 mmol) and triethyl orthoformate (5 mL, 30.1 mmol; [CAS RN 122-51-0]) in EtOH (5 mL) was heated in an oil bath to 80° C. for 12 h under an atmosphere of nitrogen. The reaction mixture was cooled to rt and concentrated under reduced pressure. The crude reaction product was partitioned between water (25 mL) and EtOAc (25 mL) and the aqueous phase extracted with EtOAc (2×25 mL). The combined organic phases were dried over anhydrous Na₂SO₄ and concentrated under reduced pressure. The crude reaction product was purified by column chromatography (100-200 mesh size silica gel) using 50% EtOAc-hexane as eluent affording the title compound as grey solid (0.75 g, 61%). MS: m/e=567.2 [M+H]⁺.

[F] 2-[6-[4-(9H-Fluoren-9-ylmethoxycarbonyl)piperazin-1-yl]-4-oxoquinazolin-3-yl]acetic acid (Intermediate A-1; [CAS RN 269078-82-2])

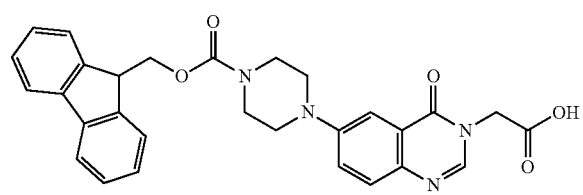 [SMILES: O=C(O)Cn1cnc2ccc(N3CCN(C(=O)OCC4c5ccccc5-c5ccccc54)CC3)cc2c1=O]

To a stirred solution of 9H-fluoren-9-ylmethyl 4-[3-[2-[(2-methylpropan-2-yl)oxy]-2-oxoethyl]-4-oxoquinazolin-6-yl]piperazine-1-carboxylate (0.6 g, 1.06 mmol) in dioxane (2.5 mL) was added 4 M HCl in dioxane (10 mL) and the reaction mixture stirred at rt for 8 h. The solvent was removed under reduced pressure, an aq. solution of 10% NaHCO₃ solution (25 mL) was added and the reaction extracted with EtOAc (3×25 mL). After that the aqueous phase was neutralized by addition of 35% conc. HCl (0.5 mL) and extracted with 5% methanol in DCM (3×25 mL).

The combined organic phases were dried over anhydrous Na₂SO₄ and concentrated under reduced pressure affording the title compound as off-white solid (0.36 g, 66%). MS: m/e=511.2 [M+H]⁺.

Intermediate A-2

2-[6-(4-Acetylpiperazin-1-yl)-4-oxoquinazolin-3-yl]acetic acid

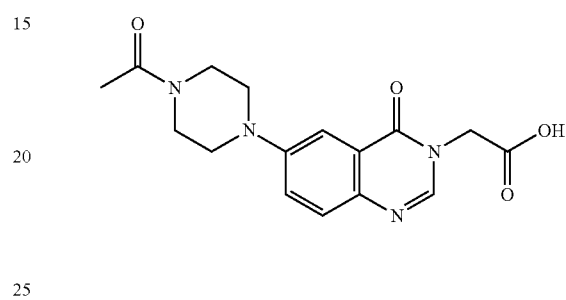

To a suspension of 2-(4-oxo-6-piperazin-1-ylquinazolin-3-yl)acetic acid (5.0 g, 17.34 mmol; [CAS RN 889958-08-1]) in DCM (100 mL) was added triethylamine (6.02 mL, 43.40 mmol) at 0° C. under an atmosphere of nitrogen. The reaction mixture was stirred at 0° C. for 15 min, then acetic anhydride (1.97 mL, 20.83 mmol) was added slowly at 0° C. and the reaction mixture was stirred at rt for 4 h. After completion of the reaction, the solvent was concentrated under reduced pressure to a minimum volume (30 mL) and the obtained solid filtered and washed with hexane. The title compound was isolated as an off-white solid (5.44 g, 95%). MS: m/e=331.2 [M+H]⁺.

Intermediate A-3

(3R)-3-[[2-[6-(4-Acetylpiperazin-1-yl)-4-oxoquinazolin-3-yl]acetyl]amino]-3-(4-chloro-phenyl)propanoic acid

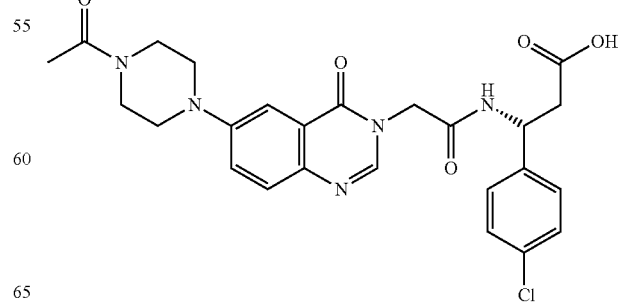

41

[A] Benzyl (3R)-3-(4-chlorophenyl)-3-[(2-methyl-propan-2-yl)oxycarbonylamino]propanoate

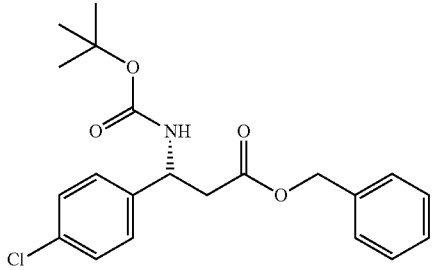

To a solution of (R)-3-(4-chlorophenyl)-3-[(2-methylpropan-2-yl)oxycarbonylamino]propanoic acid (1.0 g, 3.34 mmol; [CAS RN 479064-93-2]) in DCM (20 mL) were added EDC.HCl (1.08 g, 5.65 mmol) and HOBt (0.76 g, 5.65 mmol) at rt under an atmosphere of nitrogen. Then, DIPEA (1.97 mL, 11.30 mmol) was added and the reaction mixture was stirred at rt for 30 min, followed by the addition of benzyl alcohol (0.49 mL, 4.71 mmol). After stirring for 16 h, water was added (100 mL) and the reaction mixture extracted with DCM (2×100 mL). The combined organic phase was washed with water (50 mL), a sat. aq. solution of sodium chloride (50 mL), dried over anhydrous $Na_2SO_4$ and concentrated under reduced pressure. The crude reaction product was purified by column chromatography (100-200 mesh size silica gel) using 10% EtOAc-hexane as eluent affording the title compound as white solid (0.7 g, 54%). MS: m/e=390.4 [M+H]$^+$.

[B] Benzyl (3R)-3-amino-3-(4-chlorophenyl)propanoate hydrochloride

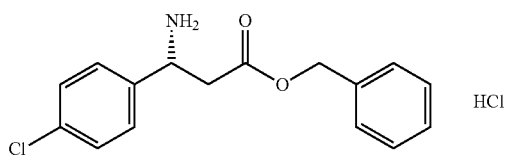

To benzyl (R)-3-(4-chlorophenyl)-3-[(2-methylpropan-2-yl)oxycarbonylamino]-propanoate (0.7 g, 1.80 mmol) was added HCl (15 mL, 4.0 M solution in dioxane) at 0° C. under an atmosphere of Ar. The reaction mixture was stirred at rt for 4 h and then concentrated under reduced pressure. The obtained solid was filtered and washed with dry diethyl ether. The title compound was isolated as white solid (0.51 g, 87%) and used in the consecutive reaction step without further purification. MS: m/e=290.1 [M+H]$^+$.

42

[C] Benzyl (3R)-3-[[2-[6-(4-acetylpiperazin-1-yl)-4-oxoquinazolin-3-yl]acetyl]amino]-3-(4-chlorophenyl)propanoate

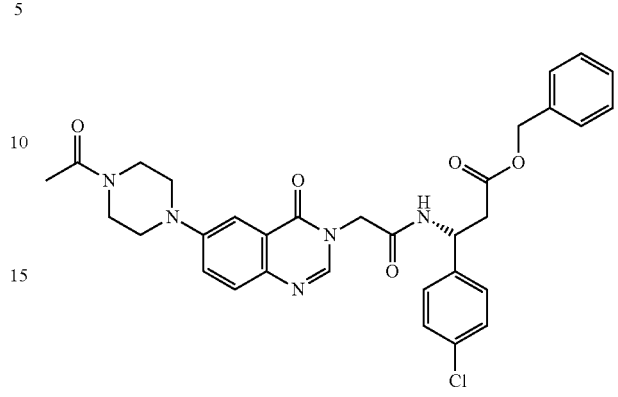

To a solution of 2-[6-(4-acetylpiperazin-1-yl)-4-oxoquinazolin-3-yl]acetic acid (intermediate A-2) (0.63 g, 1.91 mmol) in dry DMF (10 mL) were added EDC.HCl (0.50 g, 2.61 mmol) and HOBt (0.35 g, 2.61 mmol) at rt under an atmosphere of nitrogen. Then, DIPEA (0.91 mL, 5.22 mmol) was added and the reaction mixture was stirred at rt for 30 min, followed by the addition of benzyl (R)-3-amino-3-(4-chlorophenyl)propanoate hydrochloride (0.50 g, 1.73 mmol). After stirring for 16 h, the reaction mixture was quenched by addition to ice and the precipitate was washed with ice cold water (3×30 mL), diethyl ether (3×30 mL), and hexane (2×30 mL). The title compound was obtained as off-white solid (0.75 g, 65%). MS: m/e=602.2 [M+H]$^+$.

[D] (3R)-3-[[2-[6-(4-Acetylpiperazin-1-yl)-4-oxo-quinazolin-3-yl]acetyl]amino]-3-(4-chlorophenyl)propanoic acid (Intermediate A-3)

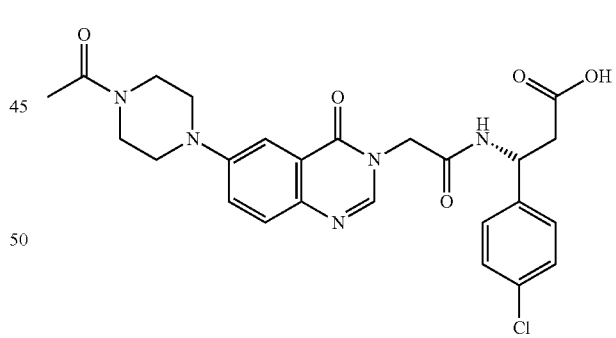

To a degassed solution of benzyl (R)-3-[[2-[6-(4-acetylpiperazin-1-yl)-4-oxoquinazolin-3-yl]acetyl]amino]-3-(4-chlorophenyl)propanoate (0.50 g, 0.83 mmol) in EtOAc (40 mL) was added 10% Pd/C (0.040 g, 0.038 mmol) and the reaction mixture stirred under hydrogen (atmospheric pressure) at rt for 4 h. The reaction mixture was filtered through Celite® using ethanol, the organic phase concentrated in vacuo and the solid material purified by washing with diethyl ether (3×20 mL) and DCM (1×30 mL). The title compound was obtained as off-white solid (0.23 g, 54%) and used in the consecutive reaction step without further purification. MS: m/e=512.3 [M+H]$^+$.

Intermediate A-4

(3R)-3-[[2-[6-(4-Acetylpiperazin-1-yl)-4-oxoquinazolin-3-yl]acetyl]amino]-3-[4-(trifluoromethyl)phenyl]propanoic acid

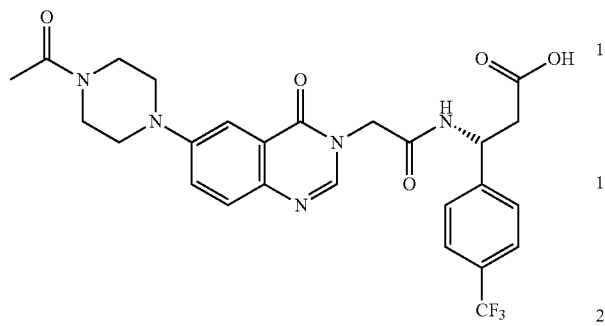

[A] Benzyl (3R)-3-[(2-methylpropan-2-yl)oxycarbonylamino]-3-[4-(trifluoromethyl)phenyl]-propanoate

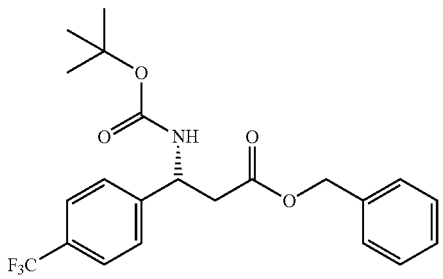

The title compound was prepared in analogy to the procedure described for the preparation of benzyl (R)-3-(4-chlorophenyl)-3-[(2-methylpropan-2-yl)oxycarbonylamino]propanoate (intermediate A-3, step A), replacing (R)-3-(4-chlorophenyl)-3-[(2-methylpropan-2-yl)oxycarbonylamino]propanoic acid with (R)-3-[(2-methylpropan-2-yl)oxycarbonylamino]-3-[4-(trifluoromethyl)phenyl]propanoic acid (1.0 g, 3.00 mmol; [CAS RN 501015-19-6]). Purification by column chromatography (100-200 mesh size silica gel) using 10% EtOAc-hexane as eluent afforded the title compound as white solid (1.11 g, 87%). MS: m/e=424.2 [M+H]$^+$.

[B] Benzyl (3R)-3-amino-3-[4-(trifluoromethyl)phenyl]propanoate hydrochloride

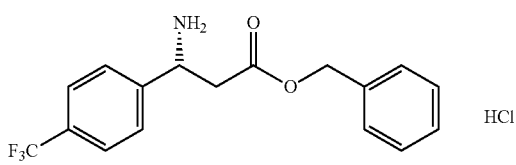

The title compound was prepared in analogy to the procedure described for the preparation of benzyl (R)-3-amino-3-(4-chlorophenyl)propanoate hydrochloride (intermediate A-3, step B), replacing benzyl (R)-3-(4-chlorophenyl)-3-[(2-methylpropan-2-yl)oxycarbonylamino]propanoate with benzyl (R)-3-[(2-methylpropan-2-yl)oxycarbonylamino]-3-[4-(trifluoromethyl)phenyl]propanoate (1.11 g, 2.62 mmol). The title compound was isolated as white solid and used in the consecutive reaction step without further purification (0.84 g, 89%). MS: m/e=324.2 [M+H]$^+$.

[C] Benzyl (3R)-3-[[2-[6-(4-Acetylpiperazin-1-yl)-4-oxoquinazolin-3-yl]acetyl]amino]-3-[4-(trifluoromethyl)phenyl]propanoate

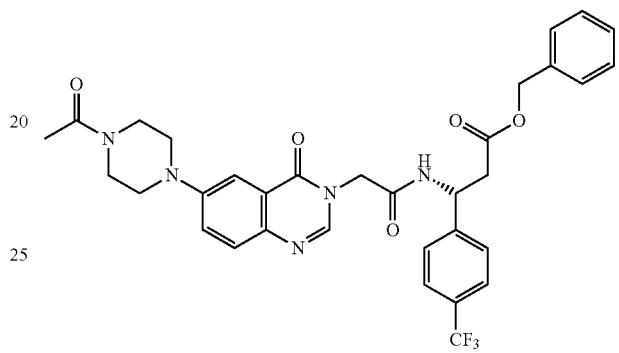

The title compound was prepared in analogy to the procedure described for the preparation of benzyl (3R)-3-[[2-[6-(4-acetylpiperazin-1-yl)-4-oxoquinazolin-3-yl]acetyl]amino]-3-(4-chlorophenyl)propanoate (intermediate A-3, step C), replacing benzyl (3R)-3-amino-3-(4-chlorophenyl)propanoate hydrochloride with benzyl (3R)-3-amino-3-[4-(trifluoromethyl)phenyl]propanoate hydrochloride (0.84 g, 2.60 mmol). The title compound was obtained as off-white solid (1.40 g, 77%). MS: m/e=636.2 [M+H]$^+$.

[D] (3R)-3-[[2-[6-(4-Acetylpiperazin-1-yl)-4-oxoquinazolin-3-yl]acetyl]amino]-3-[4-(trifluoromethyl)phenyl]propanoic acid (Intermediate A-4)

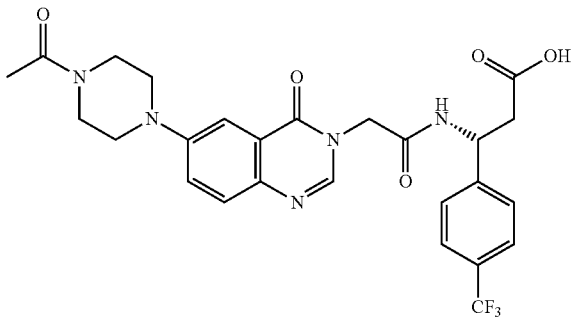

The title compound was prepared in analogy to the procedure described for the preparation of (3R)-3-[[2-[6-(4-acetylpiperazin-1-yl)-4-oxoquinazolin-3-yl]acetyl]amino]-3-(4-chlorophenyl)propanoic acid (intermediate A-3, step D), replacing benzyl (3R)-3-[[2-[6-(4-acetylpiperazin-1-yl)-4-oxoquinazolin-3-yl]acetyl]amino]-3-(4-chlorophenyl)propanoate with benzyl (3R)-3-[[2-[6-(4-acetylpiperazin-1-yl)-4-oxoquinazolin-3-yl]acetyl]amino]-3-[4-(trifluoromethyl)

phenyl]propanoate (0.70 g, 1.10 mmol). After concentration of the organic phase in vacuo the solid material was purified by washing with DCM (3×30 mL) and hexane (2×20 mL). The title compound was obtained as yellow solid (0.30 g, 50%) and used in the consecutive reaction step without further purification. MS: m/e=546.2 [M+H]$^+$.

Intermediate A-5

9H-Fluoren-9-ylmethyl 4-[3-[2-[(3,4-dichlorophenyl)methylamino]-2-oxoethyl]-4-oxoquinazolin-6-yl]piperazine-1-carboxylate

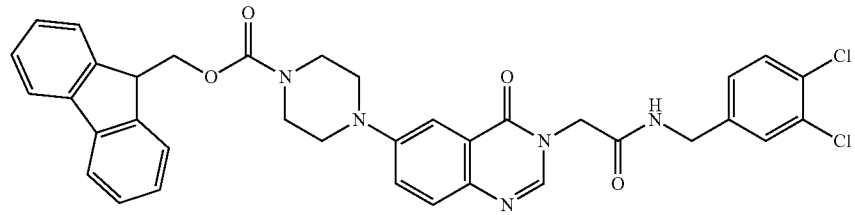 [SMILES: O=C(Cn1cnc2ccc(N3CCN(C(=O)OCC4c5ccccc5-c5ccccc54)CC3)cc2c1=O)NCc1ccc(Cl)c(Cl)c1]

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (3.0 g, 5.88 mmol) in dry DMF (30 mL) were added PYBOP (3.1 g, 5.88 mmol; [CAS RN 128625-52-5]) and DIPEA (1.23 mL, 7.05 mmol) under an atmosphere of nitrogen. Then, (3,4-dichlorophenyl)methanamine (1.24 g, 7.05 mmol; [CAS RN 102-49-8]) was added and the reaction mixture stirred at rt for 2 h. Heptane (100 mL) was added, the white precipitate filtered off, the solid material washed with heptane (50 mL) and dried under high vaccum. The title compound was obtained as white solid and used directly in the consecutive reaction step without further purification (2.20 g, 56%). MS: m/e=670.6 [M+H]$^+$.

Intermediate A-6

9H-Fluoren-9-ylmethyl 4-[3-[2-[(3,4-dichlorophenyl)methyl-methylamino]-2-oxoethyl]-4-oxoquinazolin-6-yl]piperazine-1-carboxylate

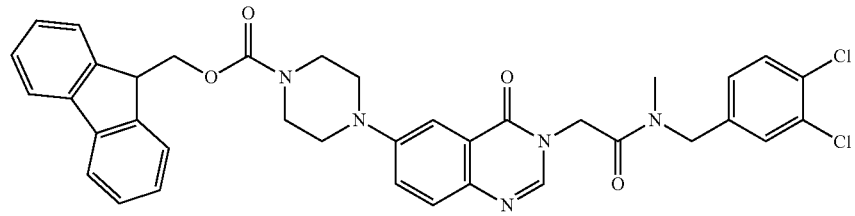 [SMILES: CN(Cc1ccc(Cl)c(Cl)c1)C(=O)Cn1cnc2ccc(N3CCN(C(=O)OCC4c5ccccc5-c5ccccc54)CC3)cc2c1=O]

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (0.75 g, 1.47 mmol) in DCM (20 mL) were added TBTU (0.71 g, 2.21 mmol; [CAS RN 125700-67-6]) and DIPEA (0.77 mL, 4.41 mmol) under an atmosphere of nitrogen. Then, 1-(3,4-dichlorophenyl)-N-methylmethanamine (0.31 g, 1.62 mmol; [CAS RN 5635-67-6]) was added and the reaction mixture stirred at rt for 2 h. Heptane (100 mL) was added, the white precipitate filtered off, the solid material washed with heptane (50 mL) and dried under high vaccum. The title compound was obtained as white solid and used directly in the consecutive reaction step without further purification (0.85 g, 85%). MS: m/e=683.3 [M+H]$^+$.

Intermediate A-7

Methyl 2-[6-(4-acetylpiperazin-1-yl)-4-oxoquinazolin-3-yl]acetate

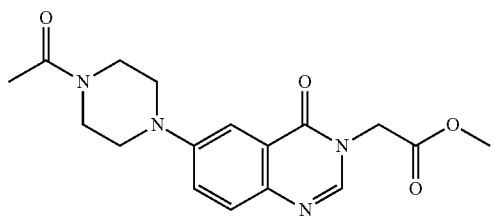 [SMILES: COC(=O)Cn1cnc2ccc(N3CCN(C(C)=O)CC3)cc2c1=O]

[A] 5-(4-Acetylpiperazin-1-yl)-2-nitrobenzoic acid

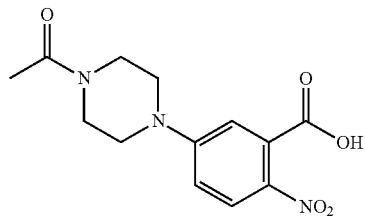 [SMILES: CC(=O)N1CCN(c2ccc([N+](=O)[O-])c(C(=O)O)c2)CC1]

A mixture of 5-chloro-2-nitrobenzoic acid (2.0 g, 9.95 mmol; [CAS RN 2516-95-2] and 1-piperazin-1-ylethanone (6.1 g, 47.7 mmol; [CAS RN 13889-98-0]) was heated at 110° C. for 18 h. Then, the reaction mixture was cooled to rt and the residue basified to pH 10-12 by addition of an aq. solution of 50% NaOH (6.0 mL) keeping the temperature at 10° C. To the clear solution was added an aq. solution of 35% HCl (1.3 mL), the formed precipiate separated by filtration, the solid material washed with EtOAc (2×20 mL) and dried under high vaccum. The title compound was obtained as light yellow solid and used directly in the consecutive reaction step without further purification (1.5 g, 51%). MS: m/e=294.1 [M+H]$^+$.

[B] Methyl 2-[[5-(4-acetylpiperazin-1-yl)-2-nitrobenzoyl]amino]acetate

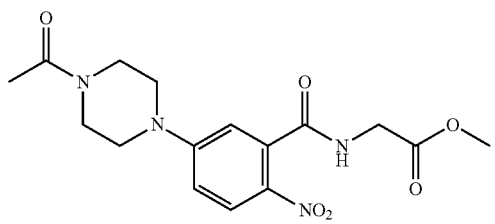 [SMILES: COC(=O)CNC(=O)c1cc(N2CCN(C(C)=O)CC2)ccc1[N+](=O)[O-]]

To a stirred solution of 5-(4-acetylpiperazin-1-yl)-2-nitrobenzoic acid (0.7 g, 2.39 mmol) in dry DMF (10 mL) was added HATU (1.36 g, 3.58 mmol; [CAS RN 148893-10-1]) and DIPEA (1.7 mL, 9.5 mmol) at rt under an atmosphere of nitrogen. After stirring for 30 min, glycine methyl ester hydrochloride (0.4 g, 3.58 mmol; [CAS RN 5680-79-5]) was added. After stirring for 18 h, the reaction mixture was concentrated under reduced pressure followed by the addition of ice water (40 mL). The obtained solid was filtered and dried under vacuum. The title compound was obtained as light yellow solid and used directly in the consecutive reaction step without further purification (0.45 g, 52%). MS: m/e=364.9 [M+H]$^+$.

[C] Methyl 2-[[5-(4-acetylpiperazin-1-yl)-2-aminobenzoyl]amino]acetate

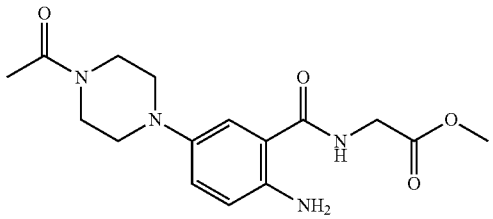 [SMILES: COC(=O)CNC(=O)c1cc(N2CCN(C(C)=O)CC2)ccc1N]

To a degassed solution of methyl 2-[[5-(4-acetylpiperazin-1-yl)-2-nitrobenzoyl]amino]acetate (3.25 g, 11.09 mmol) in methanol (50 mL) was added 10% Pd/C (0.15 g, 0.14 mmol) and the reaction mixture stirred under hydrogen (atmospheric pressure) at rt for 6 h. The reaction mixture was filtered through Celite® using methanol, the organic phase concentrated under reduced pressure and the solid material purified by washing with diethyl ether (3×20 mL). The title compound was obtained as light brown solid and used directly in the consecutive reaction step without further purification (2.75 g, 74%). MS: m/e=335.2 [M+H]$^+$.

[D] Methyl 2-[6-(4-acetylpiperazin-1-yl)-4-oxoquinazolin-3-yl]acetate (Intermediate A-7)

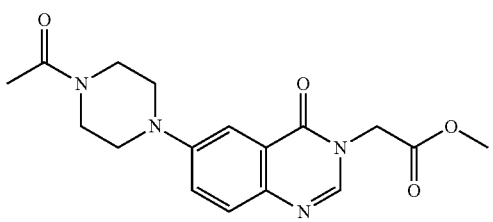 [SMILES: COC(=O)Cn1cnc2ccc(N3CCN(C(C)=O)CC3)cc2c1=O]

A solution of methyl 2-[[5-(4-acetylpiperazin-1-yl)-2-aminobenzoyl]amino]acetate (2.75 g, 8.23 mmol) in triethyl orthoformate (20 mL, 0.12 mol; [CAS RN 122-51-0]) was heated in an oil bath to 140° C. for 36 h under an atmosphere of nitrogen. The reaction mixture was cooled to rt, concentrated under reduced pressure and the crude product purified by column chromatography (100-200 mesh size silica gel) using 10% methanol-DCM as eluent. The title compound was obtained as white solid (2.0 g, 71%). MS: m/e=345.4 [M+H]$^+$.

Intermediate A-8

2-[6-[1-(9H-Fluoren-9-ylmethoxycarbonyl)-4-piperidyl]-4-oxoquinazolin-3-yl]acetic acid

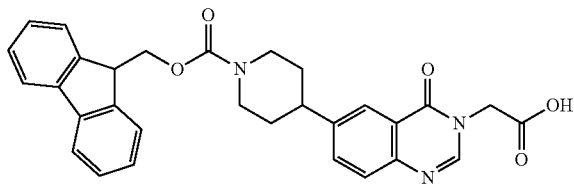

[A] Methyl 2-[(5-bromo-2-nitrobenzoyl)amino]acetate

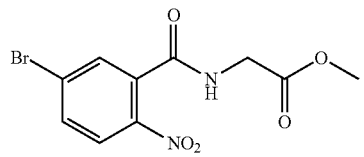 [SMILES: COC(=O)CNC(=O)c1cc(Br)ccc1[N+](=O)[O-]]

To a stirred solution of 5-bromo-2-nitrobenzoic acid (10.0 g, 40.6 mmol; [CAS RN 6950-43-2] in DMF (50 mL) were added HATU (23 g, 60 mmol) and DIPEA (35 ml, 203.2 mmol) under an atmosphere of nitrogen. Then, glycine methyl ester hydrochloride (6.0 g, 48.7 mmol; [CAS RN 5680-79-5]) was added and the reaction mixture was stirred at rt for 18 h. After completion of the reaction, the solvent was evaporated under reduced pressure providing a yellow solid. Water (25 ml) was added and the resulting yellow solid filtered off, the precipitate washed with water (4×25 mL) and dried under reduced pressure. The title compound was obtained as light yellow solid and used directly in the consecutive reaction step without further purification (7.0 g, 63%). MS: m/e=318.1 [M+H]+.

[B] tert-Butyl 4-[3-[(2-methoxy-2-oxoethyl)carbamoyl]-4-nitrophenyl]-3,6-dihydro-2H-pyridine-1-carboxylate

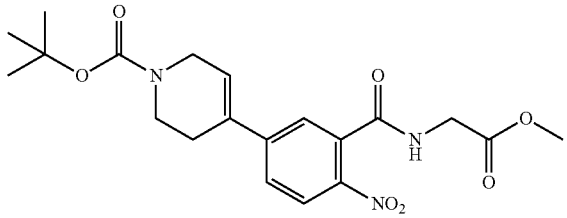 [SMILES: COC(=O)CNC(=O)c1cc(C2=CCN(C(=O)OC(C)(C)C)CC2)ccc1[N+](=O)[O-]]

To a solution of methyl 2-[(5-bromo-2-nitrobenzoyl) amino]acetate (4.0 g, 12.61 mmol) in dioxane (80 mL) were added tert-butyl 4-(tetramethyl-1,3,2-dioxaborolan-2-yl)-1,2,3,6-tetrahydropyridine-1-carboxylate (4.28 g, 13.88 mmol; [CAS RN 286961-14-6]) and carefully dried K$_2$CO$_3$ (3.91 g, 28.39 mmol). The reaction mixture was degassed for 5 min by bubbling through nitrogen and then [1,1'-bis (diphenylphosphino)ferrocene] dichloropalladium(II) dichloromethane complex (0.922 g, 1.26 mmol; [CAS RN 95464-05-4]) was added. The resultant reaction mixture was further degassed for 5 min and then stirred at 90° C. for 3 h. The reaction mixture was cooled to rt, EtOAc (250 mL) was added and the organic phase washed with water (100 mL) and a sat. solution of NaCl (100 mL). The organic layer was dried over anhydrous Na$_2$SO$_4$ and concentrated under reduced pressure. The crude reaction product was purified by column chromatography (100-200 mesh size silica gel) using 25% EtOAc-hexane as eluent affording the title compound as yellow solid (3.5 g, 62%). MS: m/e=418.2 [M−H]−.

[C] tert-Butyl 4-[4-amino-3-[(2-methoxy-2-oxoethyl)carbamoyl]phenyl]piperidine-1-carboxylate

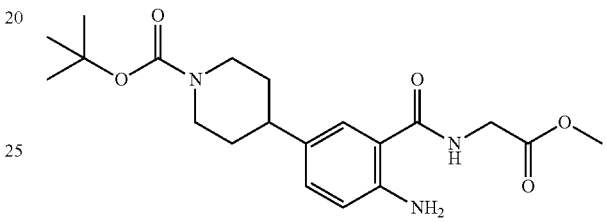

To a solution of tert-butyl 4-[3-[(2-methoxy-2-oxoethyl) carbamoyl]-4-nitrophenyl]-3,6-dihydro-2H-pyridine-1-carboxylate (2.3 g, 5.48 mmol) in methanol (50 mL) was added 10% Pd/C (0.23 g, 0.22 mmol) and the reaction mixture stirred under hydrogen (atmospheric pressure) at rt for 3 h. The reaction mixture was filtered through Celite® using methanol and the organic phase concentrated in vacuo. The crude material was obtained as off-white solid and used in the consecutive reaction step without further purification (2.0 g, crude). MS: m/e=392.0 [M+H]+.

[D] tert-Butyl 4-[3-(2-methoxy-2-oxoethyl)-4-oxoquinazolin-6-yl]piperidine-1-carboxylate

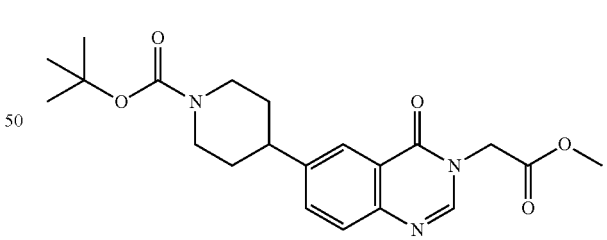

To a solution of tert-butyl 4-[4-amino-3-[(2-methoxy-2-oxoethyl)carbamoyl]phenyl]piperidine-1-carboxylate (0.5 g, 1.27 mmol) in methanol (20 mL) was added triethyl orthoformate (2 mL, 12.0 mmol; [CAS RN 122-51-0]) and the reaction mixture heated in an oil bath to 80° C. for 24 h under an atmosphere of nitrogen. The reaction mixture was cooled to rt, concentrated under reduced pressure and the crude reaction product purified by column chromatography (100-200 mesh size silica gel) using 60% EtOAc-hexane as eluent. The title compound was obtained as a sticky solid (0.30 g, 78% over 2 steps). MS: m/e=401.7 [M+H]+.

[E] 2-[6-(1-tert-Butoxycarbonyl-4-piperidyl)-4-oxo-quinazolin-3-yl]acetic acid

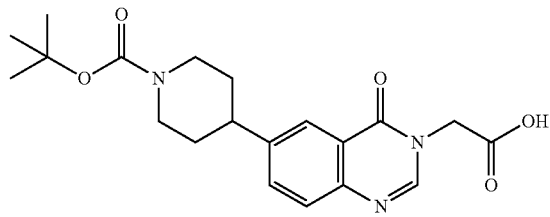 [SMILES: CC(C)(C)OC(=O)N1CCC(c2ccc3ncn(CC(=O)O)c(=O)c3c2)CC1]

To a solution of tert-butyl 4-[3-(2-methoxy-2-oxoethyl)-4-oxoquinazolin-6-yl]piperidine-1-carboxylate (5.0 g, 12.46 mmol) in THF (25 mL) was added an aq. solution of LiOH.H$_2$O (0.79 g, 18.70 mmol; [CAS RN 1310-66-3]) in water (2.5 ml). After stirring of the reaction mixture at rt for 2 h, the solvent was evaporated under reduced pressure. To the crude reaction product was added water (20 mL), the aqueous part acidified by addition of 1 N HCl (pH ca. 4) and the aqueous phase extracted with 5% MeOH in DCM (3×25 mL). The combined organic phases were dried over anhydrous Na$_2$SO$_4$ and concentrated under reduced pressure. The title compound was obtained as off-white solid (4.0 g, 83%). MS: m/e=387.7 [M+H]$^+$.

[F] 2-[6-[1-(9H-Fluoren-9-ylmethoxycarbonyl)-4-piperidyl]-4-oxoquinazolin-3-yl]acetic acid (Intermediate A-8)

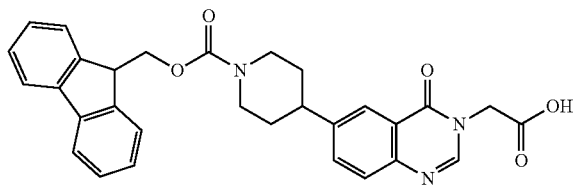 [SMILES: O=C(O)Cn1cnc2ccc(C3CCN(C(=O)OCC4c5ccccc5-c5ccccc54)CC3)cc2c1=O]

To a solution of 2-[6-(1-tert-butoxycarbonyl-4-piperidyl)-4-oxoquinazolin-3-yl]acetic acid (1.5 g, 3.87 mmol) in dioxan (15 mL) was added 4 M HCl in dioxane (15 mL) and the reaction mixture stirred at rt for 12 h. The solvent was evaporated under reduced pressure and the intermediate redissolved in dioxane (30 mL) and aq. 10% NaHCO$_3$ solution (30 mL). 9-Fluorenylmethyl chloroformate (1.69 g, 6.53 mmol; [CAS RN 28920-43-6]) was added and the reaction mixture stirred ar rt for 2 h. The crude reaction mixture was concentrated under reduce pressure and partitioned between water (50 mL) and EtOAc (50 mL). The organic phase was separated and the aqueous phase extracted with EtOAc (2×50 mL). After that the aqueous phase was acidified by addition of 25% HCl (pH ca. 3) and extracted with DCM (3×50 mL). The combined organic phases were dried over anhydrous MgSO$_4$ and concentrated under reduced pressure. The title compound was obtained as off-white solid (0.61 g, 31%). MS: m/e=510.2 [M+H]$^-$.

Intermediate A-9

N-[(3-Chloro-4-cyanophenyl)methyl]-N-methyl-2-(4-oxo-6-piperidin-4-ylquinazolin-3-yl)acetamide

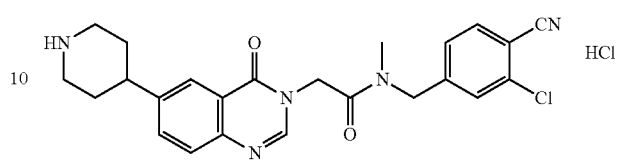

To a solution of 2-[6-[1-(9H-fluoren-9-ylmethoxycarbonyl)-4-piperidyl]-4-oxoquinazolin-3-yl]acetic acid (intermediate A-8) (0.40 g, 0.79 mmol) in DCM (8 mL) were added TBTU (0.38 g, 1.18 mmol; [CAS RN 125700-67-6]) and DIPEA (0.41 mL, 2.36 mmol) under an atmosphere of nitrogen. Then, 2-chloro-4-(methylaminomethyl)benzonitrile hydrochloride (example 56, step A) (0.17 g, 0.79 mmol) was added and the reaction mixture stirred at rt for 18 h. A solution of methanamine (4.5 mL, 3.40 g, 36.1 mmol; 33 wt. % solution in EtOH; [CAS RN 74-89-5]) was added and stirring at rt continued overnight. The crude reaction mixture was concentrated under reduced pressure, redissolved in dioxane (5 mL) and treated with 4 M HCl in dioxane (20 mL). The white precipitate was filtered off, washed with TBME (40 mL) and dried under high vaccum. The title compound was obtained as white solid and used directly in the consecutive reaction step without further purification (0.38 g, 98%). MS: m/e=450.2 [M+H]$^+$.

Example 1

(3R)-3-[[2-[6-(4-Acetylpiperazin-1-yl)-4-oxoquinazolin-3-yl]acetyl]amino]-3-(4-chlorophenyl)-N-methylpropanamide

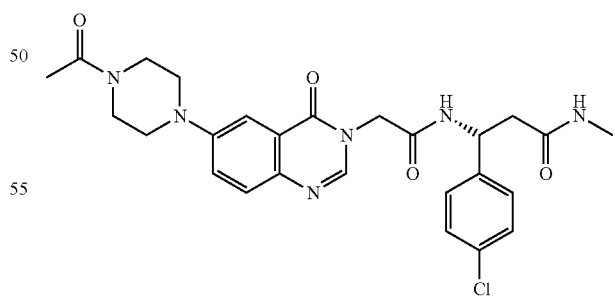

The synthesis was conducted in flow. Reagent solution A contained (3R)-3-[[2-[6-(4-acetylpiperazin-1-yl)-4-oxoquinazolin-3-yl]acetyl]amino]-3-(4-chlorophenyl)propanoic acid (intermediate A-3) (10.2 mg, 0.020 mmol), TBTU (12.8 mg, 0.040 mmol; [CAS RN 125700-67-6]) and DIPEA (7.0 µl, 0.040 mmol) in DMF (280 µl) and reagent solution B contained methanamine (100 µl, 0.80 mmol; 8.0 M solution in ethanol; [CAS RN 74-89-5]) in DMF (300 µl). The two reagent solutions were injected (300 µL of each solution) by means of Gilson LH 215 auto-sampler into the reactor sample loops (300 µL each, Gilson 819). Then, both reagent streams were combined at a T-piece connector and the reagent mixture heated at 100° C. for 10 min in a 10 ml PFA tube reactor coil. The crude product stream was purified in-line by preparative HPLC (C18 reverse phase, acetonitrile/water (0.05% triethylamine)=2:98 to 98:2) to yield the title compound as light yellow solid (3.1 mg, 30%). MS: m/e=525.3 [M+H]$^+$.

Examples 2 to 8

According to the procedure described for the synthesis of example 1 further examples were prepared from (3R)-3-[[2-[6-(4-acetylpiperazin-1-yl)-4-oxoquinazolin-3-yl]acetyl]amino]-3-(4-chlorophenyl)propanoic acid (intermediate A-3) and (3R)-3-[[2-[6-(4-acetylpiperazin-1-yl)-4-oxoquinazolin-3-yl]acetyl]amino]-3-[4-(trifluoromethyl)phenyl]propanoic acid (intermediate A-4) and the respective amine intermediates as indicated in Table 1. The results are compiled in Table 1 and comprise examples 2 to 8.

TABLE 1

| No | Compound Name & Structure | Starting Materials | MS |
|---|---|---|---|
| 2 | (3R)-3-[[2-[6-(4-Acetylpiperazin-1-yl)-4-oxoquinazolin-3-yl]acetyl]amino]-3-(4-chlorophenyl)-N,N-dimethylpropanamide | (3R)-3-[[2-[6-(4-Acetylpiperazin-1-yl)-4-oxoquinazolin-3-yl]acetyl]amino]-3-(4-chlorophenyl)propanoic acid (intermediate A-3) and N-methylmethanamine ([CAS RN 124-40-3]) | [M + H]$^+$ 539.4 |
| 3 | (3R)-3-[[2-[6-(4-Acetylpiperazin-1-yl)-4-oxoquinazolin-3-yl]acetyl]amino]-3-(4-chlorophenyl)-N-phenylpropanamide | (3R)-3-[[2-[6-(4-Acetylpiperazin-1-yl)-4-oxoquinazolin-3-yl]acetyl]amino]-3-(4-chlorophenyl)propanoic acid (intermediate A-3) and benzenamine ([CAS RN 62-53-3]) | [M + H]$^+$ 587.4 |
| 4 | (3R)-3-[[2-[6-(4-Acetylpiperazin-1-yl)-4-oxoquinazolin-3-yl]acetyl]amino]-N-methyl-3-[4-(trifluoromethyl)phenyl]propanamide | (3R)-3-[[2-[6-(4-Acetylpiperazin-1-yl)-4-oxoquinazolin-3-yl]acetyl]amino]-3-[4-(trifluoromethyl)phenyl]propanoic acid (intermediate A-4) and methanamine ([CAS RN 74-89-5]) | [M + H]$^+$ 559.4 |

TABLE 1-continued

| No | Compound Name & Structure | Starting Materials | MS |
|---|---|---|---|
| 5 | (3R)-3-[[2-[6-(4-Acetylpiperazin-1-yl)-4-oxoquinazolin-3-yl]acetyl]amino]-N,N-dimethyl-3-[4-(trifluoromethyl)phenyl]propanamide | (3R)-3-[[2-[6-(4-Acetylpiperazin-1-yl)-4-oxoquinazolin-3-yl]acetyl]amino]-3-[4-(trifluoromethyl)phenyl]propanoic acid (intermediate A-4) and N-methylmethanamine ([CAS RN 124-40-3]) | [M + H]$^+$ 573.4 |
| 6 | (3R)-3-[[2-[6-(4-Acetylpiperazin-1-yl)-4-oxoquinazolin-3-yl]acetyl]amino]-N-(2-methylpropyl)-3-[4-(trifluoromethyl)phenyl]propanamide | (3R)-3-[[2-[6-(4-Acetylpiperazin-1-yl)-4-oxoquinazolin-3-yl]acetyl]amino]-3-[4-(trifluoromethyl)phenyl]propanoic acid (intermediate A-4) and 2-methylpropan-1-amine ([CAS RN 78-81-9]) | [M + H]$^+$ 601.5 |
| 7 | (3R)-3-[[2-[6-(4-Acetylpiperazin-1-yl)-4-oxoquinazolin-3-yl]acetyl]amino]-N-phenyl-3-[4-(trifluoromethyl)phenyl]propanamide | (3R)-3-[[2-[6-(4-Acetylpiperazin-1-yl)-4-oxoquinazolin-3-yl]acetyl]amino]-3-[4-(trifluoromethyl)phenyl]propanoic acid (intermediate A-4) and benzenamine ([CAS RN 62-53-3]) | [M + H]$^+$ 621.5 |
| 8 | (3R)-3-[[2-[6-(4-Acetylpiperazin-1-yl)-4-oxoquinazolin-3-yl]acetyl]amino]-N-benzyl-3-[4-(trifluoromethyl)phenyl]propanamide | (3R)-3-[[2-[6-(4-Acetylpiperazin-1-yl)-4-oxoquinazolin-3-yl]acetyl]amino]-3-[4-(trifluoromethyl)phenyl]propanoic acid (intermediate A-4) and phenylmethanamine ([CAS RN 100-46-9]) | [M + H]$^+$ 635.5 |

Example 9

(3R)-3-[[2-[6-(4-Acetylpiperazin-1-yl)-4-oxoquinazolin-3-yl]acetyl]amino]-N-methyl-3-(4-nitrophenyl)propanamide

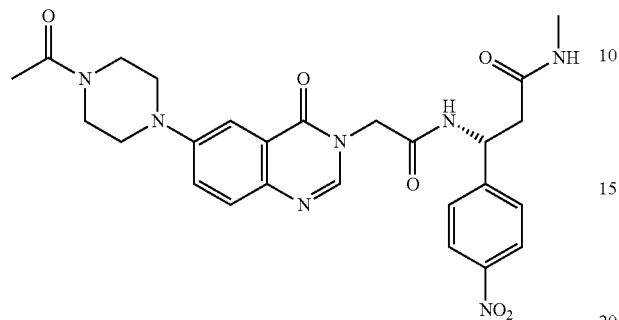

[A] (3R)-tert-Butyl N-[3-(methylamino)-1-(4-nitrophenyl)-3-oxopropyl]carbamate

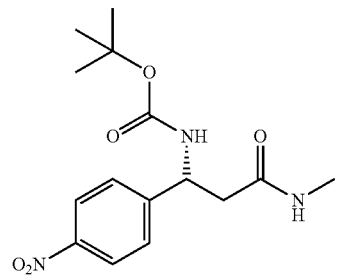

To a solution of 3-[(2-methylpropan-2-yl)oxycarbonylamino]-3-(4-nitrophenyl)propanoic acid (0.25 g, 0.80 mmol; [CAS RN 500770-85-4]) in dry DCM (20 mL) were added EDC.HCl (0.23 g, 1.20 mmol) and HOBt (0.16 g, 1.20 mmol) at rt under an atmosphere of nitrogen. Then, triethylamine (0.33 mL, 2.40 mmol) was added and the reaction mixture was stirred at rt for 30 min, followed by the addition of methanamine (0.5 mL, 1.00 mmol; 2.0 M solution in THF; [CAS RN 74-89-5]). After stirring for 16 h, the reaction mixture was quenched by addition of water (20 mL) and the aq. phase extracted with DCM (3×50 mL). The combined organic phases were dried over $Na_2SO_4$ and concentrated under reduced pressure. Purification by column chromatography (100-200 mesh size silica gel) using 2% methanol-DCM as eluent afforded the title compound as white solid (0.20 g, 77%). MS: m/e=324.3 $[M+H]^+$.

[B] (3R)-3-Amino-N-methyl-3-(4-nitrophenyl)propanamide hydrochloride

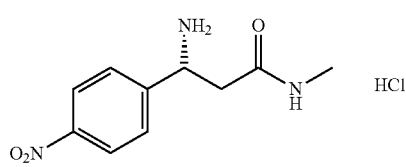

To (3R)-tert-butyl N-[3-(methylamino)-1-(4-nitrophenyl)-3-oxopropyl]carbamate (0.20 g, 0.62 mmol) was added HCl (5 mL, 4.0 M solution in dioxane) at 0° C. under an atmosphere of Ar. The reaction mixture was stirred at rt for 4 h and then concentrated under reduced pressure. The obtained solid was filtered and washed with dry diethyl ether. The title compound was isolated as moisture sensitive yellow gummy liquid (0.14 g, 87%) and used in the consecutive reaction step without further purification. MS: m/e=224.2 $[M+H]^+$.

[C] (3R)-3-[[2-[6-(4-Acetylpiperazin-1-yl)-4-oxoquinazolin-3-yl]acetyl]amino]-N-methyl-3-(4-nitrophenyl)propanamide

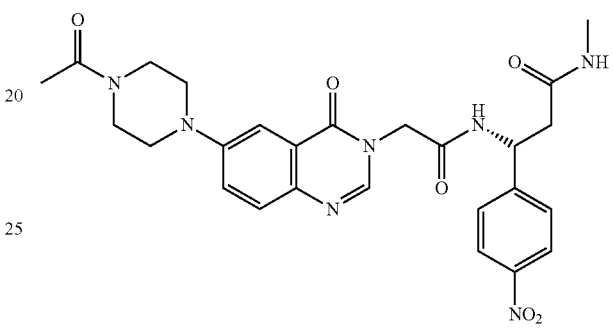

To a solution of 2-[6-(4-acetylpiperazin-1-yl)-4-oxoquinazolin-3-yl]acetic acid (intermediate A-2) (0.20 g, 0.60 mmol) in dry DMF (5 mL) were added EDC.HCl (0.17 g, 0.90 mmol) and HOBt (0.12 g, 0.90 mmol) at rt under an atmosphere of nitrogen. Then, DIPEA (0.31 mL, 1.81 mmol) was added and the reaction mixture was stirred at rt for 30 min, followed by the addition of (3R)-3-amino-N-methyl-3-(4-nitrophenyl)propanamide hydrochloride (0.14 g, 0.60 mmol). After stirring for 16 h, the reaction mixture was quenched by addition to ice and the aq. phase extracted with DCM (2×30 mL). The combined organic phase was washed with water (2×10 mL), a sat. aq. solution of sodium chloride (10 mL), dried over anhydrous $Na_2SO_4$ and concentrated under reduced pressure. The crude reaction product was triturated with 20% DCM-n-pentane to get a precipitate which was further washed with DCM. The title compound was obtained as off-white solid (0.095 g, 30%). MS: m/e=536.2 $[M+H]^+$.

Example 10

2-[6-(4-Acetylpiperazin-1-yl)-4-oxoquinazolin-3-yl]-N-[(4-chlorophenyl)methyl]acetamide

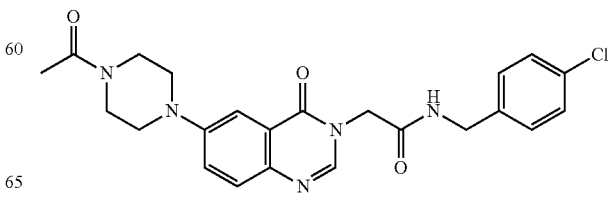

To a solution of 2-[6-(4-acetylpiperazin-1-yl)-4-oxoquinazolin-3-yl]acetic acid (intermediate A-2) (11.9 mg, 0.036 mmol) in dry DMF (1 mL) were added TBTU (17.3 mg, 0.054 mmol; [CAS RN 125700-67-6]) and DIPEA (50 µL, 0.29 mmol) under an atmosphere of nitrogen. Then, (4-chlorophenyl)methanamine (6.1 mg, 0.043 mmol; [CAS RN 104-86-9]) was added and the reaction mixture heated by mirowave irradiation to 100° C. for 15 min. Water was added (1 mL) and the crude reaction product purified by preparative HPLC on reversed phase eluting with a gradient of acetonitrile-water. The title compound was obtained as white solid (1.8 mg, 11%). MS: m/e=454.2 [M+H]$^+$.

Examples 11 to 27

According to the procedure described for the synthesis of example 10 further examples were prepared from 2-[6-(4-acetylpiperazin-1-yl)-4-oxoquinazolin-3-yl]acetic acid (intermediate A-2) and the respective amine intermediate as indicated in Table 2. Alternatively, the amide formation reaction can be conducted in flow as described in Example 1 ((3R)-3-[[2-[6-(4-acetylpiperazin-1-yl)-4-oxoquinazolin-3-yl]acetyl]amino]-3-(4-chlorophenyl)-N-methylpropanamide). The results are compiled in Table 2 and comprise examples 11 to 27.

TABLE 2

| No | Compound Name & Structure | Starting Materials | MS |
|---|---|---|---|
| 11 | 2-[6-(4-Acetylpiperazin-1-yl)-4-oxoquinazolin-3-yl]-N-[(6-chloropyridin-3-yl)methyl]acetamide | 2-[6-(4-Acetylpiperazin-1-yl)-4-oxoquinazolin-3-yl]acetic acid (intermediate A-2) and (6-chloropyridin-3-yl)methanamine ([CAS RN 97004-04-1]) | [M + H]$^+$ 455.2 |
| 12 | 2-[6-(4-Acetylpiperazin-1-yl)-4-oxoquinazolin-3-yl]-N-[(5-chloropyridin-2-yl)methyl]acetamide | 2-[6-(4-Acetylpiperazin-1-yl)-4-oxoquinazolin-3-yl]acetic acid (intermediate A-2) and (5-chloropyridin-2-yl)methanamine ([CAS RN 67938-76-5]) | [M + H]$^+$ 455.2 |
| 13 | 2-[6-(4-Acetylpiperazin-1-yl)-4-oxoquinazolin-3-yl]-N-[1-(4-chlorophenyl)ethyl]acetamide | 2-[6-(4-Acetylpiperazin-1-yl)-4-oxoquinazolin-3-yl]acetic acid (intermediate A-2) and 1-(4-chlorophenyl)ethanamine ([CAS RN 6299-02-1]) | [M + H]$^+$ 468.3 |
| 14 | 2-[6-(4-Acetylpiperazin-1-yl)-4-oxoquinazolin-3-yl]-N-[(4-fluorophenyl)methyl]acetamide | 2-[6-(4-Acetylpiperazin-1-yl)-4-oxoquinazolin-3-yl]acetic acid (intermediate A-2) and (4-fluorophenyl)methanamine ([CAS RN 140-75-0]) | [M + H]$^+$ 438.3 |

TABLE 2-continued

| No | Compound Name & Structure | Starting Materials | MS |
|----|---------------------------|--------------------|-----|
| 15 | 2-[6-(4-Acetylpiperazin-1-yl)-4-oxoquinazolin-3-yl]-N-(1,3-benzodioxol-5-ylmethyl)acetamide | 2-[6-(4-Acetylpiperazin-1-yl)-4-oxoquinazolin-3-yl]acetic acid (intermediate A-2) and 1,3-benzodioxol-5-ylmethanamine ([CAS RN 2620-50-0]) | [M + H]$^+$ 464.3 |
| 16 | 2-[6-(4-Acetylpiperazin-1-yl)-4-oxoquinazolin-3-yl]-N-[[6-(trifluoromethyl)pyridin-3-yl]methyl]acetamide | 2-[6-(4-Acetylpiperazin-1-yl)-4-oxoquinazolin-3-yl]acetic acid (intermediate A-2) and [6-(trifluoromethyl)pyridin-3-yl]methanamine ([CAS RN 387350-39-2]) | [M + H]$^+$ 489.3 |
| 17 | 2-[6-(4-Acetylpiperazin-1-yl)-4-oxoquinazolin-3-yl]-N-[[4-(trifluoromethyl)phenyl]methyl]acetamide | 2-[6-(4-Acetylpiperazin-1-yl)-4-oxoquinazolin-3-yl]acetic acid (intermediate A-2) and [4-(trifluoromethyl)phenyl]methanamine ([CAS RN 3300-51-4]) | [M + H]$^+$ 488.3 |
| 18 | 2-[6-(4-Acetylpiperazin-1-yl)-4-oxoquinazolin-3-yl]-N-[(6-cyanopyridin-3-yl)methyl]acetamide | 2-[6-(4-Acetylpiperazin-1-yl)-4-oxoquinazolin-3-yl]acetic acid (intermediate A-2) and 5-(aminomethyl)pyridine-2-carbonitrile ([CAS RN 181130-14-3]) | [M + H]$^+$ 446.3 |
| 19 | 2-[6-(4-Acetylpiperazin-1-yl)-4-oxoquinazolin-3-yl]-N-[(4-cyanophenyl)methyl]acetamide | 2-[6-(4-Acetylpiperazin-1-yl)-4-oxoquinazolin-3-yl]acetic acid (intermediate A-2) and 4-(aminomethyl)benzonitrile ([CAS RN 10406-25-4]) | [M + H]$^+$ 445.3 |

TABLE 2-continued

| No | Compound Name & Structure | Starting Materials | MS |
|---|---|---|---|
| 20 | 2-[6-(4-Acetylpiperazin-1-yl)-4-oxoquinazolin-3-yl]-N-[[4-(trifluoromethoxy)phenyl]methyl]acetamide | 2-[6-(4-Acetylpiperazin-1-yl)-4-oxoquinazolin-3-yl]acetic acid (intermediate A-2) and [4-(trifluoromethoxy)phenyl]methanamine ([CAS RN 93919-56-3]) | [M + H]$^+$ 504.3 |
| 21 | 2-[6-(4-Acetylpiperazin-1-yl)-4-oxoquinazolin-3-yl]-N-[(4-nitrophenyl)methyl]acetamide | 2-[6-(4-Acetylpiperazin-1-yl)-4-oxoquinazolin-3-yl]acetic acid (intermediate A-2) and (4-nitrophenyl)methanamine ([CAS RN 7409-30-5]) | [M + H]$^+$ 465.3 |
| 22 | 2-[6-(4-Acetylpiperazin-1-yl)-4-oxoquinazolin-3-yl]-N-[(3,4-dichlorophenyl)methyl]acetamide | 2-[6-(4-Acetylpiperazin-1-yl)-4-oxoquinazolin-3-yl]acetic acid (intermediate A-2) and (3,4-dichlorophenyl)methanamine ([CAS RN 102-49-8]) | [M + H]$^+$ 488.3 |
| 23 | 2-[6-(4-Acetylpiperazin-1-yl)-4-oxoquinazolin-3-yl]-N-[(2,4-dichlorophenyl)methyl]acetamide | 2-[6-(4-Acetylpiperazin-1-yl)-4-oxoquinazolin-3-yl]acetic acid (intermediate A-2) and (2,4-dichlorophenyl)methanamine ([CAS RN 95-00-1]) | [M + H]$^+$ 488.2 |
| 24 | 2-[6-(4-Acetylpiperazin-1-yl)-4-oxoquinazolin-3-yl]-N-[(4-chloro-3-fluorophenyl)methyl]acetamide | 2-[6-(4-Acetylpiperazin-1-yl)-4-oxoquinazolin-3-yl]acetic acid (intermediate A-2) and (4-chloro-3-fluorophenyl)methanamine ([CAS RN 72235-58-6]) | [M + H]$^+$ 472.2 |

TABLE 2-continued

| No | Compound Name & Structure | Starting Materials | MS |
|---|---|---|---|
| 25 | 2-[6-(4-Acetylpiperazin-1-yl)-4-oxoquinazolin-3-yl]-N-[(3-chloro-4-cyanophenyl)methyl]acetamide | 2-[6-(4-Acetylpiperazin-1-yl)-4-oxoquinazolin-3-yl]acetic acid (intermediate A-2) and 4-(aminomethyl)-2-chlorobenzonitrile ([CAS RN 202522-15-4]) | [M + H]+ 479.3 |
| 26 | 2-[6-(4-Acetylpiperazin-1-yl)-4-oxoquinazolin-3-yl]-N-[[4-fluoro-3-(trifluoromethoxy)phenyl]methyl]acetamide | 2-[6-(4-Acetylpiperazin-1-yl)-4-oxoquinazolin-3-yl]acetic acid (intermediate A-2) and [4-fluoro-3-(trifluoromethoxy)phenyl]methanamine ([CAS RN 886501-20-8]) | [M + H]+ 522.3 |
| 27 | (3R)-3-[[2-[6-(4-Acetylpiperazin-1-yl)-4-oxoquinazolin-3-yl]acetyl]amino]-3-(4-chlorophenyl)propanamide | 2-[6-(4-Acetylpiperazin-1-yl)-4-oxoquinazolin-3-yl]acetic acid (intermediate A-2) and (3R)-3-amino-3-(4-chlorophenyl)propanamide ([CAS RN 1307443-59-9]) | [M + H]+ 511.3 |

Example 28

2-[6-(4-Acetylpiperazin-1-yl)-4-oxoquinazolin-3-yl]-N-[(4-cyano-3-fluorophenyl)methyl]acetamide

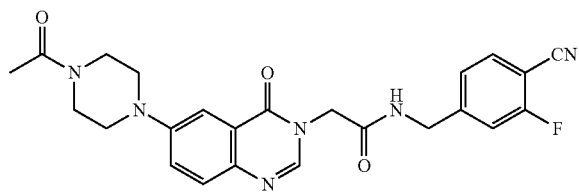

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (50 mg, 0.098 mmol) in dry DCM (2 mL) were added TBTU (47.2 mg, 0.15 mmol; [CAS RN 125700-67-6]) and DIPEA (50 μL, 0.29 mmol) under an atmosphere of nitrogen. Then, 4-(aminomethyl)-2-fluorobenzonitrile (20.1 mg, 0.11 mmol; [CAS RN 368426-73-7]) was added and the reaction mixture stirred at rt for 90 min. A solution of methanamine (2 mL, 16.0 mmol; 8.0 M solution in ethanol; [CAS RN 74-89-5]) was added and stirring at rt continued overnight. The crude reaction mixture was concentrated under reduced pressure and redissolved in dry DMF (2 mL). DIPEA (50 μL, 0.29 mmol) and acetyl chloride (7.0 μL, 0.098 mmol; [CAS RN 368426-73-7]) were added and the reaction mixture stirred at rt for 2 h under an atmosphere of nitrogen. Purification by preparative HPLC on reversed phase eluting with a gradient of acetonitrile-water provided the title compound as white solid (19 mg, 42%). MS: m/e=463.3 [M+H]+.

Examples 29 to 51

According to the procedure described for the synthesis of example 28 further examples were prepared from 2-[6-[4-(9H-fluoren-9-ylmethoxycarbonyl)piperazin-1-yl]-4-oxoquinazolin-3-yl]acetic acid (intermediate A-1) and the respective amine intermediate as indicated in Table 3. The results are compiled in Table 3 and comprise examples 29 to 51.

TABLE 3

| No | Compound Name & Structure | Starting Materials | MS |
|---|---|---|---|
| 29 | 2-[6-(4-Acetylpiperazin-1-yl)-4-oxoquinazolin-3-yl]-N-[(2-chloro-4-cyanophenyl)methyl]acetamide | 2-[6-[4-(9H-Fluoren-9-ylmethoxycarbonyl)piperazin-1-yl]-4-oxoquinazolin-3-yl]acetic acid (intermediate A-1) and 4-(aminomethyl)-3-chlorobenzonitrile ([CAS RN 202521-97-9]) | [M + H]$^+$ 479.3 |
| 30 | 2-[6-(4-Acetylpiperazin-1-yl)-4-oxoquinazolin-3-yl]-N-[(4-cyano-2-fluorophenyl)methyl]acetamide | 2-[6-[4-(9H-Fluoren-9-ylmethoxycarbonyl)piperazin-1-yl]-4-oxoquinazolin-3-yl]acetic acid (intermediate A-1) and 4-(aminomethyl)-3-fluorobenzonitrile ([CAS RN 701264-00-8]) | [M + H]$^+$ 463.3 |
| 31 | 2-[6-(4-Acetylpiperazin-1-yl)-4-oxoquinazolin-3-yl]-N-[(4-cyano-2,6-difluorophenyl)methyl]acetamide | 2-[6-[4-(9H-Fluoren-9-ylmethoxycarbonyl)piperazin-1-yl]-4-oxoquinazolin-3-yl]acetic acid (intermediate A-1) and 4-(aminomethyl)-3,5-difluorobenzonitrile ([CAS RN 633336-81-9]) | [M + H]$^+$ 481.3 |
| 32 | 2-[6-(4-Acetylpiperazin-1-yl)-4-oxoquinazolin-3-yl]-N-[(4-cyano-2-methoxyphenyl)methyl]acetamide | 2-[6-[4-(9H-Fluoren-9-ylmethoxycarbonyl)piperazin-1-yl]-4-oxoquinazolin-3-yl]acetic acid (intermediate A-1) and 4-(aminomethyl)-3-methoxybenzonitrile ([CAS RN 182159-14-4]) | [M + H]$^+$ 475.3 |
| 33 | 2-[6-(4-Acetylpiperazin-1-yl)-4-oxoquinazolin-3-yl]-N-[[4-cyano-2-(2,2,2-trifluoroethoxy)phenyl]methyl]acetamide | 2-[6-[4-(9H-Fluoren-9-ylmethoxycarbonyl)piperazin-1-yl]-4-oxoquinazolin-3-yl]acetic acid (intermediate A-1) and 4-(aminomethyl)-3-(2,2,2-trifluoroethoxy)benzonitrile ([CAS RN 1055904-78-3]) | [M + H]$^+$ 543.3 |

TABLE 3-continued

| No | Compound Name & Structure | Starting Materials | MS |
|---|---|---|---|
| 34 | 2-[6-(4-Acetylpiperazin-1-yl)-4-oxoquinazolin-3-yl]-N-[[4-chloro-3-(trifluoromethyl)phenyl]methyl]acetamide | 2-[6-[4-(9H-Fluoren-9-ylmethoxycarbonyl)piperazin-1-yl]-4-oxoquinazolin-3-yl]acetic acid (intermediate A-1) and [4-chloro-3-(trifluoromethyl)phenyl]methanamine ([CAS RN 62039-92-3]) | $[M + H]^+$ 522.3 |
| 35 | 2-[6-(4-Acetylpiperazin-1-yl)-4-oxoquinazolin-3-yl]-N-[(3-cyano-2-methylphenyl)methyl]acetamide | 2-[6-[4-(9H-Fluoren-9-ylmethoxycarbonyl)piperazin-1-yl]-4-oxoquinazolin-3-yl]acetic acid (intermediate A-1) and 3-(aminomethyl)-2-methylbenzonitrile ([CAS RN 780693-78-9]) | $[M + H]^+$ 459.4 |
| 36 | 2-[6-(4-Acetylpiperazin-1-yl)-4-oxoquinazolin-3-yl]-N-[(2-chloropyridin-4-yl)methyl]acetamide | 2-[6-[4-(9H-Fluoren-9-ylmethoxycarbonyl)piperazin-1-yl]-4-oxoquinazolin-3-yl]acetic acid (intermediate A-1) and (2-chloropyridin-4-yl)methanamine ([CAS RN 144900-57-2]) | $[M + H]^+$ 455.3 |
| 37 | 2-[6-(4-Acetylpiperazin-1-yl)-4-oxoquinazolin-3-yl]-N-[(3-nitrophenyl)methyl]acetamide | 2-[6-[4-(9H-Fluoren-9-ylmethoxycarbonyl)piperazin-1-yl]-4-oxoquinazolin-3-yl]acetic acid (intermediate A-1) and (3-nitrophenyl)methanamine ([CAS RN 26177-43-5]) | $[M + H]^+$ 465.3 |
| 38 | 2-[6-(4-Acetylpiperazin-1-yl)-4-oxoquinazolin-3-yl]-N-[[4-chloro-3-(trifluoromethoxy)phenyl]methyl]acetamide | 2-[6-[4-(9H-Fluoren-9-ylmethoxycarbonyl)piperazin-1-yl]-4-oxoquinazolin-3-yl]acetic acid (intermediate A-1) and [4-chloro-3-(trifluoromethoxy)phenyl]methanamine ([CAS RN 916210-69-0]) | $[M + H]^+$ 538.3 |

TABLE 3-continued

| No | Compound Name & Structure | Starting Materials | MS |
|---|---|---|---|
| 39 | 2-[6-(4-Acetylpiperazin-1-yl)-4-oxoquinazolin-3-yl]-N-[[4-(pentafluoro-λ⁶-sulfanyl)phenyl]methyl]acetamide | 2-[6-[4-(9H-Fluoren-9-ylmethoxycarbonyl)piperazin-1-yl]-4-oxoquinazolin-3-yl]acetic acid (intermediate A-1) and [4-(pentafluoro-λ⁶-sulfanyl)phenyl]methanamine ([CAS RN 771573-35-4]) | $[M + H]^+$ 546.3 |
| 40 | 2-[6-(4-Acetylpiperazin-1-yl)-4-oxoquinazolin-3-yl]-N-[(3-methyl-4-methylsulfonylphenyl)methyl]acetamide | 2-[6-[4-(9H-Fluoren-9-ylmethoxycarbonyl)piperazin-1-yl]-4-oxoquinazolin-3-yl]acetic acid (intermediate A-1) and (3-methyl-4-methylsulfonylphenyl)methanamine ([CAS RN 694481-22-6]) | $[M + H]^+$ 512.3 |
| 41 | 2-[6-(4-Acetylpiperazin-1-yl)-4-oxoquinazolin-3-yl]-N-[(4,5-dichloropyridin-2-yl)methyl]acetamide | 2-[6-[4-(9H-Fluoren-9-ylmethoxycarbonyl)piperazin-1-yl]-4-oxoquinazolin-3-yl]acetic acid (intermediate A-1) and (4,5-dichloropyridin-2-yl)methanamine ([CAS RN 1196157-20-6]) | $[M + H]^+$ 489.2 |
| 42 | 2-[6-(4-Acetylpiperazin-1-yl)-4-oxoquinazolin-3-yl]-N-[(3-chloro-4-methylphenyl)methyl]acetamide | 2-[6-[4-(9H-Fluoren-9-ylmethoxycarbonyl)piperazin-1-yl]-4-oxoquinazolin-3-yl]acetic acid (intermediate A-1) and (3-chloro-4-methylphenyl)methanamine ([CAS RN 67952-93-6]) | $[M + H]^+$ 468.3 |
| 43 | 2-[6-(4-Acetylpiperazin-1-yl)-4-oxoquinazolin-3-yl]-N-[(4-chlorophenyl)methyl]-N-methylacetamide | 2-[6-[4-(9H-Fluoren-9-ylmethoxycarbonyl)piperazin-1-yl]-4-oxoquinazolin-3-yl]acetic acid (intermediate A-1) and 1-(4-chlorophenyl)-N-methylmethanamine ([CAS RN 104-11-0]) | $[M + H]^+$ 468.3 |

TABLE 3-continued

| No | Compound Name & Structure | Starting Materials | MS |
|---|---|---|---|
| 44 | 2-[6-(4-Acetylpiperazin-1-yl)-4-oxoquinazolin-3-yl]-N-[(3,4-dichlorophenyl)methyl]-N-methylacetamide | 2-[6-[4-(9H-Fluoren-9-ylmethoxycarbonyl)piperazin-1-yl]-4-oxoquinazolin-3-yl]acetic acid (intermediate A-1) and 1-(3,4-dichlorophenyl)-N-methylmethanamine ([CAS RN 5635-67-6]) | [M + H]$^+$ 502.2 |
| 45 | 2-[6-(4-Acetylpiperazin-1-yl)-4-oxoquinazolin-3-yl]-N-[(4-cyano-3-fluorophenyl)methyl]-N-methylacetamide | 2-[6-[4-(9H-Fluoren-9-ylmethoxycarbonyl)piperazin-1-yl]-4-oxoquinazolin-3-yl]acetic acid (intermediate A-1) and 2-fluoro-4-(methylaminomethyl)benzonitrile ([CAS RN 1565551-88-3]) | [M + H]$^+$ 477.3 |
| 46 | 2-[6-(4-Acetylpiperazin-1-yl)-4-oxoquinazolin-3-yl]-N-[(2,6-dichloropyridin-4-yl)methyl]-N-methylacetamide | 2-[6-[4-(9H-Fluoren-9-ylmethoxycarbonyl)piperazin-1-yl]-4-oxoquinazolin-3-yl]acetic acid (intermediate A-1) and 1-(2,6-dichloropyridin-4-yl)-N-methyl-methanamine ([CAS RN 873928-49-5]) | [M + H]$^+$ 503.2 |
| 47 | 6-(4-Acetylpiperazin-1-yl)-3-[2-[2-(4-chlorophenyl)pyrrolidin-1-yl]-2-oxoethyl]quinazolin-4-one | 2-[6-[4-(9H-Fluoren-9-ylmethoxycarbonyl)piperazin-1-yl]-4-oxoquinazolin-3-yl]acetic acid (intermediate A-1) and 2-(4-chlorophenyl)pyrrolidine ([CAS RN 38944-14-8]) | [M + H]$^+$ 494.3 |
| 48 | 6-(4-Acetylpiperazin-1-yl)-3-[2-[(2R)-2-(4-methylphenyl)pyrrolidin-1-yl]-2-oxoethyl]quinazolin-4-one | 2-[6-[4-(9H-Fluoren-9-ylmethoxycarbonyl)piperazin-1-yl]-4-oxoquinazolin-3-yl]acetic acid (intermediate A-1) and (2R)-2-(4-methylphenyl)pyrrolidine ([CAS RN 1227908-77-1]) | [M + H]$^+$ 474.4 |

TABLE 3-continued

| No | Compound Name & Structure | Starting Materials | MS |
|---|---|---|---|
| 49 | 2-[6-(4-Acetylpiperazin-1-yl)-4-oxoquinazolin-3-yl]-N-[2-(3,4-dichlorophenyl)ethyl]acetamide | 2-[6-[4-(9H-Fluoren-9-ylmethoxycarbonyl)piperazin-1-yl]-4-oxoquinazolin-3-yl]acetic acid (intermediate A-1) and 2-(3,4-dichlorophenyl)ethanamine ([CAS RN 21581-45-3]) | [M + H]$^+$ 502.2 |
| 50 | 2-[6-(4-Acetylpiperazin-1-yl)-4-oxoquinazolin-3-yl]-N-[[3-(4-chlorophenyl)-1,2-oxazol-5-yl]methyl]acetamide | 2-[6-[4-(9H-Fluoren-9-ylmethoxycarbonyl)piperazin-1-yl]-4-oxoquinazolin-3-yl]acetic acid (intermediate A-1) and [3-(4-chlorophenyl)-1,2-oxazol-5-yl]methanamine ([CAS RN 66046-42-2]) | [M + H]$^+$ 521.3 |
| 51 | 2-[6-(4-Acetylpiperazin-1-yl)-4-oxoquinazolin-3-yl]-N-[[5-(4-chlorophenyl)-1,2,4-oxadiazol-3-yl]methyl]acetamide | 2-[6-[4-(9H-Fluoren-9-ylmethoxycarbonyl)piperazin-1-yl]-4-oxoquinazolin-3-yl]acetic acid (intermediate A-1) and [5-(4-chlorophenyl)-1,2,4-oxadiazol-3-yl]methanamine ([CAS RN 919750-83-7]) | [M + H]$^+$ 522.3 |

Example 52

3-[[2-[6-(4-Acetylpiperazin-1-yl)-4-oxoquinazolin-3-yl]acetyl]amino]-3-(3,4-dichlorophenyl)-N-methylpropanamide

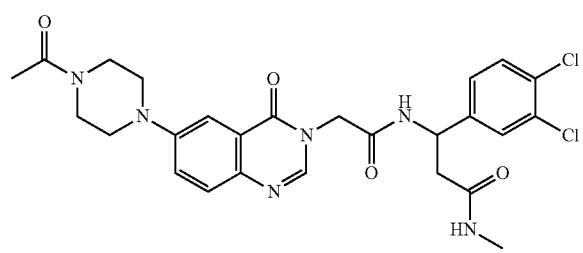 [SMILES: CNC(=O)CC(NC(=O)Cn1cnc2ccc(N3CCN(C(C)=O)CC3)cc2c1=O)c1ccc(Cl)c(Cl)c1]

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (40 mg, 0.078 mmol) in dry DCM (2 mL) were added TBTU (37.7 mg, 0.12 mmol; [CAS RN 125700-67-6]) and DIPEA (41 µL, 0.24 mmol) under an atmosphere of nitrogen. Then, ethyl 3-amino-3-(3,4-dichlorophenyl)propanoate (24.6 mg, 0.094 mmol; [CAS RN 380842-80-8]) was added and the reaction mixture stirred at rt for 90 min. A solution of methanamine (2 mL, 16.0 mmol; 8.0 M solution in ethanol; [CAS RN 74-89-5]) was added and stirring at rt continued overnight. The crude reaction mixture was concentrated under reduced pressure and redissolved in DMF (2 mL). DIPEA (41 µL, 0.24 mmol) and acetyl chloride (5.6 µL, 0.078 mmol; [CAS RN 368426-73-7]) were added and the reaction mixture stirred at rt for 2 h under an atmosphere of nitrogen. Purification by preparative HPLC on reversed phase eluting with a gradient of acetonitrile-water provided the title compound as white solid (8.4 mg, 19%). MS: m/e=559.3 [M+H]$^+$.

Example 53

Methyl 3-[[2-[6-(4-acetylpiperazin-1-yl)-4-oxoquinazolin-3-yl]acetyl]-[(3,4-dichlorophenyl)methyl]amino]propanoate

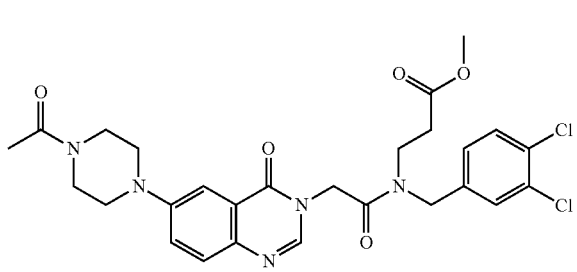 [SMILES: COC(=O)CCN(Cc1ccc(Cl)c(Cl)c1)C(=O)Cn1cnc2ccc(N3CCN(C(C)=O)CC3)cc2c1=O]

To a solution of 2-[6-(4-acetylpiperazin-1-yl)-4-oxoquinazolin-3-yl]acetic acid (intermediate A-2) (41.6 mg, 0.13 mmol) in dry DCM (1.5 mL) were added HATU (71.8 mg, 0.19 mmol) and DIPEA (66 μL, 0.38 mmol) under an atmosphere of nitrogen. Then, methyl 3-[(3,4-dichlorophenyl)methylamino]propanoate (33 mg, 0.13 mmol; [CAS RN 4020-24-0]) was added and the reaction mixture stirred at rt for 2 h. The reaction mixture was quenched by addition of a sat. aq. solution of sodium hydrogen carbonate (10 mL) and the aq. phase extracted with DCM (3×10 mL). The combined organic phases were dried over MgSO$_4$ and concentrated under reduced pressure. Purification by MPLC (20 g SiO$_2$, Telos-cartridge) eluting with a gradient of 0 to 3% methanol-DCM provided the title compound (35 mg, 48%) as white solid. MS: 574.4 (M+H)$^+$.

Example 54

3-[[2-[6-(4-Acetylpiperazin-1-yl)-4-oxoquinazolin-3-yl]acetyl]-[(3,4-dichlorophenyl)methyl]amino]propanoic acid

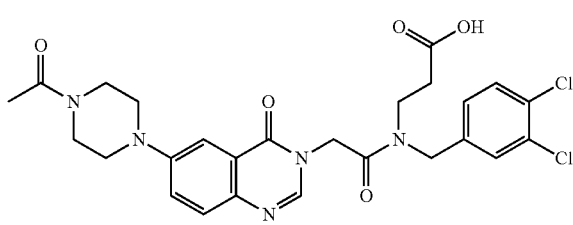 [SMILES: CC(=O)N1CCN(c2ccc3ncn(CC(=O)N(CCC(=O)O)Cc4ccc(Cl)c(Cl)c4)c(=O)c3c2)CC1]

To a solution of methyl 3-[[2-[6-(4-acetylpiperazin-1-yl)-4-oxoquinazolin-3-yl]acetyl]-[(3,4-dichlorophenyl)methyl]amino]propanoate (example 53) (26 mg, 0.045 mmol) in THF-water (0.5 mL: 1 mL) was added LiOH.H$_2$O (47.2 mg, 0.15 mmol) and the reaction mixture stirred at rt for 1 h. The reaction mixture was concentrated under reduced pressure, 1 M HCl added (5 mL) and the aq. phase extracted with DCM (3×10 mL). The combined organic phases were dried over MgSO$_4$ and concentrated under reduced pressure. Purification by preparative HPLC on reversed phase eluting with a gradient of acetonitrile-water provided the title compound as white solid (9.5 mg, 38%). MS: m/e=558.4 [M−H]$^-$.

Example 55

3-[[2-[6-(4-Acetylpiperazin-1-yl)-4-oxoquinazolin-3-yl]acetyl]-[(3,4-dichlorophenyl)methyl]amino]-N-methylpropanamide

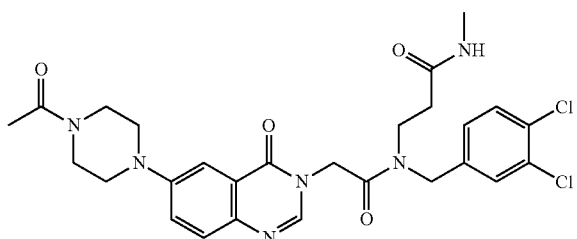

In analogy to the procedure described for the preparation of 3-[[2-[6-(4-acetylpiperazin-1-yl)-4-oxoquinazolin-3-yl]acetyl]amino]-3-(3,4-dichlorophenyl)-N-methylpropanamide (example 52), replacing ethyl 3-amino-3-(3,4-dichlorophenyl)propanoate with methyl 3-[(3,4-di chlorophenyl)methylamino]propanoate ([CAS RN 4020-24-0]). After completion of the reaction, the reaction mixture was quenched by addition of a sat. aq. solution of sodium hydrogen carbonate (10 mL) and the aq. phase extracted with DCM (3×10 mL). The combined organic phases were dried over MgSO$_4$ and concentrated under reduced pressure. Purification by MPLC (20 g SiO$_2$, Telos-cartridge) eluting with a gradient of 0 to 3% methanol-DCM provided the title compound (47 mg, 84%) as light orange solid. MS: 573.2 (M+H)$^+$.

Example 56

2-[6-(4-Acetylpiperazin-1-yl)-4-oxoquinazolin-3-yl]-N-[(3-chloro-4-cyanophenyl)methyl]-N-methylacetamide

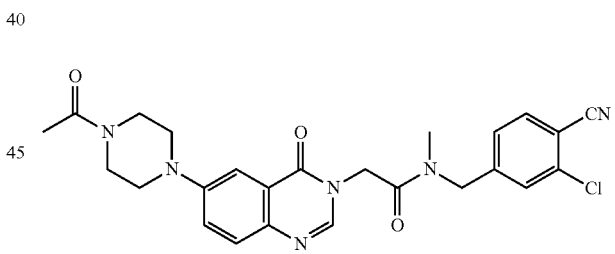

[A] 2-Chloro-4-(methylaminomethyl)benzonitrile hydrochloride

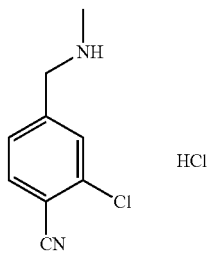

To 4-(bromomethyl)-2-chlorobenzonitrile (3.04 g, 13.2 mmol; [CAS RN 83311-25-5]) was added dropwise a solution of methanamine (20 mL, 40.0 mmol; 2.0 M solution in THF; [CAS RN 74-89-5]) at 0° C. within 30 min. The crude reaction mixture was warmed up to rt and stirring continued for 10 min. The precipiate was filtered off, washed with THE (50 mL) and the filtrate concentrated under reduced pressure. A solution of 1 M NaOH was added (50 mL) and the aq. phase extracted with DCM (3×50 mL). The combined organic phases were dried over MgSO$_4$ and concentrated under reduced pressure. The crude reaction product was dissolved in dioxane (50 mL) and treated with 4 M HCl in dioxane (20 mL). The white precipitate was filtered off, washed with TBME (40 mL) and dried under high vaccum. The title compound was obtained as white solid (1.33 g, 46%). MS: m/e=181.1 [M+H]$^+$.

[B] 2-[6-(4-Acetylpiperazin-1-yl)-4-oxoquinazolin-3-yl]-N-[(3-chloro-4-cyanophenyl)methyl]-N-methylacetamide

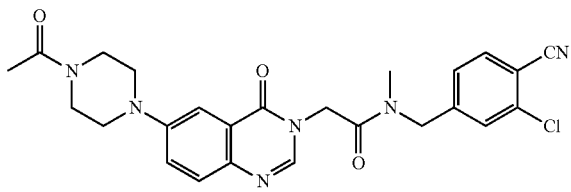 [SMILES: CC(=O)N1CCN(c2ccc3ncn(CC(=O)N(C)Cc4ccc(C#N)c(Cl)c4)c(=O)c3c2)CC1]

In analogy to the procedure described for the preparation of 2-[6-(4-acetylpiperazin-1-yl)-4-oxoquinazolin-3-yl]-N-[(4-cyano-3-fluorophenyl)methyl]acetamide (example 28), replacing 4-(aminomethyl)-2-fluorobenzonitrile with 2-chloro-4-(methylaminomethyl)benzonitrile hydrochloride. After completion of the reaction, the reaction mixture was quenched by addition of a sat. aq. solution of sodium hydrogen carbonate (10 mL) and the aq. phase extracted with DCM (3×10 mL). The combined organic phases were dried over MgSO$_4$ and concentrated under reduced pressure. Purification by MPLC (20 g SiO$_2$, Telos-cartridge) eluting with a gradient of 0 to 5% methanol-DCM provided the title compound (36 mg, 75%) as colorless oil. MS: 492.2 (M+H)$^+$.

Example 57

2-[6-(4-Acetylpiperazin-1-yl)-4-oxoquinazolin-3-yl]-N-[(4-chloro-3-cyanophenyl)methyl]-N-methylacetamide

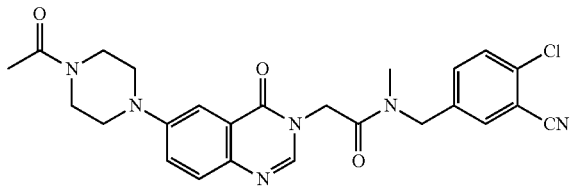 [SMILES: CC(=O)N1CCN(c2ccc3ncn(CC(=O)N(C)Cc4ccc(Cl)c(C#N)c4)c(=O)c3c2)CC1]

[A] 2-Chloro-5-(methylaminomethyl)benzonitrile hydrochloride

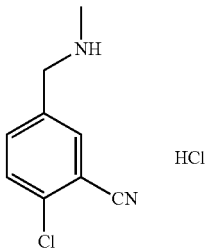

To a solution of 2-chloro-5-methylbenzonitrile (1.0 g, 6.6 mmol; [CAS RN 4387-32-0]) in carbon tetrachloride (40 mL) was added N-bromosuccinimide (1.17 g, 6.6 mmol) and benzoyl peroxide (8.0 mg, 0.033 mmol). The reaction mixture was heated to reflux and irradiated using a fluorescent lamp (λ=365 nm) for 4 h. The precipitate was filtered off and the filtrate concentrated under reduced pressure. To the crude reaction product was added dropwise a solution of methanamine (20 mL, 40.0 mmol; 2.0 M solution in THF; [CAS RN 74-89-5]) at 0° C. within 30 min. The crude reaction mixture was warmed up to rt and stirring continued for 10 min. The precipitate was filtered off, washed with THF (50 mL) and the filtrate concentrated under reduced pressure. A solution of 1 M NaOH was added (40 mL) and the aq. phase extracted with DCM (3×40 mL). The combined organic phases were dried over MgSO$_4$ and concentrated under reduced pressure. The crude reaction product was dissolved in dioxane (30 mL) and treated with 4 M HCl in dioxane (10 mL). The white precipate was filtered off, washed with TBME (30 mL) and dried under high vaccum. The title compound was obtained as white solid (0.75 g, 52%). MS: m/e=181.9 [M+H]$^+$.

[B] 2-[6-(4-Acetylpiperazin-1-yl)-4-oxoquinazolin-3-yl]-N-[(4-chloro-3-cyanophenyl)methyl]-N-methylacetamide

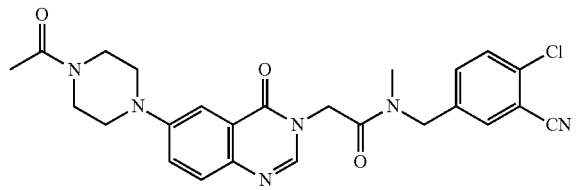 [SMILES: CC(=O)N1CCN(c2ccc3ncn(CC(=O)N(C)Cc4ccc(Cl)c(C#N)c4)c(=O)c3c2)CC1]

In analogy to the procedure described for the preparation of 2-[6-(4-acetylpiperazin-1-yl)-4-oxoquinazolin-3-yl]-N-[(4-cyano-3-fluorophenyl)methyl]acetamide (example 28), replacing 4-(aminomethyl)-2-fluorobenzonitrile with 2-chloro-5-(methylaminomethyl)benzonitrile hydrochloride. After completion of the reaction, the reaction mixture was quenched by addition of a sat. aq. solution of sodium hydrogen carbonate (10 mL) and the aq. phase extracted with DCM (3×10 mL). The combined organic phases were dried over MgSO$_4$ and concentrated under reduced pressure. Purification by MPLC (20 g SiO$_2$, Telos-cartridge) eluting with a gradient of 0 to 5% methanol-DCM provided the title compound (22 mg, 46%) as white solid. MS: 492.2 (M+H)$^+$.

Example 58

2-[6-(4-Acetylpiperazin-1-yl)-4-oxoquinazolin-3-yl]-N-[(4-cyano-3,5-difluorophenyl)methyl]-N-methyl-acetamide

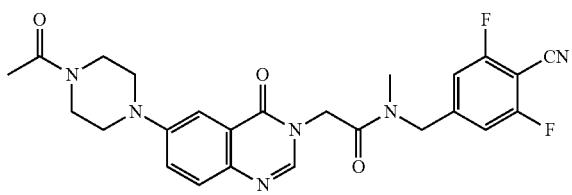 [SMILES: CC(=O)N1CCN(c2ccc3ncn(CC(=O)N(C)Cc4cc(F)c(C#N)c(F)c4)c(=O)c3c2)CC1]

[A] 2,6-Difluoro-4-(methylaminomethyl)benzonitrile

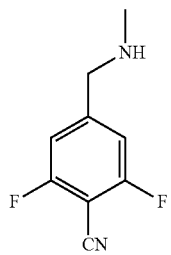

To a solution of 2,6-difluoro-4-formylbenzonitrile (0.10 g, 0.60 mmol; [CAS RN 433939-88-9]) in methanol (2 mL) was added methanamine hydrochloride (40 mg, 0.60 mmol; [CAS RN 593-51-1]) and acetic acid (3.5 μL, 0.060 mmol). After stirring of the reaction mixture at rt for 30 min, sodium cyanoborohydride (57 mg, 0.90 mmol; [CAS RN 25895-60-7]) was added in portions over 10 min. Stirring of the reaction mixture was continued for 40 min and then the reaction mixture concentrated under reduced pressure. A solution of 1 M NaOH was added (50 mL) and the aq. phase extracted with DCM (3×40 mL). The combined organic phases were dried over MgSO4 and concentrated under reduced pressure. The crude reaction product was obtained as colorless oil and used directly in the consecutive reaction step without further purification (7 mg, 6%). MS: m/e=183.1 [M+H]+.

[B] 2-[6-(4-Acetylpiperazin-1-yl)-4-oxoquinazolin-3-yl]-N-[(4-cyano-3,5-difluorophenyl)methyl]-N-methylacetamide

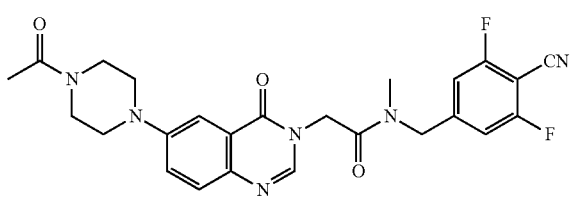 [SMILES: CC(=O)N1CCN(c2ccc3ncn(CC(=O)N(C)Cc4cc(F)c(C#N)c(F)c4)c(=O)c3c2)CC1]

To a solution of 2-[6-(4-acetylpiperazin-1-yl)-4-oxoquinazolin-3-yl]acetic acid (intermediate A-2) (11.9 mg, 0.036 mmol) in dry DCM (1.5 mL) were added HATU (20.5 mg, 0.054 mmol) and DIPEA (19 μL, 0.11 mmol) under an atmosphere of nitrogen. Then, 2,6-difluoro-4-(methylaminomethyl)benzonitrile (7 mg, 0.038 mmol) was added and the reaction mixture stirred at rt for 12 h. DCM (2 mL) and a sat. aq. solution of sodium hydrogen carbonate (5 mL) were added and the aq. phase extracted with DCM (3×10 mL). The combined organic phases were dried over MgSO4 and concentrated under reduced pressure. Purification by prep. TLC (Merck silica TLC glass plates, 20×20 cm) eluting with a mixture of toluene-acetone-methanol (5:5:1) provided the title compound as slightly yellow solid (7 mg, 37%). MS: m/e=495.3 [M+H]+.

Example 59

N-[(3,4-Dichlorophenyl)methyl]-2-[6-[4-(3-methylbutanoyl)piperazin-1-yl]-4-oxoquinazolin-3-yl]acetamide

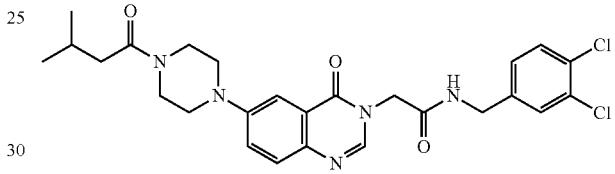

To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (15 mg, 0.022 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in DMF (1 mL). Triethylamine (30 μL, 0.22 mmol) and 3-methylbutanoyl chloride (5.2 mg, 0.043 mmol; [CAS RN 108-12-3]) were added and the reaction mixture stirred at rt overnight under an atmosphere of nitrogen. Purification by preparative HPLC on reversed phase eluting with a gradient of acetonitrile-water provided the title compound as white solid (3.6 mg, 32%). MS: m/e=530.3 [M+H]+.

Examples 60 to 69

According to the procedure described for the synthesis of example 59 further examples were prepared from 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and the respective carboxylic acid chloride as indicated in Table 4. The results are compiled in Table 4 and comprise examples 60 to 69.

TABLE 4

| No | Compound Name & Structure | Starting Materials | MS |
|---|---|---|---|
| 60 | N-[(3,4-Dichlorophenyl)methyl]-2-[4-oxo-6-(4-pentanoylpiperazin-1-yl)quinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and pentanoyl chloride ([CAS RN 638-29-9]) | [M + H]+ 530.3 |
| 61 | N-[(3,4-Dichlorophenyl)methyl]-2-[6-[4-(2-methoxyacetyl)piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 2-methoxyacetyl chloride ([CAS RN 38870-89-2]) | [M + H]+ 518.2 |
| 62 | N-[(3,4-Dichlorophenyl)methyl]-2-[4-oxo-6-[4-(2,2,2-trifluoroacetyl)piperazin-1-yl]quinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 2,2,2-trifluoroacetyl chloride ([CAS RN 354-32-5]) | [M + H]+ 542.2 |
| 63 | 2-[6-[4-(Cyclobutanecarbonyl)piperazin-1-yl]-4-oxoquinazolin-3-yl]-N-[(3,4-dichlorophenyl)methyl]acetamide | 9H-Fluoren-9-ylmethyl 4-[3-[2-[(3,4-dichlorophenyl)methyl-amino]-2-oxoethyl]-4-oxoquinazolin-6-yl]piperazine-1-carboxylate (intermediate A-5) and cyclobutanecarbonyl chloride ([CAS RN 5006-22-6]) | [M + H]+ 528.3 |
| 64 | 2-[6-[4-(Cyclopentanecarbonyl)piperazin-1-yl]-4-oxoquinazolin-3-yl]-N-[(3,4-dichlorophenyl)methyl]acetamide | 9H-Fluoren-9-ylmethyl 4-[3-[2-[(3,4-dichlorophenyl)methyl-amino]-2-oxoethyl]-4-oxoquinazolin-6-yl]piperazine-1-carboxylate (intermediate A-5) and cyclopentanecarbonyl chloride ([CAS RN 4524-93-0]) | [M + H]+ 542.3 |

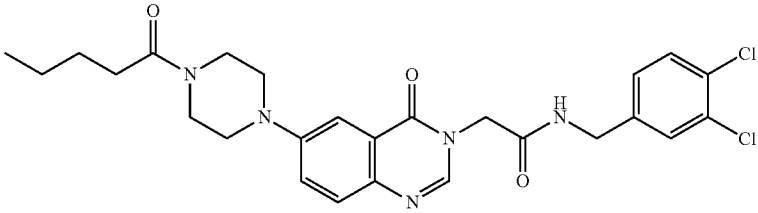

TABLE 4-continued

| No | Compound Name & Structure | Starting Materials | MS |
|---|---|---|---|
| 65 | 2-[6-[4-(Cyclohexanecarbonyl)piperazin-1-yl]-4-oxoquinazolin-3-yl]-N-[(3,4-dichlorophenyl)methyl]acetamide | 9H-Fluoren-9-ylmethyl 4-[3-[2-[(3,4-dichlorophenyl)methyl-amino]-2-oxoethyl]-4-oxoquinazolin-6-yl]piperazine-1-carboxylate (intermediate A-5) and cyclohexanecarbonyl chloride ([CAS RN 2719-27-9]) | [M + H]+ 556.3 |
| 66 | 2-N-[(3,4-Dichlorophenyl)methyl]-2-[6-[4-(oxane-4-carbonyl)piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and oxane-4-carbonyl chloride ([CAS RN 40191-32-0]) | [M + H]+ 558.3 |
| 67 | N-[(3,4-Dichlorophenyl)methyl]-2-[6-[4-(1,2-oxazole-5-carbonyl)piperazin-1-yl]-4-oxoquinazolin-3-yl]acetamide | 9H-Fluoren-9-ylmethyl 4-[3-[2-[(3,4-dichlorophenyl)methyl-amino]-2-oxoethyl]-4-oxo-quinazolin-6-yl]piperazine-1-carboxylate (intermediate A-5) and 1,2-oxazole-5-carbonyl chloride ([CAS RN 62348-13-4]) | [M + H]+ 541.2 |
| 68 | N-[(3,4-Dichlorophenyl)methyl]-N-methyl-2-[4-oxo-6-(4-propanoylpiperazin-1-yl)quinazolin-3-yl]acetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and propanoyl chloride ([CAS RN 79-03-8]) | [M + H]+ 516.4 |
| 69 | N-[(3,4-Dichlorophenyl)methyl]-N-methyl-2-[6-[4-(2-methylpropanoyl)piperazin-1-yl]-4-oxoquinazolin-3-yl]acetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-methylpropanoyl chloride ([CAS RN 79-30-1]) | [M + H]+ 530.2 |

Example 70

2-[6-[4-(3-Aminooxetane-3-carbonyl)piperazin-1-yl]-4-oxoquinazolin-3-yl]-N-[(3,4-dichlorophenyl)methyl]acetamide

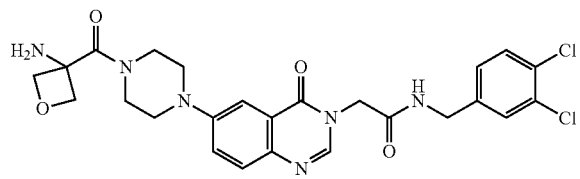 [SMILES: NC1(C(=O)N2CCN(c3ccc4ncn(CC(=O)NCc5ccc(Cl)c(Cl)c5)c(=O)c4c3)CC2)COC1]

To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (30 mg, 0.044 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in THF (2 mL). To this solution were added PYBOP (28.6 mg, 0.055 mmol; [CAS RN 128625-52-5]) and DIPEA (12 µL, 0.066 mmol) under an atmosphere of nitrogen. Then, 3-aminooxetane-3-carboxylic acid (6.4 mg, 0.055 mmol; [CAS RN 138650-24-5]) was added and the reaction mixture stirred at rt overnight. Purification by preparative HPLC on reversed phase eluting with a gradient of acetonitrile-water provided the title compound as colorless oil (2.6 mg, 11%). MS: m/e=545.3 [M+H]$^+$.

Examples 71 to 81

According to the procedure described for the synthesis of example 70 further examples were prepared from 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and the respective carboxylic acid as indicated in Table 5. The results are compiled in Table 5 and comprise examples 71 to 81.

TABLE 5

| No | Compound Name & Structure | Starting Materials | MS |
|---|---|---|---|
| 71 | N-[(3,4-Dichlorophenyl)methyl]-2-[4-oxo-6-[4-(2-sulfamoylacetyl)piperazin-1-yl]quinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 2-sulfamoylacetic acid ([CAS RN 17551-00-7]) | [M + H]$^+$ 567.2 |
| 72 | N-[(3,4-Dichlorophenyl)methyl]-2-[4-oxo-6-[4-(4-sulfamoylbutanoyl)piperazin-1-yl]quinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 4-sulfamoylbutanoic acid ([CAS RN 175476-52-5]) | [M + H]$^+$ 567.2 |
| 73 | 2-[6-[4-(Cyclobutanecarbonyl)piperazin-1-yl]-4-oxoquinazolin-3-yl]-N-[(3,4-dichlorophenyl)methyl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and cyclobutanecarboxylic acid ([CAS RN 3721-95-7]) | [M + H]$^+$ 542.3 |

TABLE 5-continued

| No | Compound Name & Structure | Starting Materials | MS |
|---|---|---|---|
| 74 | N-[(3,4-Dichlorophenyl)methyl]-2-[6-[4-(3-fluorocyclobutanecarbonyl)piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 3-fluorocyclobutane-1-carboxylate acid ([CAS RN 122665-96-7]) | [M + H]+ 560.3 |
| 75 | N-[(3,4-Dichlorophenyl)methyl]-2-[6-[4-(3,3-difluorocyclobutanecarbonyl)piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 3,3-difluorocyclo-butane-1-carboxylic acid ([CAS RN 107496-54-8]) | [M + H]+ 578.3 |
| 76 | N-[(3,4-Dichlorophenyl)methyl]-N-methyl-2-[4-oxo-6-[4-[1-(trifluoromethyl)cyclobutanecarbonyl]piperazin-1-yl]quinazolin-3-yl]acetamide | 9H-Fluoren-9-ylmethyl 4-[3-[2-[(3,4-dichloro-phenyl)methyl-methylamino]-2-oxoethyl]-4-oxoquinazolin-6-yl]piperazine-1-carboxylate (intermediate A-6) and 1-(trifluoromethyl)cyclobutane-1-carboxylic acid ([CAS RN 277756-45-3]) | [M + H]+ 610.3 |
| 77 | 2-[6-[4-(3-Chlorocyclobutanecarbonyl)piperazin-1-yl]-4-oxoquinazolin-3-yl]-N-[(3,4-dichlorophenyl)methyl]-N-methylacetamide | 9H-Fluoren-9-ylmethyl 4-[3-[2-[(3,4-dichlorophenyl)methyl-amino]-2-oxoethyl]-4-oxoquinazolin-6-yl]piperazine-1-carboxylate (intermediate A-6) and 3-chlorocyclobutane-1-carboxylic acid ([CAS RN 35207-71-7]) | [M + H]+ 578.1 |
| 78 | N-[(3,4-Dichlorophenyl)methyl]-2-[6-[4-(3-methoxycyclobutane-carbonyl)piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 3-methoxycyclo-butane-1-carboxylic acid ([CAS RN 480450-03-1]) | [M + H]+ 572.3 |

TABLE 5-continued

| No | Compound Name & Structure | Starting Materials | MS |
|---|---|---|---|
| 79 | N-[(3,4-Dichlorophenyl)methyl]-N-methyl-2-[6-[4-(oxetane-3-carbonyl)piperazin-1-yl]-4-oxoquinazolin-3-yl]acetamide 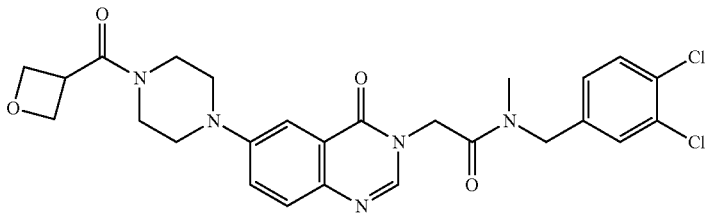 | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and oxetane-3-carboxylic acid ([CAS RN 114012-41-8]) | [M + H]⁺ 544.3 |
| 80 | N-[(3,4-Dichlorophenyl)methyl]-N-methyl-2-[6-[4-(3-methyloxetane-3-carbonyl)piperazin-1-yl]-4-oxoquinazolin-3-yl]acetamide 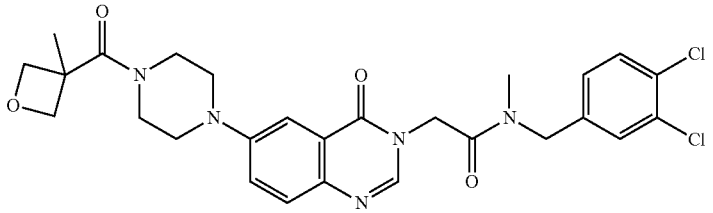 | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 3-methyloxetane-3-carboxylic acid ([CAS RN 28562-68-7]) | [M + H]⁺ 558.3 |
| 81 | 2-[6-[4-(1-Acetylazetidine-3-carbonyl)piperazin-1-yl]-4-oxoquinazolin-3-yl]-N-[(3,4-dichlorophenyl)methyl]-N-methylacetamide 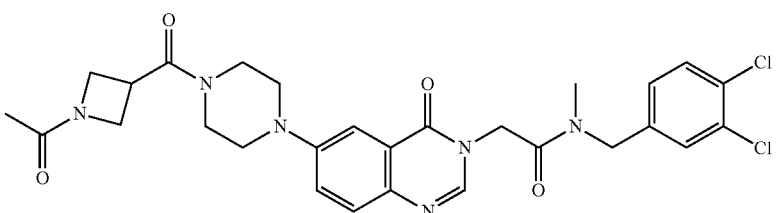 | 9H-Fluoren-9-ylmethyl 4-[3-[2-[(3,4-dichlorophenyl)methyl-methylamino]-2-oxoethyl]-4-oxoquinazolin-6-yl] piperazine-1-carboxylate (intermediate A-6) and 1-acetylazetidine-3-carboxylic acid ([CAS RN 97628-91-6]) | [M + H]⁺ 585.3 |

Example 82

4-[3-[2-[(3,4-Dichlorophenyl)methylamino]-2-oxoethyl]-4-oxoquinazolin-6-yl]-N-propan-2-ylpiperazine-1-carboxamide

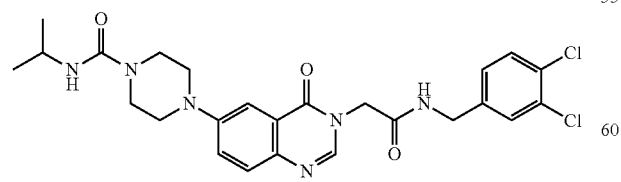

To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (30 mg, 0.044 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in dry THF (2 mL). To this solution was added 2-isocyanatopropane (4.7 mg, 0.055 mmol; [CAS RN 1795-48-8]) under an atmosphere of nitrogen and the reaction mixture stirred at rt overnight. Purification by preparative HPLC on reversed phase eluting with a gradient of acetonitrile-water provided the title compound as white solid (5.7 mg, 25%). MS: m/e=531.2 [M+H]⁺.

Examples 83 to 87

According to the procedure described for the synthesis of example 82 further examples were prepared from 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and the respective isonitrile as indicated in Table 6. The results are compiled in Table 6 and comprise examples 83 to 87.

TABLE 6

| No | Compound Name & Structure | Starting Materials | MS |
|---|---|---|---|
| 83 | N-Cyclopropyl-4-[3-[2-[(3,4-dichlorophenyl)methylamino]-2-oxoethyl]-4-oxoquinazolin-6-yl]piperazine-1-carboxamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and isocyanatocyclopropane ([CAS RN 4747-72-2]) | [M + H]$^+$ 529.2 |
| 84 | N-Cyclopentyl-4-[3-[2-[(3,4-dichlorophenyl)methylamino]-2-oxoethyl]-4-oxoquinazolin-6-yl]piperazine-1-carboxamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and isocyanatocyclopentane ([CAS RN 4747-71-1]) | [M + H]$^+$ 557.3 |
| 85 | 4-[3-[2-[(3,4-Dichlorophenyl)methylamino]-2-oxoethyl]-4-oxoquinazolin-6-yl]-N-(2-methoxyethyl)piperazine-1-carboxamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 1-isocyanato-2-methoxyethane ([CAS RN 42170-95-6]) | [M + H]$^+$ 547.3 |
| 86 | 4-[3-[2-[(3,4-Dichlorophenyl)methylamino]-2-oxoethyl]-4-oxoquinazolin-6-yl]-N-(3,5-dimethyl-1,2-oxoazol-4-yl)piperazine-1-carboxamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 4-isocyanato-3,5-dimethyl-1,2-oxazole([CAS RN 131825-41-7]) | [M + H]$^+$ 584.3 |
| 87 | 4-[3-[2-[(3,4-Dichlorophenyl)methylamino]-2-oxoethyl]-4-oxoquinazolin-6-yl]-N-pyridin-3-ylpiperazine-1-carboxamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 3-isocyanatopyridine ([CAS RN 15268-31-2]) | [M + H]$^+$ 566.2 |

Example 88

N-[(3,4-Dichlorophenyl)methyl]-2-[6-(4-methylsulfonylpiperazin-1-yl)-4-oxoquinazolin-3-yl]acetamide

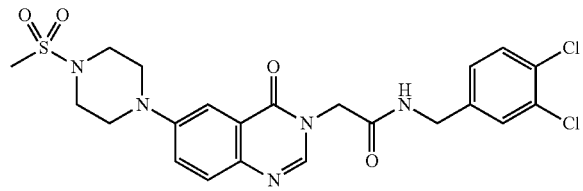 [SMILES: CS(=O)(=O)N1CCN(c2ccc3ncn(CC(=O)NCc4ccc(Cl)c(Cl)c4)c(=O)c3c2)CC1]

To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (15 mg, 0.022 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in dry DMF (1 mL). Triethylamine (30 μL, 0.22 mmol) and methanesulfonyl chloride (4.9 mg, 0.088 mmol; [CAS RN 124-63-0]) were added and the reaction mixture stirred at rt overnight under an atmosphere of nitrogen. Purification by preparative HPLC on reversed phase eluting with a gradient of acetonitrile-water provided the title compound as white solid (5.6 mg, 50%). MS: m/e=524.2 [M+H]$^+$.

Examples 89 to 92

According to the procedure described for the synthesis of example 88 further examples were prepared from 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and the respective sulfonyl chloride as indicated in Table 7. The results are compiled in Table 7 and comprise examples 89 to 92.

TABLE 7

| No | Compound Name & Structure | Starting Materials | MS |
|---|---|---|---|
| 89 | 2-[6-(4-Cyclopentylsulfonylpiperazin-1-yl)-4-oxoquinazolin-3-yl]-N-[(3,4-dichlorophenyl)methyl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and cyclopentanesulfonyl chloride ([CAS RN 26394-17-2]) | [M + H]$^+$ 578.3 |
| 90 | 2-[6-(4-Cyclohexylsulfonylpiperazin-1-yl)-4-oxoquinazolin-3-yl]-N-[(3,4-dichlorophenyl)methyl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and cyclohexanesulfonyl chloride ([CAS RN 4837-38-1]) | [M + H]$^+$ 592.3 |
| 91 | 2-[6-(4-Cyclopropylsulfonylpiperazin-1-yl)-4-oxoquinazolin-3-yl]-N-[(3,4-dichlorophenyl)methyl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and cyclopropanesulfonyl chloride ([CAS RN 139631-62-2]) | [M + H]$^+$ 564.2 |

TABLE 7-continued

| No | Compound Name & Structure | Starting Materials | MS |
|---|---|---|---|
| 92 | 2-[6-(4-Cyclobutylmethylsulfonyl)piperazin-1-yl]-4-oxoquinazolin-3-yl]-N-[(3,4-dichlorophenyl)methyl]-N-methylacetamide 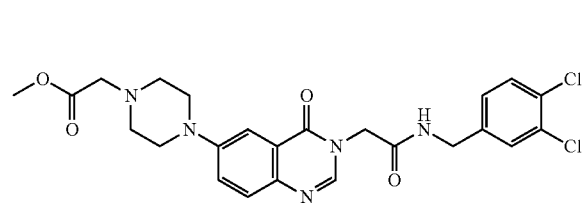 | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and cyclobutylmethane sulfonyl chloride ([CAS RN 1220695-06-6]) | [M + H]⁺ 592.2 |

Example 93

Methyl 2-[4-[3-[2-[(3,4-dichlorophenyl)methyl-amino]-2-oxoethyl]-4-oxoquinazolin-6-yl]piperazin-1-yl]acetate

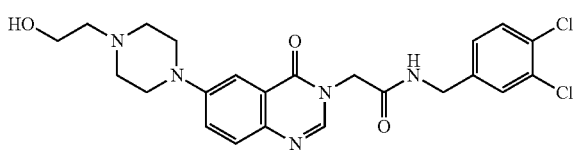 [SMILES: O=C(Cn1cnc2ccc(N3CCN(CCO)CC3)cc2c1=O)NCc1ccc(Cl)c(Cl)c1]

To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (58 mg, 0.085 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in dry THF (4 mL). To this solution was added NaH (6.8 mg, 0.17 mmol; 60% dispersion in mineral oil) and the reaction mixture stirred at rt. After 45 min, methyl 2-bromoacetate (19.5 mg, 0.13 mmol; [CAS RN 96-32-2]) was added and stirring of the reaction mixture continued at rt overnight. Purification by preparative HPLC on reversed phase eluting with a gradient of acetonitrile-water provided the title compound as white solid (4.6 mg, 10%). MS: m/e=518.2 [M+H]⁺.

Example 94

N-[(3,4-Dichlorophenyl)methyl]-2-[6-[4-(2-hydroxyethyl)piperazin-1-yl]-4-oxoquinazolin-3-yl] acetamide To a solution of 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) (30 mg, 0.044 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in dry THF (2 mL). To this solution was added 2-hydroxyacetaldehyde (4.0 mg, 0.066 mmol; [CAS RN 141-46-8]) and acetic acid (4 µL, 0.066 mmol) under an atmosphere of nitrogen and the reaction mixture stirred at rt. After 45 min, sodium cyanoborohydride (4.1 mg, 0.066 mmol; [CAS RN 25895-60-7]) was added and stirring of the reaction mixture continued at rt overnight. Purification by preparative HPLC on reversed phase eluting with a gradient of acetonitrile-water provided the title compound as white solid (2.5 mg, 12%). MS: m/e=490.2 [M+H]⁺.

Examples 95 to 103

According to the procedure described for the synthesis of example 94 further examples were prepared from 9H-fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and the respective aldehyde as indicated in Table 8. The results are compiled in Table 8 and comprise examples 95 to 103.

TABLE 8

| No | Compound Name & Structure | Starting Materials | MS |
|----|---------------------------|--------------------|----|
| 95 | N-[(3,4-Dichlorophenyl)methyl]-2-[6-[4-(2,3-dihydroxypropyl)piperazine-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 2,3-dihydroxy-propanal ([CAS RN 56-82-6]) | [M + H]$^+$ 520.2 |
| 96 | 2-[6-[4-(Cyclobutylmethyl)piperazin-1-yl]-4-oxoquinazolin-3-yl]-N-[(3,4-dichlorophenyl)methyl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and cyclobutane-carbaldehyde ([CAS RN 2987-17-9]) | [M + H]$^+$ 514.3 |
| 97 | N-[(3,4-Dichlorophenyl)methyl]-2-[4-oxo-6-[4-(oxolan-3-ylmethyl)piperazin-1-yl]quinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and oxolane-3-carbaldehyde ([CAS RN 79710-86-4]) | [M + H]$^+$ 530.3 |
| 98 | N-[(3,4-Dichlorophenyl)methyl]-2-[6-[4-(oxan-4-ylmethyl)piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and oxane-4-carbaldehyde ([CAS RN 50675-18-8]) | [M + H]$^+$ 544.3 |
| 99 | N-[(3,4-Dichlorophenyl)methyl]-2-[6-[4-[(1-methylpyrrol-2-yl)methyl]piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 1-methylpyrrole-2-carbaldehyde ([CAS RN 1192-58-1]) | [M + H]$^+$ 539.3 |

TABLE 8-continued

| No | Compound Name & Structure | Starting Materials | MS |
|---|---|---|---|
| 100 | N-[(3,4-Dichlorophenyl)methyl]-2-[6-[4-(1H-imidazol-2-ylmethyl)piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylate (intermediate A-5) and 1H-imidazole-2-carbaldehyde ([CAS RN 10111-08-7]) | [M + H]+ 526.2 |
| 101 | N-[(3,4-Dichlorophenyl)methyl]-2-[6-[4-(1H-imidazol-5-ylmethyl)piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylale (intermediate A-5) and1H-imidazole-5-carbaldehyde ([CAS RN 3034-50-2]) | [M + H]+ 526.2 |
| 102 | 3-[[4-[3-[2-[(3,4-Dichlorophenyl)methylamino]-2-oxoethyl]-4-oxoquinazolin-6-yl]piperazin-1-yl]methyl]furan-2-carboxylic acid | 9H-Fluoren-9-ylmethyl 4-[3-[2-[(3,4-dichlorophenyl)methylamino]-2-oxoethyl]-4-oxoquinazolin-6-yl]piperazine1-carboxylate (intermediate A-5) and 3-formylfuran-2-carboxylic acid ([CAS RN 29182-07-8]) | [M − H]− 568.3 |
| 103 | N-[(3,4-Dichlorophenyl)methyl]-2-[6-[4-[(2,4-dimethyl-1,3-oxazol-5-yl)methyl]piperazin-1-yl]-4-oxoquinazolin-3-yl]acetamide | 9H-Fluoren-9-ylmethyl 4-[3-[2-[(3,4-dichlorophenyl)methylamino]-2-oxoethyl]-4-oxoquinazolin-6-yl]piperazine-1-carboxylale (intermediate A-5) and 2,4-dimethyl-1,3-oxazole-5-carbaldehyde ([CAS RN 69062-86-8]) | [M + H]+ 555.3 |

Example 104

2-[6-[4-(Cyclopropylmethyl)piperazin-1-yl]-4-oxo-quinazolin-3-yl]-N-[(3,4-dichlorophenyl)methyl]-N-methylacetamide

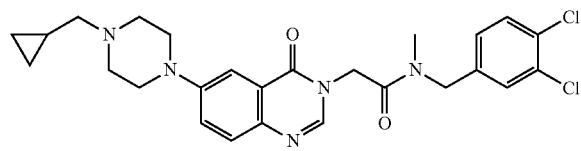 [SMILES: CN(Cc1ccc(Cl)c(Cl)c1)C(=O)Cn1cnc2ccc(N3CCN(CC4CC4)CC3)cc2c1=O]

To a solution 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) (37 mg, 0.054 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in acetonitrile (1.5 mL). To this solution were added bromomethylcyclopropane (11.0 mg, 0.081 mmol; [CAS RN 7051-34-5]) and potassium carbonate (30 mg, 0.22 mmol) and the reaction mixture heated under microwave irradiation to 120° C. for 15 min. Purification by preparative HPLC on reversed phase eluting with a gradient of acetonitrile-water provided the title compound as white solid (2.1 mg, 8%). MS: m/e=514.3 [M+H]$^+$.

Examples 105 and 106

According to the procedure described for the synthesis of example 104 further examples were prepared from 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and the respective alkyl bromide as indicated in Table 9. The results are compiled in Table 9 and comprise examples 105 and 106.

TABLE 9

| No | Compound Name & Structure | Starting Materials | MS |
|---|---|---|---|
| 105 | N-[(3,4-Dichlorophenyl)methyl]-2-[6-[4-(2-methoxyethyl)piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 1-bromo-2-methoxyethane ([CAS RN 6482-24-2]) | [M + H]$^+$ 518.3 |
| 106 | N-[(3,4-Dichlorophenyl)methyl]-N-methyl-2-[6-[4-(oxetan-3-ylmethyl)piperazin-1-yl]-4-oxoquinazolin-3-yl]acetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 3-(bromomethyl)oxetane ([CAS RN 1374014-30-8]) | [M + H]$^+$ 530.3 |

Example 107

N-[(3,4-Dichlorophenyl)methyl]-N-methyl-2-[6-[4-[2-(methylamino)-2-oxoethyl]piperazin-1-yl]-4-oxo-quinazolin-3-yl]acetamide

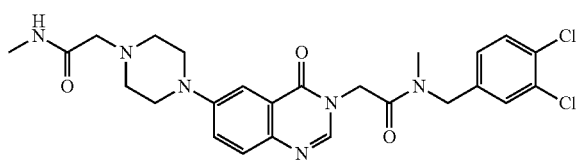 [SMILES: CNC(=O)CN1CCN(c2ccc3ncn(CC(=O)N(C)Cc4ccc(Cl)c(Cl)c4)c(=O)c3c2)CC1]

To a solution 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) (37 mg, 0.054 mmol) in dry DMF (1 mL) was added a solution of methanamine (2 mL, 16.0 mmol; 8.0 M solution in ethanol; [CAS RN 74-89-5]) and stirring at rt continued overnight. The crude reaction mixture was concentrated under reduced pressure and redissolved in dry DMF (1.5 mL). To this solution were added DIPEA (38 µL, 0.22 mmol) and 2-chloro-N-methylacetamide (11.6 mg, 0.11 mmol; [CAS RN 96-30-0]) and the reaction mixture heated under microwave irradiation to 100° C. for 10 min. Purification by preparative HPLC on reversed phase eluting with a gradient of acetonitrile-water provided the title compound as white solid (16.4 mg, 57%). MS: m/e=531.3 [M+H]$^+$.

Examples 108 to 112

According to the procedure described for the synthesis of example 107 further examples were prepared from 9H-fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and the respective alkyl chloride as indicated in Table 10. The results are compiled in Table 10 and comprise examples 108 to 112.

TABLE 10

| No | Compound Name & Structure | Starting Materials | MS |
|---|---|---|---|
| 108 | N-[(3,4-Dichlorophenyl)methyl]-2-[6-[4-[2-(dimethylamino)-2-oxoethyl]piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-chloro-N,N-dimethylacetamide ([CAS RN 2675-89-0]) | [M + H]$^+$ 545.3 |
| 109 | N-[(3,4-Dichlorophenyl)methyl]-N-methyl-2-[4-oxo-6-[4-[2-oxo-2-(propan-2-ylamino)ethyl]piperazin-1-yl]quinazolin-3-yl]acetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-chloro-N-propan-2-ylacetamide ([CAS RN 2895-21-5]) | [M + H]$^+$ 559.3 |
| 110 | N-[(3,4-Dichlorophenyl)methyl]-2-[6-[4-[2-(diethylamino)-2-oxoethyl]piperazin-1-yl]-4-oxoquinazolin-3-yl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-chloro-N,N-diethylacetamide ([CAS RN 2315-36-8]) | [M + H]$^+$ 573.3 |

TABLE 10-continued

| No | Compound Name & Structure | Starting Materials | MS |
|---|---|---|---|
| 111 | N-[(3,4-Dichlorophenyl)methyl]-N-methyl-2-[6-[4-(2-morpholin-4-yl-2-oxoethyl)piperazin-1-yl]-4-oxoquinazolin-3-yl]acetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-chloro-1-morpholin-4-ylethanone ([CAS RN 1440-61-5]) | [M + H]+ 587.3 |
| 112 | 2-[6-[4-(2-Anilino-2-oxoethyl)piperazin-1-yl]-4-oxoquinazolin-3-yl]-N-[(3,4-dichlorophenyl)methyl]-N-methylacetamide | 9H-Fluoren-9-ylmethyl 4-[3-[2-[(3,4-dichlorophenyl)methyl-methylamino]-2-oxoethyl]-4-oxoquinazolin-6-yl]piperazine-1-carboxylate (intermediate A-6) and 2-chloro-N-phenylacetamide ([CAS RN 587-65-5]) | [M + H]+ 593.3 |

Example 113

N-[(2-Chloro-4-cyanophenyl)methyl]-2-[6-[4-(oxetane-3-carbonyl)piperazin-1-yl]-4-oxoquinazolin-3-yl]acetamide

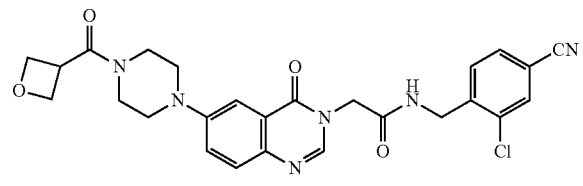 [SMILES: N#Cc1ccc(CNC(=O)Cn2cnc3ccc(N4CCN(C(=O)C5COC5)CC4)cc3c2=O)c(Cl)c1]

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (50 mg, 0.098 mmol) in dry DCM (2 mL) were added TBTU (47.2 mg, 0.15 mmol; [CAS RN 125700-67-6]) and DIPEA (50 μL, 0.29 mmol) under an atmosphere of nitrogen. Then, 4-(aminomethyl)-3-chlorobenzonitrile (20.4 mg, 0.12 mmol; [CAS RN 202521-97-9]) was added and the reaction mixture stirred at rt for 90 min. A solution of methanamine (2 mL, 16.0 mmol; 8.0 M solution in ethanol; [CAS RN 74-89-5]) was added and stirring at rt continued overnight. The crude reaction mixture was concentrated under reduced pressure and redissolved in dry DMF (2 mL). To this solution were added DIPEA (50 μL, 0.29 mmol), TBTU (47.2 mg, 0.15 mmol; [CAS RN 125700-67-6]) and oxetane-3-carboxylic acid (7.0 μL, 0.098 mmol; [CAS RN 114012-41-8]) and the reaction mixture stirred at rt for 2 h under an atmosphere of nitrogen. Purification by preparative HPLC on reversed phase eluting with a gradient of acetonitrile-water provided the title compound as light brown solid (20 mg, 39%). MS: m/e=521.3 [M+H]+.

Example 114

N-[(3-Chloro-4-cyanophenyl)methyl]-N-methyl-2-[4-oxo-6-[4-(oxolan-3-ylmethyl)piperazin-1-yl]quinazolin-3-yl]acetamide

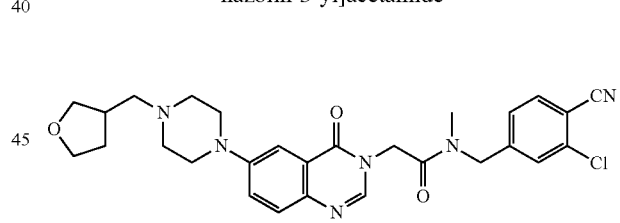

To a solution of 2-[6-[4-(9H-fluoren-9-ylmethoxycarbonyl)piperazin-1-yl]-4-oxoquinazolin-3-yl]acetic acid (intermediate A-1; [CAS RN 269078-82-2]) (50 mg, 0.098 mmol) in dry DCM (2 mL) were added TBTU (47.2 mg, 0.15 mmol; [CAS RN 125700-67-6]) and DIPEA (50 μL, 0.29 mmol) under an atmosphere of nitrogen. Then, 2-chloro-4-(methylaminomethyl)benzonitrile hydrochloride (26.7 mg, 0.12 mmol; example 56, step A) was added and the reaction mixture stirred at rt for 90 min. A solution of methanamine (2 mL, 16.0 mmol; 8.0 M solution in ethanol; [CAS RN 74-89-5]) was added and stirring at rt continued overnight. The crude reaction mixture was concentrated under reduced pressure and redissolved in methanol (2 mL). To this solution was added oxolane-3-carbaldehyde (27 μL, 29.4 mg, 0.15 mmol; 50 wt. % sol. in water; [CAS RN 79710-86-4]) and acetic acid (9 μL, 0.15 mmol) under an atmosphere of nitrogen and the reaction mixture stirred at rt. After 45 min, sodium cyanoborohydride (9.2 mg, 0.15 mmol; [CAS RN 25895-60-7]) was added and stirring of the reaction mixture continued at rt overnight. The crude reaction mixture was concentrated under reduced pressure, a sat. aq. solution of sodium hydrogen carbonate (20 mL) was added and the aq. phase extracted with DCM (3×20 mL). The combined organic phases were dried over MgSO4 and concentrated under reduced pressure. Purification by column chromatography (100-200 mesh size silica gel) eluting with a gradient of 0 to 4% methanol-DCM and crystallization from methanol afforded the title compound as white solid (25 mg, 48%). MS: m/e=535.4 [M+H]+.

Example 115

N-[(4-Chloro-3-cyanophenyl)methyl]-N-methyl-2-[4-oxo-6-[4-(oxolan-3-ylmethyl)piperazin-1-yl]quinazolin-3-yl]acetamide

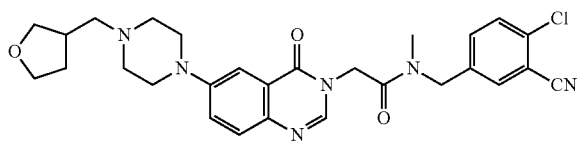 [SMILES: CN(Cc1ccc(Cl)c(C#N)c1)C(=O)Cn1cnc2ccc(N3CCN(CC4CCOC4)CC3)cc2c1=O]

In analogy to the procedure described for the preparation of N-[(3-chloro-4-cyanophenyl)methyl]-N-methyl-2-[4-oxo-6-[4-(oxolan-3-ylmethyl)piperazin-1-yl]quinazolin-3-yl]acetamide (example 114), replacing 2-chloro-4-(methylaminomethyl)benzonitrile hydrochloride with 2-chloro-5-(methylaminomethyl)benzonitrile hydrochloride (example 57, step A). Purification by column chromatography (100-200 mesh size silica gel) eluting with a gradient of 0 to 4% methanol-DCM afforded the title compound as colorless oil (26 mg, 50%). MS: m/e=535.3 [M+H]+.

Example 116

2-[6-(4-Acetylpiperazin-1-yl)-4-oxoquinazolin-3-yl]-N-[(3,4-dichlorophenyl)methyl]-N-ethylacetamide

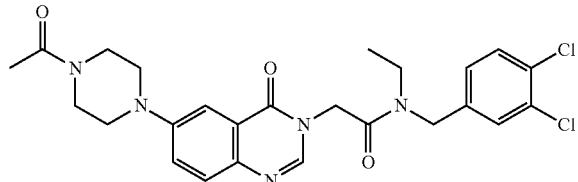

[A] N-[(3,4-Dichlorophenyl)methyl]ethanamine hydrochloride

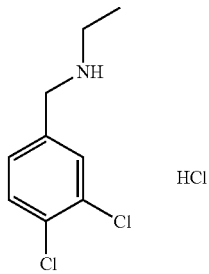

To a solution of 3,4-dichlorobenzaldehyde (1.0 g, 5.71 mmol; [CAS RN 6287-38-3]) and ethanamine (5.71 mL, 11.4 mmol; 2.0 M solution in THF; [CAS RN 75-04-7]) in isopropanol (12 mL) was added acetic acid (0.34 mL, 5.71 mmol) under an atmosphere of nitrogen and the reaction mixture stirred at rt. After 45 min, sodium cyanoborohydride (0.72 g, 5.71 mmol; [CAS RN 25895-60-7]) was added and stirring of the reaction mixture continued at rt overnight. The crude reaction mixture was concentrated under reduced pressure, EtOAc (50 mL) was added and the organic phase extracted with an aq. solution of 0.1 M HCl (3×20 mL). The combined aqueous phases were set to pH 14 upon addition of solid NaOH and the aq. phase extracted with EtOAc (3×100 mL). The combined organic phases were dried over MgSO4 and concentrated under reduced pressure. The crude reaction product was dissolved in dioxane (50 mL) and treated with 4 M HCl in dioxane (20 mL). The white precipitate was filtered off, washed with TBME (30 mL) and dried under high vaccum. The title compound was obtained as white solid (0.95 g, 69%). MS: m/e=204.0 [M+H]+.

[B] 2-[6-(4-Acetylpiperazin-1-yl)-4-oxoquinazolin-3-yl]-N-[(3,4-dichlorophenyl)methyl]-N-ethyl-acetamide

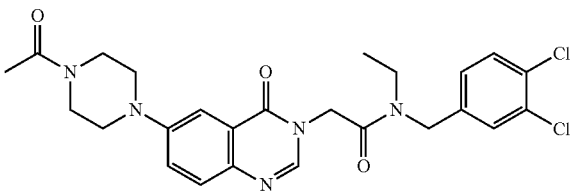 [SMILES: CCN(Cc1ccc(Cl)c(Cl)c1)C(=O)Cn1cnc2ccc(N3CCN(C(C)=O)CC3)cc2c1=O]

To a suspension of methyl 2-[6-(4-acetylpiperazin-1-yl)-4-oxoquinazolin-3-yl]acetate (intermediate A-7) (50 mg, 0.15 mmol) and N-[(3,4-dichlorophenyl)methyl]ethanamine hydrochloride (38.1 mg, 0.16 mmol) in dry THF (2 mL) was added bis(trimethylaluminium)-1,4-diazabicyclo[2.2.2]octane adduct (44.7 mg, 0.17 mmol; [CAS RN 137203-34-0]) under an atmosphere of nitrogen and the reaction mixture heated under microwave irradiation to 130° C. for 1 h. Purification by preparative HPLC on reversed phase eluting with a gradient of acetonitrile-water provided the title compound as white solid (7.6 mg, 10%). MS: m/e=516.3 [M+H]+.

Example 117

2-[6-(4-Acetylpiperazin-1-yl)-4-oxoquinazolin-3-yl]-N-[(3,4-dichlorophenyl)methyl]-N-propan-2-ylacetamide

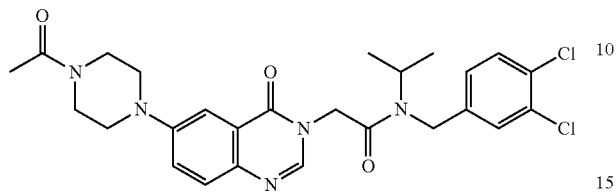

[A] N-[(3,4-Dichlorophenyl)methyl]propan-2-amine hydrochloride

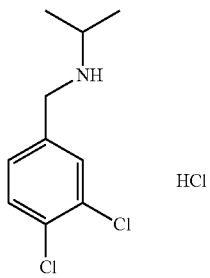

In analogy to the procedure described for the preparation of N-[(3,4-dichlorophenyl)methyl]ethanamine hydrochloride (example 116, step A), replacing ethanamine with 2-propanamine ([CAS RN 75-31-0]). The title compound was obtained as white solid (1.10 g, 73%). MS: m/e=218.1 [M+H]⁻.

[B] 2-[6-(4-Acetylpiperazin-1-yl)-4-oxoquinazolin-3-yl]-N-[(3,4-dichlorophenyl)methyl]-N-isopropyl-acetamide

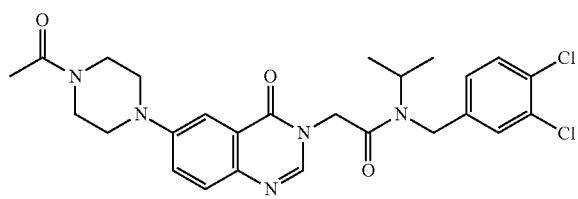 [SMILES: CC(=O)N1CCN(c2ccc3ncn(CC(=O)N(Cc4ccc(Cl)c(Cl)c4)C(C)C)c(=O)c3c2)CC1]

In analogy to the procedure described for the preparation of 2-[6-(4-acetylpiperazin-1-yl)-4-oxoquinazolin-3-yl]-N-[(3,4-dichlorophenyl)methyl]-N-ethyl-acetamide (example 116, step B), replacing N-[(3,4-dichlorophenyl)methyl]ethanamine hydrochloride with N-[(3,4-dichlorophenyl)methyl]propan-2-amine hydrochloride. Purification by preparative HPLC on reversed phase eluting with a gradient of acetonitrile-water provided the title compound as white solid (7.9 mg, 10%). MS: m/e=530.3 [M+H]⁺.

Example 118

2-[6-(4-Acetyl-1,4-diazepan-1-yl)-4-oxoquinazolin-3-yl]-N-[(3,4-dichlorophenyl)methyl]acetamide

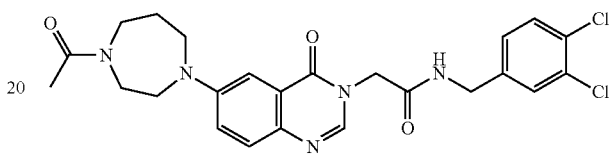

To a solution of 2-[6-[4-(9H-fluoren-9-ylmethoxycarbonyl)-1,4-diazepan-1-yl]-4-oxoquinazolin-3-yl]acetic acid (prepared as described in US2010/0069307A1, pp. 12; [CAS RN 1217190-17-2]) (50 mg, 0.095 mmol) in dry DMF (0.5 mL) were added TBTU (45.9 mg, 0.14 mmol; [CAS RN 125700-67-6]) and DIPEA (50 µL, 0.29 mmol) under an atmosphere of nitrogen. Then, (3,4-dichlorophenyl)methanamine (20.1 mg, 0.11 mmol; [CAS RN 102-49-8]) was added and the reaction mixture stirred at rt for 5 h. A solution of methanamine (60 µL, 0.48 mmol; 8.0 M solution in ethanol; [CAS RN 74-89-5]) was added and stirring at rt continued overnight. The crude reaction mixture was concentrated under reduced pressure and redissolved in dry DMF (0.5 mL). DIPEA (50 µL, 0.29 mmol) and acetyl chloride (34 µL, 0.48 mmol; [CAS RN 368426-73-7]) were added and the reaction mixture stirred at rt for 16 h under an atmosphere of nitrogen. Purification by preparative HPLC on reversed phase eluting with a gradient of acetonitrile-water provided the title compound as light yellow solid (17.7 mg, 37%). MS: m/e=463.3 [M+H]⁺.

Examples 119 to 127

According to the procedure described for the synthesis of example 118 further examples were prepared from 2-[6-[4-(9H-fluoren-9-ylmethoxycarbonyl)-1,4-diazepan-1-yl]-4-oxoquinazolin-3-yl]acetic acid (prepared as described in US2010/0069307A1, pp. 12; [CAS RN 1217190-17-2]) and 2-[6-[1-(9H-fluoren-9-ylmethoxycarbonyl)-4-piperidyl]-4-oxoquinazolin-3-yl]acetic acid (intermediate A-8) and the respective amine intermediate as indicated in Table 11. The results are compiled in Table 11 and comprise examples 119 to 127.

TABLE 11

| No | Compound Name & Structure | Starting Materials | MS |
|---|---|---|---|
| 119 | 2-[6-(4-Acetyl-1,4-diazepan-1-yl)-4-oxoquinazolin-3-yl]-N-[[4-(trifluoromethyl)phenyl]methyl]acetamide | 2-[6-[4-(9H-Fluoren-9-ylmethoxycarbonyl)-1,4-diazepan-1-yl]-4-oxoquinazolin-3-yl]acetic acid and [4-(trifluoromethyl)phenyl]methanamine ([CAS RN 3300-51-4]) | [M + H]+ 502.2 |
| 120 | 2-[6-(4-Acetyl-1,4-diazepan-1-yl)-4-oxoquinazolin-3-yl]-N-[(3-chloro-4-cyanophenyl)methyl]-N-methylacetamide | 2-[6-[4-(9H-Fluoren-9-ylmethoxycarbonyl)-1,4-diazepan-1-yl]-4-oxoquinazolin-3-yl]acetic acid and 2-chloro-4-(methylaminomethyl)benzonitrile hydrochloride (example 56, step A) | [M + H]+ 507.3 |
| 121 | 2-[6-(4-Acetyl-1,4-diazepan-1-yl)-4-oxoquinazolin-3-yl]-N-[(4-chloro-3-cyanophenyl)methyl]-N-methylacetamide | 2-[6-[4-(9H-Fluoren-9-ylmethoxycarbonyl)-1,4-diazepan-1-yl]-4-oxoquinazolin-3-yl]acetic acid and 2-chloro-5-(methylaminomethyl)benzonitrile hydrochloride (example 57, step A) | [M + H]+ 507.2 |
| 122 | 2-[6-(1-Acetylpiperidin-4-yl)-4-oxoquinazolin-3-yl]-N-[(3,4-dichlorophenyl)methyl]acetamide | 2-[6-[1-(9H-Fluoren-9-ylmethoxycarbonyl)-4-piperidyl]-4-oxoquinazolin-3-yl]acetic acid (intermediate A-8) and (3,4-dichlorophenyl)methanamine ([CAS RN 102-49-8]) | [M + H]+ 487.1 |
| 123 | 2-[6-(1-Acetylpiperidin-4-yl)-4-oxoquinazolin-3-yl]-N-[[4-(trifluoromethyl)phenyl]methyl]acetamide | 2-[6-[1-(9H-Fluoren-9-ylmethoxycarbonyl)-4-piperidyl]-4-oxoquinazolin-3-yl]acetic acid (intermediate A-8) and [4-(trifluoromethyl)phenyl]methanamine ([CAS RN 3300-51-4]) | [M + H]+ 487.2 |

TABLE 11-continued

| No | Compound Name & Structure | Starting Materials | MS |
|---|---|---|---|
| 124 | 2-[6-(1-Acetylpiperidin-4-yl)-4-oxoquinazolin-3-yl]-N-[(3,4-dichlorophenyl)methyl]-N-methylacetamide | 2-[6-[1-(9H-Fluoren-9-ylmethoxycarbonyl)-4-piperidyl]-4-oxoquinazolin-3-yl]acetic acid (intermediate A-8) and 1-(3,4-dichlorophenyl)-N-methylmethanamine ([CAS RN 5635-67-6]) | [M + H]$^+$ 501.2 |
| 125 | 2-[6-(1-Acetylpiperidin-4-yl)-4-oxoquinazolin-3-yl]-N-[(3-chloro-4-cyanophenyl)methyl]-N-methylacetamide | 2-[6-[1-(9H-Fluoren-9-ylmethoxycarbonyl)-4-piperidyl]-4-oxoquinazolin-3-yl]acetic acid (intermediate A-8) and 2-chloro-4-(methylaminomethyl)benzonitrile hydrochloride (example 56, step A) | [M + H]$^+$ 492.2 |
| 126 | 2-[6-(1-Acetylpiperidin-4-yl)-4-oxoquinazolin-3-yl]-N-[(4-chloro-3-cyanophenyl)methyl]-N-methylacetamide | 2-[6-[1-(9H-Fluoren-9-ylmethoxycarbonyl)-4-piperidyl]-4-oxoquinazolin-3-yl]acetic acid (intermediate A-8) and 2-chloro-5-(methylaminomethyl)benzonitrile hydrochloride (example 57, step A) | [M + H]$^+$ 492.2 |
| 127 | 2-[6-(1-Acetylpiperidin-4-yl)-4-oxoquinazolin-3-yl]-N-[(4-cyano-3-fluorophenyl)methyl]-N-methylacetamide | 2-[6-[1-(9H-Fluoren-9-ylmethoxycarbonyl)-4-piperidyl]-4-oxoquinazolin-3-yl]acetic acid (intermediate A-8) and 2-fluoro-4-(methylaminomethyl)benzonitrile ([CAS RN 1565551-88-3]) | [M + H]$^+$ 476.2 |

Example 128

2-[6-(1-Acetylpiperidin-4-yl)-4-oxoquinazolin-3-yl]-N-[[4-chloro-3-(trifluoromethoxy)phenyl]methyl]-N-methylacetamide

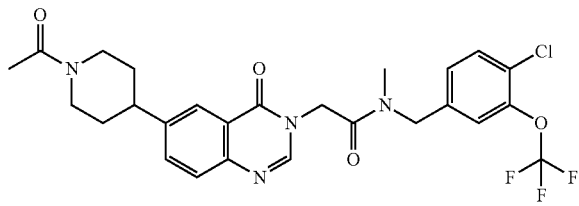 [SMILES: CC(=O)N1CCC(c2ccc3ncn(CC(=O)N(C)Cc4ccc(Cl)c(OC(F)(F)F)c4)c(=O)c3c2)CC1]

[A] 1-[4-Chloro-3-(trifluoromethoxy)phenyl]-N-methyl-methanamine

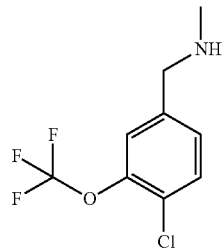

To a solution of 4-chloro-3-(trifluoromethoxy)benzaldehyde (0.30 g, 1.34 mmol; [CAS RN 886499-59-8]) in methanol (3 mL) was added methanamine (0.22 mL, 0.16 g, 1.74 mmol; 33 wt. % solution in EtOH; [CAS RN 74-89-5]) and acetic acid (0.10 mL, 1.74 mmol). After stirring of the reaction mixture at rt for 30 min, sodium cyanoborohydride (86 mg, 2.61 mmol; [CAS RN 25895-60-7]) was added in portions over 10 min. Stirring of the reaction mixture was continued for 40 min and then the reaction mixture concentrated under reduced pressure. A solution of 1 M NaOH was added (50 mL) and the aq. phase extracted with DCM (3×50 mL). The combined organic phases were dried over MgSO$_4$ and concentrated under reduced pressure. The crude reaction product was obtained as colorless oil and used directly in the consecutive reaction step without further purification (70 mg, 22%). MS: m/e=240.1 [M+H]$^+$.

[B] 2-[6-(1-Acetyl-4-piperidyl)-4-oxoquinazolin-3-yl]-N-[[4-chloro-3-(trifluoromethoxy)phenyl]methyl]-N-methyl-acetamide

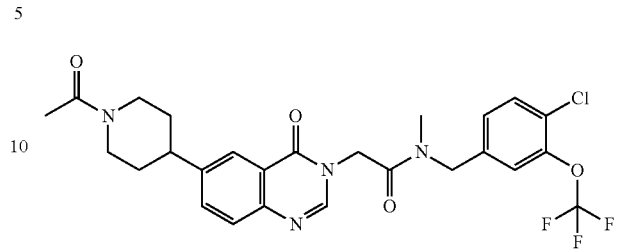

In analogy to the procedure described for the preparation of 2-[6-(4-acetyl-1,4-diazepan-1-yl)-4-oxoquinazolin-3-yl]-N-[(3,4-dichlorophenyl)methyl]acetamide (example 118), replacing 2-[6-[4-(9H-fluoren-9-ylmethoxycarbonyl)-1,4-diazepan-1-yl]-4-oxoquinazolin-3-yl]acetic acid with 2-[6-[1-(9H-fluoren-9-ylmethoxycarbonyl)-4-piperidyl]-4-oxoquinazolin-3-yl]acetic acid (intermediate A-8) and (3,4-dichlorophenyl)methanamine with 1-[4-chloro-3-(trifluoromethoxy)phenyl]-N-methyl-methanamine, respectively. Purification by column chromatography (100-200 mesh size silica gel) eluting with a gradient of 0 to 3% methanol-DCM afforded the title compound as white solid (38 mg, 73%). MS: m/e=551.2 [M+H]$^+$.

Example 129

N-[(3-Chloro-4-cyanophenyl)methyl]-N-methyl-2-[4-oxo-6-[4-(oxolan-3-ylmethyl)-1,4-diazepan-1-yl]quinazolin-3-yl]acetamide

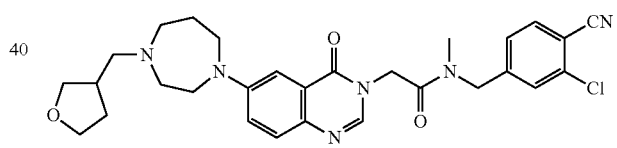

To a solution of 2-[6-[4-(9H-fluoren-9-ylmethoxycarbonyl)-1,4-diazepan-1-yl]-4-oxoquinazolin-3-yl]acetic acid (prepared as described in US2010/0069307A1, pp. 12; [CAS RN 1217190-17-2]) (50 mg, 0.095 mmol) in dry DMF (0.5 mL) were added TBTU (45.9 mg, 0.14 mmol; [CAS RN 125700-67-6]) and DIPEA (50 µL, 0.29 mmol) under an atmosphere of nitrogen. Then, 2-chloro-4-(methylaminomethyl)benzonitrile hydrochloride (23.9 mg, 0.11 mmol; example 56, step A) was added and the reaction mixture stirred at rt for 5 h. A solution of methanamine (60 µL, 0.48 mmol; 8.0 M solution in ethanol; [CAS RN 74-89-5]) was added and stirring at rt continued overnight. The crude reaction mixture was concentrated under reduced pressure and redissolved in methanol (2 mL). To this solution was added oxolane-3-carbaldehyde (27 µL, 29.4 mg, 0.15 mmol; 50 wt. % solution in water; [CAS RN 79710-86-4]) and acetic acid (9 µL, 0.15 mmol) under an atmosphere of nitrogen and the reaction mixture stirred at rt. After 45 min, sodium cyanoborohydride (9.2 mg, 0.15 mmol; [CAS RN 25895-60-7]) was added and stirring of the reaction mixture continued at rt overnight. The crude reaction mixture was concentrated under reduced pressure, a sat. aq. solution of sodium hydrogen carbonate (20 mL) was added and the aq. phase extracted with DCM (3×20 mL). The combined organic phases were dried over MgSO₄ and concentrated under reduced pressure. Purification by column chromatography (100-200 mesh size silica gel) eluting with a gradient of 0 to 5% methanol-DCM afforded the title compound as colorless oil (19 mg, 36%). MS: m/e=549.3 [M+H]⁺.

Example 130

N-[(4-Chloro-3-cyanophenyl)methyl]-N-methyl-2-[4-oxo-6-[4-(oxolan-3-ylmethyl)-1,4-diazepan-1-yl]quinazolin-3-yl]acetamide

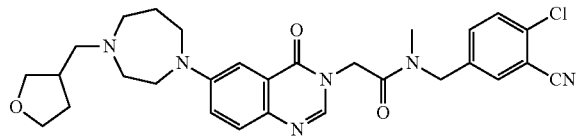 [SMILES: CN(Cc1ccc(Cl)c(C#N)c1)C(=O)Cn1cnc2ccc(N3CCCN(CC4CCOC4)CC3)cc2c1=O]

In analogy to the procedure described for the preparation of N-[(3-chloro-4-cyanophenyl)methyl]-N-methyl-2-[4-oxo-6-[4-(tetrahydrofuran-3-ylmethyl)-1,4-diazepan-1-yl]quinazolin-3-yl]acetamide (example 129), replacing 2-chloro-4-(methylaminomethyl)benzonitrile hydrochloride with 2-chloro-5-(methylaminomethyl)benzonitrile hydrochloride (example 57, step A). Purification by column chromatography (100-200 mesh size silica gel) eluting with a gradient of 0 to 5% methanol-DCM afforded the title compound as colorless oil (31 mg, 60%). MS: m/e=549.4 [M+H]⁺.

Example 131

N-[(3-Chloro-4-cyanophenyl)methyl]-2-[6-[1-(2-hydroxyacetyl)piperidin-4-yl]-4-oxoquinazolin-3-yl]-N-methylacetamide

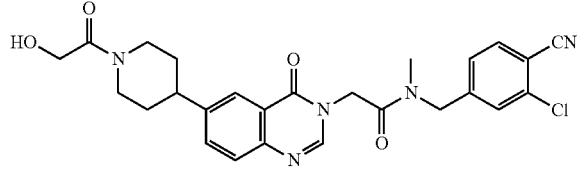 [SMILES: CN(Cc1ccc(C#N)c(Cl)c1)C(=O)Cn1cnc2ccc(C3CCN(C(=O)CO)CC3)cc2c1=O]

To a solution of N-[(3-chloro-4-cyanophenyl)methyl]-N-methyl-2-(4-oxo-6-piperidin-4-ylquinazolin-3-yl)acetamide (intermediate A-9) (27 mg, 0.056 mmol) in dry DMF (1.5 mL) were added TBTU (27 mg, 0.083 mmol; [CAS RN 125700-67-6]) and DIPEA (50 μL, 0.29 mmol) under an atmosphere of nitrogen. Then, 2-hydroxyacetic acid (5.1 mg, 0.067 mmol; [CAS RN 79-14-1]) was added and the reaction mixture stirred at rt for 18 h. Purification by preparative HPLC on reversed phase eluting with a gradient of acetonitrile-water provided the title compound as white solid (10.7 mg, 38%). MS: m/e=508.3 [M+H]⁺.

Examples 132 to 142

According to the procedure described for the synthesis of example 131 further examples were prepared from N-[(3-chloro-4-cyanophenyl)methyl]-N-methyl-2-(4-oxo-6-piperidin-4-ylquinazolin-3-yl)acetamide (intermediate A-9) and the respective carboxylic acid as indicated in Table 12. The results are compiled in Table 12 and comprise examples 132 to 142.

TABLE 12

| No | Compound Name & Structure | Starting Materials | MS |
|---|---|---|---|
| 132 | N-[(3-Chloro-4-cyanophenyl)methyl]-2-[6-[1-(2-methoxyacetyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 2-methoxyacetic acid ([CAS RN 625-45-6]) | [M + H]⁺ 522.2 |
| 133 | N-[(3-Chloro-4-cyanophenyl)methyl]-2-[6-[1-(2-methoxypropanoyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 2-methoxypropanoic acid ([CAS RN 4324-37-2]) | [M + H]⁺ 536.3 |

TABLE 12-continued

| No | Compound Name & Structure | Starting Materials | MS |
|---|---|---|---|
| 134 | N-[(3-Chloro-4-cyanophenyl)methyl]-2-[6-[1-(3-methoxypropanoyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 3-methoxypropanoic acid ([CAS RN 2544-06-1]) | [M + H]$^+$ 536.3 |
| 135 | N-[(3-Chloro-4-cyanophenyl)methyl]-N-methyl-2-[4-oxo-6-[1-(2-propan-2-yloxyacetyl)piperidin-4-yl]quinazolin-3-yl]acetamide | N-[(3-Chloro-4-cyanophenyl)methyl]-N-methyl-2-(4-oxo-6-piperidin-4-ylquinazolin-3-yl)acetamide (intermediate A-9) and 2-isopropoxyacetic acid ([CAS RN 33445-07-7]) | [M + H]$^+$ 550.3 |
| 136 | N-[(3-Chloro-4-cyanophenyl)methyl]-2-[6-[1-(cyclopropanecarbonyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and cyclopropanecarboxylic acid ([CAS RN 1759-53-1]) | [M + H]$^+$ 518.3 |
| 137 | N-[(3-Chloro-4-cyanophenyl)methyl]-2-[6-[1-(cyclobutanecarbonyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and cyclobutanecarboxylic acid ([CAS RN 3721-95-7]) | [M + H]$^+$ 532.3 |
| 138 | N-[(3-Chloro-4-cyanophenyl)methyl]-2-[6-[1-(3-fluorocyclobutanecarbonyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 3-fluorocyclobutane carboxylic acid ([CAS RN 122665-96-7]) | [M + H]$^+$ 550.3 |

TABLE 12-continued

| No | Compound Name & Structure | Starting Materials | MS |
|----|---------------------------|--------------------|----|
| 139 | N-[(3-Chloro-4-cyanophenyl)methyl]-2-[6-[1-(3-chlorocyclobutanecarbonyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 3-chlorocyclobutane-1-carboxylic acid ([CAS RN 35207-71-7]) | [M + H]+ 566.3 |
| 140 | N-[(3-Chloro-4-cyanophenyl)methyl]-2-[6-[1-(3,3-difluorocyclobutanecarbonyl)piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and 3,3-difluorocyclobutane-1-carboxylic acid ([CAS RN 107496-54-8]) | [M + H]+ 568.6 |
| 141 | N-[(3-Chloro-4-cyanophenyl)methyl]-N-methyl-2-[6-[1-(oxetane-2-carbonyl)piperidin-4-yl]-4-oxoquinazolin-3-yl]acetamide | N-[(3-Chloro-4-cyanophenyl)methyl]-N-methyl-2-(4-oxo-6-piperidin-4-ylquinazolin-3-yl)acetamide (intermediate A-9) and oxetane-2-carboxylic acid ([CAS RN 864373-47-7]) | [M + H]+ 534.3 |
| 142 | N-[(3-Chloro-4-cyanophenyl)methyl]-N-methyl-2-[6-[1-(oxetane-3-carbonyl)piperidin-4-yl]-4-oxoquinazolin-3-yl]acetamide | N-[(3-Chloro-4-cyanophenyl)methyl]-N-methyl-2-(4-oxo-6-piperidin-4-ylquinazolin-3-yl)acetamide (intermediate A-9) and oxetane-3-carboxylic acid ([CAS RN 114012-41-8]) | [M + H]+ 534.3 |

Example 143

N-[(3-Chloro-4-cyanophenyl)methyl]-N-methyl-2-[4-oxo-6-[1-(oxolan-3-ylmethyl)piperidin-4-yl]quinazolin-3-yl]acetamide

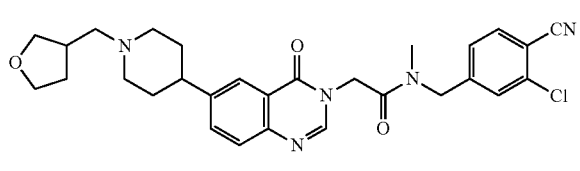 [SMILES: CN(Cc1ccc(C#N)c(Cl)c1)C(=O)Cn1cnc2ccc(C3CCN(CC4CCOC4)CC3)cc2c1=O]

In analogy to the procedure described for the preparation of N-[(3-chloro-4-cyanophenyl)methyl]-N-methyl-2-[4-oxo-6-[4-(tetrahydrofuran-3-ylmethyl)-1,4-diazepan-1-yl]quinazolin-3-yl]acetamide (example 129), replacing 2-[6-[4-(9H-fluoren-9-ylmethoxycarbonyl)-1,4-diazepan-1-yl]-4-oxoquinazolin-3-yl]acetic acid with 2-[6-[1-(9H-fluoren-9-ylmethoxycarbonyl)-4-piperidyl]-4-oxoquinazolin-3-yl]acetic acid (intermediate A-8). Purification by preparative HPLC on reversed phase eluting with a gradient of acetonitrile-water provided the title compound as colorless oil (14.2 mg, 28%). MS: m/e=536.4 [M+H]$^+$.

Example 144

N-[(4-Chloro-3-cyanophenyl)methyl]-N-methyl-2-[4-oxo-6-[1-(oxolan-3-ylmethyl)piperidin-4-yl]quinazolin-3-yl]acetamide

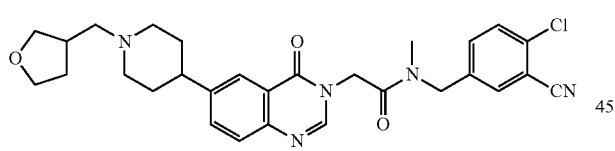

In analogy to the procedure described for the preparation of N-[(3-chloro-4-cyanophenyl)methyl]-N-methyl-2-[4-oxo-6-[4-(tetrahydrofuran-3-ylmethyl)-1,4-diazepan-1-yl]quinazolin-3-yl]acetamide (example 129), replacing 2-[6-[4-(9H-fluoren-9-ylmethoxycarbonyl)-1,4-diazepan-1-yl]-4-oxoquinazolin-3-yl]acetic acid with 2-[6-[1-(9H-fluoren-9-ylmethoxycarbonyl)-4-piperidyl]-4-oxoquinazolin-3-yl]acetic acid (intermediate A-8) and 2-chloro-4-(methylaminomethyl)benzonitrile hydrochloride with 2-chloro-5-(methylaminomethyl)benzonitrile hydrochloride (example 57, step A). Purification by column chromatography (100-200 mesh size silica gel) eluting with a gradient of 0 to 5% methanol-DCM afforded the title compound as colorless oil (21.3 mg, 42%). MS: m/e=534.3 [M+H]$^+$.

Example 145

N-[(3-Chloro-4-cyanophenyl)methyl]-N-methyl-2-[6-(1-methylsulfonylpiperidin-4-yl)-4-oxoquinazolin-3-yl]acetamide

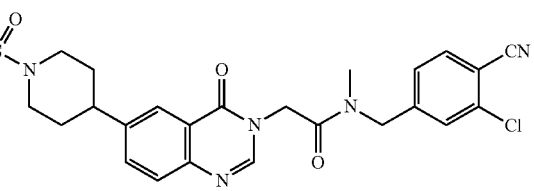

To a solution of N-[(3-chloro-4-cyanophenyl)methyl]-N-methyl-2-(4-oxo-6-piperidin-4-ylquinazolin-3-yl)acetamide (intermediate A-9) (22 mg, 0.045 mmol) in dry DMF (1.5 mL) was added DIPEA (25 μL, 0.15 mmol) and methanesulfonyl chloride (6.2 mg, 0.054 mmol; [CAS RN 124-63-0]) and the reaction mixture stirred at rt overnight under an atmosphere of nitrogen. Purification by preparative HPLC on reversed phase eluting with a gradient of acetonitrile-water provided the title compound as white solid (12.8 mg, 54%). MS: m/e=528.2 [M+H]$^+$.

Example 146

N-Cyclopropyl-N-[(3,4-dichlorophenyl)methyl]-2-[6-[1-(2-methoxyacetyl)piperidin-4-yl]-4-oxoquinazolin-3-yl]acetamide

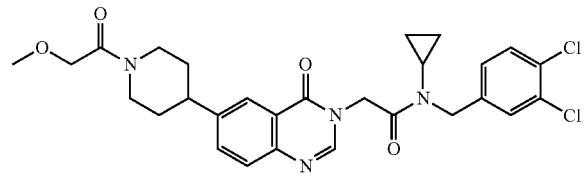 [SMILES: COCC(=O)N1CCC(c2ccc3ncn(CC(=O)N(Cc4ccc(Cl)c(Cl)c4)C4CC4)c(=O)c3c2)CC1]

[A] N-[(3,4-Dichlorophenyl)methyl]cyclopropanamine hydrochloride

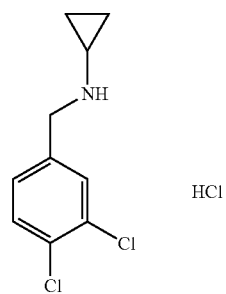 [SMILES: Clc1ccc(CNC2CC2)cc1Cl ; Cl]

In analogy to the procedure described for the preparation of N-[(3,4-dichlorophenyl)methyl]ethanamine hydrochloride (example 116, step A), replacing ethanamine with cyclopropanamine ([CAS RN 765-30-0]). The title compound was obtained as white solid (0.46 g, 32%). MS: m/e=216.1 [M+H]$^+$.

[B] N-Cyclopropyl-N-[(3,4-dichlorophenyl)methyl]-2-[6-[1-(2-methoxyacetyl)-4-piperidyl]-4-oxoquinazolin-3-yl]acetamide

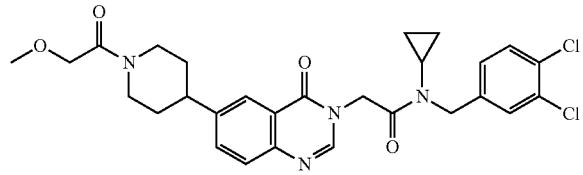 [SMILES: COCC(=O)N1CCC(c2ccc3ncn(CC(=O)N(Cc4ccc(Cl)c(Cl)c4)C4CC4)c(=O)c3c2)CC1]

In analogy to the procedure described for the preparation of 2-[6-(4-acetyl-1,4-diazepan-1-yl)-4-oxoquinazolin-3-yl]-N-[(3,4-dichlorophenyl)methyl]acetamide (example 118), replacing 2-[6-[4-(9H-fluoren-9-ylmethoxycarbonyl)-1,4-diazepan-1-yl]-4-oxoquinazolin-3-yl]acetic acid with 2-[6-[1-(9H-fluoren-9-ylmethoxycarbonyl)-4-piperidyl]-4-oxoquinazolin-3-yl]acetic acid (intermediate A-8), (3,4-dichlorophenyl)methanamine with N-[(3,4-dichlorophenyl)methyl]cyclopropanamine hydrochloride and acetyl chloride with 2-methoxyacetyl chloride ([CAS RN 38870-89-2]), respectively. Purification by preparative HPLC on reversed phase eluting with a gradient of acetonitrile-water provided the title compound as white solid (11.1 mg, 21%). MS: m/e=557.6 [M+H]$^+$.

Example 147

2-[6-[2-Acetyl-2-azabicyclo[2.2.1]heptan-5-yl]-4-oxoquinazolin-3-yl]-N-[(3,4-dichlorophenyl)methyl]acetamide

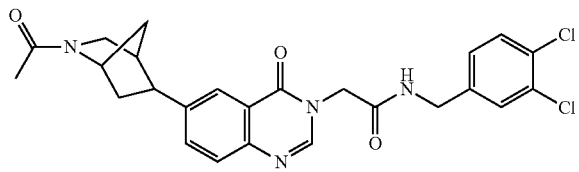 [SMILES: CC(=O)N1CC2CC1CC2c1ccc2ncn(CC(=O)NCc3ccc(Cl)c(Cl)c3)c(=O)c2c1]

In analogy to the procedure described for the preparation of 2-[6-(4-acetyl-1,4-diazepan-1-yl)-4-oxoquinazolin-3-yl]-N-[(3,4-dichlorophenyl)methyl]acetamide (example 118), replacing 2-[6-[4-(9H-fluoren-9-ylmethoxycarbonyl)-1,4-diazepan-1-yl]-4-oxoquinazolin-3-yl]acetic acid with 2-[6-[2-(9H-fluoren-9-ylmethoxycarbonyl)-2-azabicyclo[2.2.1]heptan-5-yl]-4-oxoquinazolin-3-yl]acetic acid (prepared as described in US2010/0069307A1, pp. 19; [CAS RN 1217190-42-5]). Purification by preparative HPLC on reversed phase eluting with a gradient of acetonitrile-water provided the title compound as light yellow solid (17 mg, 36%). MS: m/e=499.1 [M+H]$^+$.

Example 148

2-[6-(4-Acetylpiperazin-1-yl)-4-oxoquinazolin-3-yl]-N-[(3,4-dichlorophenyl)methyl]propanamide

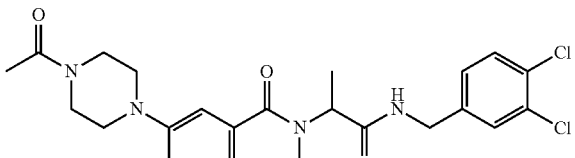

[A] tert-Butyl N-[1-[(3,4-dichlorophenyl)methylamino]-1-oxopropan-2-yl]carbamate

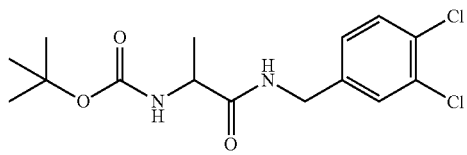 [SMILES: CC(NC(=O)OC(C)(C)C)C(=O)NCc1ccc(Cl)c(Cl)c1]

To a solution of 2-(tert-butoxycarbonylamino)propanoic acid (1.0 g, 5.3 mmol; [CAS RN 3744-87-4]) in DCM (40 mL) were added HATU (2.4 g, 5.3 mmol; [CAS RN 148893-10-1]) and triethylamine (1.4 mL, 10.6 mmol) under an atmosphere of nitrogen. Then, (3,4-dichlorophenyl)methanamine (0.9 g, 5.3 mmol; [CAS RN 102-49-8]) was added and the reaction mixture stirred at rt overnight. A 1 M solution of citric acid (20 mL) was added and the aq. phase extracted with DCM (3×20 mL). The combined organic phases were dried over MgSO$_4$ and concentrated under reduced pressure. Purification by column chromatography (100-200 mesh size silica gel) eluting with a gradient of 1:20 to 1:1 EtOAc-petroleum ether afforded the title compound as white solid (1.6 g, 87%). MS: m/e=347.1 [M+H]$^+$.

[B] 2-Amino-N-[(3,4-dichlorophenyl)methyl]propanamide hydrochloride

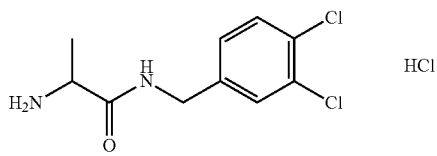

A solution of tert-butyl N-[1-[(3,4-dichlorophenyl)methylamino]-1-oxopropan-2-yl]carbamate (1.6 g, 4.6 mmol) in EtOAc (10 mL) was treated with 4 M HCl in dioxane (10 mL) and the recation mixture stirred at rt for 2 h. The white precipitate was filtered off, washed with TBME (40 mL) and dried under high vaccum. The title compound was obtained as white solid and used crude in the consecutive reaction step (1.2 g, 92%). MS: m/e=247.0 [M+H]$^+$.

[C] 5-(4-Acetylpiperazin-1-yl)-N-[1-[(3,4-dichlorophenyl)methylamino]-1-oxopropan-2-yl]-2-nitrobenzamide

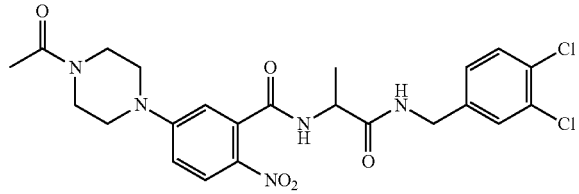

To a solution of 5-(4-acetylpiperazin-1-yl)-2-nitrobenzoic acid (intermediate A-7, step A) (0.51 g, 2.1 mmol) in DCM (40 mL) were added HATU (0.78 g, 2.1 mmol; [CAS RN 148893-10-1]) and triethylamine (0.5 mL, 3.4 mmol) under an atmosphere of nitrogen. Then, 2-amino-N-[(3,4-dichlorophenyl)methyl]propanamide hydrochloride (0.50 g, 1.7 mmol) was added and the reaction mixture stirred at rt overnight. A 1 M solution of citric acid (40 mL) was added and the aq. phase extracted with DCM (3×40 mL). The combined organic phases were dried over MgSO$_4$ and concentrated under reduced pressure. Purification by column chromatography (100-200 mesh size silica gel) eluting with a gradient of 1:80 to 1:30 methanol-DCM afforded the title compound as yellow solid (0.44 g, 50%). MS: m/e=522.1 [M+H]$^+$.

[D] 5-(4-Acetylpiperazin-1-yl)-2-amino-N-[1-[(3,4-dichlorophenyl)methylamino]-1-oxopropan-2-yl]benzamide

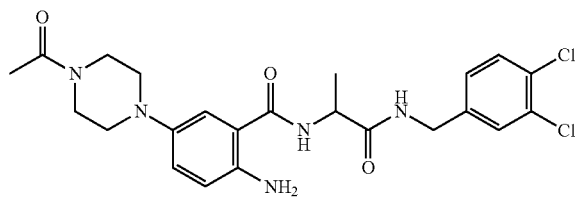

To 5-(4-acetylpiperazin-1-yl)-N-[1-[(3,4-dichlorophenyl)methylamino]-1-oxopropan-2-yl]-2-nitrobenzamide (0.44 g, 0.84 mmol) dissolved in ethanol (20 mL) was added dropwise a solution of tin(II) chloride dihydrate (1.1 g, 5.05 mmol) in conc. HCl (2 mL) at rt. After stirring of the reaction mixture for 2 h, an aq. solution of 10% sodium carbonate (50 mL) was added, the reaction filtered and the aq. phase extracted with DCM (3×40 mL). The combined organic phases were dried over Na$_2$SO$_4$ and concentrated under reduced pressure. Purification by column chromatography (100-200 mesh size silica gel) eluting with a gradient of 1:50 to 1:20 methanol-DCM afforded the title compound as light brown solid (0.20 g, 48%). MS: m/e=492.1 [M+H]$^+$.

[E] 2-[6-(4-Acetylpiperazin-1-yl)-4-oxoquinazolin-3-yl]-N-[(3,4-dichlorophenyl)methyl]propanamide

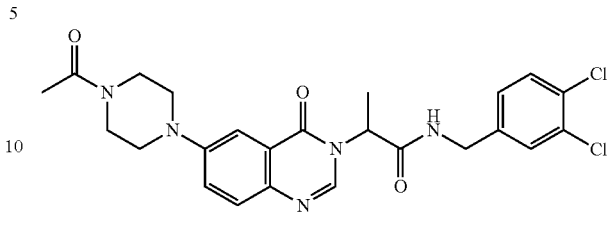

To a solution of 5-(4-acetylpiperazin-1-yl)-2-amino-N-[1-[(3,4-dichlorophenyl)methylamino]-1-oxopropan-2-yl]benzamide (100 mg, 0.20 mmol) in ethanol (5 mL) was added acetic acid (12 µg, 0.20 mmol) and trimethyl orthoformate (22 mg, 0.20 mmol; [CAS RN 149-73-5]) and the reaction mixture heated to 60° C. for 12 h. The crude reaction mixture was concentrated under reduced pressure and purified by preparative HPLC on reversed phase eluting with a gradient of acetonitrile-water. The title compound was obtained as white solid (47 mg, 46%). MS: m/e=502.1 [M+H]$^+$.

Example 149

2-[6-(4-Acetylpiperazin-1-yl)-4-oxoquinazolin-3-yl]-N-[(3,4-dichlorophenyl)methyl]-N-methylpropanamide

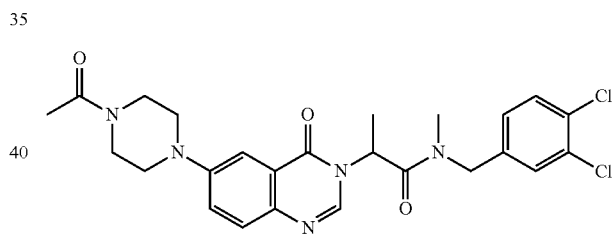

[A] tert-Butyl N-[1-[(3,4-dichlorophenyl)methyl-methylamino]-1-oxopropan-2-yl]carbamate

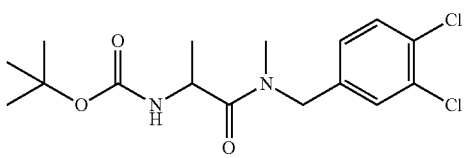 [SMILES: CC(NC(=O)OC(C)(C)C)C(=O)N(C)Cc1ccc(Cl)c(Cl)c1]

In analogy to the procedure described for the preparation of tert-butyl N-[1-[(3,4-dichlorophenyl)methylamino]-1-oxopropan-2-yl]carbamate (example 148, step A), replacing (3,4-dichlorophenyl)methanamine with 1-(3,4-dichlorophenyl)-N-methyl-methanamine ([CAS RN 5635-67-6]). Purification by column chromatography (100-200 mesh size silica gel) eluting with a gradient of 1:10 to 1:3 EtOAc-petroleum ether afforded the title compound as colorless oil (1.7 g, 90%). MS: m/e=362.3 [M+H]$^+$.

[B] 2-Amino-N-[(3,4-dichlorophenyl)methyl]-N-methylpropanamide hydrochloride

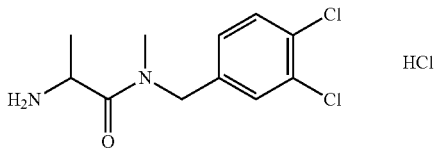 [SMILES: CC(N)C(=O)N(C)Cc1ccc(Cl)c(Cl)c1 ; Cl]

In analogy to the procedure described for the preparation of 2-amino-N-[(3,4-dichlorophenyl)methyl]propanamide hydrochloride (example 148, step B), replacing tert-butyl N-[1-[(3,4-dichlorophenyl)methylamino]-1-oxopropan-2-yl]carbamate with tert-butyl N-[1-[(3,4-dichlorophenyl)methyl-methylamino]-1-oxopropan-2-yl]carbamate. The title compound was obtained as white solid and used crude in the consecutive reaction step (1.0 g, 71%). MS: m/e=261.1 [M+H]⁺.

[C] 5-(4-Acetylpiperazin-1-yl)-N-[1-[(3,4-dichlorophenyl)methyl-methylamino]-1-oxopropan-2-yl]-2-nitrobenzamide

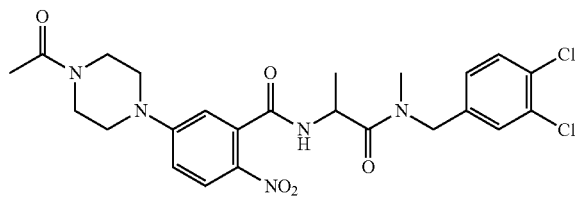 [SMILES: CC(=O)N1CCN(c2ccc(N)c(C(=O)NC(C)C(=O)N(C)Cc3ccc(Cl)c(Cl)c3)c2)CC1]

In analogy to the procedure described for the preparation of 5-(4-acetylpiperazin-1-yl)-N-[1-[(3,4-dichlorophenyl)methylamino]-1-oxopropan-2-yl]-2-nitrobenzamide (example 148, step C), replacing 2-amino-N-[(3,4-dichlorophenyl)methyl]propanamide hydrochloride with 2-amino-N-[(3,4-dichlorophenyl)methyl]-N-methylpropanamide hydrochloride. Purification by column chromatography (100-200 mesh size silica gel) eluting with a gradient of 1:80 to 1:30 methanol-DCM afforded the title compound as red solid (2.0 g, 58%; 53% purity). MS: m/e=536.0 [M+H]⁺.

[D] 5-(4-Acetylpiperazin-1-yl)-2-amino-N-[1-[(3,4-dichlorophenyl)methyl-methylamino]-1-oxopropan-2-yl]benzamide

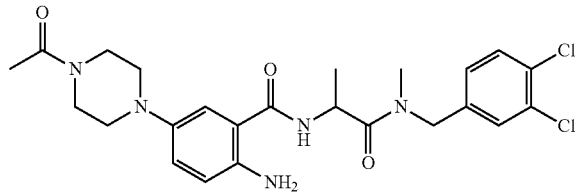

In analogy to the procedure described for the preparation of 5-(4-acetylpiperazin-1-yl)-2-amino-N-[1-[(3,4-dichlorophenyl)methylamino]-1-oxopropan-2-yl]benzamide (example 148, step D), replacing 5-(4-acetylpiperazin-1-yl)-N-[1-[(3,4-dichlorophenyl)methylamino]-1-oxopropan-2-yl]-2-nitrobenzamide with 5-(4-acetylpiperazin-1-yl)-N-[1-[(3,4-dichlorophenyl)methyl-methylamino]-1-oxopropan-2-yl]-2-nitrobenzamide. Purification by column chromatography (100-200 mesh size silica gel) eluting with a gradient of 1:30 to 1:10 methanol-DCM afforded the title compound as light yellow oil (0.45 g, 31%; 65% purity). MS: m/e=506.0 [M+H]⁺.

[E] 2-[6-(4-Acetylpiperazin-1-yl)-4-oxoquinazolin-3-yl]-N-[(3,4-dichlorophenyl)methyl]-N-methylpropanamide

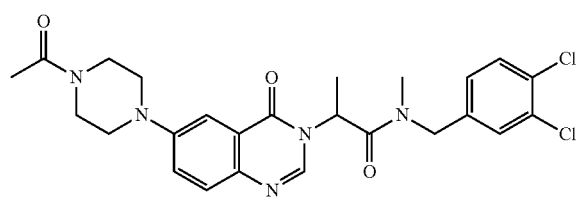 [SMILES: CC(=O)N1CCN(c2ccc3ncn(C(C)C(=O)N(C)Cc4ccc(Cl)c(Cl)c4)c(=O)c3c2)CC1]

In analogy to the procedure described for the preparation of 2-[6-(4-acetylpiperazin-1-yl)-4-oxoquinazolin-3-yl]-N-[(3,4-dichlorophenyl)methyl]propanamide (example 148, step E), replacing 5-(4-acetylpiperazin-1-yl)-2-amino-N-[1-[(3,4-dichlorophenyl)methylamino]-1-oxopropan-2-yl]benzamide with 5-(4-acetylpiperazin-1-yl)-2-amino-N-[1-[(3,4-dichlorophenyl)methyl-methylamino]-1-oxopropan-2-yl]benzamide. Purification by preparative HPLC on reversed phase eluting with a gradient of acetonitrile-water provided the title compound as white solid (25 mg, 13%). MS: m/e=515.2 [M+H]⁺.

Example 150

1-[6-(4-Acetylpiperazin-1-yl)-4-oxoquinazolin-3-yl]-N-[(3,4-dichlorophenyl)methyl]cyclopropane-1-carboxamide

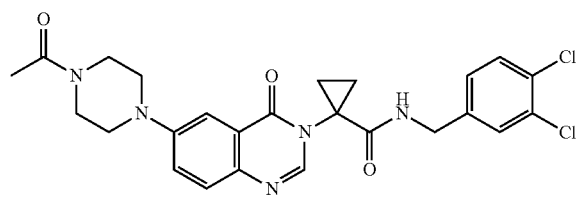 [SMILES: CC(=O)N1CCN(c2ccc3ncn(C4(C(=O)NCc5ccc(Cl)c(Cl)c5)CC4)c(=O)c3c2)CC1]

[A] tert-Butyl N-[1-[(3,4-dichlorophenyl)methylcarbamoyl]cyclopropyl]carbamate

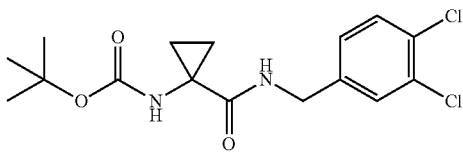 [SMILES: CC(C)(C)OC(=O)NC1(C(=O)NCc2ccc(Cl)c(Cl)c2)CC1]

In analogy to the procedure described for the preparation of tert-butyl N-[1-[(3,4-dichlorophenyl)methylamino]-1- oxopropan-2-yl]carbamate (example 148, step A), replacing 2-(tert-butoxycarbonylamino)propanoic acid with 1-(tert-butoxycarbonylamino)cyclopropanecarboxylic acid ([CAS RN 88950-64-5]). Purification by column chromatography (100-200 mesh size silica gel) eluting with a gradient of 1:20 to 1:1 EtOAc-petroleum ether afforded the title compound as colorless oil (2.0 g, 90%; 66% purity). MS: m/e=381.0 [M+H]+.

[B] 1-Amino-N-[(3,4-dichlorophenyl)methyl]cyclo-propanecarboxamide hydrochloride

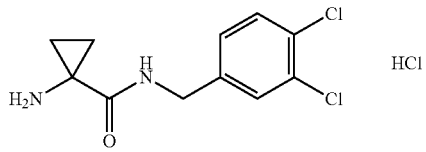 [SMILES: NC1(C(=O)NCc2ccc(Cl)c(Cl)c2)CC1 ; Cl]

In analogy to the procedure described for the preparation of 2-amino-N-[(3,4-dichlorophenyl)methyl]propanamide hydrochloride (example 148, step B), replacing tert-butyl N-[1-[(3,4-dichlorophenyl)methylamino]-1-oxopropan-2-yl]carbamate with tert-butyl N-[1-[(3,4-di chlorophenyl)methylcarbamoyl]cyclopropyl]carbamate. The title compound was obtained as white solid and used crude in the consecutive reaction step (1.0 g, 61%). MS: m/e=259.1 [M+H]+.

[C] 5-(4-Acetylpiperazin-1-yl)-N-[1-[(3,4-dichloro-phenyl)methylcarbamoyl]cyclopropyl]-2-nitrobenz-amide

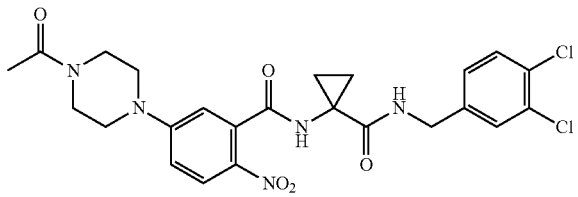 [SMILES: CC(=O)N1CCN(c2ccc([N+](=O)[O-])c(C(=O)NC3(C(=O)NCc4ccc(Cl)c(Cl)c4)CC3)c2)CC1]

In analogy to the procedure described for the preparation of 5-(4-acetylpiperazin-1-yl)-N-[1-[(3,4-dichlorophenyl) methylamino]-1-oxopropan-2-yl]-2-nitrobenzamide (example 148, step C), replacing 2-amino-N-[(3,4-dichlorophenyl)methyl]propanamide hydrochloride with 1-amino-N-[(3,4-dichlorophenyl)methyl]cyclopropanecarboxamide hydrochloride. Purification by column chromatography (100-200 mesh size silica gel) eluting with a gradient of 1:80 to 1:30 methanol-DCM afforded the title compound as red solid (1.1 g, 60%). MS: m/e=534.1 [M+H]+.

[D] 5-(4-Acetylpiperazin-1-yl)-2-amino-N-[1-[(3,4-dichlorophenyl)methylcarbamoyl]cyclopropyl]benz-amide

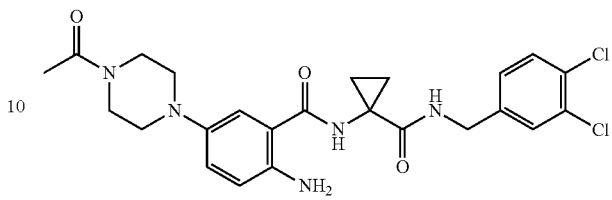

In analogy to the procedure described for the preparation of 5-(4-acetylpiperazin-1-yl)-2-amino-N-[1-[(3,4-dichloro-phenyl)methylamino]-1-oxopropan-2-yl]benzamide (example 148, step D), replacing 5-(4-acetylpiperazin-1-yl)-N-[1-[(3,4-dichlorophenyl)methylamino]-1-oxopropan-2-yl]-2-nitrobenzamide with 5-(4-acetylpiperazin-1-yl)-N-[1-[(3,4-dichlorophenyl)methylcarbamoyl]cyclopropyl]-2-nitrobenzamide. The title compound was isolated as light yellow solid (0.35 g, 69%). MS: m/e=557.3 [M+H]+.

[E] 1-[6-(4-Acetylpiperazin-1-yl)-4-oxoquinazolin-3-yl]-N-[(3,4-dichlorophenyl)methyl]cyclopropane-1-carboxamide

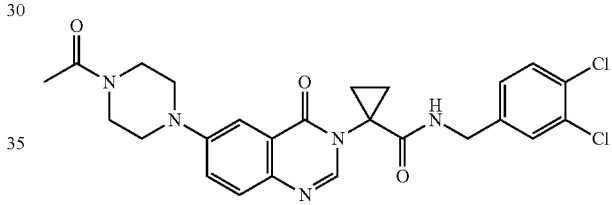

In analogy to the procedure described for the preparation of 2-[6-(4-acetylpiperazin-1-yl)-4-oxoquinazolin-3-yl]-N-[(3,4-dichlorophenyl)methyl]propanamide (example 148, step E), replacing 5-(4-acetylpiperazin-1-yl)-2-amino-N-[1-[(3,4-dichlorophenyl)methylamino]-1-oxopropan-2-yl]benzamide with 5-(4-acetylpiperazin-1-yl)-2-amino-N-[1-[(3,4-dichlorophenyl)methylcarbamoyl]cyclopropyl]benzamide. Purification by preparative HPLC on reversed phase eluting with a gradient of acetonitrile-water provided the title compound as white solid (25 mg, 16%). MS: m/e=514.0 [M+H]+.

Example 151

2-[6-(4-Acetylpiperazin-1-yl)-2-methyl-4-oxoqui-nazolin-3-yl]-N-[(3,4-dichlorophenyl)methyl]acet-amide

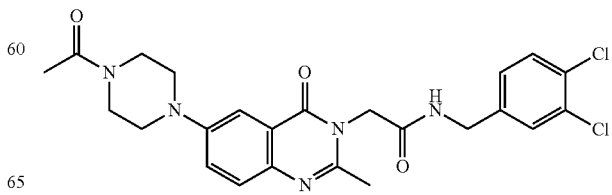

[A] tert-Butyl N-[2-[(3,4-dichlorophenyl)methylamino]-2-oxoethyl]carbamate

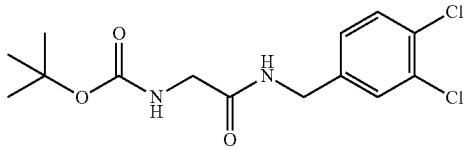 [SMILES: CC(C)(C)OC(=O)NCC(=O)NCc1ccc(Cl)c(Cl)c1]

In analogy to the procedure described for the preparation of tert-butyl N-[1-[(3,4-dichlorophenyl)methylamino]-1-oxopropan-2-yl]carbamate (example 148, step A), replacing 2-(tert-butoxycarbonylamino)propanoic acid with 2-(tert-butoxycarbonylamino)acetic acid ([CAS RN 4530-20-5]). Purification by column chromatography (100-200 mesh size silica gel) eluting with a gradient of 1:20 to 1:1 EtOAc-petroleum ether afforded the title compound as white solid (2.5 g, 66%). MS: m/e=276.8 [M+H-tert-Bu]$^+$.

[B] 2-Amino-N-[(3,4-dichlorophenyl)methyl]acetamide hydrochloride

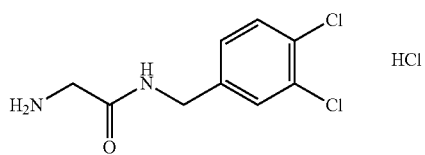 [SMILES: NCC(=O)NCc1ccc(Cl)c(Cl)c1 ; Cl]

In analogy to the procedure described for the preparation of 2-amino-N-[(3,4-dichlorophenyl)methyl]propanamide hydrochloride (example 148, step B), replacing tert-butyl N-[1-[(3,4-dichlorophenyl)methylamino]-1-oxopropan-2-yl]carbamate with tert-butyl N-[2-[(3,4-dichlorophenyl)methylamino]-2-oxoethyl]carbamate. The title compound was obtained as white solid and used crude in the consecutive reaction step (1.3 g, 67%). MS: m/e=233.1 [M+H]$^+$.

[C] 5-(4-Acetylpiperazin-1-yl)-N-[2-[(3,4-dichlorophenyl)methylamino]-2-oxoethyl]-2-nitrobenzamide

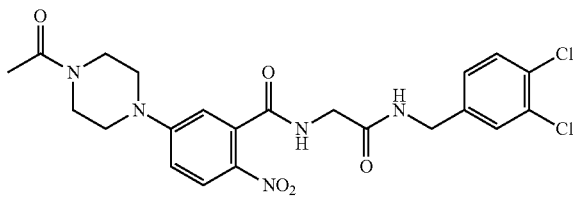 [SMILES: CC(=O)N1CCN(c2ccc([N+](=O)[O-])c(C(=O)NCC(=O)NCc3ccc(Cl)c(Cl)c3)c2)CC1]

In analogy to the procedure described for the preparation of 5-(4-acetylpiperazin-1-yl)-N-[1-[(3,4-dichlorophenyl)methylamino]-1-oxopropan-2-yl]-2-nitrobenzamide (example 148, step C), replacing 2-amino-N-[(3,4-dichlorophenyl)methyl]propanamide hydrochloride with 2-amino-N-[(3,4-dichlorophenyl)methyl]acetamide hydrochloride. Purification by column chromatography (100-200 mesh size silica gel) eluting with a gradient of 1:100 to 1:20 methanol-DCM afforded the title compound as yellow solid (1.6 g, 71%). MS: m/e=508.6 [M+H]$^+$.

[D] 5-(4-Acetylpiperazin-1-yl)-2-amino-N-[2-[(3,4-dichlorophenyl)methylamino]-2-oxoethyl]benzamide

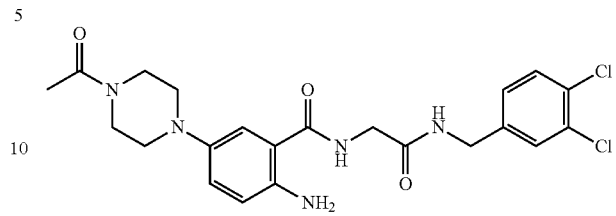

In analogy to the procedure described for the preparation of 5-(4-acetylpiperazin-1-yl)-2-amino-N-[1-[(3,4-dichlorophenyl)methylamino]-1-oxopropan-2-yl]benzamide (example 148, step D), replacing 5-(4-acetylpiperazin-1-yl)-N-[1-[(3,4-dichlorophenyl)methylamino]-1-oxopropan-2-yl]-2-nitrobenzamide with 5-(4-acetylpiperazin-1-yl)-N-[2-[(3,4-dichlorophenyl)methylamino]-2-oxoethyl]-2-nitrobenzamide. Purification by column chromatography (100-200 mesh size silica gel) eluting with a gradient of 1:100 to 1:20 methanol-DCM afforded the title compound as light brown solid (0.9 g, 60%). MS: m/e=478.1 [M+H]$^+$.

[E] 2-[6-(4-Acetylpiperazin-1-yl)-2-methyl-4-oxoquinazolin-3-yl]-N-[(3,4-dichlorophenyl)methyl]acetamide

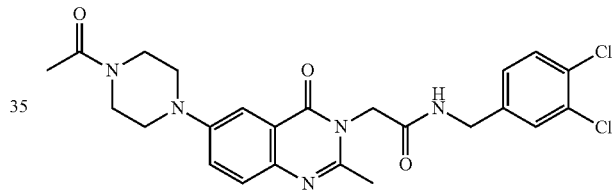

To a solution of 5-(4-acetylpiperazin-1-yl)-2-amino-N-[2-[(3,4-dichlorophenyl)methylamino]-2-oxoethyl]benzamide (200 mg, 0.42 mmol) in ethanol (10 mL) was added acetic acid (24 µg, 0.42 mmol) and trimethyl orthoacetate (50 mg, 0.42 mmol; [CAS RN 1445-45-0]) and the reaction mixture heated to reflux overnight. The crude reaction mixture was concentrated under reduced pressure and purified by preparative HPLC on reversed phase eluting with a gradient of acetonitrile-water. The title compound was obtained as white solid (120 mg, 57%). MS: m/e=502.1 [M+H].

Example 152

2-[6-(4-Acetylpiperazin-1-yl)-2,4-dioxo-1H-quinazolin-3-yl]-N-[(3,4-dichlorophenyl)methyl]acetamide

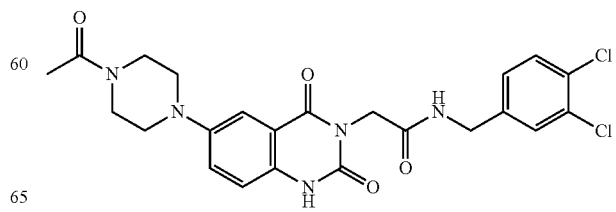

To a solution of 5-(4-acetylpiperazin-1-yl)-2-amino-N-[2-[(3,4-dichlorophenyl)methylamino]-2-oxoethyl]benzamide (example 151, step D) (200 mg, 0.42 mmol) in DCM (10 mL) was added N,N'-carbonyldiimidazole (102 mg, 0.63 mmol; [CAS RN 530-62-1]) and the reaction mixture heated to 80° C. overnight. The crude reaction mixture was concentrated under reduced pressure and purified by preparative HPLC on reversed phase eluting with a gradient of acetonitrile-water. The title compound was obtained as white solid (100 mg, 47%). MS: m/e=504.1 [M+H]$^+$.

Example 153

2-[6-(4-Acetylpiperazin-1-yl)-4-oxoquinazolin-3-yl]-N-[1-(3,4-dichlorophenyl)-3-methoxypropyl]acetamide

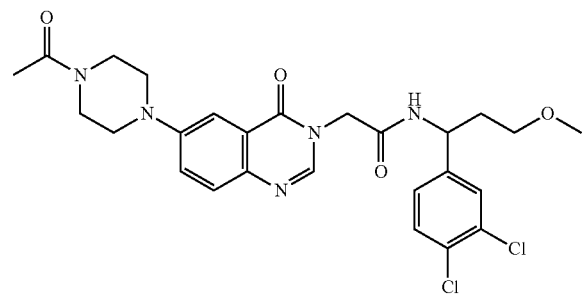 [SMILES: COCCC(NC(=O)Cn1cnc2ccc(N3CCN(C(C)=O)CC3)cc2c1=O)c1ccc(Cl)c(Cl)c1]

To a solution of 2-[6-(4-acetylpiperazin-1-yl)-4-oxoquinazolin-3-yl]acetic acid (intermediate A-2) (11.9 mg, 0.036 mmol) in dry DMF (1 mL) were added HATU (20.5 mg, 0.054 mmol; [CAS RN 148893-10-1]) and DIPEA (50 μL, 0.29 mmol) under an atmosphere of nitrogen. Then, 1-(3,4-dichlorophenyl)-3-methoxypropan-1-amine hydrochloride (11.6 mg, 0.043 mmol; [CAS RN 1803587-38-3]) was added and the reaction mixture heated by microwave irradiation to 100° C. for 10 min. Water was added (1 mL) and the crude reaction product purified by preparative HPLC on reversed phase eluting with a gradient of acetonitrile-water. The title compound was obtained as white solid (1.4 mg, 7%). MS: m/e=546.1 [M+H]$^+$.

Example 154

N-[(3-Chloro-4-cyanophenyl)methyl]-2-[6-[1-(2-cyanoacetyl)piperidin-4-yl]-4-oxoquinazolin-3-yl]-N-methylacetamide

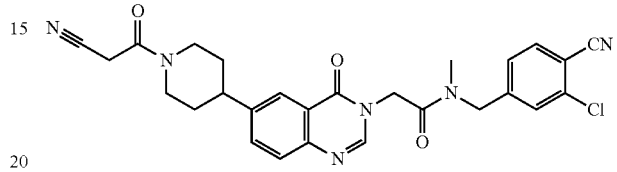

To a solution of N-[(3-chloro-4-cyanophenyl)methyl]-N-methyl-2-(4-oxo-6-piperidin-4-ylquinazolin-3-yl)acetamide (intermediate A-9) (68 mg, 0.15 mmol) in DCM (2 mL) were added HATU (86.2 mg, 0.23 mmol; [CAS RN 148893-10-1]) and DIPEA (79 μL, 0.45 mmol) under an atmosphere of nitrogen. Then, 2-cyanoacetic acid (19.3 mg, 0.23 mmol; [CAS RN 372-09-8]) was added and the reaction mixture heated by microwave irradiation to 100° C. for 10 min. Purification by preparative HPLC on reversed phase eluting with a gradient of acetonitrile-water provided the title compound as light yellow solid (35.1 mg, 45%). MS: m/e=517.2 [M+H]$^+$.

Example 155

N-[(3-Chloro-4-cyanophenyl)methyl]-2-[6-[1-(3-cyanopropanoyl)piperidin-4-yl]-4-oxoquinazolin-3-yl]-N-methylacetamide

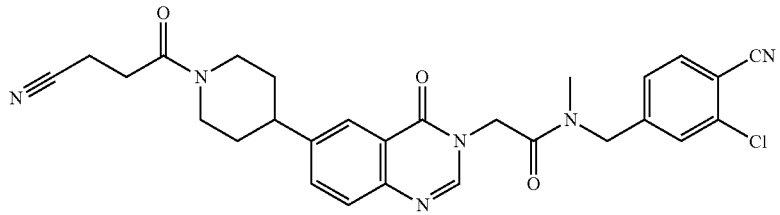 [SMILES: CN(Cc1ccc(C#N)c(Cl)c1)C(=O)Cn1cnc2ccc(C3CCN(C(=O)CCC#N)CC3)cc2c1=O]

To a solution of N-[(3-chloro-4-cyanophenyl)methyl]-N-methyl-2-(4-oxo-6-piperidin-4-ylquinazolin-3-yl)acetamide (intermediate A-9) (50 mg, 0.11 mmol) in dry DMF (2 mL) were added (benzotriazol-1-yloxy)tripyrrolidinophosphonium hexafluorophosphate (69.4 mg, 0.13 mmol; PyBOP; [CAS RN 128625-52-5]) and DIPEA (97 μL, 0.56 mmol) under an atmosphere of nitrogen. Then, 3-cyanopropanoic acid (13.2 mg, 0.13 mmol; [CAS RN 16051-87-9]) was added and the reaction mixture stirred at rt for 1 h. Purification by preparative HPLC on reversed phase eluting with a gradient of acetonitrile-water provided the title compound as white solid (5 mg, 9%). MS: m/e=531.3 [M+H]$^+$.

Examples 156 to 159

According to the procedure described for the synthesis of example 155 further examples were prepared from N-[(3-chloro-4-cyanophenyl)methyl]-N-methyl-2-(4-oxo-6-piperidin-4-ylquinazolin-3-yl)acetamide (intermediate A-9) and the respective carboxylic acid as indicated in Table 13. The results are compiled in Table 13 and comprise examples 156 to 159.

TABLE 13

| No | Compound Name & Structure | Starting Materials | MS |
|---|---|---|---|
| 156 | N-[(3-Chloro-4-cyanophenyl)methyl]-2-[6-[1-[(2R)-2-hydroxypropanoyl]piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and (R)-2-hydroxypropanoic acid ([CAS RN 10326-41-7]) | [M + H]$^+$ 522.3 |
| 157 | N-[(3-Chloro-4-cyanophenyl)methyl]-2-[6-[1-[(2R)-2-hydroxy-3-methylbutanoyl]piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and (R)-2-hydroxy-3-methylbutanoic acid ([CAS RN 17407-56-6]) | [M + H]$^+$ 550.4 |
| 158 | N-[(3-Chloro-4-cyanophenyl)methyl]-2-[6-[1-[(2R)-2-methoxypropanoyl]piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and (R)-2-methoxypropanoic acid ([CAS RN 23943-96-6]) | [M + H]$^+$ 536.3 |
| 159 | N-[(3-Chloro-4-cyanophenyl)methyl]-2-[6-[1-[(2S)-2-methoxypropanoyl]piperidin-4-yl]-4-oxoquinazolin-3-yl]-N-methylacetamide | N-[(3-Chloro-4-cyanophenyl)methyl]-N-methyl-2-(4-oxo-6-piperidin-4-ylquinazolin-3-yl)acetamide (intermediate A-9) and (S)-2-methoxypropanoic acid ([CAS RN 23953-00-6]) | [M + H]$^+$ 536.3 |

Example 160

Methyl 4-[3-[2-[(3-chloro-4-cyanophenyl)methyl-methylamino]-2-oxoethyl]-4-oxoquinazolin-6-yl]piperidine-1-carboxylate

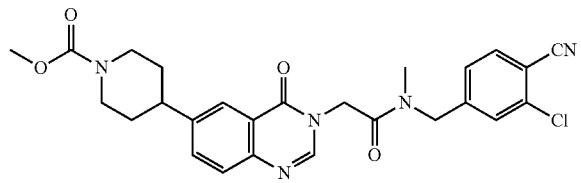 [SMILES: COC(=O)N1CCC(c2ccc3ncn(CC(=O)N(C)Cc4ccc(C#N)c(Cl)c4)c(=O)c3c2)CC1]

To a solution of N-[(3-chloro-4-cyanophenyl)methyl]-N-methyl-2-(4-oxo-6-piperidin-4-ylquinazolin-3-yl)acetamide (intermediate A-9) (50 mg, 0.11 mmol) in dry DMF (2 mL) were added methyl chloroformate (10 µL, 0.13 mmol; [CAS RN 79-22-1]) and DIPEA (97 µL, 0.56 mmol) and the reaction mixture stirred at rt for 1 h under an atmosphere of nitrogen. Purification by preparative HPLC on reversed phase eluting with a gradient of acetonitrile-water provided the title compound as white solid (40 mg, 70%). MS: m/e=508.3 [M+H]$^+$.

Example 161

2-[6-(1-Acetylpiperidin-4-yl)-4-oxoquinazolin-3-yl]-N-[[3-chloro-5-(trifluoromethyl)phenyl]methyl]acetamide

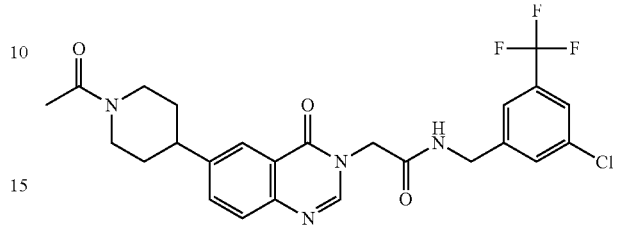

To a solution of 2-[6-(1-tert-butoxycarbonyl-4-piperidyl)-4-oxoquinazolin-3-yl]acetic acid (intermediate A-8, step E) (100 mg, 0.26 mmol) in DCM (2 mL) were added (benzotriazol-1-yloxy)tripyrrolidinophosphonium hexafluorophosphate (161 mg, 0.31 mmol; PyBOP; [CAS RN 128625-52-5]) and DIPEA (225 µL, 1.29 mmol) under an atmosphere of nitrogen. Then, (3-chloro-5-(trifluoromethyl)phenyl)methanamine (59.5 mg, 0.28 mmol; [CAS RN 400771-41-7]) was added and the reaction mixture stirred at rt for 1 h. The solvent was evaporated under reduced pressure and 4 M HCl in dioxane (2 mL) was added. After stirring at rt for 15 min, the reaction mixture was concentrated under reduced pressure and the crude reaction mixture redissolved in dry DMF (2 mL). DIPEA (500 µL, 2.86 mmol), (benzotriazol-1-yloxy)tripyrrolidinophosphonium hexafluorophosphate (161 mg, 0.31 mmol; PyBOP; [CAS RN 128625-52-5]) and acetic acid (30 µL, 0.52 mmol) were added and the reaction mixture stirred at rt for 1 h under an atmosphere of nitrogen. Purification by preparative HPLC on reversed phase eluting with a gradient of acetonitrile-water provided the title compound as white solid (46 mg, 35%). MS: m/e=521.3 [M+H]$^+$.

Examples 162 to 164

According to the procedure described for the synthesis of example 161 further examples were prepared from 2-[6-(1-tert-butoxycarbonyl-4-piperidyl)-4-oxoquinazolin-3-yl]acetic acid (intermediate A-8, step E) and the respective benzylamine as indicated in Table 14. The results are compiled in Table 14 and comprise examples 162 to 164.

TABLE 14

| No | Compound Name & Structure | Starting Materials | MS |
|---|---|---|---|
| 162 | 2-[6-(1-Acetylpiperidin-4-yl)-4-oxoquinazolin-3-yl]-N-[[4-fluoro-3-(trifluoromethyl)phenyl]methyl]acetamide | 2-[6-(1-tert-Butoxycarbonyl-4-piperidyl)-4-oxoquinazolin-3-yl]acetic acid (intermediate A-8, step E) and (4-fluoro-3-(trifluoromethyl)phenyl)methanamine ([CAS RN 67515-74-6]) | [M + H]$^+$ 505.2 |

TABLE 14-continued

| No | Compound Name & Structure | Starting Materials | MS |
|---|---|---|---|
| 163 | 2-[6-(1-Acetylpiperidin-4-yl)-4-oxoquinazolin-3-yl]-N-[[4-chloro-3-(trifluoromethyl)phenyl]methyl]acetamide | 2-[6-(1-tert-Butoxycarbonyl-4-piperidyl)-4-oxoquinazolin-3-yl]acetic acid (intermediate A-8, step E) and (4-chloro-3-(trifluoromethyl)phenyl)methanamine ([CAS RN 62039-92-3]) | [M + H]+ 521.4 |
| 164 | 2-[6-(1-Acetylpiperidin-4-yl)-4-oxoquinazolin-3-yl]-N-[(3,5-dichlorophenyl)methyl]acetamide | 2-[6-(1-tert-Butoxycarbonyl-4-piperidyl)-4-oxoquinazolin-3-yl]acetic acid (intermediate A-8, step E) and (3,5-dichlorophenyl)methanamine ([CAS RN 39989-43-0]) | [M + H]+ 487.3 |

Example 165

N-[(3,4-Dichlorophenyl)methyl]-N-methyl-2-[4-oxo-6-[1-(2-sulfamoylacetyl)piperidin-4-yl]quinazolin-3-yl]acetamide

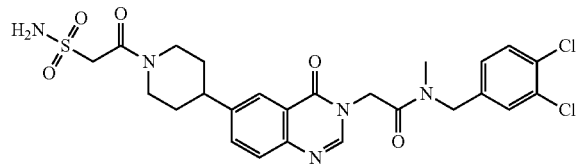 [SMILES: CN(Cc1ccc(Cl)c(Cl)c1)C(=O)Cn1cnc2ccc(C3CCN(C(=O)CS(N)(=O)=O)CC3)cc2c1=O]

[A] N-[(3,4-Dichlorophenyl)methyl]-N-methyl-2-(4-oxo-6-piperidin-4-ylquinazolin-3-yl)acetamide

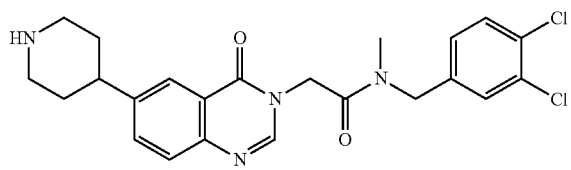 [SMILES: CN(Cc1ccc(Cl)c(Cl)c1)C(=O)Cn1cnc2ccc(C3CCNCC3)cc2c1=O]

To a solution of 2-[6-(1-tert-butoxycarbonyl-4-piperidyl)-4-oxoquinazolin-3-yl]acetic acid (intermediate A-8, step E) (2.03 g, 5.23 mmol) in DCM (50 mL) were added HATU (2.98 g, 7.84 mmol; [CAS RN 148893-10-1]) and DIPEA (2.74 mL, 15.7 mmol) under an atmosphere of nitrogen. Then, 1-(3,4-dichlorophenyl)-N-methylmethanamine (1.0 g, 5.23 mmol; [CAS RN 5635-67-6]) was added and the reaction mixture stirred at rt for 1 h. To the reaction mixture was added 4 M HCl in dioxane (15 mL) and stirring at rt continued overnight. The reaction mixture was set to pH 14 by addition of a solution of 2 M sodium hydroxide and the aq. phase extracted with DCM (3×200 mL). The combined organic phases were dried over MgSO4 and concentrated under reduced pressure. Purification by MPLC (20 g SiO2, Telos-cartridge) eluting with a gradient of 0 to 5% methanol-DCM provided the title compound as light brown solid (0.77 g, 32%). MS: 459.3 (M+H)+.

[B] N-[(3,4-Dichlorophenyl)methyl]-N-methyl-2-[4-oxo-6-[1-(2-sulfamoylacetyl)piperidin-4-yl]quinazolin-3-yl]acetamide

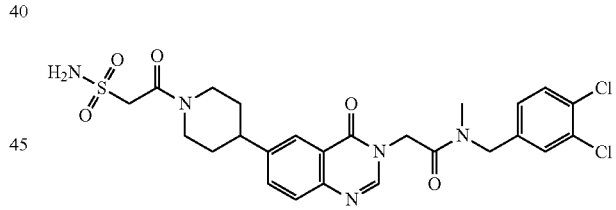

To a solution of N-[(3,4-dichlorophenyl)methyl]-N-methyl-2-(4-oxo-6-piperidin-4-ylquinazolin-3-yl)acetamide (50 mg, 0.11 mmol) in dry DMF (2 mL) were added HATU (62.1 mg, 0.16 mmol; [CAS RN 148893-10-1]) and DIPEA (150 µL, 0.86 mmol) under an atmosphere of nitrogen. Then, 2-sulfamoylacetic acid (23.9 mg, 0.16 mmol; [CAS RN 17551-00-7]) was added and the reaction mixture heated by mirowave irradiation to 100° C. for 10 min. Purification by preparative HPLC on reversed phase eluting with a gradient of acetonitrile-water provided the title compound as colorless oil (19 mg, 30%). MS: m/e=580.1 [M+H]+.

Examples 166 to 183

According to the procedure described for the synthesis of example 165 further examples were prepared from N-[(3,4-dichlorophenyl)methyl]-N-methyl-2-(4-oxo-6-piperidin-4-ylquinazolin-3-yl)acetamide (Example 165, step A) and the respective carboxylic acid as indicated in Table 15. The results are compiled in Table 15 and comprise examples 166 to 183.

TABLE 15

| No | Compound Name & Structure | Starting Materials | MS |
|---|---|---|---|
| 166 | N-[(3,4-Dichlorophenyl)methyl]-2-[6-[1-[2-(2-methoxyethoxy)acetyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 2-(2-methoxyethoxy)acetic acid ([CAS RN 16024-56-9]) | [M + H]+ 575.2 |
| 167 | N-[(3,4-Dichlorophenyl)methyl]-2-[6-[1-[(2R)-2-methoxypropanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (R)-2-methoxypropanoic acid ([CAS RN 23943-96-6]) | [M + H]+ 545.2 |
| 168 | N-[(3,4-Dichlorophenyl)methyl]-2-[6-[1-[(2S)-2-methoxypropanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (S)-2-methoxypropanoic acid ([CAS RN 23953-00-6]) | [M + H]+ 545.2 |
| 169 | N-[(3,4-Dichlorophenyl)methyl]-2-[6-[1-[(2R)-2-hydroxy-3-methylbutanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (R)-2-hydroxy-3-methylbutanoic acid ([CAS RN 17407-56-6]) | [M + H]+ 559.2 |
| 170 | N-[(3,4-Dichlorophenyl)methyl]-2-[6-[1-[(2S)-2-hydroxy-3-methylbutanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (S)-2-hydroxy-3-methylbutanoic acid ([CAS RN 17407-55-5]) | [M + H]+ 559.2 |

TABLE 15-continued

| No | Compound Name & Structure | Starting Materials | MS |
|---|---|---|---|
| 171 | N-[(3,4-Dichlorophenyl)methyl]-2-[6-[1-(2-methoxyacetyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 2-methoxyacetyl chloride ([CAS RN 38870-89-2]) | [M + H]$^+$ 531.1 |
| 172 | N-[(3,4-Dichlorophenyl)methyl]-2-[6-[1-(2-hydroxy-2-methylpropanoyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 2-hydroxy-2-methylpropanoic acid ([CAS RN 594-61-6]) | [M + H]$^+$ 545.2 |
| 173 | N-[(3,4-Dichlorophenyl)methyl]-2-[6-[1-(2-methoxypropanoyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 2-methoxypropanoic acid ([CAS RN 4324-37-2]) | [M + H]$^+$ 545.1 |
| 174 | N-[(3,4-Dichlorophenyl)methyl]-2-[6-[1-[(2R)-2-hydroxypropanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (R)-2-hydroxypropanoic acid ([CAS RN 10326-41-7]) | [M + H]$^+$ 531.1 |
| 175 | N-[(3,4-Dichlorophenyl)methyl]-2-[6-[1-[(2S)-2-hydroxypropanoyl]piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and (S)-2-hydroxypropanoic acid ([CAS RN 79-33-4]) | [M + H]$^+$ 531.1 |

TABLE 15-continued

| No | Compound Name & Structure | Starting Materials | MS |
|---|---|---|---|
| 176 | N-[(3,4-Dichlorophenyl)methyl]-2-[6-[1-(1-hydroxycyclobutanecarbonyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 1-hydroxycyclobutanecarboxylic acid ([CAS RN 41248-13-9]) | [M + H]$^+$ 557.1 |
| 177 | N-[(3,4-Dichlorophenyl)methyl]-2-[6-[1-(2,3-dihydroxypropanoyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 2,3-dihydroxypropanoic acid (40% in water) ([CAS RN 600-19-1]) | [M + H]$^+$ 547.1 |
| 178 | N-[(3,4-Dichlorophenyl)methyl]-2-[6-[1-(1,4-dioxane-2-carbonyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 1,4-dioxane-2-carboxylic acid ([CAS RN 89364-41-0]) | [M + H]$^+$ 573.1 |
| 179 | N-[(3,4-Dichlorophenyl)methyl]-2-[6-[1-(1-hydroxycyclopropanecarbonyl)piperidin-4-yl]-4-oxoquinazolin-3-yl]-N-methylacetamide | N-[(3,4-Dichlorophenyl)methyl]-N-methyl-2-(4-oxo-6-piperidin-4-ylquinazolin-3-yl)acetamide (Example 165, step A) and 1-hydroxycyclopropanecarboxylic acid ([CAS RN 17994-25-1]) | [M + H]$^+$ 543.1 |
| 180 | N-[(3,4-Dichlorophenyl)methyl]-N-methyl-2-[4-oxo-6-[1-(oxolane-2-carbonyl)piperidin-4-yl]quinazolin-3-yl]acetamide | N-[(3,4-Dichlorophenyl)methyl]-N-methyl-2-(4-oxo-6-piperidin-4-ylquinazolin-3-yl)acetamide (Example 165, step A) and tetrahydrofuran-2-carboxylic acid ([CAS RN 16874-33-2]) | [M + H]$^+$ 557.1 |

TABLE 15-continued

| No | Compound Name & Structure | Starting Materials | MS |
|---|---|---|---|
| 181 | N-[(3,4-Dichlorophenyl)methyl]-N-methyl-2-[6-[1-(2-methyloxolane-2-carbonyl)piperidin-4-yl]-4-oxoquinazolin-3-yl]acetamide | N-[(3,4-Dichlorophenyl)methyl]-N-methyl-2-(4-oxo-6-piperidin-4-ylquinazolin-3-yl)acetamide (Example 165, step A) and 2-methyltetrahydrofuran-2-carboxylic acid ([CAS RN 61449-65-8]) | [M + H]+ 571.2 |
| 182 | N-[(3,4-Dichlorophenyl)methyl]-N-methyl-2-[4-oxo-6-[1-(oxolane-3-carbonyl)piperidin-4-yl]quinazolin-3-yl]acetamide | N-[(3,4-Dichlorophenyl)methyl]-N-methyl-2-(4-oxo-6-piperidin-4-ylquinazolin-3-yl)acetamide (Example 165, step A) and tetrahydrofuran-3-carboxylic acid ([CAS RN 89364-31-8]) | [M + H]+ 557.1 |
| 183 | N-[(3,4-Dichlorophenyl)methyl]-N-methyl-2-[6-[1-(1,3-oxazole-5-carbonyl)piperidin-4-yl]-4-oxoquinazolin-3-yl]acetamide | N-[(3,4-Dichlorophenyl)methyl]-N-methyl-2-(4-oxo-6-piperidin-4-ylquinazolin-3-yl)acetamide (Example 165, step A) and oxazole-5-carboxylic acid ([CAS RN 118994-90-4]) | [M + H]+ 554.2 |

Example 184

2-[6-(1-Acetyl-4-hydroxypiperidin-4-yl)-4-oxoquinazolin-3-yl]-N-[(3,4-dichlorophenyl)methyl]-N-methylacetamide

[A] tert-Butyl 4-hydroxy-4-(4-oxo-3H-quinazolin-6-yl)piperidine-1-carboxylate

To a solution of 6-bromo-3,4-dihydroquinazolin-4-one (100 mg, 0.44 mmol; [CAS RN 32084-59-6]) in THF (12.5 mL) at −78° C. was added MeLi (0.2 mL, 0.58 mmol) dropwise over 5 min. After 10 min, 1.6 M n-BuLi in hexane (1.8 mL, 1.33 mmol) was added dropwise over 10 min and stirring continued at −78° C. for 1 h. A solution of tert-butyl 4-oxopiperidine-1-carboxylate (900 mg, 0.44 mmol) in THF (2.5 mL) was added dropwise over 10 min at −78° C. and stirring continued for 2 h. The reaction mixture was quenched by addition of a sat. solution of NH₄Cl (25 mL) and the aq. phase extracted with EtOAc (3×10 mL). The combined organic phases were dried over anhydrous Na₂SO₄ and concentrated under reduced pressure. The crude reaction product was purified by column chromatography (100-200 mesh size silica gel) using 80% EtOAc-hexane as eluent affording the title compound as light yellow solid (600 mg, 39%). MS: 346.3 (M+H)⁺.

[B] tert-Butyl 4-hydroxy-4-[3-(2-methoxy-2-oxo-ethyl)-4-oxoquinazolin-6-yl]piperidine-1-carboxylate

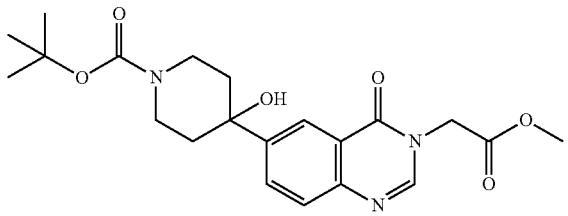 [SMILES: COC(=O)Cn1cnc2ccc(C3(O)CCN(C(=O)OC(C)(C)C)CC3)cc2c1=O]

A suspension of tert-butyl 4-hydroxy-4-(4-oxo-3H-quinazolin-6-yl)piperidine-1-carboxylate (2.0 g, 5.80 mmol), K₂CO₃ (1.60 g, 11.59 mmol) and methyl bromo acetate (1.15 g, 7.54 mmol) in CH₃CN (25 mL) was stirred at reflux temperature for 6 h. The reaction mixture was cooled to rt and volatiles removed under reduced pressure. The crude reaction product was diluted with EtOAc (100 mL) and washed with H₂O (2×50 mL) and a sat. solution of NaCl (50 mL). The combined organic phases were dried over anhydrous Na₂SO₄ and concentrated under reduced pressure to provide the title compound as brown solid (1.60 g, 66%), which was used in the consecutive reaction step without further purification. MS: 417.9 (M+H)⁺.

[C] 2-[6-[4-Hydroxy-1-[(2-methylpropan-2-yl)oxycarbonyl]piperidin-4-yl]-4-oxoquinazolin-3-yl]acetic acid

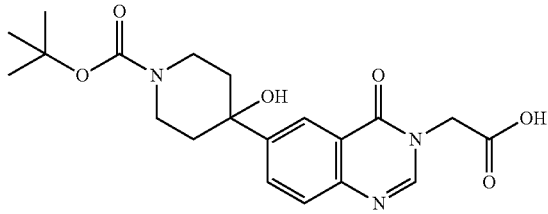 [SMILES: CC(C)(C)OC(=O)N1CCC(O)(c2ccc3ncn(CC(=O)O)c(=O)c3c2)CC1]

To a cooled solution of tert-butyl 4-hydroxy-4-[3-(2-methoxy-2-oxoethyl)-4-oxoquinazolin-6-yl]piperidine-1-carboxylate (1.40 g, 3.36 mmol) in THF (20 mL) at 0° C. was added a solution of LiOH.H₂O (420 mg, 10.07 mmol) in H₂O (2.5 mL) dropwise over 5 min, followed by stirring at rt for 3 h. The crude reaction mixture was concentrated under reduced pressure and the obtained residue diluted with H₂O (25 mL) and washed with diethyl ether. The aq. phase was neutralized by addition of a 1 M solution of HCl and then concentrated under reduced pressure to afford the title compound as brown solid (1.20 g, crude). The crude material was used in the consecutive reaction step without further purification. MS: 404.1 (M+H)⁺.

[D] tert-Butyl 4-[3-[2-[(3,4-dichlorophenyl)methyl-methylamino]-2-oxoethyl]-4-oxoquinazolin-6-yl]-4-hydroxypiperidine-1-carboxylate

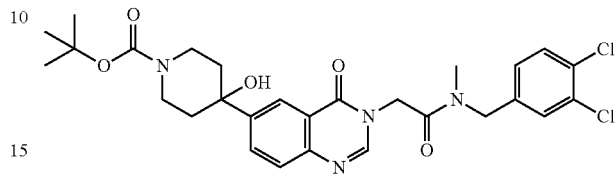

To a solution of 2-[6-[4-hydroxy-1-[(2-methylpropan-2-yl)oxycarbonyl]piperidin-4-yl]-4-oxoquinazolin-3-yl]acetic acid (1.20 g, 2.98 mmol) and 1-(3,4-dichlorophenyl)-N-methylmethanamine (622 mg, 3.28 mmol; [CAS RN 5635-67-6]) in DMF (20 mL) was added TBTU (1.19 g, 3.72 mmol; [CAS RN 125700-67-6]) and N-methylmorpholine (0.61 mL, 5.96 mmol) under an atmosphere of nitrogen. After stirring of the reaction mixture at rt for 12 h, the solvent was removed under reduced pressure and the obtained residue diluted with EtOAc (100 mL), followed by washing with H₂O (3×50 mL) and a sat. solution of NaCl (2×50 mL). The combined organic phases were dried over anhydrous Na₂SO₄ and concentrated under reduced pressure. The crude reaction product was purified by column chromatography (100-200 mesh size silica gel) using 80% EtOAc-hexane as eluent affording the title compound as off white solid (800 mg, 42% over two steps). MS: 575.1 (M+H)⁺.

[E] 2-[6-(1-Acetyl-4-hydroxypiperidin-4-yl)-4-oxoquinazolin-3-yl]-N-[(3,4-di chlorophenyl)methyl]-N-methylacetamide

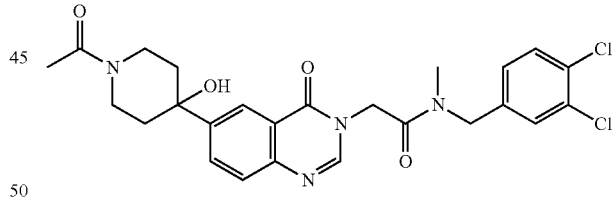

To a stirred solution of tert-butyl 4-[3-[2-[(3,4-dichlorophenyl)methyl-methylamino]-2-oxoethyl]-4-oxoquinazolin-6-yl]-4-hydroxypiperidine-1-carboxylate (500 mg, 0.87 mmol) in dioxane (10 mL) was added 4 M HCl in dioxane (5 mL) at 0° C. and the reaction mixture stirred at rt for 4 h. The reaction mixture was concentrated under reduced pressure and the crude material purified by trituration with TBME (2×10 mL). To the precipitate was added DCM (10 mL) and Et₃N (0.35 mL, 0.25 mmol) at 0° C., followed by a solution of acetyl chloride (0.09 mL, 1.27 mmol) in DCM (5 mL) dropwise over 5 min. After stirring of the reaction mixture at rt for 6 h, DCM (10 mL) was added and the organic phase washed with H₂O (10 mL) and a sat. solution of NaCl (10 mL). The combined organic phases were dried over anhydrous Na₂SO₄ and concentrated under reduced pressure. The crude reaction product was purified by column chromatography (100-200 mesh size silica gel) eluting with a gradient of 1:50 to 1:40 methanol-EtOAc affording the title compound as off white solid (150 mg, 33% over two steps). MS: 517.2 (M+H)+.

Example 185

2-[6-(1-Acetyl-4-hydroxypiperidin-4-yl)-4-oxoquinazolin-3-yl]-N-[(3-chloro-4-cyanophenyl)methyl]-N-methylacetamide

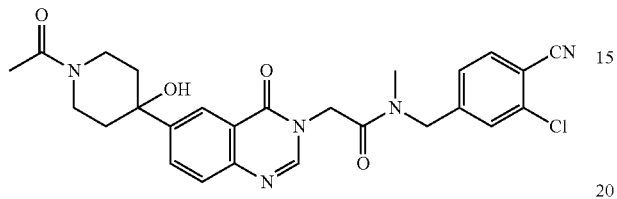

The title compound was prepared in analogy to the procedure described for the preparation of 2-[6-(1-acetyl-4-hydroxypiperidin-4-yl)-4-oxoquinazolin-3-yl]-N-[(3,4-dichlorophenyl)methyl]-N-methylacetamide (example 184), replacing in step D 1-(3,4-dichlorophenyl)-N-methylmethanamine [CAS RN 5635-67-6] with 2-chloro-4-(methylaminomethyl)benzonitrile hydrochloride (example 56, step A). Purification by column chromatography (100-200 mesh size silica gel) eluting with a gradient of 1:50 to 1:40 methanol-EtOAc affording the title compound as off white solid (80 mg, 34% over last two steps). MS: 508.2 (M+H)+.

Example 186

[2-[4-[3-[2-[(3-Chloro-4-cyanophenyl)methyl-methylamino]-2-oxoethyl]-4-oxoquinazolin-6-yl]piperidin-1-yl]-2-oxoethyl]nitrate

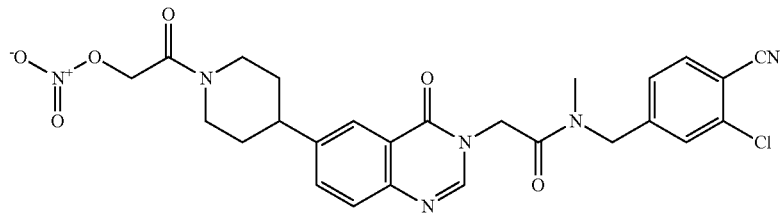

[A] 2-[6-[1-(2-Bromoacetyl)piperidin-4-yl]-4-oxoquinazolin-3-yl]-N-[(3-chloro-4-cyanophenyl)methyl]-N-methylacetamide

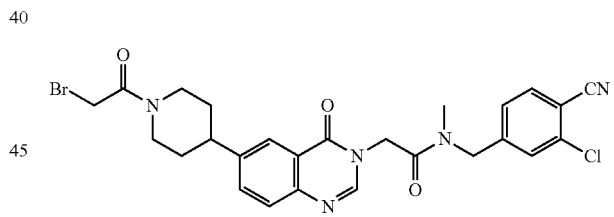

To a solution of N-[(3-chloro-4-cyanophenyl)methyl]-N-methyl-2-(4-oxo-6-piperidin-4-ylquinazolin-3-yl)acetamide (intermediate A-9) (25 mg, 0.056 mmol) in DCM (2.5 mL) were added Et$_3$N (23 µL, 0.17 mmol) under an atmosphere of nitrogen. Then, a solution of bromo acetyl chloride (6 µL, 0.084 mmol) in DCM (0.5 mL) at 0° C. was added and the reaction mixture stirred for 1 h. The solvent was removed under reduced pressure and the obtained residue diluted with H$_2$O (5 mL) and extracted with DCM (2×10 mL). The combined organic phases were dried over anhydrous Na$_2$SO$_4$ and concentrated under reduced pressure. Purification by prep. TLC (Merck silica TLC glass plates, 20×20 cm) eluting with a mixture of heptane-EtOAc (10:1) provided the title compound as off white solid (15 mg, 44%). MS: m/e=571.0 [M+H]+.

[B] [2-[4-[3-[2-[(3-Chloro-4-cyanophenyl)methyl-methylamino]-2-oxoethyl]-4-oxoquinazolin-6-yl]piperidin-1-yl]-2-oxoethyl]nitrate

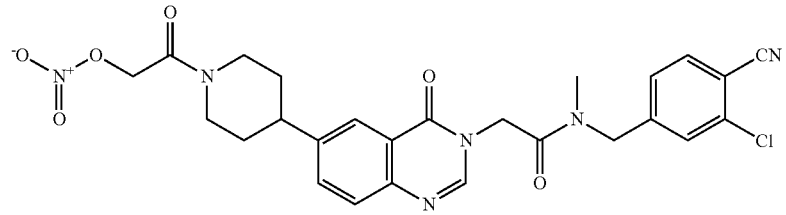

To a solution of 2-[6-[1-(2-bromoacetyl)piperidin-4-yl]-4-oxoquinazolin-3-yl]-N-[(3-chloro-4-cyanophenyl)methyl]-N-methylacetamide (0.18 g, 0.30 mmol) in acetonitrile (10 mL) was added silver nitrate (0.20 g, 0.11 mmol) and the reation mixture was stirred at 70° C. for 24 h under an atmosphere of nitrogen. Evaporation of the solvent and purification by preparative HPLC on reversed phase eluting with a gradient of acetonitrile-water provided the title compound as off white solid (30 mg, 18%). MS: m/e=552.6 [M+H]$^+$.

Example 187

2-[6-(1-Acetylpiperidin-4-yl)-8-fluoro-4-oxoquinazolin-3-yl]-N-[(3-chloro-4-cyanophenyl)methyl]-N-methylacetamide

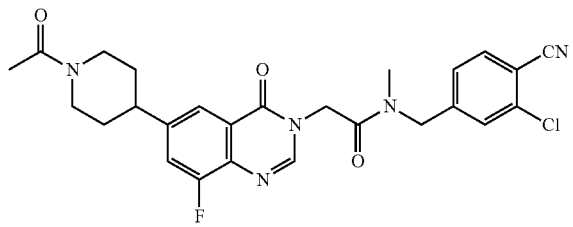 [SMILES: CC(=O)N1CCC(c2cc(F)c3ncn(CC(=O)N(C)Cc4ccc(C#N)c(Cl)c4)c(=O)c3c2)CC1]

[A] 6-Bromo-8-fluoro-3H-quinazolin-4-one

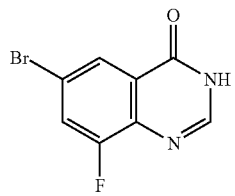 [SMILES: O=c1[nH]cnc2c(F)cc(Br)cc12]

A suspension of 2-amino-5-bromo-3-fluorobenzoic acid (1.0 g, 4.27 mmol; [CAS RN 874784-14-2]) and formamidine acetate (0.89 g, 8.55 mmol; [CAS RN 3473-63-0]) in 2-methoxyethanol (12 mL) was heated under microwave irradiation to 150° C. for 45 min. The formed precipitate was filtered off, the crystalls washed with a small amount of EtOH and dried under reduced pressure. The title compound was isolated as white powder (0.80 g, 77%). MS: m/e=245.0 [M+H]$^+$.

[B] Methyl 2-(6-bromo-8-fluoro-4-oxoquinazolin-3-yl)acetate

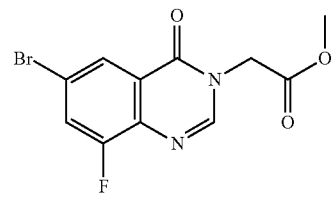 [SMILES: COC(=O)Cn1cnc2c(F)cc(Br)cc2c1=O]

A suspension of 6-bromo-8-fluoro-3H-quinazolin-4-one (0.8 g, 3.29 mmol), methyl 2-bromoacetate (1.01 g, 0.61 mL, 6.58 mmol; [CAS RN 96-32-2]) and potassium carbonate (1.36 g, 9.88 mmol) in DMF (12 mL) was heated under microwave irradiation to 80° C. for 30 min. The crude reaction product was purified by column chromatography (100-200 mesh size silica gel) eluting with a gradient of 0:1 to 1:0 EtOAc-hexane affording the title compound as light yellow solid (0.67 g, 64%). MS: 317.0 (M+H)$^+$.

[C] 2-(6-Bromo-8-fluoro-4-oxoquinazolin-3-yl)-N-[(3-chloro-4-cyanophenyl)methyl]-N-methylacetamide

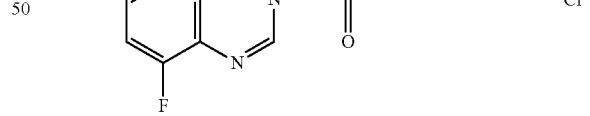

To a solution of methyl 2-(6-bromo-8-fluoro-4-oxoquinazolin-3-yl)acetate (0.65 g, 2.06 mmol) and 2-chloro-4-(methylaminomethyl)benzonitrile hydrochloride (example 56, step A) (0.47 g, 2.17 mmol) in THF (10 mL) was added bis(trimethylaluminium)-1,4-diazabicyclo[2.2.2]octane adduct (0.64 g, 2.48 mmol; [CAS RN 137203-34-0]) and the reaction mixture heated under microwave irradiation to 130° C. for 30 min under an atmosphere of Ar. The crude reaction product was purified by column chromatography (100-200 mesh size silica gel) eluting with a gradient of 0:1 to 1:0 EtOAc-hexane affording the title compound as light yellow solid (0.54 g, 47%). MS: 465.1 (M+H)$^+$.

[D] tert-Butyl 4-[3-[2-[(3-chloro-4-cyanophenyl)methyl-methylamino]-2-oxoethyl]-8-fluoro-4-oxoquinazolin-6-yl]-3,6-dihydro-2H-pyridine-1-carboxylate

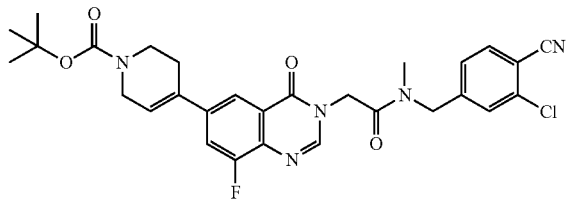 [SMILES: CN(Cc1ccc(C#N)c(Cl)c1)C(=O)Cn1cnc2c(F)cc(C3=CCN(C(=O)OC(C)(C)C)CC3)cc2c1=O]

A solution of 2-(6-bromo-8-fluoro-4-oxoquinazolin-3-yl)-N-[(3-chloro-4-cyanophenyl)methyl]-N-methylacetamide (0.54 g, 0.97 mmol), tert-butyl 4-(4,4,5,5-tetramethyl-1,3,2-dioxaborolan-2-yl)-5,6-dihydropyridine-1(2H)-carboxylate (0.30 g, 0.97 mmol; [CAS RN 286961-14-6]), triphenylphosphine (51 mg, 0.19 mmol; CAS RN 603-35-0]) and tripotassium phosphate (0.21 g, 0.97 mmol; [CAS RN 7778-53-2]) in a mixture of water (2.5 mL) and 1,2-diethoxyethan (10 mL) was degassed by Ar by sonication for 10 min. Finally, Pd(OAc)$_2$ (22 mg, 0.097 mmol; [CAS RN 3375-31-3]) was added and the reaction mixture heated to 90° C. for 90 min under an atmosphere of Ar. The reaction mixture was evaporated under reduced pressure and then purified by column chromatography (100-200 mesh size silica gel) eluting with a gradient of 0:1 to 1:0 EtOAc-hexane affording the title compound as light yellow solid (0.40 g, 62%). MS: 568.4 (M+H)$^+$.

[E] N-[(3-Chloro-4-cyanophenyl)methyl]-2-(8-fluoro-4-oxo-6-piperidin-4-ylquinazolin-3-yl)-N-methylacetamide

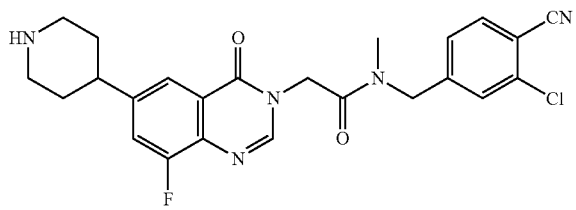 [SMILES: CN(Cc1ccc(C#N)c(Cl)c1)C(=O)Cn1cnc2c(F)cc(C3CCNCC3)cc2c1=O]

To a degassed solution of tert-butyl 4-[3-[2-[(3-chloro-4-cyanophenyl)methyl-methyl amino]-2-oxoethyl]-8-fluoro-4-oxoquinazolin-6-yl]-3,6-dihydro-2H-pyridine-1-carboxylate (0.40 g, 0.60 mmol) in MeOH (10 mL) was added 20% Pd(OH)$_2$/C (0.042 g, 0.060 mmol; [CAS RN 12135-22-7]) and the reaction mixture stirred under hydrogen (atmospheric pressure) at rt for 2 h. The reaction mixture was filtered through Celite® and the organic phase concentrated in vacuo. The residue was redissolved in dioxane (5 mL), 4 M HCl in dioxane (5 mL) was added and the reaction mixture stirred at rt for 2 h. The reaction mixture was set to pH 14 by addition of a solution of 2 M sodium hydroxide and the aq. phase extracted with DCM (3×200 mL). The combined organic phases were dried over MgSO$_4$ and concentrated under reduced pressure providing the title compound as light brown solid (0.22 g, 37%; 48% purity according to LC-MS). MS: 468.3 (M+H)$^+$.

[F] 2-[6-(1-Acetylpiperidin-4-yl)-8-fluoro-4-oxoquinazolin-3-yl]-N-[(3-chloro-4-cyanophenyl)methyl]-N-methylacetamide

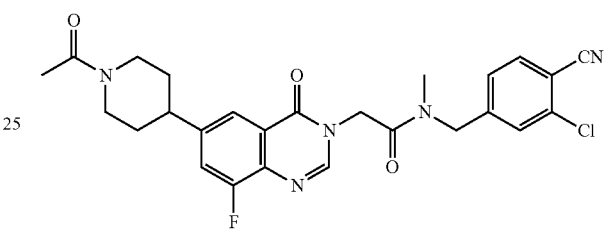

To a solution of N-[(3-chloro-4-cyanophenyl)methyl]-2-(8-fluoro-4-oxo-6-piperidin-4-ylquinazolin-3-yl)-N-methylacetamide (108 mg, 0.11 mmol; 48% purity) in dry DMF (2 mL) were added (benzotriazol-1-yloxy)tripyrrolidinophosphonium hexafluorophosphate (69.4 mg, 0.13 mmol; PyBOP; [CAS RN 128625-52-5]) and DIPEA (97 μL, 0.56 mmol) under an atmosphere of nitrogen. Then, acetic acid (8.0 mg, 0.13 mmol) was added and the reaction mixture stirred at rt overnight. Purification by preparative HPLC on reversed phase eluting with a gradient of acetonitrile-water provided the title compound as off-white solid (4.4 mg, 8%). MS: m/e=510.4 [M+H]$^+$.

Example 188

N-[(3-Chloro-4-cyanophenyl)methyl]-2-[8-fluoro-6-[1-(3-methoxypropanoyl)piperidin-4-yl]-4-oxoquinazolin-3-yl]-N-methylacetamide

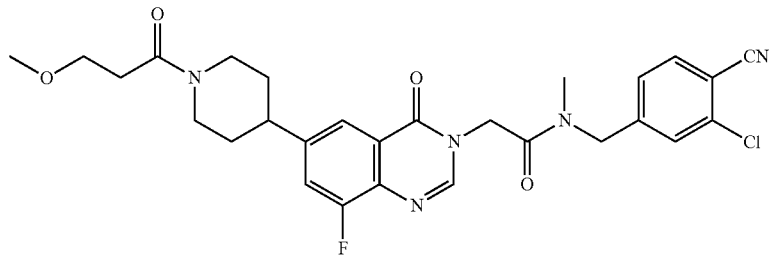 [SMILES: COCCC(=O)N1CCC(c2cc(F)c3ncn(CC(=O)N(C)Cc4ccc(C#N)c(Cl)c4)c(=O)c3c2)CC1]

The title compound was prepared in analogy to the procedure described for the preparation of 2-[6-(1-acetylpiperidin-4-yl)-8-fluoro-4-oxoquinazolin-3-yl]-N-[(3-chloro-4-cyanophenyl)methyl]-N-methylacetamide (example 187), replacing in step F acetic acid with 3-methoxypropanoic acid ([CAS RN 2544-06-1]). Purification by preparative HPLC on reversed phase eluting with a gradient of acetonitrile-water provided the title compound as off-white solid (6.6 mg, 11%). MS: m/e=554.4 [M+H]+.

Example 189

2-[6-(1-Acetylpiperidin-4-yl)-4-oxopyrido[3,4-d]pyrimidin-3-yl]-N-[(3-chloro-4-cyanophenyl)methyl]-N-methylacetamide

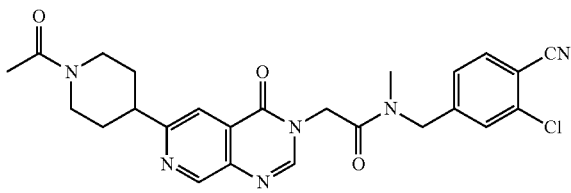

The title compound was prepared in analogy to the procedure described for the preparation of 2-[6-(1-acetylpiperidin-4-yl)-8-fluoro-4-oxoquinazolin-3-yl]-N-[(3-chloro-4-cyanophenyl)methyl]-N-methylacetamide (example 187), replacing in step A 2-amino-5-bromo-3-fluorobenzoic acid with 5-amino-2-bromopyridine-4-carboxylic acid ([CAS RN 1242336-80-6]). Purification by preparative HPLC on reversed phase eluting with a gradient of acetonitrile-water provided the title compound as white solid (8.1 mg, 15%). MS: m/e=493.4 [M+H]+.

Example 190

N-[(3-Chloro-4-cyanophenyl)methyl]-2-[6-[1-(3-methoxypropanoyl)piperidin-4-yl]-4-oxopyrido[3,4-d]pyrimidin-3-yl]-N-methylacetamide

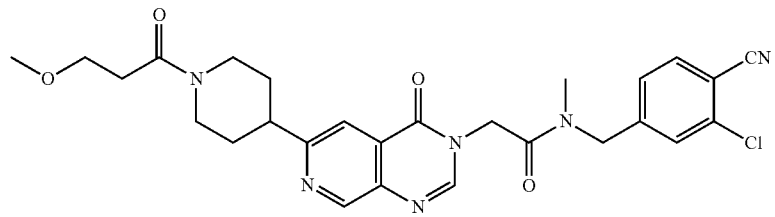 [SMILES: COCCC(=O)N1CCC(c2cc3c(=O)n(CC(=O)N(C)Cc4ccc(C#N)c(Cl)c4)cnc3cn2)CC1]

The title compound was prepared in analogy to the procedure described for the preparation of 2-[6-(1-acetylpiperidin-4-yl)-4-oxopyrido[3,4-d]pyrimidin-3-yl]-N-[(3-chloro-4-cyanophenyl)methyl]-N-methylacetamide (example 189), replacing in step F acetic acid with 3-methoxypropanoic acid ([CAS RN 2544-06-1]). Purification by preparative HPLC on reversed phase eluting with a gradient of acetonitrile-water provided the title compound as white solid (10 mg, 17%). MS: m/e=537.4 [M+H]+.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I)

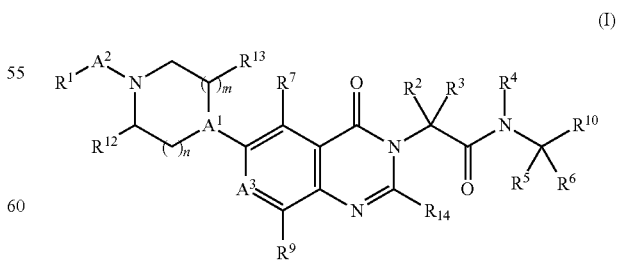

(I) wherein $R^1$ is hydroxycycloalkyl, alkoxy, haloalkoxy, alkoxyalkoxyalkyl, alkoxyalkyl, haloalkoxyalkyl, alkyl, haloalkyl, alkyl sulfonyl, haloalkyl sulfonyl, aminosulfonylalkyl, cyanoalkyl, nitratealkyl, substituted cycloalkyl, substituted cycloalkylalkyl, hydroxyalkyl, dihydroxyalkyl, substituted heteroaryl, substituted heterocycloalkyl or substituted aryl, wherein substituted cycloalkyl, substituted cycloalkylcycloalkylalkyl, substituted heteroaryl, substituted heterocycloalkyl and substituted aryl are substituted with one to three substituents selected from H, amino, alkyl, haloalkyl, alkoxy, haloalkoxy, alkylcarbonyl, carboxy, halogen and cyano;

$R^2$ and $R^3$ are independently selected from H, alkyl and cycloalkyl;

or $R^2$ and $R^3$ together with the carbon to which they are attached form a cycloalkyl;

$A^1$ is —CH—, —C(OH)— or —N—;

$A^2$ is —C(O)—, —C(O)CH$_2$—, —CH$_2$—, —NR$^{11}$C(O)—, —NR$^{11}$C(O)CH$_2$—, or —S(O)$_2$—;

$A^3$ is —CR$^8$— or —N—;

one of $R^4$ and $R^5$ is H or alkyl and the other is H, alkoxyalkyl, alkoxycarbonylalkyl, haloalkoxycarbonylalkyl, alkyl, haloalkyl, carboxyalkyl, cycloalkyl or substituted aminocarbonylalkyl, wherein substituted aminocarbonylalkyl is substituted on the nitrogen atom by two substituents independently selected from H, alkyl, cycloalkyl and substituted phenyl, wherein substituted phenyl is substituted with one to three substituents independently selected from H, alkyl, haloalkyl and cycloalkyl;

or $R^4$ and $R^5$ together with the nitrogen and carbon atoms to which they are attached form a heterocycloalkyl;

$R^6$ is H or alkyl;

$R^7$, $R^8$ and $R^9$ are independently H, alkyl, cycloalkyl, halogen or cyano;

$R^{10}$ is substituted aryl or substituted heteroaryl, wherein substituted aryl and substituted heteroaryl are substituted with one to three substituents selected from H, alkyl, haloalkyl, alkoxy, haloalkoxy, halogen, nitro, cyano, alkylsulfonyl, haloalkylsulfonyl and pentafluoro-$\lambda^6$-sulfanyl;

$R^{11}$ is H, alkyl or cycloalkyl;

$R^{12}$ and $R^{13}$ are both H or $R^{12}$ and $R^{13}$ together form —(CH$_2$)$_p$—;

$R^{14}$ is H, alkyl or hydroxy; and n, m and p are independently zero, 1 or 2;

or a pharmaceutically acceptable salt thereof

2. A compound according to claim 1, wherein $R^1$ is alkoxy, haloalkoxy, alkoxyalkyl, haloalkoxyalkyl, alkyl, haloalkyl, alkyl sulfonyl, haloalkylsulfonyl, aminosulfonylalkyl, substituted cycloalkyl, substituted cycloalkylalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, haloalkoxy, alkylcarbonyl, carboxy, halogen and cyano;

$R^2$ and $R^3$ are independently selected from H, alkyl and cycloalkyl;

or $R^2$ and $R^3$ together with the carbon to which they are attached form a cycloalkyl;

$A^1$ is —CH— or —N—;

$A^2$ is —C(O)—, —C(O)CH$_2$—, —CH$_2$—, —NR$^{11}$C(O)—, —NR$^{11}$C(O)CH$_2$—, or —S(O)$_2$—;

one of $R^4$ and $R^5$ is H or alkyl and the other is H, alkoxycarbonylalkyl, haloalkoxycarbonylalkyl, alkyl, haloalkyl, carboxyalkyl, cycloalkyl or substituted aminocarbonylalkyl, wherein substituted aminocarbonylalkyl is substituted on the nitrogen atom by two substituents independently selected from H, alkyl, cycloalkyl and substituted phenyl, wherein substituted phenyl is substituted with one to three substituents independently selected from H, alkyl, haloalkyl and cycloalkyl;

or $R^4$ and $R^5$ together with the nitrogen and carbon atoms to which they are attached form a heterocycloalkyl;

$R^6$ is H or alkyl;

$R^7$, $R^8$ and $R^9$ are independently H, alkyl, cycloalkyl, halogen or cyano;

$R^{10}$ is substituted aryl or substituted heteroaryl, wherein substituted aryl and substituted heteroaryl are substituted with one to three substituents selected from H, alkyl, haloalkyl, alkoxy, haloalkoxy, halogen, nitro, cyano, alkylsulfonyl, haloalkylsulfonyl and pentafluoro-$\lambda^6$-sulfanyl;

$R^{11}$ is H, alkyl or cycloalkyl;

$R^{12}$ and $R^{13}$ are both H or $R^{12}$ and $R^{13}$ together form —(CH$_2$)$_p$—;

$R^{14}$ is H, alkyl or hydroxy; and n, m and p are independently zero, 1 or 2;

or a pharmaceutically acceptable salt thereof

3. A compound according to claim 1, or a pharmaceutically acceptable salt thereof, wherein $R^1$ is hydroxycycloalkyl, alkoxy, alkoxyalkoxyalkyl, alkoxyalkyl, alkyl, alkyl sulfonyl, aminosulfonylalkyl, cyanoalkyl, nitratealkyl, substituted cycloalkyl, substituted cycloalkylalkyl, haloalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, alkylcarbonyl, carboxy and halogen.

4. A compound according to claim 1, or a pharmaceutically acceptable salt thereof, wherein $R^1$ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted heteroaryl, substituted heterocycloalkyl or substituted aryl, wherein substituted cycloalkyl, substituted cycloalkylalkyl, substituted heteroaryl, substituted heterocycloalkyl and substituted aryl are substituted with one to three substituents selected from H, amino, alkyl, haloalkyl, alkoxy, alkylcarbonyl, carboxy and halogen.

5. A compound according to claim 1, or a pharmaceutically acceptable salt thereof, wherein $R^1$ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted dioxanyl, substituted azetidinyl, substituted morpholinyl or substituted phenyl, wherein substituted cycloalkyl, substituted cycloalkylalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted dioxanyl, substituted azetidinyl, substituted morpholinyl and substituted phenyl are substituted with one to three substituents selected from H, amino, alkyl, haloalkyl, alkoxy, alkylcarbonyl, carboxy and halogen.

6. A compound according to claim 1, or a pharmaceutically acceptable salt thereof, wherein $R^1$ is alkoxy, alkoxyalkyl, alkyl, alkylsulfonyl, aminosulfonylalkyl, substituted cycloalkyl, substituted cycloalkylalkyl, haloalkyl, hydroxyalkyl, dihydroxyalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted azetidinyl, substituted morpholinyl or substituted phenyl, wherein substituted cycloalkyl, substituted cycloalkylalkyl, substituted furanyl, substituted oxazolyl, substituted isoxazolyl, substituted imidazolyl, substituted pyrrolyl, substituted pyridinyl, substituted oxetanyl, substituted tetrahydrofuranyl, substituted tetrahydropyranyl, substituted azetidinyl, substituted morpholinyl and substituted phenyl are substituted with one to three substituents selected from H, amino, alkyl, haloalkyl, alkoxy, alkylcarbonyl, carboxy and halogen.

7. A compound according to claim 1, or a pharmaceutically acceptable salt thereof, wherein $R^1$ is alkoxyalkyl, alkyl, substituted cycloalkyl or substituted cycloalkylalkyl, wherein substituted cycloalkyl and substituted cycloalkylalkyl are substituted with one to three substituents selected from H, haloalkyl and halogen.

8. A compound according to claim 1, or a pharmaceutically acceptable salt thereof, wherein $R^1$ is alkoxyalkyl or alkyl.

9. A compound according to claim 1, or a pharmaceutically acceptable salt thereof, wherein $R^1$ is alkyl.

10. A compound according to claim 1, or a pharmaceutically acceptable salt thereof, wherein $A^1$ is —CH— or —N—.

11. A compound according to claim 1, or a pharmaceutically acceptable salt thereof, wherein $R^2$ is H or alkyl.

12. A compound according to claim 1, or a pharmaceutically acceptable salt thereof, wherein $R^3$ is H.

13. A compound according to claim 1, or a pharmaceutically acceptable salt thereof, wherein le and $R^3$ are H.

14. A compound according to claim 1, or a pharmaceutically acceptable salt thereof, wherein $R^4$ is H, alkoxycarbonylalkyl, alkyl, carboxyalkyl, cycloalkyl or aminocarbonylalkyl substituted on the nitrogen atom by one H and one alkyl.

15. A compound according to claim 1, or a pharmaceutically acceptable salt thereof, wherein $R^5$ is H, alkoxyalkyl, alkyl or aminocarbonylalkyl substituted on the nitrogen atom by two substituents independently selected from H and alkyl.

16. A compound according to claim 1, or a pharmaceutically acceptable salt thereof, wherein $R^5$ is H, alkyl or aminocarbonylalkyl substituted on the nitrogen atom by two substituents independently selected from H and alkyl.

17. A compound according to claim 1, or a pharmaceutically acceptable salt thereof, wherein $R^4$ is H or alkyl; and $R^5$ is H.

18. A compound according to claim 1, or a pharmaceutically acceptable salt thereof, wherein $R^6$ is H.

19. A compound according to claim 1, or a pharmaceutically acceptable salt thereof, wherein $R^7$, $R^8$ and $R^9$ are H.

20. A compound according to claim 1, or a pharmaceutically acceptable salt thereof, wherein $R^{10}$ is substituted phenyl, substituted benzodioxolyl, substituted isoxazolyl, substituted oxadiazolyl or substituted pyridinyl, wherein substituted phenyl, substituted benzodioxolyl, substituted isoxazolyl, substituted oxadiazolyl and substituted pyridinyl are substituted with one to three substituents selected from H, alkyl, haloalkyl, alkoxy, haloalkoxy, halogen, nitro, cyano, alkylsulfonyl and pentafluoro-$\lambda^6$-sulfanyl.

21. A compound according to claim 1, or a pharmaceutically acceptable salt thereof, wherein $R^{10}$ is phenyl substituted with one to three substituents selected from halogen and cyano.

22. A compound according to claim 1, or a pharmaceutically acceptable salt thereof, wherein $R^{11}$ is H or alkyl.

23. A compound according to claim 1, or a pharmaceutically acceptable salt thereof, wherein n is 1; and m is 1 or 2.

24. A compound according to claim 1, or a pharmaceutically acceptable salt thereof, wherein n and m are 1.

25. A compound according to claim 1, or a pharmaceutically acceptable salt thereof, wherein p is 1.

26. A compound according to claim 1, or a pharmaceutically acceptable salt thereof, wherein $R^{12}$ and $R^{13}$ are both H.

27. A compound according to claim 1, or a pharmaceutically acceptable salt thereof, wherein $R^{14}$ is H.

28. A compound according to claim 1, or a pharmaceutically acceptable salt thereof, wherein $A^2$ is —C(O)—.

29. A compound according to claim 1, or a pharmaceutically acceptable salt thereof, wherein $A^3$ is —$CR^8$—.

30. A compound according to claim 1, wherein $R^1$ is alkoxyalkyl or alkyl;
$R^2$, $R^3$, $R^5$, $R^6$, $R^7$, $R^8$, $R^9$, $R^{12}$, $R^{13}$ and $R^{14}$ are all H;
$A^1$ is —CH— or —N—;
$A^2$ is -C(O)-;
$R^4$ is H or alkyl;
$R^{10}$ is phenyl substituted with one to three substituents selected from halogen and cyano; and
n and m are 1;
or a pharmaceutically acceptable salt thereof 31. A compound according to claim 1, selected from
(3R)-3-[[2-[6-(4-acetylpiperazin-1-yl)-4-oxoquinazolin-3-yl]acetyl]amino]-3-(4-chlorophenyl)-N-methylpropanamide;
(3R)-3-[[2-[6-(4-acetylpiperazin-1-yl)-4-oxoquinazolin-3-yl]acetyl]amino]-3-(4-chlorophenyl)-N,N-dimethylpropanamide;
(3R)-3-[[2-[6-(4-acetylpiperazin-1-yl)-4-oxoquinazolin-3-yl]acetyl]amino]-3-(4-chlorophenyl)-N-phenylpropanamide;
(3R)-3-[[2-[6-(4-acetylpiperazin-1-yl)-4-oxoquinazolin-3-yl]acetyl]amino]-N-methyl-3-[4-(trifluoromethyl)phenyl]propanamide;
(3R)-3-[[2-[6-(4-acetylpiperazin-1-yl)-4-oxoquinazolin-3-yl]acetyl]amino]-N,N-dimethyl-3-[4-(trifluoromethyl)phenyl]propanamide;
(3R)-3-[[2-[6-(4-acetylpiperazin-1-yl)-4-oxoquinazolin-3-yl]acetyl]amino]-N-(2-methylpropyl)-3-[4-(trifluoromethyl)phenyl]propanamide;
(3R)-3-[[2-[6-(4-acetylpiperazin-1-yl)-4-oxoquinazolin-3-yl]acetyl]amino]-N-phenyl-3-[4-(trifluoromethyl)phenyl]propanamide;
(3R)-3-[[2-[6-(4-acetylpiperazin-1-yl)-4-oxoquinazolin-3-yl]acetyl]amino]-N-methyl-3-(4-nitrophenyl)propanamide;
2-[6-(4-acetylpiperazin-1-yl)-4-oxoquinazolin-3-yl]-N-[(4-chlorophenyl)methyl]acetamide;
2-[6-(4-acetylpiperazin-1-yl)-4-oxoquinazolin-3-yl]-N-[(6-chloropyridin-3-yl)methyl]acetamide;
2-[6-(4-acetylpiperazin-1-yl)-4-oxoquinazolin-3-yl]-N-[(5-chloropyridin-2-yl)methyl]acetamide;
2-[6-(4-acetylpiperazin-1-yl)-4-oxoquinazolin-3-yl]-N-[1-(4-chlorophenyl)ethyl]acetamide;
2-[6-(4-acetylpiperazin-1-yl)-4-oxoquinazolin-3-yl]-N-[(4-fluorophenyl)methyl]acetamide;

2-[6-(4-acetylpiperazin-1-yl)-4-oxoquinazolin-3-yl]-N-(1,3-benzodioxol-5-ylmethyl)acetamide;

2-[6-(4-acetylpiperazin-1-yl)-4-oxoquinazolin-3-yl]-N-[[6-(trifluoromethyl)pyridin-3-yl]methyl]acetamide;

2-[6-(4-acetylpiperazin-1-yl)-4-oxoquinazolin-3-yl]-N-[[4-(trifluoromethyl)phenyl]methyl]acetamide;

2-[6-(4-acetylpiperazin-1-yl)-4-oxoquinazolin-3-yl]-N-[(6-cyanopyridin-3-yl)methyl]acetamide;

2-[6-(4-acetylpiperazin-1-yl)-4-oxoquinazolin-3-yl]-N-[(4-cyanophenyl)methyl]acetamide;

2-[6-(4-acetylpiperazin-1-yl)-4-oxoquinazolin-3-yl]-N-[[4-(trifluoromethoxy)phenyl]methyl]acetamide;

2-[6-(4-acetylpiperazin-1-yl)-4-oxoquinazolin-3-yl]-N-[(4-nitrophenyl)methyl]acetamide;

2-[6-(4-acetylpiperazin-1-yl)-4-oxoquinazolin-3-yl]-N-[(3,4-dichlorophenyl)methyl]acetamide;

2-[6-(4-acetylpiperazin-1-yl)-4-oxoquinazolin-3-yl]-N-[(2,4-dichlorophenyl)methyl]acetamide;

2-[6-(4-acetylpiperazin-1-yl)-4-oxoquinazolin-3-yl]-N-[(4-chloro-3-fluorophenyl)methyl]acetamide;

2-[6-(4-acetylpiperazin-1-yl)-4-oxoquinazolin-3-yl]-N-[(3-chloro-4-cyanophenyl)methyl]acetamide;

2-[6-(4-acetylpiperazin-1-yl)-4-oxoquinazolin-3-yl]-N-[[4-fluoro-3-(trifluoromethoxy)phenyl]methyl]acetamide;

(3R)-3[[2-[6-(4-acetylpiperazin-1-yl)-4-oxoquinazolin-3-yl]acetyl]amino]-3-(4-chlorophenyl)propanamide;

2-[6-(4-acetylpiperazin-1-yl)-4-oxoquinazolin-3-yl]-N-[(4-cyano-3-fluorophenyl)methyl]acetamide;

2-[6-(4-acetylpiperazin-1-yl)-4-oxoquinazolin-3-yl]-N-[(2-chloro-4-cyanophenyl)methyl]acetamide;

2-[6-(4-acetylpiperazin-1-yl)-4-oxoquinazolin-3-yl]-N-[(4-cyano-2-fluorophenyl)methyl]acetamide;

2-[6-(4-acetylpiperazin-1-yl)-4-oxoquinazolin-3-yl]-N-[(4-cyano-2,6-difluorophenyl)methyl]acetamide;

2-[6-(4-acetylpiperazin-1-yl)-4-oxoquinazolin-3-yl]-N-[(4-cyano-2-methoxyphenyl)methyl]acetamide;

2-[6-(4-acetylpiperazin-1-yl)-4-oxoquinazolin-3-yl]-N4 [4-cyano-2-(2,2,2-trifluoroethoxy)phenyl]methyl]acetamide;

2-[6-(4-acetylpiperazin-1-yl)-4-oxoquinazolin-3-yl]-N4 [4-chloro-3-(trifluoromethyl)phenyl]methyl]acetamide;

2-[6-(4-acetylpiperazin-1-yl)-4-oxoquinazolin-3-yl]-N-[(3-cyano-2-methylphenyl)methyl]acetamide;

2-[6-(4-acetylpiperazin-1-yl)-4-oxoquinazolin-3-yl]-N-[(2-chloropyridin-4-yl)methyl]acetamide;

2-[6-(4-acetylpiperazin-1-yl)-4-oxoquinazolin-3-yl]-N-[(3-nitrophenyl)methyl]acetamide;

2-[6-(4-acetylpiperazin-1-yl)-4-oxoquinazolin-3-yl]-N-[[4-chloro-3-(trifluoromethoxy)phenyl]methyl]acetamide;

2-[6-(4-acetylpiperazin-1-yl)-4-oxoquinazolin-3-yl]-N-[[4-(pentafluoro-$\lambda^6$-sulfanyl)phenyl]methyl]acetamide;

2-[6-(4-acetylpiperazin-1-yl)-4-oxoquinazolin-3-yl]-N-[(3-methyl-4-methylsulfonylphenyl)methyl]acetamide;

2-[6-(4-acetylpiperazin-1-yl)-4-oxoquinazolin-3-yl]-N-[(4,5-dichloropyridin-2-yl)methyl]acetamide;

2-[6-(4-acetylpiperazin-1-yl)-4-oxoquinazolin-3-yl]-N-[(3-chloro-4-methylphenyl)methyl]acetamide;

2-[6-(4-acetylpiperazin-1-yl)-4-oxoquinazolin-3-yl]-N-[(4-chlorophenyl)methyl]-N-methylacetamide;

2-[6-(4-acetylpiperazin-1-yl)-4-oxoquinazolin-3-yl]-N-[(3,4-dichlorophenyl)methyl]-N-methylacetamide;

2-[6-(4-acetylpiperazin-1-yl)-4-oxoquinazolin-3-yl]-N-[(4-cyano-3-fluorophenyl)methyl]-N-methylacetamide;

2-[6-(4-acetylpiperazin-1-yl)-4-oxoquinazolin-3-yl]-N-[(2,6-dichloropyridin-4-yl)methyl]-N-methylacetamide;

6-(4-acetylpiperazin-1-yl)-3-[2-[2-(4-chlorophenyl)pyrrolidin-l-yl]-2-oxoethyl]quinazolin-4-one;

6-(4-acetylpiperazin-1-yl)-3-[2-[(2R)-2-(4-methylphenyl)pyrrolidin-l-yl]-2-oxoethyl]quinazolin-4-one;

3-[[2-[6-(4-acetylpiperazin-1-yl)-4-oxoquinazolin-3-yl]acetyl]amino]-3-(3,4-dichlorophenyl)-N-methylpropanamide;

methyl 3-[[2-[6-(4-acetylpiperazin-1-yl)-4-oxoquinazolin-3-yl]acetyl]-[(3,4-dichlorophenyl)methyl]amino]propanoate;

3-[[2-[6-(4-acetylpiperazin-1-yl)-4-oxoquinazolin-3-yl]acetyl]-[(3,4-dichlorophenyl)methyl]amino]propanoic acid;

3-[[2-[6-(4-acetylpiperazin-1-yl)-4-oxoquinazolin-3-yl]acetyl]-[(3,4-dichlorophenyl)methyl]amino]-N-methylpropanamide;

2-[6-(4-acetylpiperazin-1-yl)-4-oxoquinazolin-3-yl]-N-[(3-chloro-4-cyanophenyl)methyl]-N-methylacetamide;

2-[6-(4-acetylpiperazin-1-yl)-4-oxoquinazolin-3 -yl]-N-[(4-chloro-3-cyanophenyl)methyl] -N-methylacetamide;

2-[6-(4-acetylpiperazin-1-yl)-4-oxoquinazolin-3 -yl]-N-[(4-cyano-3,5-difluorophenyl)methyl]-N-methylacetamide;

N-[(3,4-dichlorophenyl)methyl]-2-[6-[4-(3-methylbutanoyl)piperazin-1-yl]-4-oxoquinazolin-3 -yl]acetamide;

N-[(3,4-dichlorophenyl)methyl]-2-[4-oxo-6-(4-pentanoylpiperazin-1-yl)quinazolin-3 -yl]acetamide;

N-[(3,4-dichlorophenyl)methyl]-2-[6-[4-(2-methoxyacetyl)piperazin-1-yl]-4-oxoquinazolin-3 -yl]acetamide;

N-[(3,4-dichlorophenyl)methyl]-2-[4-oxo-6-[4-(2,2,2-trifluoroacetyl)piperazin- 1-yl]quinazolin-3-yl]acetamide;

2-[6-[4-(cyclobutanecarbonyl)piperazin-1-yl]-4-oxoquinazolin-3-yl]-N-[(3,4-dichlorophenyl)methyl]acetamide;

2-[6-[4-(cyclopentanecarbonyl)piperazin-1-yl]-4-oxoquinazolin-3 -yl]-N-[(3,4-dichlorophenyl)methyl]acetamide;

2-[6-[4-(cyclohexanecarbonyl)piperazin-1-yl]-4-oxoquinazolin-3-yl]-N-[(3,4-dichlorophenyl)methyl]acetamide;

N-[(3,4-dichlorophenyl)methyl]-2-[6-[4-(oxane-4-carbonyl)piperazin- 1-yl]-4-oxoquinazolin-3-yl]acetamide;

N-[(3,4-dichlorophenyl)methyl]-2-[6-[4-(1,2-oxazole-5-carbonyl)piperazin-1-yl]-4-oxoquinazolin-3-yl]acetamide;

N-[(3,4-dichlorophenyl)methyl]-N-methyl-2-[4-oxo-6-(4-propanoylpiperazin-1-yl)quinazolin-3-yl]acetamide;

N-[(3,4-dichlorophenyl)methyl]-N-methyl-2-[6-[4-(2-methylpropanoyl)piperazin-1-yl]-4-oxoquinazolin-3 -yl]acetamide;

2-[6-[4-(3-aminooxetane-3-carbonyl)piperazin- 1-yl]-4-oxoquinazolin-3-yl]-N-[(3,4-dichlorophenyl)methyl]acetamide;

N-[(3,4-dichlorophenyl)methyl]-2- [4-oxo-6-[4-(2-sulfamoylacetyl)piperazin-1-yl]quinazolin-3-yl]acetamide;

N-[(3,4-dichlorophenyl)methyl]-2-[4-oxo-6-[4-(4-sulfamoylbutanoyl)piperazin-1-yl]quinazolin-3-yl]acetamide;

2-[6-[4-(cyclobutanecarbonyl)piperazin-1-yl]-4-oxoquinazolin-3-yl]-N-[(3,4-dichlorophenyl)methyl]-N-methylacetamide;

N-[(3,4-dichlorophenyl)methyl]-2-[6-[4-(3-fluorocyclobutanecarbonyl)piperazin-1-yl]-4-oxoquinazolin-3-yl]-N-methylacetamide;

N-[(3,4-dichlorophenyl)methyl]-2-[6-[4-(3,3-difluorocyclobutanecarbonyl)piperazin-1-yl]-4-oxoquinazolin-3-yl]-N-methylacetamide;

N-[(3,4-dichlorophenyl)methyl]-N-methyl-2-[4-oxo-6-[4-[1-(trifluoromethyl)cyclobutanecarbonyl]piperazin-1-yl]quinazolin-3-yl]acetamide;

2[6-[4-(3-chlorocyclobutanecarbonyl)piperazin-l-yl]-4-oxoquinazolin-3-yl]-N-[(3,4-dichlorophenyl)methyl]-N-methylacetamide;

N-[(3,4-dichlorophenyl)methyl]-2-[6-[4-(3-methoxycyclobutanecarbonyl)piperazin-1-yl]-4-oxoquinazolin-3-yl]-N-methylacetamide;

N-[(3,4-dichlorophenyl)methyl]-N-methyl-2-[6-[4-(oxetane-3-carbonyl)piperazin-1-yl]-4-oxoquinazolin-3-yl]acetamide;

N-[(3,4-dichlorophenyl)methyl]-N-methyl-2-[6-[4-(3-methyloxetane-3-carbonyl)piperazin-1-yl]-4-oxoquinazolin-3-yl]acetamide;

2-[6-[4-(1-acetylazetidine-3-carbonyl)piperazin-1-yl]-4-oxoquinazolin-3-yl]-N-[(3,4-dichlorophenyl)methyl]-N-methylacetamide;

4-[3-[2-[(3,4-dichlorophenyl)methylamino]-2-oxoethyl]-4-oxoquinazolin-6-yl]-N-propan-2-ylpiperazine-1-carboxamide;

N-cyclopropyl-4-[3-[2-[(3,4-dichlorophenyl)methylamino]-2-oxoethyl]-4-oxoquinazolin-6-yl]piperazine-1-carboxamide;

N-cyclopentyl-4-[3-[2-[(3,4-dichlorophenyl)methylamino]-2-oxoethyl]-4-oxoquinazolin-6-yl]piperazine-1-carboxamide;

4-[3-[2-[(3,4-dichlorophenyl)methylamino]-2-oxoethyl]-4-oxoquinazolin-6-yl]-N-(2-methoxyethyl)piperazine-1-carboxamide;

4-[3-[2-[(3,4-dichlorophenyl)methylamino]-2-oxoethyl]-4-oxoquinazolin-6-yl]-N-(3,5-dimethyl-1,2-oxazol-4-yl)piperazine-1-carboxamide;

4-[3-[2-[(3,4-dichlorophenyl)methylamino]-2-oxoethyl]-4-oxoquinazolin-6-yl]-N-pyridin-3-ylpiperazine-1-carboxamide;

N-[(3,4-dichlorophenyl)methyl]-2-[6-(4-methylsulfonylpiperazin-1-yl)-4-oxoquinazolin-3-yl]acetamide;

2-[6-(4-cyclopentylsulfonylpiperazin-1-yl)-4-oxoquinazolin-3-yl]-N-[(3,4-dichlorophenyl)methyl]acetamide;

2-[6-(4-cyclohexylsulfonylpiperazin-1-yl)-4-oxoquinazolin-3-yl]-N-[(3,4-dichlorophenyl)methyl]acetamide;

2-[6-(4-cyclopropylsulfonylpiperazin-1-yl)-4-oxoquinazolin-3-yl]-N-[(3,4-dichlorophenyl)methyl]-N-methylacetamide;

2-[6-[4-(cyclobutylmethylsulfonyl)piperazin-1-yl]-4-oxoquinazolin-3-yl]-N-[(3,4-dichlorophenyl)methyl]-N-methylacetamide;

methyl 2-[4-[3-[2-[(3,4-dichlorophenyl)methylamino]-2-oxoethyl]-4-oxoquinazolin-6-yl]piperazin-1-yl]acetate;

N-[(3,4-dichlorophenyl)methyl]-2-[6-[4-[4-(2-hydroxyethyl)piperazin-1-yl]-4-oxoquinazolin-3-yl]acetamide;

N-[(3,4-dichlorophenyl)methyl]-2-[6-[4-(2,3-dihydroxypropyl)piperazin-1-yl]-4-oxoquinazolin-3-yl]acetamide;

2-[6-[4-(cyclobutylmethyl)piperazin-1-yl]-4-oxoquinazolin-3-yl]-N-[(3,4-dichlorophenyl)methyl]acetamide;

N-[(3,4-dichlorophenyl)methyl]-2-[4-oxo-[4-(oxolan-3-ylmethyl)piperazin-1-yl]quinazolin-3-yl]acetamide;

N-[(3,4-dichlorophenyl)methyl]-2-[6-[4-(oxan-4-ylmethyl)piperazin-1-yl]-4-oxoquinazolin-3-yl]acetamide;

N-[(3,4-dichlorophenyl)methyl]-2-[6-[4-[(1-methylpyrrol-2-yl)methyl]piperazin-1-yl]-4-oxoquinazolin-3-yl]acetamide;

N-[(3,4-dichlorophenyl)methyl]-2-[6-[4-(1H-imidazol-2-ylmethyl)piperazin-1-yl]-4-oxoquinazolin-3-yl]acetamide;

N-[(3,4-dichlorophenyl)methyl]-2-[6-[4-(1H-imidazol-5-ylmethyl)piperazin-1-yl]-4-oxoquinazolin-3-yl]acetamide;

3-[[4-[3-[2-[(3,4-dichlorophenyl)methylamino]-2-oxoethyl]-4-oxoquinazolin-6-yl]piperazin-1-yl]methyl]furan-2-carboxylic acid;

N-[(3,4-dichlorophenyl)methyl]-2-[6-[4-[(2,4-dimethyl-1,3-oxazol-5-yl)methyl]piperazin-1-yl]-4-oxoquinazolin-3-yl]acetamide;

2-[6-[4-(cyclopropylmethyl)piperazin-1-yl]-4-oxoquinazolin-3-yl]-N-[(3,4-dichlorophenyl)methyl]-N-methylacetamide;

N-[(3,4-dichlorophenyl)methyl]-2-[6-[4-(2-methoxyethyl)piperazin-1-yl]-4-oxoquinazolin-3-yl]-N-methylacetamide;

N-[(3,4-dichlorophenyl)methyl]-N-methyl-2-[6-[4-(oxetan-3-ylmethyl)piperazin-1-yl]-4-oxoquinazolin-3-yl]acetamide;

N-[(3,4-dichlorophenyl)methyl]-N-methyl-2-[6-[4-[2-(methylamino)-2-oxoethyl]piperazin-1-yl]-4-oxoquinazolin-3-yl]acetamide;

N-[(3,4-dichlorophenyl)methyl]-2-[6-[4-[2-(dimethylamino)-2-oxoethyl]piperazin-1-yl]-4-oxoquinazolin-3-yl]-N-methylacetamide;

N-[(3,4-dichlorophenyl)methyl]-N-methyl-2-[4-oxo-6-[4-[2-oxo-2-(propan-2-ylamino)ethyl]piperazin-1-yl]quinazolin-3-yl]acetamide;

N-[(3,4-dichlorophenyl)methyl]-2-[6-[4-[2-(diethylamino)-2-oxoethyl]piperazin-1-yl]-4-oxoquinazolin-3-yl]-N-methylacetamide;

N-[(3,4-dichlorophenyl)methyl]-N-methyl-2-[6-[4-(2-morpholin-4-yl-2-oxoethyl)piperazin-l-yl]-4-oxoquinazolin-3-yl]acetamide;

2-[6-[4-(2-anilino-2-oxoethyl)piperazin-1-yl]-4-oxoquinazolin-3-yl]-N-[(3,4-dichlorophenyl)methyl]-N-methylacetamide;

N-[(2-chloro-4-cyanophenyl)methyl]-2-[6-[4-(oxetane-3-carbonyl)piperazin-1-yl]-4-oxoquinazolin-3-yl]acetamide;

N-[(3-chloro-4-cyanophenyl)methyl]-N-methyl-2-[4-oxo-6-[4-(oxolan-3-ylmethyl)piperazin-1-yl]quinazolin-3-yl]acetamide;

N-[(4-chloro-3-cyanophenyl)methyl]-N-methyl-2-[4-oxo-6-[4-(oxolan-3-ylmethyl)piperazin-1-yl]quinazolin-3-yl]acetamide;

2-[6-(4-acetylpiperazin-1-yl)-4-oxoquinazolin-3-yl]-N-[(3,4-dichlorophenyl)methyl]-N-ethylacetamide;

2-[6-(4-acetylpiperazin-1-yl)-4-oxoquinazolin-3-yl]-N-[(3,4-dichlorophenyl)methyl]-N-propan-2-ylacetamide;

2-[6-(4-acetyl-1,4-diazepan-1-yl)-4-oxoquinazolin-3-yl]-N-[(3,4-dichlorophenyl)methyl]acetamide;

2-[6-(4-acetyl-1,4-diazepan-1-yl)-4-oxoquinazolin-3-yl]-N-[[4-(trifluoromethyl)phenyl]methyl]acetamide;
2-[6-(4-acetyl-1,4-diazepan-1-yl)-4-oxoquinazolin-3-yl]-N-[(3-chloro-4-cyanophenyl)methyl]-N-methylacetamide;
2-[6-(4-acetyl-1,4-diazepan-1-yl)-4-oxoquinazolin-3-yl]-N-[(4-chloro-3-cyanophenyl)methyl]-N-methylacetamide;
2-[6-(1-acetylpiperidin-4-yl)-4-oxoquinazolin-3-yl]-N-[(3,4-dichlorophenyl)methyl]acetamide;
2-[6-(1-acetylpiperidin-4-yl)-4-oxoquinazolin-3-yl]-N-[[4-(trifluoromethyl)phenyl]methyl]acetamide;
2-[6-(1-acetylpiperidin-4-yl)-4-oxoquinazolin-3-yl]-N-[(3,4-dichlorophenyl)methyl]-N-methylacetamide;
2-[6-(1-acetylpiperidin-4-yl)-4-oxoquinazolin-3-yl]-N-[(3-chloro-4-cyanophenyl)methyl]-N-methylacetamide;
2-[6-(1-acetylpiperidin-4-yl)-4-oxoquinazolin-3-yl]-N-[(4-chloro-3-cyanophenyl)methyl]-N-methylacetamide;
2-[6-(1-acetylpiperidin-4-yl)-4-oxoquinazolin-3-yl]-N-[(4-cyano-3-fluorophenyl)methyl]-N-methylacetamide;
2-[6-(1-acetylpiperidin-4-yl)-4-oxoquinazolin-3-yl]-N4 [4-chloro-3-(trifluoromethoxy)phenyl]methyl]-N-methylacetamide;
N-[(3-chloro-4-cyanophenyl)methyl]-N-methyl-2-[4-oxo-6-[4-(oxolan-3-ylmethyl)-1,4-diazepan-1-yl]quinazolin-3-yl]acetamide;
N-[(4-chloro-3-cyanophenyl)methyl]-N-methyl-2-[4-oxo-6-[4-(oxolan-3-ylmethyl)-1,4-diazepan-1-yl]quinazolin-3-yl]acetamide;
N-[(3-chloro-4-cyanophenyl)methyl]-2-[6-[1-(2-hydroxyacetyl)piperidin-4-yl]-4-oxoquinazolin-3-yl]-N-methylacetamide;
N-[(3-chloro-4-cyanophenyl)methyl]-2-[6-[1-(2-methoxyacetyl)piperidin-4-yl]-4-oxoquinazolin-3-yl]-N-methylacetamide;
N-[(3-chloro-4-cyanophenyl)methyl]-2-[6-[1-(2-methoxypropanoyl)piperidin-4-yl]-4-oxoquinazolin-3-yl]-N-methylacetamide;
N-[(3-chloro-4-cyanophenyl)methyl]-2-[6-[1-(3-methoxypropanoyl)piperidin-4-yl]-4-oxoquinazolin-3-yl]-N-methylacetamide;
N-[(3-chloro-4-cyanophenyl)methyl]-N-methyl-2-[4-oxo-6-[1-(2-propan-2-yloxyacetyl)piperidin-4-yl]quinazolin-3-yl]acetamide;
N-[(3-chloro-4-cyanophenyl)methyl]-2-[6-[1-(cyclopropanecarbonyl)piperidin-4-yl]-4-oxoquinazolin-3-yl]-N-methylacetamide;
N-[(3-chloro-4-cyanophenyl)methyl]-2-[6-[1-(cyclobutanecarbonyl)piperidin-4-yl]-4-oxoquinazolin-3-yl]-N-methylacetamide;
N-[(3-chloro-4-cyanophenyl)methyl]-2-[6-[1-(3-fluorocyclobutanecarbonyl)piperidin-4-yl]-4-oxoquinazolin-3-yl]-N-methylacetamide;
N-[(3-chloro-4-cyanophenyl)methyl]-2-[6-[1-(3-chlorocyclobutanecarbonyl)piperidin-4-yl]-4-oxoquinazolin-3-yl]-N-methylacetamide;
N-[(3-chloro-4-cyanophenyl)methyl]-2-[6-[1-(3,3-difluorocyclobutanecarbonyl)piperidin-4-yl]-4-oxoquinazolin-3-yl]-N-methylacetamide;
N-[(3-chloro-4-cyanophenyl)methyl]-N-methyl-2-[6-[1-(oxetane-2-carbonyl)piperidin-4-yl]-4-oxoquinazolin-3-yl]acetamide;
N-[(3-chloro-4-cyanophenyl)methyl]-N-methyl-2-[6-[1-(oxetane-3-carbonyl)piperidin-4-yl]-4-oxoquinazolin-3-yl]acetamide;
N-[(3 -chloro-4-cyanophenyl)methyl]-N-methyl-2-[4-oxo-6-[1-(oxolan-3-ylmethyl)piperidin-4-yl]quinazolin-3-yl]acetamide;
N-[(4-chloro-3-cyanophenyl)methyl]-N-methyl-2-[4-oxo-6-[1-(oxolan-3-ylmethyl)piperidin-4-yl]quinazolin-3-yl]acetamide;
N-[(3-chloro-4-cyanophenyl)methyl]-N-methyl-2-[6-(1-methylsulfonylpiperidin-4-yl)-4-oxoquinazolin-3-yl]acetamide;
N-cyclopropyl-N-[(3,4-dichlorophenyl) methyl]-2-[6-[1-(2-methoxyacetyl)piperidin-4-yl]-4-oxoquinazolin-3-yl]acetamide;
2-[6-[2-acetyl-2-azabicyclo[2.2.1]heptan-5-yl]-4-oxoquinazolin-3-yl]-N-[(3,4-dichlorophenyl)methyl]acetamide;
2-[6-(4-acetylpiperazin-1-yl)-4-oxoquinazolin-3-yl]-N-[(3,4-dichlorophenyl)methyl]propanamide;
2-[6-(4-acetylpiperazin-1-yl)-4-oxoquinazolin-3-yl]-N-[(3,4-dichlorophenyl)methyl]-N-methylpropanamide;
1-[6-(4-acetylpiperazin-1-yl)-4-oxoquinazolin-3-yl]-N-[(3,4-dichlorophenyl)methyl]cyclopropane-1-carboxamide; and
2-[6-(4-acetylpiperazin-1-yl)-2-methyl-4-oxoquinazolin-3-yl]-N-[(3,4-dichlorophenyl)methyl]acetamide;
or a pharmaceutically acceptable salt thereof 32. A compound according to claim 1, selected from
2-(6-(4-acetylpiperazin-l-yl)-4-oxoquinazolin-3(4H)-yl)-N-(1-(3,4-dichlorophenyl)-3-methoxypropyl)acetamide;
N-(3-chloro-4-cyanobenzyl)-2-(6-(1-(2-cyanoacetyl)piperidin-4-yl)-4-oxoquinazolin-3(4H)-yl)-N-methylacetamide;
N-(3-chloro-4-cyanobenzyl)-2-(6-(1-(3-cyanopropanoyl)piperidin-4-yl)-4-oxoquinazolin-3(4H)-yl)-N-methylacetamide;
(R)-N-(3-chloro-4-cyanobenzyl)-2-(6-(1-(2-hydroxypropanoyl)piperidin-4-yl)-4-oxoquinazolin-3(4H)-yl)-N-methylacetamide;
(R)-N-(3-chloro-4-cyanobenzyl)-2-(6-(1-(2-hydroxy-3-methylbutanoyl)piperidin-4-yl)-4-oxoquinazolin-3 (4H)-yl)-N-methylacetamide;
(R)-N-(3-chloro-4-cyanobenzyl)-2-(6-(1-(2-methoxypropanoyl)piperidin-4-yl)-4-oxoquinazolin-3(4H)-yl)-N-methylacetamide;
(S)-N-(3-chloro-4-cyanobenzyl)-2-(6-(1-(2-methoxypropanoyl)piperidin-4-yl)-4-oxoquinazolin-3(4H)-yl)-N-methylacetamide;
methyl 4-(3-(2-((3-chloro-4-cyanobenzyl)(methyl)amino)-2-oxoethyl)-4-oxo-3,4-dihydroquinazolin-6-yl)piperidine-l-carboxylate;
2-(6-(1-acetylpiperidin-4-yl)-4-oxoquinazolin-3(4H)-yl)-N-(3-chloro-5-(trifluoromethyl)benzyl)acetamide;
2-(6-(1-acetylpiperidin-4-yl)-4-oxoquinazolin-3(4H)-yl)-N-(4-fluoro-3-(trifluoromethyl)benzyl)acetamide;
2-(6-(1-acetylpiperidin-4-yl)-4-oxoquinazolin-3(4H)-yl)-N-(4-chloro-3-(trifluoromethyl)benzyl)acetamide;
2-(6-(1-acetylpiperidin-4-yl)-4-oxoquinazolin-3(4H)-yl)-N-(3,5-dichlorobenzyl)acetamide;
N-(3,4-dichlorobenzyl)-N-methyl-2-(4-oxo-6-(1-(2-sulfamoylacetyl)piperidin-4-yl)quinazolin-3(4H)-yl)acetamide;
N-(3,4-dichlorobenzyl)-2-(6-(1-(2-(2-methoxyethoxy)acetyl)piperidin-4-yl)-4-oxoquinazolin-3(4H)-yl)-N-methylacetamide;

(R)-N-(3,4-dichlorobenzyl)-2-(6-(1-(2-methoxypropanoyl)piperidin-4-yl)-4-oxoquinazolin-3(4H)-yl)-N-methylacetamide;
(S)-N-(3,4-dichorobenzyl)-2-(6-(1-(2-methoxypropanoyl)piperidin-4-yl)-4-oxoquinazolin-3(4H)-yl)-N-methylacetamide;
(R)-N-(3,4-dichlorobenzyl)-2-(6-(1-(2-hydroxy-3-methylbutanoyl)piperidin-4-yl)-4-oxoquinazolin-3(4H)-yl)-N-methylacetamide;
(S)-N-(3,4-dichlorobenzyl)-2-(6-(1-(2-hydroxy-3-methylbutanoyl)piperidin-4-yl)-4-oxoquinazolin-3(4H)-yl)-N-methylacetamide;
N-(3,4-dichlorobenzyl)-2-(6-(1-(2-methoxyacetyl)piperidin-4-yl)-4-oxoquinazolin-3(4H)-yl)-N-methylacetamide;
N-(3,4-dichlorobenzyl)-2-(6-(1-(2-hydroxy-2-methylpropanoyl)piperidin-4-yl)-4-oxoquinazolin-3(4H)-yl)-N-methylacetamide;
N-(3,4-dichlorobenzyl)-2-(6-(1-(2-methoxypropanoyl)piperidin-4-yl)-4-oxoquinazolin-3(4H)-yl)-N-methylacetamide;
(R)-N-(3,4-dichlorobenzyl)-2-(6-(1-(2-hydroxypropanoyl)piperidin-4-yl)-4-oxoquinazol in-3(4H)-yl)-N-methylacetamide;
(S)-N-(3,4-dichlorobenzyl)-2-(6-(1-(2-hydroxypropanoyl)piperidin-4-yl)-4-oxoquinazolin-3(4H)-yl)-N-methylacetamide;
N-(3,4-dichlorobenzyl)-2-(6-(1-(1-hydroxycyclobutanecarbonyl)piperidin-4-yl)-4-oxoquinazol in-3(4H)-yl)-N-methylacetamide;
N-(3,4-dichlorobenzyl)-2-(6-(1-(2,3-dihydroxypropanoyl)piperidin-4-yl)-4-oxoquinazolin-3(4H)-yl)-N-methylacetamide;
2-(6-(1-(1,4-dioxane-2-carbonyl)piperidin-4-yl)-4-oxoquinazolin-3(4H)-yl)-N-(3,4-dichlorobenzyl)-N-methylacetamide;
N-(3,4-dichlorobenzyl)-2-(6-(1-(1-hydroxycyclopropanecarbonyl)piperidin-4-yl)-4-oxoquinazolin-3(4H)-yl)-N-methylacetamide;
N-(3,4-dichlorobenzyl)-N-methyl-2-(4-oxo-6-(1-(tetrahydrofuran-2-carbonyl)piperidin-4-yl)quinazolin-3(4H)-yl)acetamide;
N-(3,4-dichlorobenzyl)-N-methyl-2-(6-(1-(2-methyltetrahydrofuran-2-carbonyl)piperidin-4-yl)-4-oxoquinazolin-3(4H)-yl)acetamide;
N-(3,4-dichlorobenzyl)-N-methyl-2-(4-oxo-6-(1-(tetrahydrofuran-3-carbonyl)piperidin-4-yl)quinazolin-3(4H)-yl)acetamide;
N-(3,4-dichlorobenzyl)-N-methyl-2-(6-(1-(oxazole-5-carbonyl)piperidin-4-yl)-4-oxoquinazolin-3(4H)-yl)acetamide;
2-[6-(1-acetyl-4-hydroxypiperidin-4-yl)-4-oxoquinazolin-3-yl]-N-[(3,4-dichlorophenyl)methyl]-N-methylacetamide;
2-[6-(1-acetyl-4-hydroxypiperidin-4-yl)-4-oxoquinazolin-3-yl]-N-[(3-chloro-4-cyanophenyl)methyl]-N-methylacetamide;
[2-[4-[3-[2-[(3-chloro-4-cyanophenyl)methyl-methylamino]-2-oxoethyl]-4-oxoquinazolin-6-yl]piperidin-1-yl]-2-oxoethyl]nitrate;
2-(6-(1-acetylpiperidin-4-yl)-8-fluoro-4-oxoquinazolin-3(4H)-yl)-N-(3-chloro-4-cyanobenzyl)-N-methylacetamide;
N-(3-chloro-4-cyanobenzyl)-2-(8-fluoro-6-(1-(3-methoxypropanoyl)piperidin-4-y1)-4-oxoquinazolin-3(4H)-yl)-N-methylacetamide;
2-(6-(1-acetylpiperidin-4-yl)-4-oxopyrido[3,4-d]pyrimidin-3(4H)-yl)-N-(3-chloro-4-cyanobenzyl)-N-methylacetamide; and
N-(3-chloro-4-cyanobenzyl)-2-(6-(1-(3-methoxypropanoyl)piperidin-4-yl)-4-oxopyrido[3,4-d]pyrimidin-3(4H)-yl)-N-methylacetamide;
or a pharmaceutically acceptable salt thereof.

33. A compound according to claim 1, selected from
2-[6-(4-acetylpiperazin-1-yl)-4-oxoquinazolin-3-yl]-N-[(4-chloro-3-fluorophenyl)methyl]acetamide;
2-[6-(4-acetylpiperazin-1-yl)-4-oxoquinazolin-3-yl]-N-[(3-chloro-4-cyanophenyl)methyl]acetamide;
2-[6-(4-acetylpiperazin-1-yl)-4-oxoquinazolin-3-yl]-N-[(4-cyano-3-fluorophenyl)methyl]acetamide;
2-[6-(4-acetylpiperazin-1-yl)-4-oxoquinazolin-3-yl]-N-[(3,4-dichlorophenyl)methyl]-N-methylacetamide;
2-[6-(4-acetylpiperazin-1-yl)-4-oxoquinazolin-3-yl]-N-[(3-chloro-4-cyanophenyl)methyl]-N-methylacetamide;
2-[6-(1-acetylpiperidin-4-yl)-4-oxoquinazolin-3-yl]-N-[(3-chloro-4-cyanophenyl)methyl]-N-methylacetamide; and
N-[(3-chloro-4-cyanophenyl)methyl]-2-[6-[1-(2-methoxyacetyl)piperidin-4-yl]-4-oxoquinazolin-3-yl]-N-methylacetamide;
or a pharmaceutically acceptable salt thereof.

34. A process to prepare a compound according to claim 1, or a pharmaceutically acceptable salt thereof, comprising the reaction of a compound of formula (VI) in the presence of a compound of formula (VII), wherein $A^2$ is —C(O)—

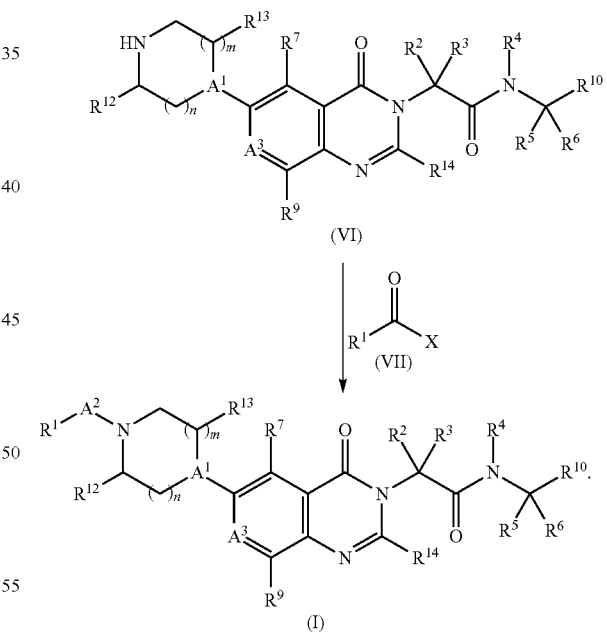

35. A pharmaceutical composition comprising a compound according to claim 1, or a pharmaceutically acceptable salt thereof, and a therapeutically inert carrier.

36. A method for the treatment of glaucoma, which method comprises administering to an individual in need thereof an effective amount of a compound according to claim 1, or a pharmaceutically acceptable salt thereof 37. A compound according to claim 1, or a pharmaceutically acceptable salt thereof, when manufactured according to a process comprising the reaction of a compound of formula (VI) in the presence of a compound of formula (VII), wherein $A^2$ is —C(O)—

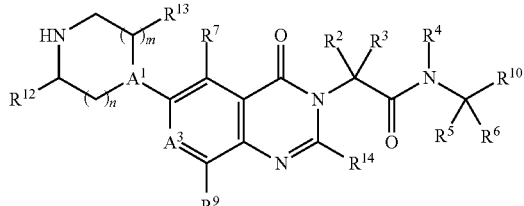

(VI)

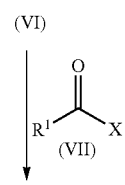

(VII)

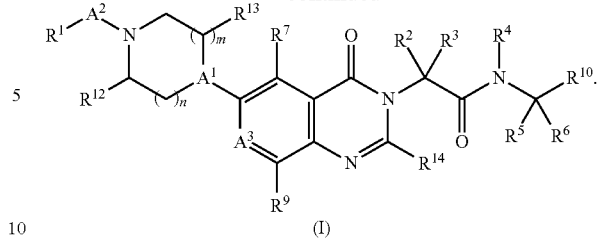

(I)

38. A compound that is N-[(3-chloro-4-cyanophenyl)methyl]-2-[6-[1-(3-methoxypropanoyl)piperidin-4-yl]-4-oxoquinazolin-3-yl]-N-methylacetamide, or a pharmaceutically acceptable salt thereof 39. A pharmaceutical composition comprising the compound according to claim 38, or a pharmaceutically acceptable salt thereof, and a therapeutically inert carrier.

* * * * *